(12) United States Patent
Sugiyama et al.

(10) Patent No.: US 11,161,884 B2
(45) Date of Patent: Nov. 2, 2021

(54) MODIFIED BIOTIN, STREPTAVIDIN MUTANT, AND USAGE OF THEM

(71) Applicant: SAVID THERAPEUTICS INC., Tokyo (JP)

(72) Inventors: Akira Sugiyama, Tokyo (JP); Hirofumi Doi, Chiba (JP); Tatsuhiko Kodama, Tokyo (JP); Tsuyoshi Inoue, Osaka (JP); Eiichi Mizohata, Osaka (JP); Tatsuya Kawato, Tokushima (JP); Tomohiro Meshizuka, Osaka (JP); Motomu Kanai, Tokyo (JP); Yohei Shimizu, Tokyo (JP); Noriaki Takasu, Mie (JP); Mari Takatsu, Tokyo (JP)

(73) Assignee: SAVID THERAPEUTICS INC., Tokyo (JP)

( * ) Notice: Subject to any disclaimer, the term of this patent is extended or adjusted under 35 U.S.C. 154(b) by 0 days.

(21) Appl. No.: 16/512,894

(22) Filed: Jul. 16, 2019

(65) Prior Publication Data

US 2020/0017558 A1 Jan. 16, 2020

Related U.S. Application Data

(62) Division of application No. 15/119,441, filed as application No. PCT/JP2015/054431 on Feb. 18, 2015.

(30) Foreign Application Priority Data

Feb. 18, 2014 (JP) ................................ 2014-028525
Oct. 17, 2014 (JP) ................................ 2014-212861

(51) Int. Cl.
| | | |
|---|---|---|
| *A61B 5/00* | (2006.01) |
| *A61B 8/00* | (2006.01) |
| *A61B 10/00* | (2006.01) |
| *C07K 14/36* | (2006.01) |
| *A61K 49/00* | (2006.01) |
| *C07D 519/00* | (2006.01) |
| *C07D 495/04* | (2006.01) |
| *C07K 16/22* | (2006.01) |
| *C07K 16/28* | (2006.01) |
| *C09B 23/10* | (2006.01) |
| *C07K 14/00* | (2006.01) |

(52) U.S. Cl.
CPC .......... *C07K 14/36* (2013.01); *A61K 49/0032* (2013.01); *A61K 49/0052* (2013.01); *A61K 49/0058* (2013.01); *C07D 495/04* (2013.01); *C07D 519/00* (2013.01); *C07K 16/22* (2013.01); *C07K 16/2887* (2013.01); *C09B 23/107* (2013.01); *C07K 14/00* (2013.01); *C07K 2317/24* (2013.01); *C07K 2317/622* (2013.01); *C07K 2319/21* (2013.01); *C07K 2319/22* (2013.01); *C07K 2319/33* (2013.01)

(58) Field of Classification Search
None
See application file for complete search history.

(56) References Cited

U.S. PATENT DOCUMENTS

| | | |
|---|---|---|
| 6,153,442 A | 11/2000 | Pirio et al. |
| 7,842,475 B2 | 11/2010 | Zheng |
| 9,670,255 B2 | 6/2017 | Sugiyama |
| 2002/0068367 A1 | 6/2002 | Coffen et al. |
| 2009/0176213 A1 | 7/2009 | Zheng et al. |
| 2012/0039879 A1 | 2/2012 | Kodama et al. |
| 2012/0214970 A1 | 8/2012 | Howarth |
| 2014/0011255 A1 | 1/2014 | Ying et al. |

FOREIGN PATENT DOCUMENTS

| | | |
|---|---|---|
| CN | 1353609 | 6/2002 |
| CN | 1457260 | 11/2003 |
| CN | 102325884 | 1/2012 |
| CN | 103298949 A | 9/2013 |
| CN | 104995196 A | 10/2015 |
| EP | 1304331 | 4/2003 |
| EP | 2 335 721 A1 | 6/2011 |
| EP | 2 960 243 A1 | 12/2015 |
| JP | 2006-275865 | 10/2006 |
| JP | 6096371 | 3/2017 |
| WO | 00/76505 | 12/2000 |
| WO | 01/95857 | 12/2001 |
| WO | 2009/089262 | 7/2009 |
| WO | 2010/095455 | 8/2010 |
| WO | 2012/023579 | 2/2012 |
| WO | 2012/023580 | 2/2012 |
| WO | 2012/058635 | 5/2012 |
| WO | 2014/129446 | 8/2014 |

OTHER PUBLICATIONS

Wilbur et al., Bioconj. Chem., 2010, 21, 1225-1238.
Pratesi et al., J. Med. Chem., 2010, 53, 432-440.
Wilbur et al, Bioconj. Chem., 2000, 11, 584-598.
Press et al., "A comparative evaluation of conventional and pretargeted radioimmunotherapy of CD20-expressing lymphoma xenografts", Blood, vol. 98, No. 8, pp. 2535-2543, The American Society of Hematology, Oct. 15, 2001.
Office Action issued in JP Patent Application No. 2016-249039, dated Oct. 30, 2018, along with an English-language (machine) translation.

(Continued)

*Primary Examiner* — Michael G. Hartley
*Assistant Examiner* — Melissa J Perreira
(74) *Attorney, Agent, or Firm* — Greenblum & Bernstein, P.L.C.

(57) ABSTRACT

An object of this invention is to provide a streptavidin mutant reduced in affinity to the naturally-occurring biotin, and to provide a modified biotin which shows a high affinity to such streptavidin mutant reduced in affinity to the naturally-occurring biotin. This invention can provide a compound composed of a dimer of modified biotin, a streptavidin mutant, angsd usage of them.

9 Claims, 18 Drawing Sheets

Specification includes a Sequence Listing.

(56) References Cited

OTHER PUBLICATIONS

Office Action issued in EP Patent Application No. 15 751 807.7, dated Oct. 11, 2018.
Office Action issued in CN Patent Application No. 201580020296.6, dated Sep. 4, 2018, along with an English-language (machine) translation.
Chinese Office Action issued in CN Patent Application No. 201580020296.6, dated Dec. 5, 2017, along with an English-language (machine) translation.
Extended European Search Report issued in EP Patent Application No. 15751807.7, dated Nov. 22, 2017.
Melkko et al., "On the Magnitude of the Chelate Effect for the Recognition of Proteins by Pharmacophores Scaffolded by Self-Assembling Oligonucleotides", *Chemistry & Biology*, 13, pp. 225-231, 2006.
Partial Supplementary European Search Report issued in EP Patent Application No. 15751807.7, dated Aug. 21, 2017.
Fairhead et al., "SpyAvidin Hubs Enable Precise and Ultrastable Orthogonal Nanoassembly," *J. Am. Chem. Soc.*, vol. 136, No. 35, pp. 12355-12363, 2014.
Fairhead et al., "Plug-and-Play Pairing via Defined Divalent Streptavidins," *J. Mol. Biol.*, vol. 426, No. 1, pp. 199-214, 2014.
Green et al., "The Use of Bifunctional Biotinyl Compounds to Determine the Arrangement of Subunits in Avidin," *Biochem J.*, vol. 125, No. 3, pp. 781-791, 1971.
Green, "Avidin," *Adv. Protein Chem.*, vol. 29, pp. 85-133, 1975.
Green, "Avidin and Streptavidin," *Methods Enzymol.*, vol. 184, pp. 51-67, 1990.
Hnatowich et al., "Investigations of Avidin and Biotin for Imaging Applications," *J. Nucl. Med.*, vol. 28, pp. 1294-1302, 1987.
Paganelli et al., "Three-Step Monoclonal Antibody Tumor Targeting in Carcinoembryonic Antigen-Positive Patients," *Cancer Research*, vol. 51, pp. 5960-5966, 1991.
Park et al., "Pretargeted Radioimmunotherapy Using Genetically Engineered Antibody-Streptavidin Fusion Proteins for Treatment of Non-Hodgkin Lymphoma," *Clin. Cancer Res.*, vol. 17, No. 23, pp. 7373-7382, 2011.
Wilbur et al., "Design and Synthesis of Bis-Biotin-Containing Reagents for Applications Utilizing Monoclonal Antibody-Based Pretargeting Systems with Streptavidin Mutants," *Bioconjugate Chem.*, vol. 21. No. 7, pp. 1225-1238, 2010.
International Search Report & Search Opinion issued in PCT/JP2015/054431, dated May 19, 2015, along with an English-language translation.
International Preliminary Report on Patentability issued in PCT/JP2015/054431, dated Sep. 1, 2016, along with an English-language translation.
Final Office Action, USPTO, dated Jan. 31, 2020 issued in the parent U.S. Appl. No. 15/119,441.
Office Action issued in the corresponding European Patent Application No. 15751807.7, dated Aug. 30, 2019.
Office Action issued in the corresponding Parent U.S. Appl. No. 15/119,441, dated Jul. 8, 2019.
Office Action issued in the corresponding Parent U.S. Appl. No. 15/119,441, dated Jan. 30, 2019.
Office Action issued in Parent U.S. Appl. No. 15/119,441, dated Aug. 10, 2020.
Office Action issued in parent U.S. Appl. No. 15/119,441, dated Mar. 10, 2021.
Partial European Search Report issued in corresponding European patent application No. 20217008.0, dated Mar. 15, 2021.
Extended European Search Report issued in corresponding European patent application No. 20217008.0, dated Jun. 8, 2021.
Office Action issued in corresponding Chinese Patent Application No. 201810634531.4, dated May 6, 2021, with English machine translation.
Genbank Database, RecName_Full=Streptavidin; Flags_Precursor, UniProtKB/Swiss-Prot: Sequence updated: Aug. 1, 1991; Annotation updated: Apr. 7, 2021.
Office Action issued in parent U.S. Appl. No. 15/119,441, dated Jul. 9, 2021.
Office Action issued in corresponding Chinese Patent App. No. 201910863438.5 dated Aug. 11, 2021, along with an English Machine Translation.
Kong Lingqing et al., "Biotin-Avidin labeling technology", Progress in Veterinary Medicine, 2008, 29(4): 100-102, along with English Machine Translation of Abstract.

The data shown in above are average of three independent analysis and error bar shows ±SD.

MODIFIED BIOTIN, STREPTAVIDIN MUTANT, AND USAGE OF THEM

CROSS-REFERENCE TO RELATED APPLICATIONS

The present application is a Divisional of U.S. application Ser. No. 15/119,441, filed Aug. 17, 2016, which is a National stage of International Patent Application No. PCT/JP2015/054431, filed Feb. 18, 2015, which claims priority to Japanese Application No. 2014-212861, filed Oct. 17, 2014 and Japanese Application No. 2014-028525, filed Feb. 18, 2014, the contents of which are expressly incorporated by reference herein in their entireties.

TECHNICAL FIELD

This invention relates to compound composed of a dimer of modified biotin, a streptavidin mutant, and usage of them.

BACKGROUND ART

Avidin and biotin, or, streptavidin and biotin show a very strong affinity ($Kd=10^{-15}$ to $10^{-14}$ M), which is one of the strongest interactions between two biomolecules. Today, the avidin/streptavidin-biotin interaction has been widely used in the fields of biochemistry, molecular biology, and medicine (Green, (1975), *Adv. Protein Chem.*, 29: 85-133; Green, (1990), *Methods Enzymol.*, 184: 51-67). Avidin is a basic glycoprotein derived from albumen, and has an isoelectric point above 10. Meanwhile, streptavidin is derived from *Streptomyces* (*Streptomyces avidinii*), has the isoelectric point at around the neutral point, and has no sugar chain. Both proteins can form a tetramer, and can bind one biotin molecule per one subunit. The molecular weight it at around 60 kDa.

In recent years, there has been proposed the pretargeting method, as a method of drug delivery making use of the high binding ability of avidin/streptavidin with biotin, combined with an antigen molecule (Hnatowich, (1987), *J. Nucl. Med.*, 28, 1294-1302). Chicken avidin and bacterial streptavidin are, however, highly immunogenic to human body, and produces an anti-avidin/streptavidin antibody in the early stage after being administered to human. This has been an inhibiting factor against implementation of the pretargeting method (Paganelli, (1991), *Cancer Res.*, 51, 5960-5966). As a solution to this problem, a low-immunogenic streptavidin has been reported (International Patent WO2010/095455).

Also the pretargeting method using bisbiotin (compound obtained by combining two biotin molecules with a linker) and a streptavidin mutant (Park et al., *Clin. Cancer Res.;* 17(23); 7373-82, 2011) has been reported. This method has successfully solved a problem of endogenous biotin, by using a streptavidin mutant having an amino acid mutation denoted as S45A or Y43A. More specifically, while the streptavidin mutant with S45A or Y43A can bind biotin only weakly as compared with the wild-type streptavidin, the streptavidin mutant becomes to bind more strongly with bisbiotin after being converted into a bis-form compound.

PRIOR ART LITERATURES

Patent Literature

[Patent Literature 1] International Publication WO2010/095455

Non-Patent Literature

[Non-Patent Literature 1] Green, (1975), *Adv. Protein Chem.*, 29: 85-133;

[Non-Patent Literature 2] Green, (1990), *Methods Enzymol.*, 184: 51-67

[Non-Patent Literature 3] Hnatowich, (1987), *J. Nucl. Med*, 28, 1294-1302

[Non-Patent Literature 4] Paganelli, (1991), *Cancer Res.*, 51, 5960-5966).

[Non-Patent Literature 5] Park et al., *Clin. Cancer Res.;* 17(23); 7373-82, 2011

SUMMARY OF THE INVENTION

Object to be Solved by the Invention

The low-immunogenic streptavidin described above, although reduced in the immunogenicity to human, still has affinity to endogenous biotin inhuman body, so that it would elevate the background level in diagnostic applications, or it would fail in achieving a disease-specific drug effect in therapeutic applications. It is therefore an object of this invention to provide a streptavidin mutant reduced in affinity to the natural-occurring biotin, and also to provide a modified biotin which shows a high affinity to such streptavidin mutant reduced in affinity to the naturally-occurring biotin. It is a further object of this invention to provide a diagnostic/therapeutic drug based on combination of the streptavidin mutant and the modified biotin, and a diagnostic/therapeutic kit based on combination of the streptavidin mutant and the modified biotin.

Means for Solving the Object

After thorough investigations aimed at solving the problems above, the present inventors succeeded in obtaining a streptavidin mutant having a reduced affinity to the naturally-occurring biotin, by further introducing predetermined amino acid mutations into the low-immunogenic streptavidin mutant having been described in International Patent WO2010/095455. The present inventors concurrently synthesized a dimeric compound of modified biotin by partially modifying the biotin structure. The present inventors then examined affinity between the streptavidin mutant and the dimeric compound of modified biotin, and found out combinations thereof having high-affinity. The findings led us to work out this invention.

[1] A compound represented by Formula (1) below:

[Chemical Formula 1]

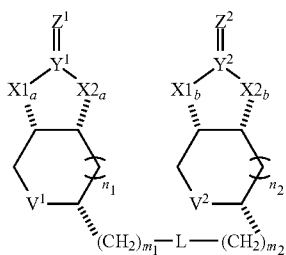
(1)

(in Formula, each of X1a, X1b, X2a and X2b independently represents O or NH, each of $Y^1$ and $Y^2$ independently represents C or S, each of $Z^1$ and $Z^2$ independently represents O, S or NH, each of $V^1$ and $V^2$ independently represents S or $S^+$—$O^-$, each of n1 and n2 independently represents 0 or 1, each of m1 and m2 independently represents an integer from 1 to 10, and L represents a linking group.)

[2] The compound of [1], wherein both of n1 and n2 represent 0, and being represented by Formula (2) below:

[Chemical Formula 2] (2)

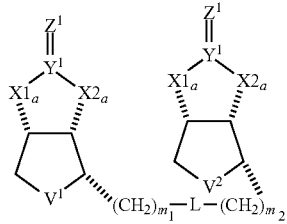

(in Formula, X1a, X1b, X2a, X2b, $Y^1$, $Y^2$, $Z^1$, $Z^2$, $V^1$, $V^2$, m1, m2 and L are synonymous to those in Claim 1).

[3] The compound of [1] or [2], wherein L represents —CONH—, —NHCO—, —O—, alkylene group having 1 to 10 carbon atoms, optionally substituted phenylene group, or any of combinations of them.

[4] The compound of any one of [1] to [3], wherein L represents —CONH—$(CH_2)_p$—CONH—$(CH_2)_q$—O—$(CH_2)_r$—NHCO$(CH_2)_s$—NH—CO—, —CONH—$(CH_2)_p$—CONH—$(CH_2)_q$—NHCO—$(CH_2)_s$—NH—CO—, —CONH—$(CH_2)_p$—CONH-(optionally substituted phenylene group)-NHCO—$(CH_2)_s$—NH—CO—, —CONH—CH($COOCH_3$)—$(CH_2)_p$—NHCO-(optionally substituted phenylene group)-CONH—$(CH_2)_s$—CH($COOCH_3$)—NH—CO—, or —CONH—$(CH_2)_p$—O—$(CH_2)_r$—NHCO-(optionally substituted phenylene group)-CONH—$(CH_2)_s$—O—$(CH_2)_u$—NH—CO— (in Formulae, each of p, q, r, s, t and u independently represents an integer from 1 to 10).

[5] A compound represented by any one of Formulae below:

[Chemical Formula 3]

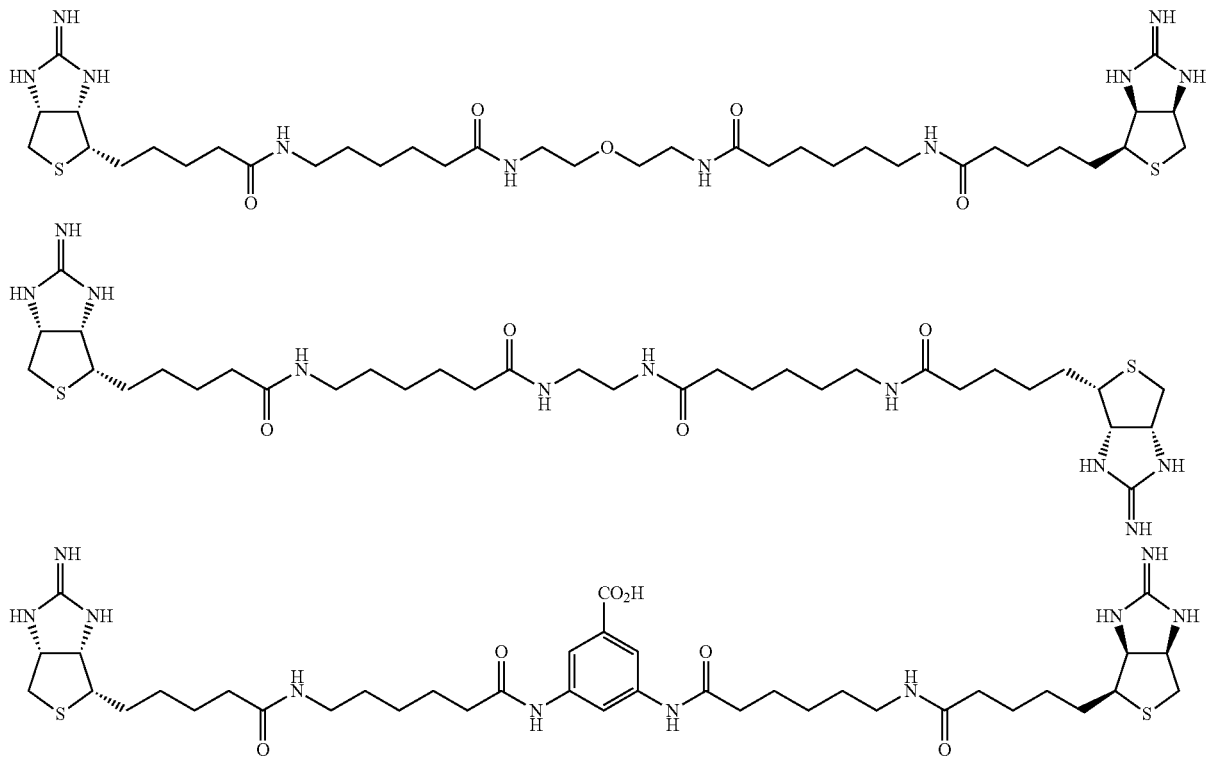

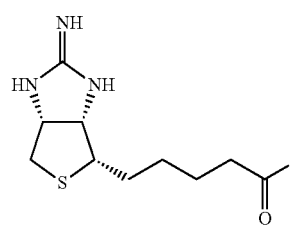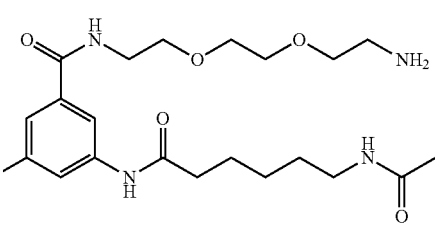
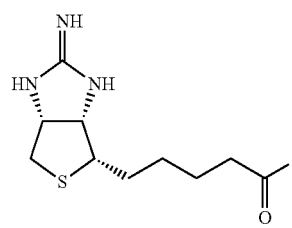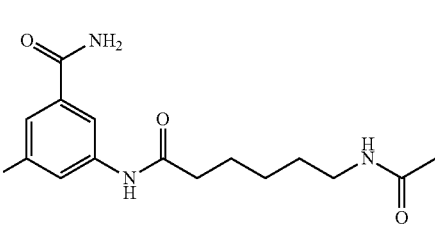
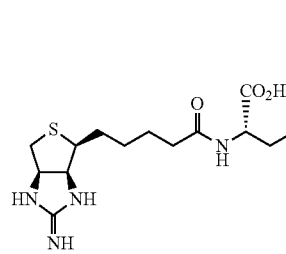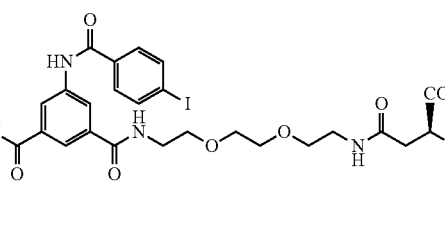
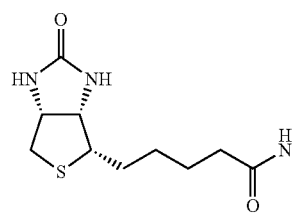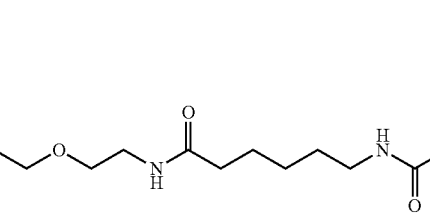
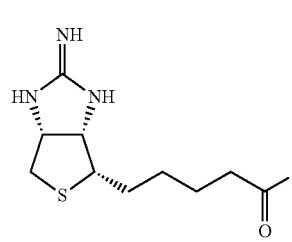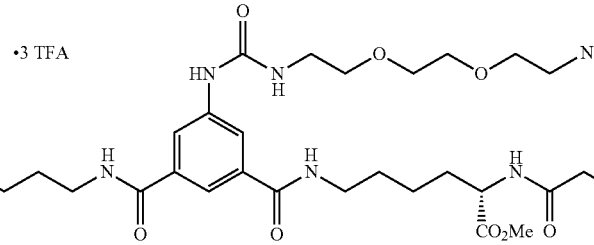
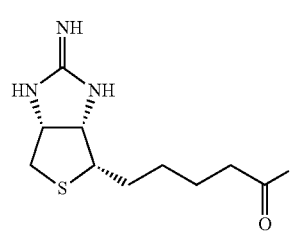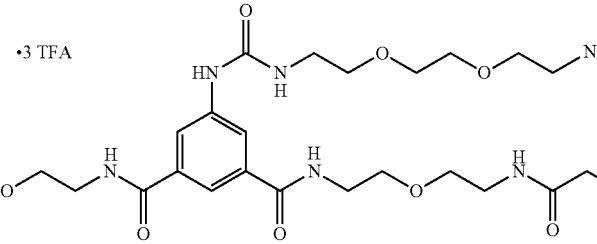

[6] A compound comprising the compound of any one of [1] to [5], bound with a chelate group capable of capturing a radioisotope.
[7] A compound comprising the compound of any one of [1] to [5], bound with a fluorescent compound or a drug compound.
[8] A compound represented by any one of formulae below:
[Chemical Formula 4]
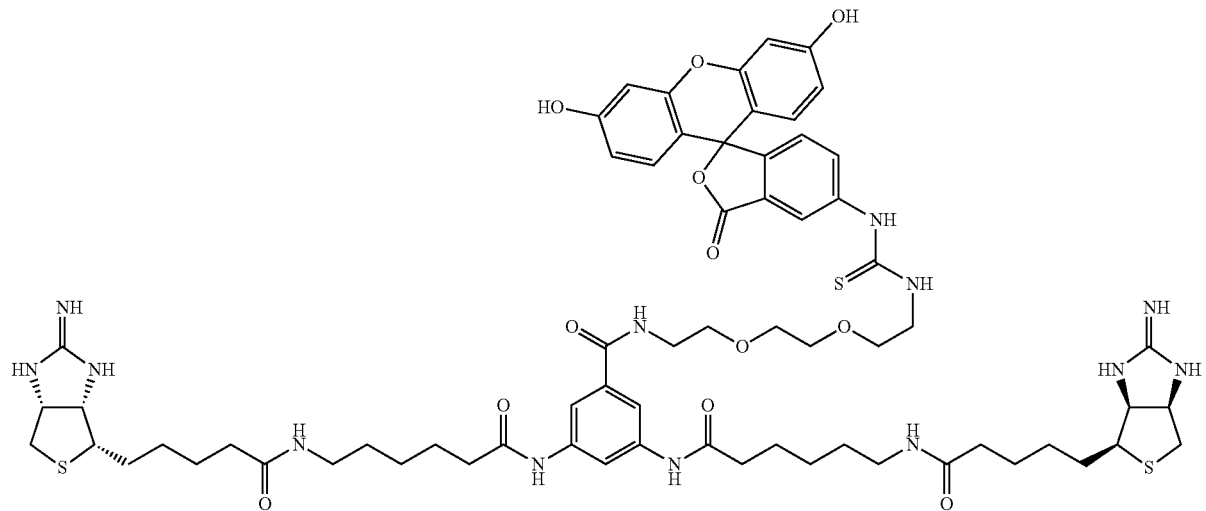
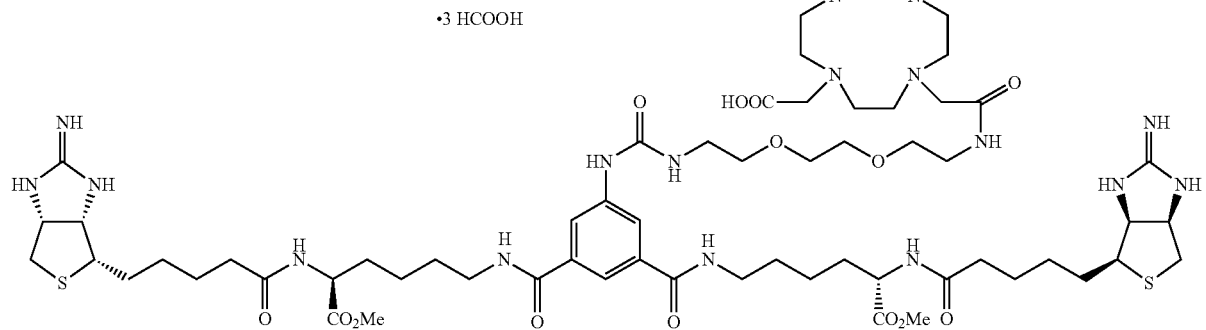

-continued
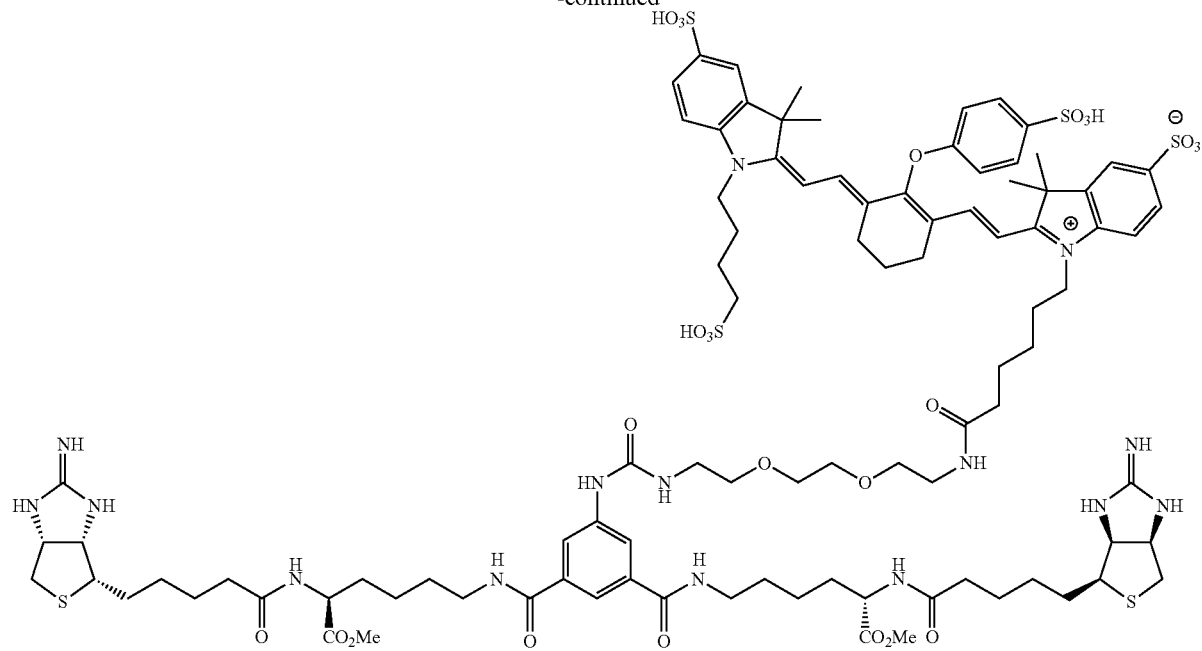
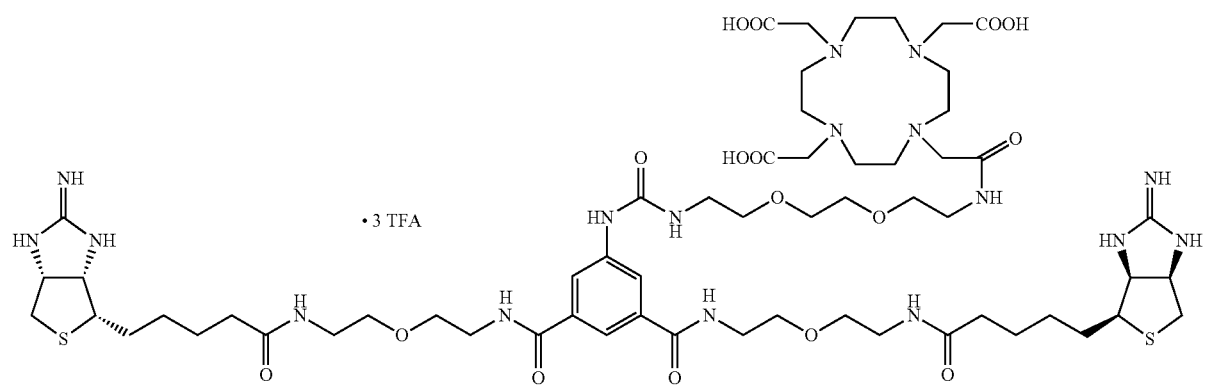
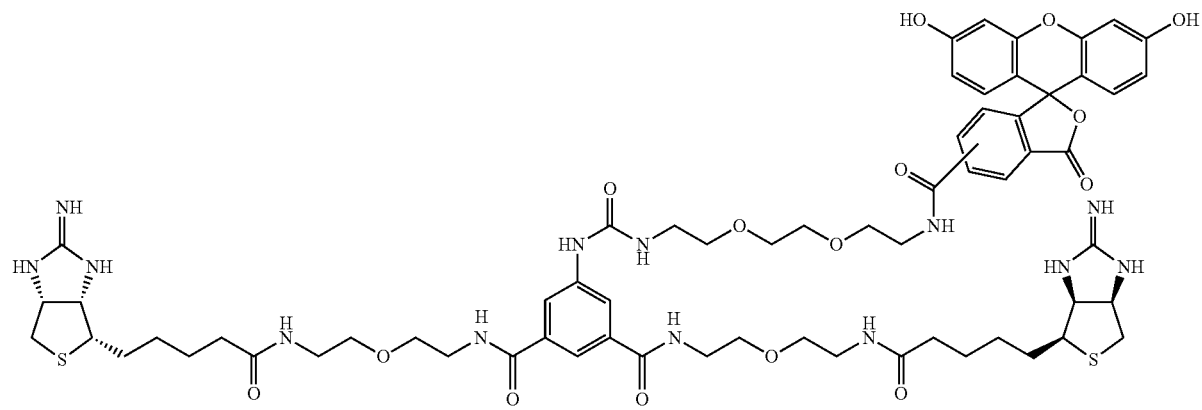

-continued

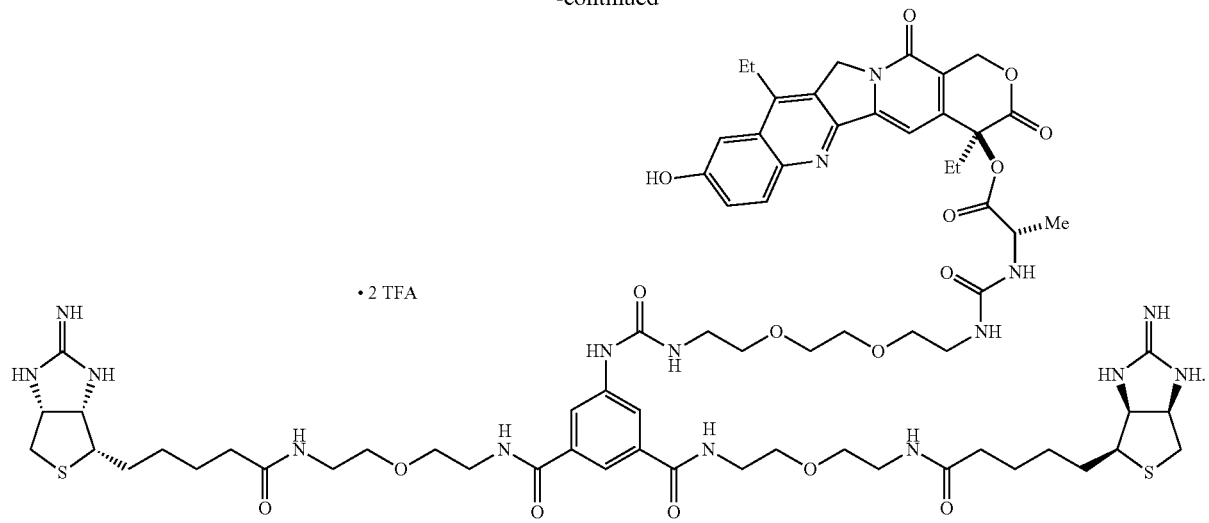

[9] A streptavidin mutant comprising an amino acid sequence in which Asn at amino acid residue 37 in the amino acid sequence represented by SEQ ID NO: 3 is substituted with other amino acid residue.

[10] A streptavidin mutant comprising an amino acid sequence represented by SEQ ID NO: 4.

[11] A DNA encoding the streptavidin mutant described in [9] or [10].

[12] A streptavidin mutant-molecular probe conjugate, obtained by combining the streptavidin mutant described in [9] or [10] with a molecular probe.

[13] The streptavidin mutant-molecular probe conjugate of [12], wherein the molecular probe is an anti-human CD20 antibody.

[14] The streptavidin mutant-molecular probe conjugate of [12], wherein the molecular probe is rituximab.

[15] The streptavidin mutant-molecular probe conjugate of [12], wherein the molecular probe is an anti-epiregulin single chain antibody.

[16] A therapeutic agent, or in vivo or in vitro diagnostic agent, comprising the streptavidin mutant-molecular probe conjugate described in any one of [12] to [15].

[17] A therapeutic, or in vivo or in vitro diagnostic kit, comprising (a) the streptavidin mutant-molecular probe conjugate described in any one of [12] to [15]; and (b) an in vivo or in vitro diagnostic substance, or a therapeutic substance, labeled with the compound described in any one of [1] to [5].

Advantageous Effects of Invention

According to this invention, there is provided a combination of the streptavidin mutant having a reduced immunogenicity and a reduced affinity to the naturally-occurring biotin, and a dimeric compound of modified biotin having a high affinity to such streptavidin mutant. The combination of the streptavidin mutant and the dimeric compound of modified biotin of this invention is useful in diagnostic/therapeutic processes based on the pretargeting method.

EMBODIMENTS FOR CARRYING OUT THE INVENTION

Figure 1:
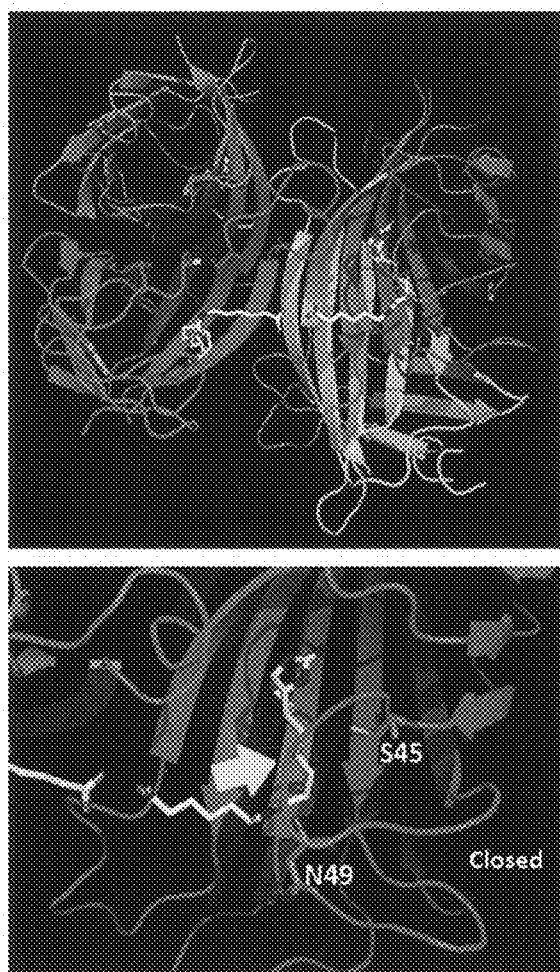
FIG. 1 shows a result of crystallographic analysis.

This invention will further be detailed below.

(1) Dimeric Compound of Modified Biotin

A dimeric compound of modified biotin of this invention is a compound represented by formula (1) below, and preferably a compound represented by formula (2) where n1 and n2 in formula (1) represent 0.

[Chemical Formula 5]

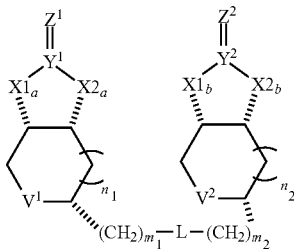

(1)

[Chemical Formula 6]

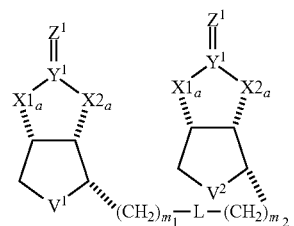

(2)

(in Formulae, each of X1a, X1b, X2a and X2b independently represents O or NH, each of $Y^1$ and $Y^2$ independently represents C or S, each of $Z^1$ and $Z^2$ independently represents O, S or NH, each of $V^1$ and $V^2$ independently represents S or $S^+$—$O^-$, each of n1 and n2 independently represents an integer of 0 or 1, each of m1 and m2 independently represents integer from 1 to 10, and L represents a linking group.)

In formula (1) and formula (2), portions represented by the structures below:

[Chemical Formula 7]

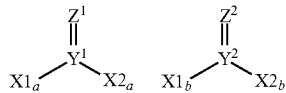

are preferably any one of; but not limited to, the structures below:

[Chemical Formula 8]

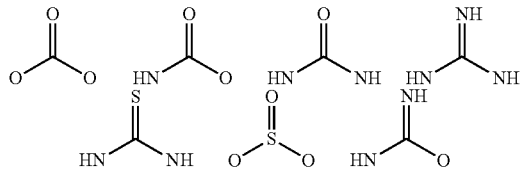

Each of m1 and m2 represents an integer from 1 to 10, preferably from 2 to 10, more preferably from 2 to 8, and even more preferably from 2 to 6.

L preferably represents —CONH—, —NHCO—, —O—, alkylene group having 1 to 10 carbon atoms, optionally substituted phenylene group, or linking group composed of combination thereof. L more preferably represents —CONH—$(CH_2)_p$—CONH—$(CH_2)_q$—O—$(CH_2)_r$—NHCO—$(CH_2)_s$—NH—CO—, —CONH—$(CH_2)_p$—CONH—$(CH_2)_q$—NHCO—$(CH_2)_s$—NH—CO—, —CONH—$(CH_2)_p$—CONH-(optionally substituted phenylene group)-NHCO—$(CH_2)_s$—NH—CO—, —CONH—CH(COOCH$_3$)—$(CH_2)_p$—NHCO-(optionally substituted phenylene group)-CONH—$(CH_2)_s$—CH(COOCH$_3$)—NH—CO—, or —CONH—$(CH_2)_p$—O—$(CH_2)_r$—NHCO-(optionally substituted phenylene group)-CONH—$(CH_2)_s$—O—$(CH_2)_u$—NH—CO— (in the formulae, each of p, q, r, s, t, and u independently represents an integer of 1 to 10). More preferably, each of p, q, r and s independently represents an integer of 2 to 8, and even more preferably an integer of 2 to 6. Even more preferably, each of t and u independently represents an integer of 1 to 4. Substituent on the phenylene group is exemplified by —COOH, —CONH$_2$, optionally substituted amido group, and —CO—NH$_2$.

The compounds represented by formula (1) or formula (2) of this invention may be synthesized by the methods described later in Example 1. Compounds 5, 7, 11, 13, 15, 22, 24, 36 and 50 in Example 1 are the compounds represented by formula (1) or formula (2) of this invention.

Method of Synthesizing Compound 5

To an ethyl acetate solution of Compound 1, are added 1-ethyl-3-(3-dimethylaminopropyl)carbodiimide hydrochloride and N,N-dimethylformamide. The mixture is added with 2,2'-oxybis(ethylamine) preliminarily dissolved in a mixed solvent of chloroform and N,N-dimethylformamide, and the mixture is allowed to react at room temperature, to obtain tert-butyl 6,6'-[2,2'-oxybis(ethane-2,1-diyl)bis(azanediyl)]bis(6-oxohexane-6,1-diyl)dicarbonate (Compound 2). To a dichloromethane solution of dicarbamate Compound 2, trifluoroacetic acid is added, and the mixture is allowed to react at room temperature for 30 minutes, to obtain N,N'-[2,2'-oxybis(ethane-2,1-diyl)]bis(6-aminohexanamido) (Compound 3). To a mixed solvent of N,N-dimethylformamide and pyridine containing diamine 3, EZ-Link® NHS-Iminobiotin is added, and the mixture is allowed to react at room temperature. The crude product is dissolved into a mixed solvent of dioxane and water, added with a 25% aqueous ammonia solution, and the mixture is allowed to react at room temperature, to obtain (3aS,3a'S,4S,4'S,6aR,6a'R)-4,4'-(5,12,20,27-tetraoxo-16-oxa-6,13,19,26-tetraazahentriacontane-1,3H-diyl)bis[tetrahydro-1H-thieno[3,4-d]imidazole-2(3H)-iminium] di(2,2,2-trifluoroacetate) (Compound 5).

Method of Synthesizing Compound 7

To a mixed solvent of N,N-dimethylformamide and pyridine containing diamine 6, EZ-Link® NHS-Iminobiotin is added, and the mixture is allowed to react at room temperature. After the solvent is evaporated off under reduced pressure, the residue is dissolved in dioxane, added with 25% aqueous ammonia, and the mixture is allowed to react at room temperature, to obtain (3aS,3a'S,4S,4'S,6aR,6a'R)-4,4'-(5,12,18,25-tetraoxo-6,13,17,24-tetraazanonacosane-1,29-diyl)bis[tetrahydro-1H-thieno[3,4-d]imidazole-2(3H)-iminium] di(2,2,2-trifluoroacetate) (Compound 7).

Method of Synthesizing Compound 11

To an N,N-dimethylformamide solution of Compound 1, 1-ethyl-3-(3-dimethylaminopropyl)carbodiimide hydrochloride is added, then ethyl 3,5-diaminobenzoate (Compound 8) dissolved in N,N-dimethylformamide is added, and the mixture is allowed to react at room temperature, to obtain ethyl 3,5-bis[6-(tert-butoxycarbonylamino)hexanamido]benzoate (Compound 9). To a dioxane solution of dicarbamate Compound 9, a 4-N hydrogen chloride solution in dioxane is added, and the mixture is allowed to react at room temperature, to obtain 6,6'-[5-(ethoxycarbonyl)-1,3-phenylene]bis(azanediyl)bis(6-oxohexane-1-ammonium) dichloride (Compound 10). The ammonium salt 10 is added with N,N-dimethylformamide, and then with triethylamine for solubilization. The mixture is then added with EZ-Link® NHS-Iminobiotin, and allowed to react at room temperature. The crude product is dissolved into methanol, added with a 2-N aqueous sodium hydroxide solution, and the mixture is stirred at room temperature for 22 hours, to obtain (3aS,3a'S,4S,4'S,6aR,6a'R)-4,4'-{5,5'-[6,6'-(5-carboxy-1,3-phenylene)bis(azanediyl)bis(6-oxohexane-6,1-diyl)]bis(azanediyl)bis(5-oxopentane-5,1-diyl)}bis(tetrahydro-1H-thieno[3,4-d]imidazole-2(3)-iminium) di(2,2,2-trifluoroacetate) (Compound 11).

Method of Synthesizing Compound 13

To a N,N-dimethylformamide solution of bisiminobiotin 11, added are N,N'-diisopropylcarbodiimide and 1-hydroxybenzotriazole monohydrate, further added is an N,N-dimethylformamide solution of amine 12, and the mixture is allowed to react at 60° C., to obtain (3aS,3a'S,4S,4'S,6aR,6a'R)-4,4'-{5,5'-[6,6'-(5-(2-(2-(2-aminoethoxy)ethoxy)ethylcarbonyl)-1,3-phenylene)bis(azanediyl)bis(6-oxohexane-6,1-diyl)]bis(azanediyl)bis(5-oxopentane-5,1-diyl)}bis(tetrahydro-1H-thieno [3,4-d]imidazole-2(3H)-iminium) tri(2,2,2-trifluoroacetate) (Compound 13).

Method of Synthesizing Compound 15

Diamine 10 is added with dioxane and pyridine, further with EZ-Link® NHS-Iminobiotin, and the mixture is allowed to react at room temperature. The solvent is evaporated off under reduced pressure, the crude product is dissolved in dioxane and water, added with 28% aqueous ammonium, and the mixture is allowed to react at room temperature, to obtain (3aS,3a'S,4S,4'S,6aR,6a'R)-4,4'-{5, 5'-[6,6'-(5-carbamoyl-1,3-phenylene)bis(azanediyl)bis(6-oxohexane-6,1-diyl)]bis(azanediyl)bis(5-oxopentane-5,1-diyl)}bis[tetrahydro-1H-thieno[3,4-d]imidazole-2(3H)-iminium]di(2,2,2-trifluoroacetate) (Compound 15).

Method of Synthesizing Compound 22

To an N,N-dimethylformamide solution of 5-(4-iodobenzamido)isophthalic acid, added are 1-ethyl-3-(3-dimethylaminopropyl)carbodiimide hydrochloride and 1-hydroxybenzotriazole monohydrate, further added is an N,N-dimethylformamide solution of amine 12, and the mixture is allowed to react at room temperature, to obtain $N^1,N^3$-bis{2-[2-(2-(tert-butoxycarbonylamino)ethoxy)ethoxy]ethyl}-5-(4-iodobenzamido)isophthalamide (Compound 17).

To a dichloromethane solution of dicarbamate Compound 17, trifluoroacetic acid is added, and the mixture is allowed to react at room temperature, to obtain $N^1,N^3$-bis{2-[2-(2-aminoethoxy)ethoxy]ethyl}-5-(4-iodobenzamido)isophthalamide (Compound 18).

To a N,N-dimethylformamide solution containing Boc-Asp(O$^t$Bu)—OH (Compound 19a) and N-hydroxysuccinimide, added is 1-ethyl-3-(3-dimethylaminopropyl)carbodiimide hydrochloride, and the mixture is allowed to react at room temperature, to obtain (S)-1-tert-butyl 4-(2,5-dioxopyrrolidine-1-yl) 2-(tert-butoxycarbonylamino)succinate (Compound 19).

To a mixed solvent of dioxane and pyridine containing diamine Compound 18, activated ester 19 is added, the mixture is allowed to react at room temperature, Compound 19 is further added, and the mixture is allowed to react at room temperature, to obtain tert-butyl (14S,14'S)-1,1'-[5-(4-iodobenzamido)-1,3-phenylene]bis[4-(tert-butoxycarbonylamino)-1,12-dioxo-5,8-dioxa-2,11-diazapentadecanoate] (Compound 20).

Compound 20 is added with trifluoroacetic acid, and the mixture is allowed to react at room temperature, to obtain (14S,14'S)-1,1'-[5-(4-iodobenzamido)-1,3-phenylene]bis (14-carboxy-1,12-dioxo-5,8-dioxa-2,11-diazatetradecane-14-ammonium) di(2,2,2-trifluoroacetate) (Compound 21).

Bisamino acid 21 is suspended into a mixed solvent of dioxane and water, a 1-N aqueous sodium hydroxide solution is added, the mixture is stirred at room temperature for solubilization, added with EZ-Link® NHS-Iminobiotin, and is allowed to react at room temperature. A 2-N aqueous sodium hydroxide solution is added, and the mixture is further allowed to react at room temperature, to obtain (3aS,3a'S,4S,4'S,6aR,6a'R)-4,4'-{(14S,4'S)-1,1'-[5-(4-iodobenzamido)-1,3-phenylene]bis(14-carboxy-1,12,16-trioxo-5,8-dioxa-2,11,15-triazaeicosane-20,1-diyl)}bis(tetrahydro-1H-thieno[3,4-d]imidazole-2(3H)-iminium) di(2,2,2-trifluoroacetate) (Compound 22).

Method of Synthesizing Compound 24

To an N,N-dimethylformamide solution of diamine 3, biotin N-hydroxysuccinimide ester (Compound 23) is added, and the mixture is allowed to react at room temperature, to obtain N,N'-[2,2'-oxybis(ethane-2,1-diyl)]bis{6-[5-((3a,4S,6aR)-2-oxohexahydro-1H-thieno[3,4-d]imidazole-4-yl)pentanamido]hexanamide} (Compound 24).

Method of Synthesizing Compound 36

2-Iminobiotin 39 is added with trifluoroacetic acid, the mixture is stirred, and an excessive portion of trifluoroacetic acid is removed by evaporation under reduced pressure. To an acetonitrile solution of the obtained white solid, added are pyridine and disuccinimide 40, and the mixture is stirred at 30° C. After the solvent is evaporated off under reduced pressure, the residue is dried in vacuo, to obtain Compound 41. To a mixed solvent of N,N-dimethylformamide and triethylamine containing diamine 34 is added ester 41 prepared from 2-iminobiotin 39, the mixture is stirred at room temperature, the solvent is evaporated off under reduced pressure, the obtained crude product is purified by reversed-phase silica gel column chromatography (water/methanol=2:1→1:2), to obtain Compound 35. To an aqueous solution of bisiminobiotin 35, trifluoroacetic acid is added, the mixture is stirred at 50° C. for 4 hours, the solvent is evaporated off under reduced pressure, and the obtained crude product is purified by reversed-phase silica gel column chromatography (water/methanol=2:1→1:2), to obtain Compound 36.

Method of Synthesizing Compound 50

To an N,N-dimethylformamide solution of disuccinimide compound 30, added is an N,N-dimethylformamide solution of amine 45, and the mixture is stirred at room temperature. An additional N,N-dimethylformamide solution of amine 45 is added, and the mixture is stirred at room temperature. After the solvent is evaporated off under reduced pressure, the residue is added with ethyl acetate, washed successively with 1-M aqueous sodium hydroxide solution, 1-M hydrochloric acid, and a saturated sodium chloride solution, the organic layer is dried over sodium sulfate, the solvent is evaporated off under reduced pressure, the obtained crude product is purified by silica gel column chromatography (dichloromethane/hexane=1:30→1:20→1:10→1:5), to obtain Compound 46. An aqueous solution of dicarbamate Compound 47 obtained above is added with trifluoroacetic acid under cooling on ice, stirred, heated to room temperature, and further stirred. After the solvent is evaporated off under reduced pressure, the residue is dried in vacuo, to obtain a crude product containing Compound 48. To a test tube containing Compound 41 prepared from 2-iminobiotin 39 are added an N,N-dimethylfomamide solution of diamine 48 and diisopropylethylamine, and the mixture is stirred at room temperature. The solvent is evaporated off under reduced pressure, and the obtained crude product is purified by reversed-phase silica gel column chromatography (methanol/water=2:1, 0.3% TFA), to obtain Compound 49. Bisiminobiotin 49 is then added with a mixed solvent of trifluoroacetic acid and water, the mixture is heated to 50° C. and stirred. After the solvent is evaporated off under reduced pressure, the residue is dried in vacuo, to obtain Compound 50.

According to this invention, there is also provided a compound composed of a dimeric compound of modified biotin of this invention, bound with a chelate group capable of capturing a radioisotope. The chelete group usable in this invention includes DOTA (1,4,7,10-tetraazacyclododecane-N,N',N",N"'-tetraacetate), DTPA (diethylenetriamine pentaacetate), TETA (1,4,8,11-tetraazacyclotetradecane-N, N', N", N"'-tetraacetate), N2S2, MAG3 and CHX-A-DTPA.

According to this invention, there is also provided a compound composed of the above-described compound bound with a chelete group, and a radioisotope captured thereon. Among the radioisotopes possibly captured by the chelete group, those available for imaging include gamma-ray emitting nuclides ($^{67}$Ga, $^{99m}$Tc, $^{111}$In, $^{123}$I) and positron emitting nuclides ($^{18}$F, $^{62}$Cu, $^{64}$Cu, $^{66}$Ga, $^{68}$Ga, $^{76}$Br, $^{86}$Y, $^{89}$Zr, $^{4}$Tc, $^{124}$I). Those suitably used as therapeutic radioisotope include beta-ray emitting nuclides ($^{32}$P, $^{67}$Cu, $^{89}$Sr, $^{90}$Y, $^{114m}$In, $^{117m}$Sn, $^{131}$I, $^{153}$Sm, $^{166}$Ho, $^{177}$Lu, $^{186}$Re, $^{188}$Re, etc.), alpha-ray emitting nuclides ($^{211}$At, $^{212}$Bi, $^{212}$Pb, $^{213}$Bi, $^{223}$Ra, $^{225}$Ac, etc.) and Auger electron emitting nuclides ($^{125}$I, $^{165}$Er, etc.). Among these nuclides, $^{64}$Cu, $^{124}$I, $^{76}$Br, $^{68}$Ga, $^{99m}$Tc, $^{123}$I, $^{131}$I and $^{90}$Y are preferably used.

According to this invention, there is also provided a compound composed of the above-described dimeric compound of modified biotin of this invention bound with a fluorescent compound or drug compound (e.g., anticancer drug).

The fluorescent compound suitably used in this invention is exemplified by fluorescein-5-isothiocyanate (FITC), IRDye (registered trademark) 800, and fluorescein. The drug (e.g., anticancer drug) suitably used in this invention is exemplified by PBD (pyrrolobenzodiazepin) class (e.g., SJG-136, SG2202, etc.), maytansine analogues (e.g., DM1, DM4, etc.), dolastatin analogues (e.g., monomethyl auristatin E (MMAE), monomethyl auristatin F (MMAF), dolastatin 10, tubulysin, etc.), duocarmycin analogues (e.g., DC1, DC4, DC44, etc.), camptothecin analogues (e.g., SN-38 etc.), and others (e.g., methotrexate, vinblastine, calicheamicin, α-amanitin, doxorubicin, and melphalan).

Specific examples of the compound composed of the compound represented by formula (1) or formula (2) of this invention bound with a chelate group capable of capturing a radioisotope, and the compound composed of the compound represented by formula (1) or formula (2) of this invention bound with a fluorescent compound or a drug compound, are exemplified by Compounds 14, 42, 44, 51, 52 and 59 in Example 1, which may be synthesized according to the synthetic methods described later in Example 1.

Method of Synthesizing Compound 14

A methanol solution of bisiminobiotin 13 is added with triethylamine and fluorescein-5-isothiocyanate, and the mixture is allowed to react at room temperature, to obtain (3aS,3a'S,4S,4'S,6aR,6a'R)-4,4'-{5,5'-[6,6'-(5-(2-(2-(2-(3-(3',6'-dihydroxy-3-oxo-3H-spiro[isobenzofuran-1,9'-xanthene]-5-yl)thioureido)ethoxy)ethoxy)ethylcarbamoyl)-1,3-phenylene)bis(azanediyl)bis(6-oxohexane-6,1-diyl)]bis(azanediyl)bis(5-oxopentane-5,1-diyl)}bis(tetrahydro-1H-thieno[3,4-d]imidazole-2(3H)-iminium) di(2,2,2-trifluoroacetate) (Compound 14).

Method of Synthesizing Compound 42

To a mixed solvent of methanol and triethylamine containing bisiminobiotin 36, DOTA-NHS-ester 37 was added, and the mixture is stirred at room temperature. The solvent is evaporated off under reduced pressure, and the obtained crude product is purified by reversed-phase HPLC (0.0-20.0-20.5-60.5-61.0-75.0 min; 5.0-5.0-17.5-57.5-100.0-100.0% CH$_3$CN in 0.1% HCOOH in MQ, ramp time=40 min (17.5-57.5%), t$_r$=31.5 min), to obtain Compound 42.

Method of Synthesizing Compound 44

To a mixed solvent of N,N-dimethylformamide and triethylamine containing bisiminobiotin 36, IRDye® 800CW NHS Ester is added, and the mixture is stirred at room temperature. The solvent is evaporated off under reduced pressure, and the obtained crude product is purified by reversed-phase HPLC (0.0-20.0-20.5-60.5-61.0-75.0 min; 5.0-5.0-17.5-57.5-100.0-100.0% CH$_3$CN in 0.1% TFA in MQ, ramp time=40 min (17.5-57.5%), t$_r$=40.9 min), to obtain Compound 44.

Method of Synthesizing Compound 51

To a mixed solvent of methanol and triethylamine containing bisiminobiotin 50, DOTA-NHS-ester 37 is added, and the mixture is stirred at room temperature. The solvent is evaporated off under reduced pressure, and the obtained crude product is purified by reversed-phase HPLC (0.0-20.0-20.5-60.5-61.0-75.0 min; 5.0-5.0-17.5-57.5-100.0-100.0% CH$_3$CN in 0.1% TFA in MQ, ramp time=40 min (17.5-57.5%), t$_r$=32.6 min), to obtain Compound 51.

Method of Synthesizing Compound 52

To a mixed solvent of methanol and triethylamine containing bisiminobiotin 50, 5(6)-carboxyfluorescein N-hydroxysuccinimide ester 51 is added, and the mixture is stirred at room temperature. The solvent is evaporated off under reduced pressure, the obtained crude product is purified by reversed-phase column chromatography (methanol/water=1:1→2:1, 0.5% TEA), and further purified through Sephadex 20LH (methanol, 1% TFA), to obtain Compound 52.

Method of Synthesizing Compound 59

To a dichloromethane solution containing SN38 Boc-protected compound 53 and Cbz-Ala-OH 54 is added 1-ethyl-3-(3-dimethylaminopropyl)carbodiimide hydrochloride and dimethylaminopyridine under cooling on ice, the mixture is gradually heated to room temperature, and stirred. The mixture is added with dichloromethane, washed successively with an aqueous sodium hydrogen carbonate solution, water, 0.1-M hydrochloric acid, and a saturated sodium chloride solution, the organic layer is dried over sodium sulfate, the solvent is evaporated off under reduced pressure, and the obtained crude product is purified by silica gel column chromatography (dichloromethane/methanol=30:1), to obtain Compound 55. To an ethyl acetate solution of Compound 55, Pd/C is added, the atmosphere in the reaction vessel is replaced with hydrogen, the mixture is stirred at room temperature, then stirred at 40° C., and filtered through celite. The solvent is evaporated off under reduced pressure, and the obtained crude product is purified by thin layer chromatography (dichloromethane/methanol=30:1), to obtain Compound 56. To a dichloromethane solution of Compound 56, triphosgene and pyridine are added under cooling on ice, the mixture is heated to room temperature and stirred. After the solvent is evaporated off under reduced pressure, the residue is dried in vacuo, to obtain a crude product (brown liquid) containing Compound 57. To a methanol solution of crude product containing bisiminobiotin 50 and Compound 57, triethylamine is added, and the mixture is stirred at room temperature. The solvent is evaporated off under reduced pressure, and the obtained crude product is purified by reversed-phase thin layer chromatography (methanol/water=3:1, 1% TFA), to obtain Compound 58. To an aqueous solution of bisiminobiotin 58, trifluoroacetic acid is added, and the mixture is stirred at room temperature. The solvent is evaporated off under reduced pressure, and the obtained crude product is purified by reversed-phase thin layer chromatography (methanol/water=3:1, 1% TFA), to obtain Compound 59.

(2) Streptavidin Mutant

The streptavidin mutant characteristically contains mutation of predetermined amino acids in the amino acid sequence of the core streptavidin represented by SEQ ID NO: 2, and is reduced in immunogenicity as compared with the wild-type streptavidin, and is also reduced in affinity to the naturally-occurring biotin or biocytin.

The amino acid sequence of wild-type (native) core streptavidin is represented by SEQ TD NO: 2 in the Sequence Listing, and the nucleotide sequence encoding it is represented by SEQ ID NO: 1 in the sequence listing.

The streptavidin mutant of this invention is specifically exemplified by a streptavidin mutant composed of an amino acid sequence in which, in the amino acid sequence represented by SEQ ID NO: 3, Asn at the 37th amino acid residue is substituted with other amino acid residue. It is more preferably a streptavidin mutant containing the amino acid sequence represented by SEQ ID NO: 4.

The amino acid sequence represented by SEQ ID NO: 3 has the mutations listed below in streptavidin whose amino acid sequence is represented by SEQ ID NO: 2:
(1) mutation given by substitution of tyrosine at position 10 with serine;
(2) mutation given by substitution of tyrosine at position 71 with serine;
(3) mutation given by substitution of arginine at position 72 with lysine;
(4) mutation given by substitution of glutamic acid at position 89 with aspartic acid;
(5) mutation given by substitution of arginine at position 91 with substituted with lysine;
(6) mutation given by substitution of glutamic acid at position 104 with asparagine;
(7) mutation given by substitution of asparagine at position 11 with aspartic acid;
(8) mutation given by substitution of serine at position 15 with aspartic acid; and
(9) mutation given by substitution of serine at position 33 with asparagine.

The amino acid sequence represented by SEQ ID NO: 4 additionally contains the mutation below, in the amino acid sequence represented by SEQ ID NO: 3:
(10) mutation given by substation of asparagine at position 37 with glycine:

In this invention, the phrase stating that " . . . is reduced in immunogenicity as compared with the wild-type streptavidin" means that the immunogenicity is reduced when the streptavidin mutant was administered to mammals including human. Reduction in immunogenicity may be confirmed typically by the method below. That is, the streptavidin mutant of this invention is analyzed to find how it is reactive with an anti-streptavidin antiserum obtained from a crab-eating monkey immunized with wild-type streptavidin, and reduction in immunogenicity, from the level shown by the wild-type streptavidin, is determined if the reactivity to the anti-streptavidin antiserum is found to be decreased from that of the wild-type streptavidin. According to the way of determining such reduction in immunogenicity, the immunogenicity of the streptavidin mutant of this invention is decreased preferably down to 80% or below, more preferably 60% or below, more preferably 20% or below, even more preferably 15% or below, yet more preferably 10% or below, and particularly 5% or below, of the level shown by the wild-type streptavidin.

In this invention, the phrase stating that " . . . is reduced in affinity to the naturally-occurring biotin or biocytin" means that binding potential of the streptavidin mutant with the naturally-occurring biotin or biocytin is lowered from the binding potential of streptavidin with the naturally-occurring biotin or biocytin. Affinity/binding potential of the streptavidin mutant with the naturally-occurring biotin or biocytin may be evaluated typically by SPR analysis. Affinity of the streptavidin mutant of this invention with the naturally-occurring biotin or biocytin has been decreased preferably down to 80% or below, more preferably 70% or below, more preferably 60% or below, even more preferably 50% or below, and yet more preferably 40% or below, of the level shown by the wild-type streptavidin.

According to this invention, there is also provided a DNA encoding the streptavidin mutant of this invention. The DNA of this invention may be produced by site-directed mutagenesis of DNA encoding the wild-type (native) streptavidin.

The DNA encoding the streptavidin mutant of this invention may be used after being introduced into a vector. In particular, the streptavidin mutant of this invention may be produced by introducing the DNA encoding the streptavidin mutant of this invention into an expression vector, and then transforming a host with the expression vector, so as to express the streptavidin mutant of this invention.

When *E. coli* is used as a host, the vector used in this invention preferably has a replication origin (ori), and also has a gene for selecting the transformed host (e.g., drug-resistance gene resistant to drugs including ampicillin, tetracycline, kanamycin or chloramphenicol, etc.). The expression vector preferably has a promoter capable of efficiently expressing the streptavidin mutant of this invention in the host, such as lacZ promoter or T7 promoter Examples of such vector include M13 vector, pUC vector, pBR322, pBluescript, pCR-Script, pGEX-5X-1 (Pharmacia), "QIA-express system" (QIAGEN), pEGFP, and pET (in this case, BL21 having T7 RNApolymeraze expressed therein is preferably used as a host). The vector may also be attached with a signal sequence or the like, so as to increase the yield of the streptavidin mutant of this invention.

The vector may be introduced into the host cell typically by the calcium chloride method or electroporation. The vector may also be attached with a sequence capable of encoding a tag for improving solubility, such as glutathione-S-transferase, thioredoxin or maltose-binding protein. The vector may also be attached with a sequence capable of encoding atag designed for simplifying the purification, such as polyhistidine tag, Myc epitope, hemagglutinin (HA) epitope, T7 epitope, Xpress tag, FLAG peptide tag, or other known sequences.

Examples of the expression vector other than *E. coli* include mammal-derived expression vectors (e.g., pcDNA3 (Invitrogen), pEGF-BOS (*Nucleic Acids. Res.* 1990,18(17), p 5322), pEF, pCDM8); insect cell-derived expression vectors (e.g., "Bac-to-BAC baculovirus expression system" (from Gibco-BRL), pBacPAK8); plant-derived expression vectors (e.g., pMH1, pMH2); animal virus-derived expression vectors (e.g., pHSV, pMV, pAdexLew); retrovirus-derived expression vectors (e.g., pZIPneo); yeast-derived expression vectors (e.g., "*Pichia* Expression Kit" (Invitrogen), pNV11, SP-Q01); and hay *bacillus* (*Bacillus subtilis*)-derived expression vector (e.g., pPL608, pKTH50).

For the purpose of expression in an animal cell such as CHO cell, COS cell, NIH3T3 cell or the like, it is essential for the expression vector to have a promoter which is necessary for the expression in the cell, such as SV40 promoter (Mulligan et al., *Nature* (1979) 277, 108), MMLV-LTR promoter, EF1α promoter (Mizushima et al., *Nucleic Acids Res.* (1990) 18, 5322), or CMV promoter. The expression vector more preferably has a gene for selecting transformation of the cell (e.g., drug-resistance gene identifiable by drugs (neomycin, G418, etc.). Examples of such vector include pMAM, pDR2, pBK-RSV, pBK-CMV, pOPRSV and pOP13.

Host cell into which the vector is introduced may be either prokaryotes or eukaryotes, without special limitation. For example, *E. coli* and various types of animal cells may be used.

As the eukaryotic cells, for example, animal cell, plant cell, or fungal cell may be used as the host. Animal cell suitably used herein include mammalian cells such as CHO cell, COS cell, 3T3 cell, HeLa cell and Vero cell; and insect cells such as Sf9, Sf21 and Tn5. For the purpose of mass expression in the animal cell, CHO cell is particularly preferable. The vector may be introduced into the host cell typically by calcium phosphate method, DEAE dextran method, a method using cationic ribosome DOTAP (from Boehringer Mannheim), electroporation method, lipofection or the like.

As for the plant cells, a well known example of protein-producing system is *Nicotiana tabacum*-derived cell, which may be cultured using callus. Known examples of fungal cell include those of yeast fungi, including genus *Saccharomyces*, represented by *Saccharomyces cerevisiae*; and filamentous fungus including genus *Aspergillus*, represented by *Aspergillus niger*.

As the procaryotic cells suitably used herein, exemplified are *Escherichia coli* (*E. coli*), such as JM109, DH5α and HB101; and hay *bacillus* (*Bacillus subtilis*).

The streptavidin mutant of this invention may be obtained by transforming these cells using the DNA of this invention, and by culturing the transformed cells in vitro. The cells may be cultured by any of known methods. For example, DMEM, MEM, RPMI1640 or IMDM may be used as a culture medium for the animal cells. The culture in this case may be allowed to proceed in the presence of serum such as fetal calf serum (FCS), or may be in accordance with serum-flee culture. The culture is preferably allowed to proceed at pH6 to 8 or around. The culture is typically allowed to proceed at approximately 30 to 40° C. for approximately 15 to 200 hours, with optional replacement of medium, ventilation and stirring. Also a growth factor may be added in order to promote the growth of the cells.

(3) Use of Streptavidin Mutant and Modified Biotin

According to this invention, there is also provided a streptavidin mutant-molecular probe conjugate, obtained by combining the streptavidin mutant of this invention with a molecular probe; and a therapeutic agent or diagnostic agent containing the streptavidin mutant-molecular probe conjugate. Moreover, the streptavidin mutant-molecular probe conjugate may be provided as a therapeutic or diagnostic kit, after combining it with a diagnostic or therapeutic substance labeled with the modified biotin which shows affinity to the streptavidin mutant of this invention. The molecular probe suitably used herein is exemplified by antibody, peptide, nucleic acid, and aptamer, and more specifically, by antibody, peptide, nucleic acid and aptamer which are targeted at antigens specifically expressed in cancer, the antigen includes:

epiregulin, ROBO1,2,3,4, 1-40-β-amyloid, 4-1BB, 5AC, 5T4, ACVR2B, adenocarcinoma antibody, α-fetoprotein, angiopoietin2, anthrax toxin, AOC3 (VAP-1), B-lymphoma cell, B7-H3, BAFF, β amyloid, C242 antibody, C5, CA-125, carbonic anhydraze 9 (CA-IX), cardiac myosin, CCL11 (eotaxin-1), CCR4, CCR5, CD11, CD18, CD125, CD140a, CD147 (basigin), CD147 (basigin), CD15, CD152, CD154 (CD40L), CD154, CD19, CD2, CD20, CD200, CD22, CD221, CD23 (IgE receptor), CD25 (α chain of IL-2 receptor), CD28, CD3, CD30 (TNFRSF8), CD33, CD37, CD38 (cyclic ADP ribose hydrolase), CD4, CD40, CD41 (integrin α-IIib), CD44 v6, CD5, CD51, CD52, CD56, CD6, CD70, CD74, CD79B, CD80, CEA, CFD, ch4D5, CLDN18.2, *Clostridium difficile*, clumping factor A, CSF2, CTLA-4, cytomegalovirus, cytomegalovirusglycoprotein B, DLL4, DR5, *E. coli* Shiga Toxin 1, *E. coli* Shiga Toxin 2, EGFL7, EGFR, endotoxin, EpCAM, episialin, ERBB3, *Escherichia coli*, F (fusion) protein of respiratory syncytial virus, FAP, fibrin IIβ chain, fibronectin extra domain-B, folic acid receptor 1, Frizzled receptor, GD2, GD3 ganglioside, GMCSF receptor a chain, GPNMB, hepatitis B surface antigen, hepatitis B virus, HER1, HER2/neu, HER3, HGF, HIV-1, HLA-DRβ, HNGF, Hsp90, human β amyloid, human scatter factor receptor kinase, human TNF, ICAM-1 (CD54), IFN-α, IFN-γ, IgE, IgE Fc region, IGF-1 receptor, IGF-I, IgG4, IGHE, IL-1β, IL-12, IL-13, IL-17, IL-17A, IL-22, IL-23, IL-4, IL-5, IL-6, IL-6 receptor, IL-9, ILGF2, influenza A hemagglutinin, insulin-like growth factor I receptor, integrin α4, integrin α4β7, integrin α5β1, integrin α7β7, integrin αIIbβ3, integrin αvβ3, integrin γ derived protein, interferon receptor, interferon α/β receptor, ITGA2, ITGB2 (CD18), KIR2D, L-selectin(CD62L), Lewis-Y antigen, LFA-1 (CD11a), lipoteichoic acid, LOXL2, LTA, MCP-1, mesothelin, MS4A1, MUC1, mucin CanAg, myostatin, N-glycolylneuraminic acid, NARP-1, NCA-90 (granulocyte antigen), NGF, NOGO-A, NRP1, *Oryctolagus cuniculus*, OX-40, oxLDL, PCSK9, PD-1, PDCD1, PDGF-R α, phosphatidylserine, prostate cancer cell, *Pseudomonas aeruginosa*, rabies virus glycoprotein, RANKL, respiratory syncytial virus, RHD, Rh (Rhesus) factor, RON, RTN4, sclerostin, SDC1, selectin P, SLAMF7, SOST, sphingosine-1-phosphate, TAG-72, TEM1, tenascin C, TFPI, TGFβ1, TGFβ2, TGF-β, TNF-α, TRAIL-R1, TRAIL-R2, tumor antigen CTAA16.88, tumor-specific glycosilation of MUC1, TWEAK receptor, TYRP1 (glycoprotein 75), VEGF-A, VEGFR-1, VEGFR2, vimentin, VWF Preferable examples of the molecular probe include anti-human CD20 antibody (e.g., Rituximab), and anti-epiregulin single chain antibody.

Rituximab is an anti-human CD20 antibody, where human CD20 is expressed only in B cell. A therapeutic drug for B cell non-Hodgkin's lymphoma and mantle cell lymphona, obtained by isotopic labeling of murine anti-CD20 monoclonal antibody with $^{90}$Y, is commercially available under the registered trademark of "Zevalin". This drug has an RI label directly bound to the anti-CD20 antibody, and needs several days after in vivo administration up to tumor accumulation, with an anxiety of serious side effect such as bone-marrow suppression induced by RI. As a solution to these problems, the pre-targeting method has been proposed (Non-Patent Literature 3). Pagneli et al. has investigated into the pre-targeting method using a fusion protein of anti-CD20 antibody-scFv and a streptavidin mutant, and RI-labeled biotin or bisbiotin (Non-Patent Literature 5).

Epiregulin is a member of epidermal growth factor, and is known to function as a cancer growth inhibitor capable of inducing changes in cytomorphology of HeLa cell. Aburatani et al. have produced an anti-epiregulin antibody (WO2008/047723). Lee et al. has humanized and evaluated an anti-epiregulin antibody (Biochemical and Biophysical Research communications, 444(2013), 1011-1017).

According to this invention, the streptavidin mutant of this invention may specifically be accumulated to cancer cell, by preparing a fused body of a molecular probe such as a cancer antigen-specific antibody molecule with the streptavidin mutant of this invention, and by administering it to a patient. Then by administering a diagnostic or therapeutic substance bound with the modified biotin which shows affinity to the streptavidin mutant (fluorescent dye, chemoluminescence agent, radioisotope, sensitizer composed of metal compound or the like, neutron capturing agent composed of metal compound or the like, low molecular weight compound such as drug, micro or nanobubble, protein, etc.) to a patient, the substance may specifically be accumulated to the cancer cell. In this invention, antibody production may be suppressed as a result of reduction in immunogenicity, and thereby it now becomes possible to avoid early in vivo clearance of the mutant streptavidin due to antibody, and a shock such as anaphylaxis. According to this invention, by using the streptavidin combined with patient's tissue, serum or the like as an in vitro diagnostic drug or a clinical reagent, the noise assignable to biotin or biotin-binding protein contained in the tissue, serum or the like, may be reduced, and this enables diagnosis or examination with higher S/N.

Alternatively, in this invention, a fused body of a molecular probe such as a cancer antigen-specific antibody molecule with the streptavidin mutant of this invention may be combined with a diagnostic or therapeutic substance bound with the modified biotin which shows affinity to the streptavidin mutant (fluorescent dye, chemoluminescence agent, radioisotope, sensitizer composed of metal compound or the like, neutron capturing agent composed of metal compound or the like, low molecular weight compound such as drug, micro or nanobubble, protein, etc.) to prepare a conjugate, and the obtained conjugate may be administered to a patient.

Various types of molecules may be used as the antibody to be bound to the streptavidin mutant. Either polyclonal antibody or monoclonal antibody may be used. IgG and in particular IgG$_1$ is preferable, without special limitation on subclass of the antibody. The "antibody" herein includes all of modified antibodies and antibody fragments. Examples of the antibody include humanized antibody; human-type antibody; human antibody; antibodies derived from various animals including mouse, rabbit, rat, guinea pig and monkey; chimeric antibodies formed between human antibody and antibodies derived from various animals; diabody; scFv; Fd; Fab; Fab'; and F(ab)'$_2$, but not limited thereto.

The conjugate of the streptavidin mutant and an antibody may be obtained by a method known to those skilled in the art. For example, the conjugate may be obtained by chemical binding (U.S. Pat. No. 5,608,060); or may be obtained in the form of fusion protein, by ligating a DNA encoding the streptavidin mutant and a DNA encoding the antibody, and then allowing it to be expressed in a host cell typically by using a vector. The DNA encoding the streptavidin mutant and the DNA encoding the antibody may be ligated via a DNA encoding an appropriate peptide, called linker. The streptavidin mutant-antibody conjugate is preferably produced, while maintaining the specific binding ability between the antibody and a target molecule.

This invention will further be detailed referring to Examples below, to which this invention is not limited.

EXAMPLES

Example 1A: Synthesis of Dimeric Compound of Modified Biotin

General Method

Nuclear magnetic resonance (NMR) spectrum was measured using JEOL ECX500 ($^1$H NMR: 500 MHz), or JEOL ECS400 ($^1$H NMR: 400 MHz) spectrometer. Chemical shift was given in ppm, as a value away from an internal reference peak assignable to a residual solvent in a deuterated solvent (CDCl$_3$: δ=7.26 ppm, CD$_3$OD: δ=3.31 ppm). Low-resolution mass spectrum (LRMS) was measured using an ESI-MS system named Waters ZQ4000 spectrometer. Column chromatography was carried out using silica gel Merk 60 (230-400 mesh ASTM). The reactions were monitored by way of thin layer chromatography (TLC), or low-resolution mass spectrometry (LRMS).

Reversed-phase high performance liquid chromatography (HPLC) was carried out using JASCO-HPLC system. Ultraviolet radiation of 210 nm or 254 nm was used for detection, and a gradient solvent system (acetonitrile/0.1% trifluoroacetic acid in MQ) was used as the mobile phase. Analyses were carried out using YMC-Pack ODS-AM (150×4.6 mL) or YMC-Triart-C18 (150×4.6 mL) column, at a flow rate of 1 mL/min. Fractionation was carried out using YMC-Pack ODS-AM (250×20 mL) or YMC-Triart-C18 (250×10 mL) column, at a flow rate of 8 to 10 mL/min for the former, and at a flow rate of 3 mL/min for the latter.

EZ-Link (registered trademark) NHS-Iminobiotin was purchased from Thermo Fisher Scientific Inc. Other reagents were purchased from Aldrich, Tokyo Chemical Industry Co., Ltd. (TCI), Kanto Chemical Co., Inc. (Kanto), Wako Pure Chemical Industries, Ltd., and Watanabe Chemical Industries, Ltd. All reagents and solvents were used as sold, unless otherwise specifically noted.

Tert-butyl 6,6'-[2,2'-oxybis(ethane-2,1-diyl)bis(azanediyl)]bis(6-oxohexane-6,1-diyl)dicarbonate (2)

[Chemical Formula 9]

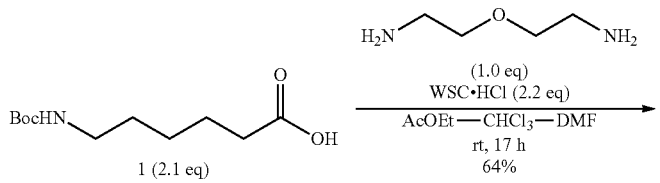

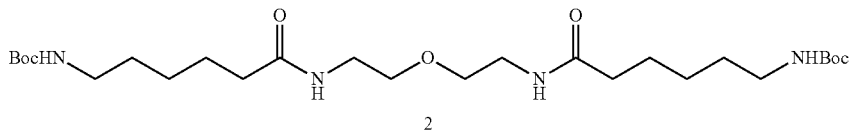

To an ethyl acetate (12 mL) solution of Compound 1 (1.40 g, 6.05 mmol) synthesized by a known method (Carlescu et al., Carbohydr. Res., (2010) 345, 33) were added 1-ethyl-3-(3-dimethylaminopropyl)carbodiimide hydrochloride (WSC.HCl, 1.22 g, 6.34 mmol) and N,N-dimethylformamide (6 mL), and the mixture was cooled on an ice bath. After adding 2,2'-oxybis(ethylamine) (0.30 g, 2.88 mmol) dissolved in a mixed solvent of chloroform (24 mL) and N,N-dimethylformamide (6 mL) to the reaction mixture, the mixture was stirred at room temperature for 17 hours. The mixture was then added with a saturated sodium chloride solution, the product was extracted into ethyl acetate, the organic layer was washed twice with a 0.5-N hydrochloric acid solution, then washed twice with an aqueous saturated sodium hydrogen carbonate solution, and further washed with a saturated sodium chloride solution. The organic layer was then dried over sodium sulfate, the solvent was evaporated off under reduced pressure, and the obtained crude product was purified by silica gel column chromatography (dichloromethane/methanol=20:1). Title Compound 2 (0.982 g, yield 64%, highly viscous yellow oil) was thus obtained.

$^1$H NMR (500 MHz, CD$_3$OD) δ: 1.29-1.36 (m, 4H), 1.43 (s, 18H), 1.48 (quint., 4H, J=7.5 Hz), 1.62 (quint., 4H, J=7.5 Hz), 2.20 (t, 4H, J=7.5 Hz), 3.02 (t, 4H, J=7.5 Hz), 3.35 (t, 4H, J=5.7 Hz), 3.51 (t, 4H, J=5.7 Hz); LRMS (ESI): m/z 553 [M+Na]$^+$.

N,N'-[2,2'-Oxybis(ethane-2,1-diyl)]bis(6-aminohexanamido) (3)

[Chemical Formula 10]

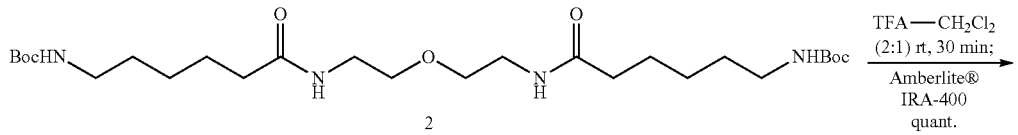

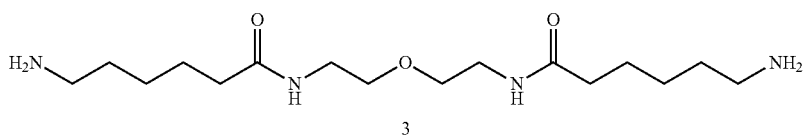

To a dichloromethane (6 mL) solution containing dicarbamate Compound 2 (0.917 g, 1.73 mmol) was added trifluoroacetic acid (12 mL), and the mixture was stirred at room temperature for 30 minutes. After the solvent was evaporated off under reduced pressure, the residue was dissolved into methanol (1 mL), applied to Amberlite® IRA-400 column (basic resin, 20 mm×200 mm), and eluted with methanol. After the solvent was evaporated off under reduced pressure, the residue was dried in vacuo. Title Compound 3 (0.57 g, quant., pale yellowish white solid) was thus obtained.

$^1$H NMR (500 MHz, CD$_3$OD) δ: 1.35-1.40 (m, 4H), 1.53 (quint., 4H, J=7.5 Hz), 1.63 (quint., 4H, J=7.5 Hz), 2.22 (t, 4H, J=7.5 Hz), 2.70 (t, 4H, J=7.5 Hz), 3.35 (t, 4H, J=5.7 Hz), 3.51 (t, 4H, J=5.7 Hz);

LRMS (ESI): m/z 166 [M+2H]$^{2+}$.

(3aS,3a'S,4S,4'S,6aR,6a'R)-4,4'-(5,12,20,27-Tetraoxo-16-oxa-6,13,19,26-tetraazahentriacontane-1,3H-diyl) bis[tetrahydro-1H-thieno[3,4-d]imidazole-2 (3H)-iminium] di(2,2,2-trifluoroacetate) (5)

ture was stirred at room temperature for 7 hours. After the solvent was evaporated off under reduced pressure, a mixed solvent (1:1) of acetone and diethyl ether was added to the residue, and sonicated. The deposited solid was collected by filtration, washed with the same solvent, and dried under reduced pressure. The crude product was dissolved into a mixed solvent of dioxane (1.2 mL) and water (0.8 mL), 25% aqueous ammonia (4.8 mL) was added, and the mixture was stirred at room temperature for 6 hours. The aqueous layer was washed with diethyl ether, and the solvent was evaporated off under reduced pressure. The obtained crude product was purified by reversed-phase HPLC (0-10-11-41-42-55 min; 0-0-22-52-100-100% CH$_3$CN in 0.1% TFA in MQ, ramp time=30 min (22-52%), t$_r$=22.0 min). Title Compound 5 (10.8 mg, two-step yield=65%, colorless amorphous matter) was thus obtained.

$^1$H NMR (500 MHz, CD$_3$OD) δ: 1.35 (quint., 4H, J=7.5 Hz), 1.46 (quint., 4H, J=7.5 Hz), 1.52 (quint., 4H, J=7.5 Hz), 1.55-1.72 (m, 10H), 1.78 (sext., 2H, J=7.5 Hz), 2.21 (t, 8H, J=7.5 Hz), 2.83 (d, 2H, J=13.2 Hz), 3.01 (dd, 2H, J=13.2, 5.2 Hz), 3.17 (t, 2H, J=7.5 Hz), 3.32 (ddd, 2H, J=10.3, 5.8, 4.6),

[Chemical Formula 11]

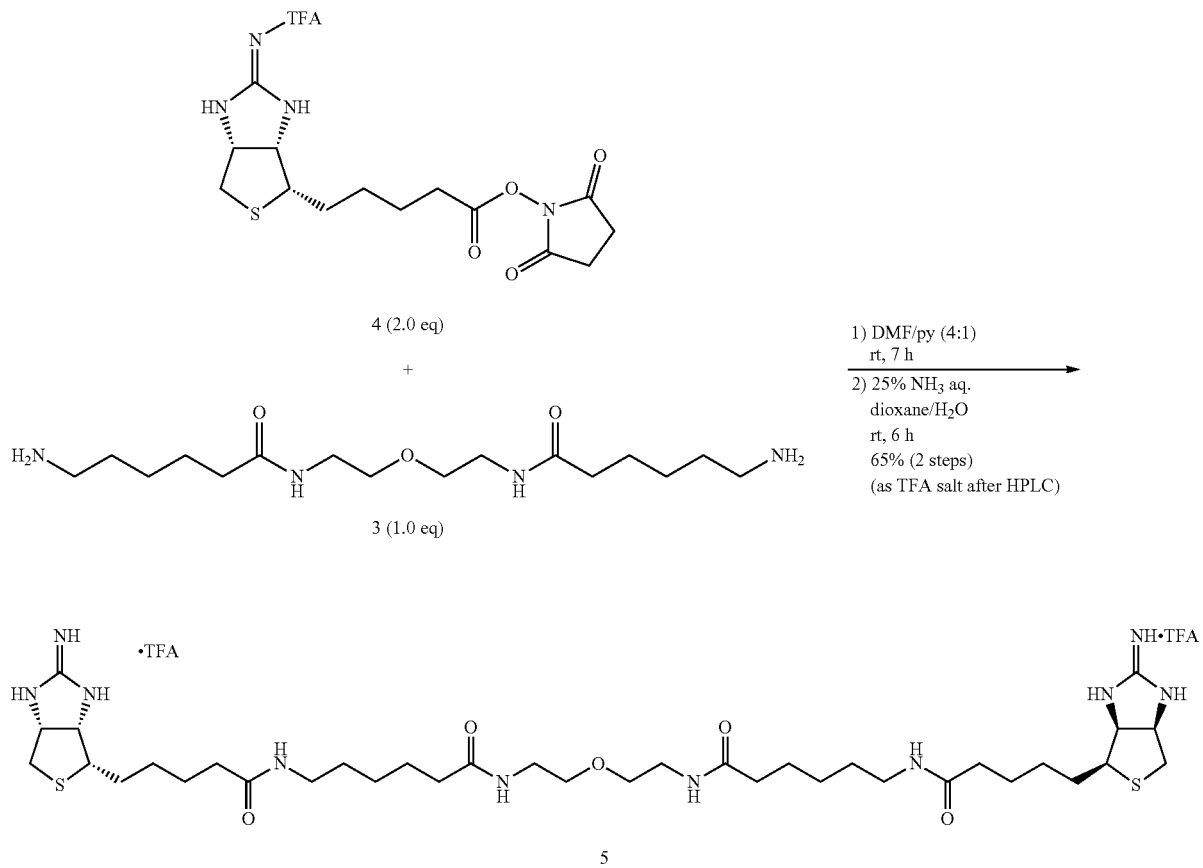

To a solution of diamine 3 (7.0 mg, 0.0212 mmol) dissolved in a mixed solvent of N,N-dimethylformamide (0.4 mL) and pyridine (0.1 mL) was added EZ-Link® NHS-Iminobiotin (4, 18.4 mg, 0.0424 mmol), and the mixture 3.36 (t, 4H, J=5.2 Hz), 3.51 (t, 4H, J=5.2 Hz), 4.54 (dd, 2H, J=7.5, 4.6 Hz), 4.73 (dd, 2H, J=7.5, 5.2 Hz);

LRMS (ESI): m/z 391 [M+2H]$^{2+}$.

(3aS,3a'S,4S,4'S,6aR,6a'R)-4,4'-(5,12,17,24-Tetraoxo-6,13,16,23-tetraazaoctacosane-1,28-diyl)bis[tetrahydro-1H-thieno[3,4-d]imidazole-2(3H)-iminium] di(2,2,2-trifluoroacetate) (7)

[Chemical Formula 12]

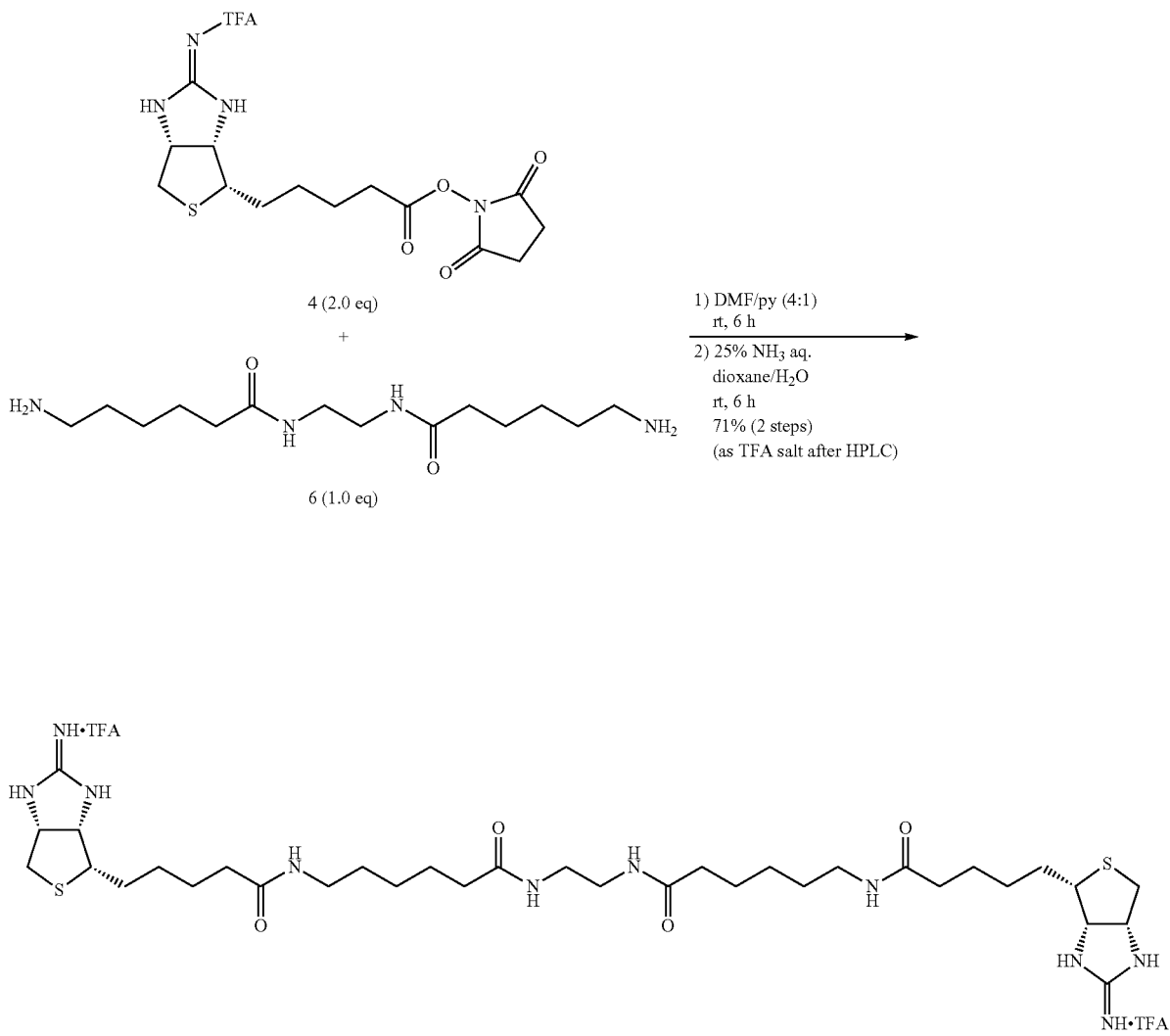

To a solution of diamine 6 (3.3 mg, 0.0115 mmol) synthesized by a known method and dissolved in a mixed solvent of N,N-dimethylformamide (0.4 mL) and pyridine (0.1 mL) was added EZ-Link® NHS-Iminobiotin (4, 10 mg, 0.0230 mmol), and the mixture was stirred at room temperature for 6 hours. After the solvent was evaporated off under reduced pressure, the residue was dissolved into dioxane (0.5 mL), 25% aqueous ammonia (2.0 mL) was added, and the mixture was stirred at room temperature for 6 hours. The aqueous layer was washed with diethyl ether, and the solvent was evaporated off under reduced pressure. The obtained crude product was purified by reversed-phase HPLC (YMC-Pack ODS-AM, gradient: 0-10-11-36-37-50 min; 0-0-17-42-100-100% $CH_3CN$ in 0.1% TFA in MQ, ramp time=25 min (17-42%), $t_r$=26.7 min). Title Compound 7 (7.9 mg, two-stage yield=71%, colorless amorphous matter) was thus obtained.

$^1$H NMR (400 MHz, $CD_3OD$) δ: 1.31-1.38 (m, 4H), 1.42-1.55 (m, 8H), 1.56-1.70 (m, 10H), 1.78 (sext., 2H, J=8.0 Hz), 2.20 (q, 8H, J=7.2 Hz), 2.83 (d, 2H, J=13.4 Hz), 3.01 (dd, 2H, J=13.4, 4.5 Hz), 3.17 (t, 4H, J=8.0), 3.27 (s,4H), 3.30-3.33 (m, 2H), 4.54 (dd, 2H, J=8.0, 4.5 Hz), 4.73 (dd, 2H, J=7.6 4.5 Hz);

LRMS (ESI): m/z 369 $[M+2H]^{2+}$.

Ethyl 3,5-bis[6-(Tert-butoxycarbonylamino)hexanamido]benzoate (9)

[Chemical Formula 13]

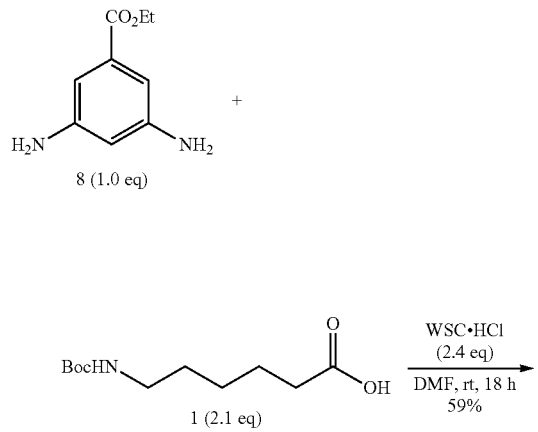

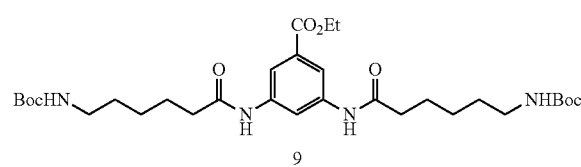

To a solution of Compound 1 (2.82 g, 11.2 mmol) synthesized by a known method (Carlescu et al., *Carbohydr. Res.* (2010) 345, 33) and dissolved in N,N-dimethylformamide (25 mL) were added 1-ethyl-3-(3-dimethylaminopropyl)carbodiimide hydrochloride (WSC·HCl, 2.66 g, 12.8 mmol) and ethyl 3,5-diaminobenzoate 8 (0.96 g, 5.33 mmol) dissolved in N,N-dimethylformamide (10 mL), and the mixture was stirred at room temperature for 2 hours. The mixture was added with a saturated sodium chloride solution and 1-N hydrochloric acid, the product was extracted into ethyl acetate, and the organic layer was washed twice with 0.5-N hydrochloric acid, then washed twice with an aqueous saturated sodium hydrogen carbonate solution, and further washed with a saturated sodium chloride solution. The organic layer was then dried over sodium sulfate, the solvent was evaporated off under reduced pressure, and the obtained crude product was purified by silica gel column chromatography (hexane/ethyl acetate=1:1→1:3). Title Compound 9 (2.27 g, yield 59%, yellow oil) was thus obtained.

$^1$H NMR (400 MHz, cdcl$_3$) δ: 1.30-1.35 (m, 6H), 1.35-1.50 (m, 22H), 1.66 (quint., 4H, J=7.6 Hz), 2.31 (t, 4H, J=7.6 Hz), 3.05 (q, 4H, J=6.7 Hz), 4.30 (q, 4H, J=7.2 Hz), 4.76 (brs, 2H), 7.91 (s, 2H), 8.05 (s, 1H), 8.54 (s, 2H); LRMS (ESI): m/z 629 [M+Na]$^+$.

6,6'-[5-(Ethoxycarbonyl)-1,3-phenylene]bis(azanediyl)bis(6-oxohexane-1-ammonium) dichloride (10)

[Chemical Formula 14]

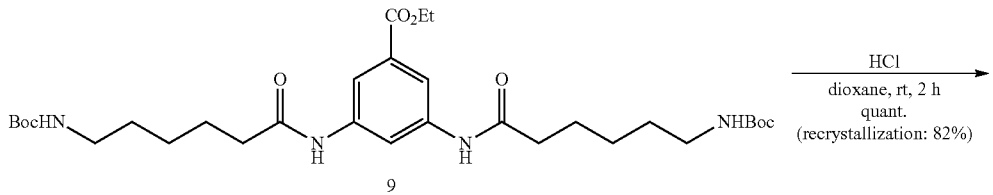

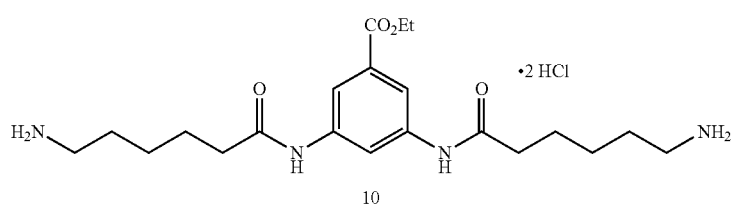

To a dioxane (20 mL) solution of dicarbamate compound 9 (2.27 g, 3.74 mmol) was added a 4-N hydrogen chloride solution in dioxane (20 mL), and the mixture was stirred at room temperature for 2 hours. The produced solid was washed with diethyl ether, and dried in vacuo. Ammonium salt 10 was quantitatively obtained. The solid was further dissolved into a small amount of dichloromethane, diethyl ether was added thereto, the produced solid was collected by filtration, and then washed with diethyl ether. A white solid of highly purified Compound 23 (1.47 g, yield 82%) was obtained.

$^1$H NMR (500 MHz, CD$_3$OD) δ: 139 (t, 3H, J=7.5 Hz), 1.48 (quint, 4H, J=7.5 Hz), 1.71 (quint., 4H, J=7.5 Hz), 1.75 (quint., 4H, J=7.5 Hz), 2.44 (t, 4H, J=7.5 Hz), 2.95 (t, 4H, J=7.5 Hz), 4.36 (q, 2H, J=7.5 Hz), 7.97 (d, 2H, J=1.8 Hz), 8.19 (s, 1H); LRMS (ESI): m/z 407 [M+H]$^+$.

(3aS,3a'S,4S,4'S,6aR,6a'R)-4,4'-{5,5'-[6,6'-(5-Carboxy-1,3-phenylene)bis(azanediyl)bis(6-oxohexane-6,1-diyl)]bis(azanediyl)bis(5-oxopentane-5,1-diyl)}bis(tetrahydro-1H-thieno[3,4-d]imidazole-2(3H)-iminium) di(2,2-trifluoroacetate) (11)

added, and the mixture was stirred at room temperature for 14 hours. The solvent was evaporated off under reduced pressure, the crude product was dissolved into methanol (0.5 mL), a 2-N aqueous sodium hydroxide solution (138 μL, 0.276 mmol) was added, and the mixture was stirred at room temperature for 22 hours. The produced white suspension was added with water (0.5 mL), the solid was washed with diethyl ether, collected by filtration, and further washed with an excessive amount of diethyl ether. The obtained crude product was purified by reversed-phase HPLC (YMC-Pack ODS-AM, gradient: 0-10-11-36-37-50 min; 0-0-2045-100-100% CH$_3$CN in 0.1% TFA in MQ, ramp time=25 min (20-45%), t$_r$=24.9 min). Title Compound 11 (26.0 mg, yield=71%, pale yellow amorphous matter) was thus obtained.

$^1$H NMR (500 MHz, CD$_3$OD) δ: 1.43 (quint., 8H, J=7.5 Hz), 1.56 (quint., 6H, J=7.5 Hz), 1.60-1.67 (m, 4H), 1.73 (quint., 6H, J=7.5 Hz), 2.19 (t, 4H, J=7.5 Hz), 2.40 (t, 4H, J=7.5 Hz), 2.81 (d, 2H, J=13.2 Hz), 2.99 (dd, 2, J=13.2, 4.6 Hz), 3.19 (td, 4H, J=6.9, 1.7 Hz), 3.27 (ddd, 2H, J=10.3, 5.8,

[Chemical Formula 15]

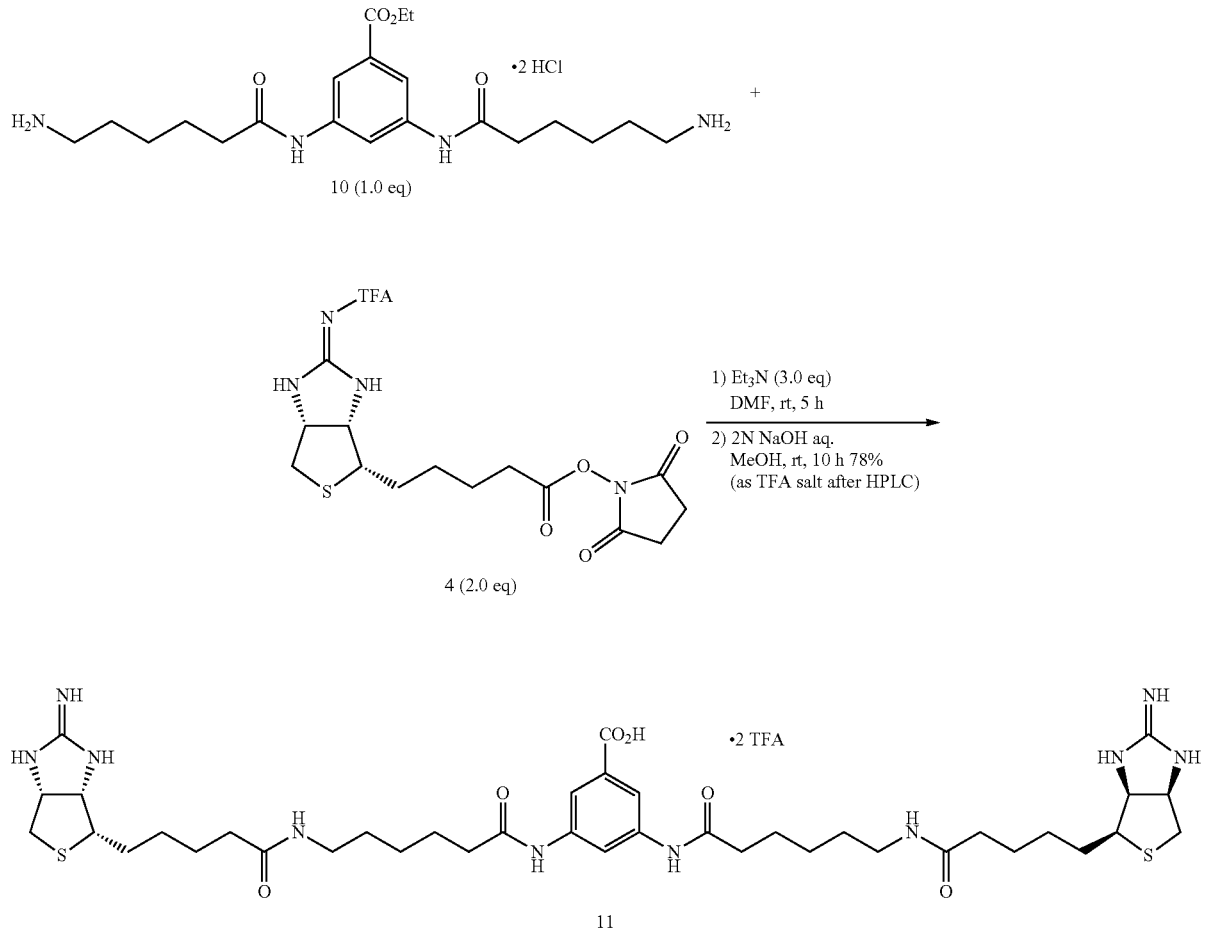

N,N-Dimethylformamide (0.6 mL) was added to ammonium salt 10 (16.6 mg, 0.0346 mmol), and triethylamine (14 μL, 0.104 mmol) was then added to dissolve the salt. EZ-Link® NHS-Iminobiotin (4, 30 mg, 0.0691 mmol) was 4.6 Hz), 4.52 (dd, 2H, J=8.0, 4.6 HZ), 4.71 (2H, J=8.0, 4.6 Hz), 7.95 (d, 2H, J=1.8 Hz), 8.17 (d, 1H, J=1.8 Hz);

LRMS (ESI): m/z 415 [M+2H]$^{2+}$.

(3aS,3a'S,4S,4'S,6aR,6a'R)-4,4'-{5,5'-[6,6'-(5-(2-(2-Aminoethoxy)ethoxy)ethylcarbonyl)-1,3-phenylene)bis(azanediyl)bis(6-oxohexane-6,1-diyl)]bis(azanediyl)bis(5-oxopentane-5,1-diyl)}bis(tetrahydro-1H-thieno[3,4-d]imidazole-2(3H)-iminium) tri(2,2,2-trifluoroacetate) (13)

[Chemical Formula 16]

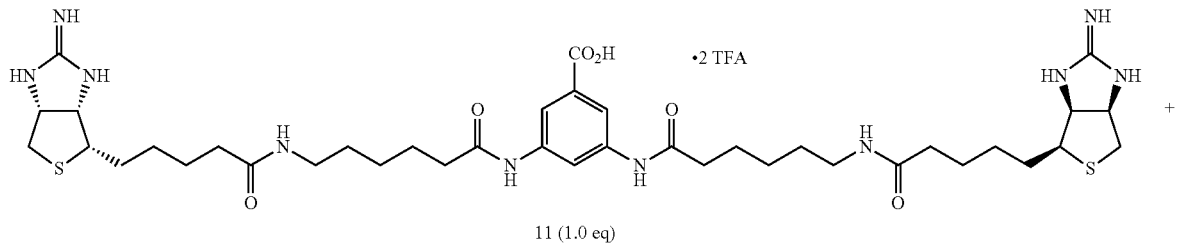

11 (1.0 eq)

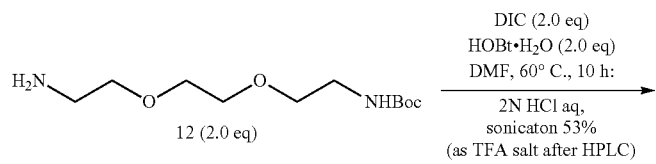

12 (2.0 eq)

DIC (2.0 eq)
HOBt·H₂O (2.0 eq)
DMF, 60° C., 10 h:
2N HCl aq,
sonicaton 53%
(as TFA salt after HPLC)

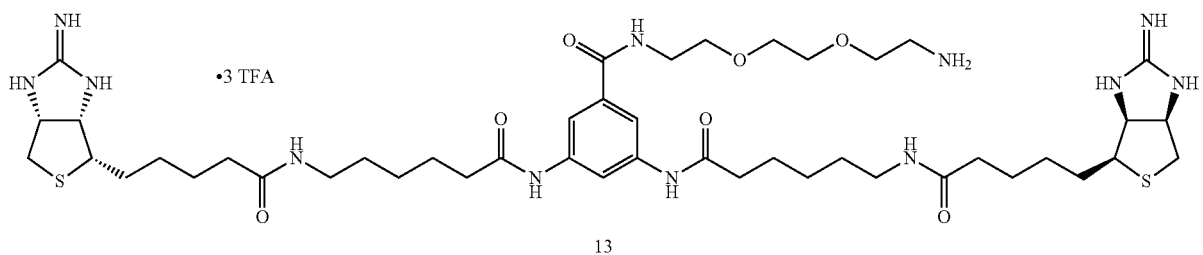

13

To a N,N-dimethylformamide (0.3 mL) solution of bisiminobiotin 11 (17 mg, 0.0161 mmol) were added N,N'-diisopropylcarbodiimide (DIC, 5.0 μL, 0.0322 mmol) and 1-hydroxybenzotriazole monohydrate (HOBt.H₂O, 4.9 mg, 0.0322 mmol). An N,N-dimethylformamide (0.15 mL) solution of amine 12 (8.0 mg, 0.0322 mmol) synthesized by a known method (Wilbur et al., *Bioconjugate. Chem.* (2010) 21, 1225) was added, and the mixture was stirred at 60° C. for 10 hours. The solvent was evaporated off under reduced pressure, water (1 mL) was added, the aqueous layer was washed with a mixed solvent (1:1) of ethyl acetate and diethyl ether, and the solvent was evaporated off under reduced pressure. The residue was added with a 2-N hydrochloric acid (1 mL), and then sonicated to dissolve the crude product. Water (1 mL) was then added, the aqueous layer was washed with diethyl ether and ethyl acetate, and the solvent was evaporated off under reduced pressure. The obtained crude product was purified by reversed-phase HPLC (YMC-Pack ODS-AM, gradient: 0-10-50-51-65 min; 10-10-30-100-100% $CH_3CN$ in 0.1% TFA in MQ, ramp time=40 min (10-30%), $t_r$=43.5 min). Title Compound 13 (11.2 mg, yield=53%, pale yellow amorphous matter) was thus obtained.

$^1$H NMR (500 MHz, $CD_3OD$) δ: 1.39-1.48 (m, 8H), 1.56 (quint, 6H, J=7.5 Hz), 1.65 (sext., 4H, J=6.9 Hz), 1.69-1.80 (m, 6H), 2.20 (t, 4H, J=7.5 Hz), 2.40 (t, 4H, J=7.5 Hz), 2.82 (d, 2H, J=13.2 Hz), 2.99 (dd, 2H, J=13.2, 4.6 Hz), 3.10 (t, 2H, J=5.2 Hz), 3.18 (t, 4H, J=7.5 Hz), 3.29 (ddd, 2H, J=10.3, 5.8, 4.6 Hz), 3.58 (t, 2H, J=5.2 Hz), 3.69 (quint, 8H, J=5.2 Hz), 4.52 (dd, 2H, J=8.0, 4.6 Hz), 4.72 (2H, dd, J=8.0, 4.6 Hz), 7.77 (d, 2H, J=1.7 Hz), 7.90 (d, 1H, J=1.7 Hz); LRMS (ESI): m/z 480 $[M+2H]^{2+}$.

(3aS,3a'S,4S,4'S,6aR,6a'R)-4,4'-{5,5'-[6,6'-(5-(2-(2-(2-(3-(3',6'-Dihydroxy-3-oxo-3H-spiro[isobenzofuran-1,9'-xanthene]-5-yl)thioureido)ethoxy)ethoxy)ethylcarbamoyl)-1,3-phenylene)bis(azanediyl)bis(6-oxohexane-6,1-diyl)]bis(azanediyl)bis(5-oxopentane-5,1-diyl)}bis(tetrahydro-1H-thieno[3,4-d]imidazole-2(3H)-iminium) di(2,22-trifluoroacetate) (14)

[Chemical Formula 17]

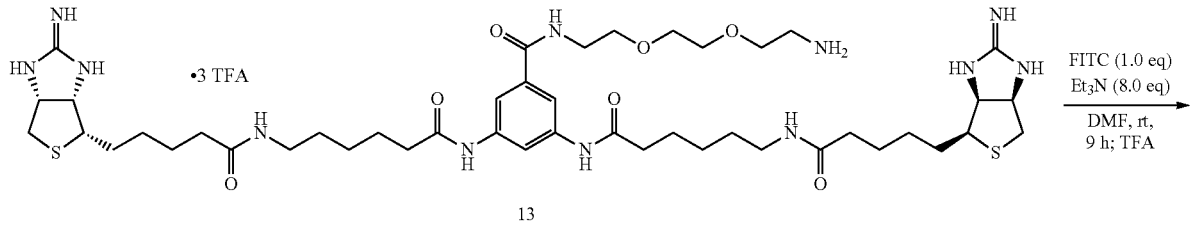

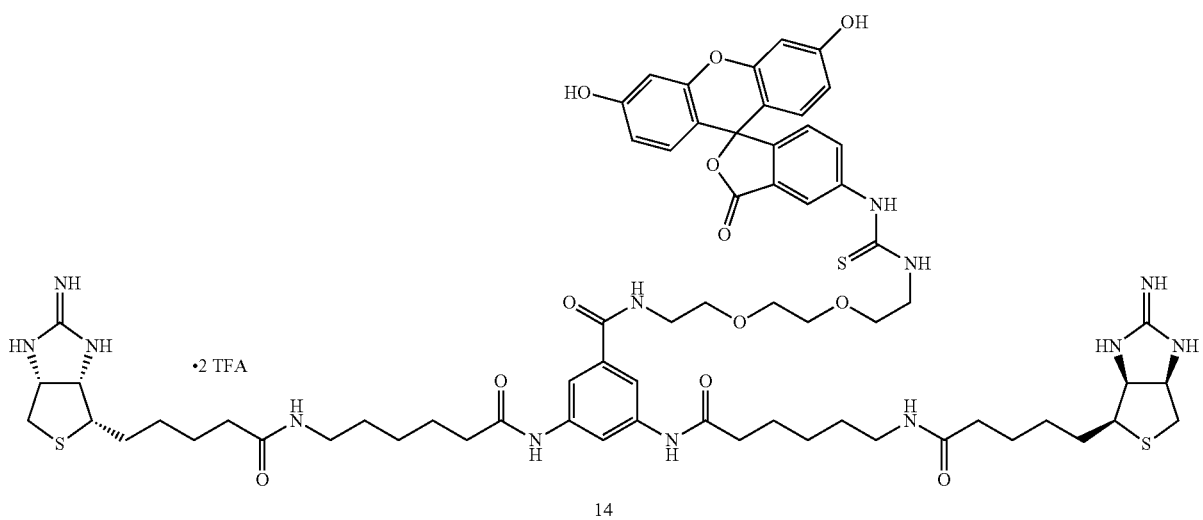

To a methanol (02 mL) solution of bisiminobiotin 13 (5 mg, 3.84 μmol) were added triethylamine (4.3 μL, 30.7 μmol) and fluorescein-5-isothiocyanate (FITC, 1.6 mg, 4.03 μmol). The mixture, with a reddish brown solid deposited therein, was stirred at room temperature for 10 hours. Methanol (1 mL) was added, the mixture was sonicated, the solid was collected by suction filtration, and then washed with methanol. The solid was dissolved into a methanol solution containing 10% of trifluoroacetic acid. The solvent was evaporated off under reduced pressure, and the obtained yellow crude product was purified by reversed-phase HPLC (YMC-Triart-C18, detected at 270 nm, gradient: 0-10-11-4142-55 min; 20-20-30-60-100-100% $CH_3CN$ in 0.1% TFA in MQ, ramp time=30 min (30-60%), $t_r$=25.7 min). Title Compound 14 (4.8 mg, yield=79%, pale yellow amorphous matter) was thus obtained.

$^1$H NMR (500 MHz, $CD_3OD$) δ: 1.41 (quint., 8H, J=7.5 Hz), 1.54 (quint., 6H, J=7.5 Hz), 1.63 (sext., 4H, J=6.9 Hz), 1.66-1.78 (m, 6H), 2.18 (t, 4H, J=7.5 Hz), 2.38 (t, 4H, J=7.5 Hz), 2.80 (2H, d, J=13.2 Hz), 2.97 (dd, 2H, J=13.2, 4.6 Hz), 3.17 (t, 4H, J=6.9 Hz), 3.26 (ddd, 2H, J=10.3, 5.8, 4.6 Hz), 3.57 (t, 2H, J=5.2 Hz), 3.68-3.74 (m, 8H), 3.81 (brs, 2H), 4.50 (dd, 2H, J=8.0, 4.6 Hz), 4.70 (d, 2H, J=7.5, 4.6 Hz), 6.73 (d, 2H, J=8.0 Hz), 6.87 (s, 2H), 6.92 (d, 2H, J=8.0 Hz), 720 (d, 1H, J=8.1 Hz), 7.72 (s, 2H), 7.82 (d, 1H, J=8.1 Hz), 7.96 (s, 1H), 828 (s, 1H); LRMS (ESI): m/z 675 [M+2H]$^{2+}$.

(3aS,3a'S,4S,4'S,6aR,6a'R)-4,4'-{5,5'-[6,6'-(5-Carbamoyl-1,3-phenylene)bis(azanediyl)bis(6-oxohexane-6,1-diyl)]bis(azanediyl)bis(5-oxopentane-5,1-diyl)}bis[tetrahydro-1H-thieno[3,4-d]imidazole-2(3H)-iminium]di(2,2,2-trifluoroacetate) (15)

[Chemical Formula 18]

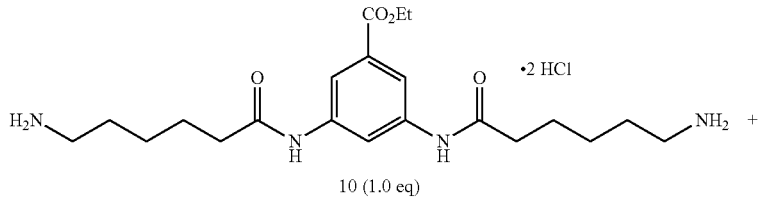

10 (1.0 eq)

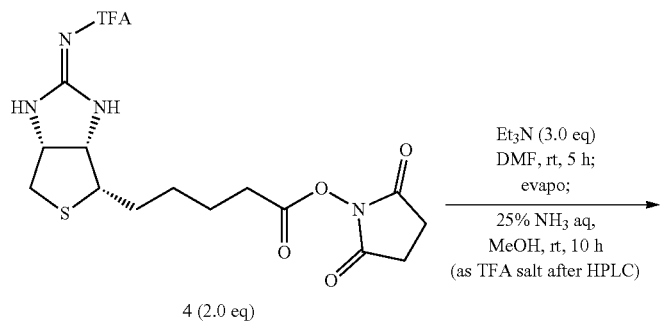

4 (2.0 eq)

Et₃N (3.0 eq)
DMF, rt, 5 h;
evapo;

25% NH₃ aq,
MeOH, rt, 10 h
(as TFA salt after HPLC)

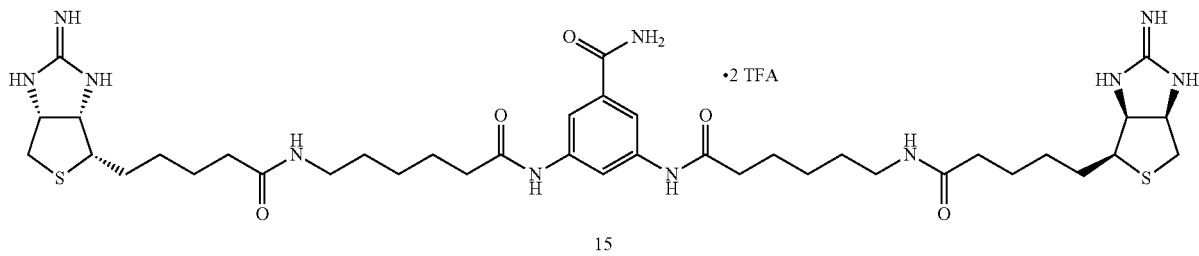

15

N,N-Dimethylformamide (0.23 mL) and triethylamine (4.8 μL, 0.034 μmmol) were added to diamine 10 (5.5 mg, 0.011XX mmol), EZ-Link® NHS-Iminobiotin 4 (10 mg, 0.023 mmol) was then added, and the mixture was stirred at room temperature for 6 hours. The solvent was evaporated off under reduced pressure, the crude product was dissolved into methanol (0.5 mL), 25% aqueous ammonia (2 mL) was added, and the mixture was stirred at 35° C. for 12 hours. The solvent was evaporated off under reduced pressure, and the obtained crude product was purified by reversed-phase HPLC (YMC-Pack ODS-AM, gradient: 0-10-11-36-37-50 min; 0-0-20-45-100-100% CH₃CN in 0.1% TFA in MQ, ramp time=25 min (20-45%), $t_r$=23.1 min). Title Compound 15 (5.9 mg, yield=49%) was thus obtained.

$^1$H NMR (500 MHz, CD₃OD) δ: 1.38-1.46 (m, 8H), 1.56 (quint, 6H, J=7.5 Hz), 1.64 (sext, 4H, J=6.9 Hz), 1.73 (quint, 6H, J=7.5 Hz), 2.19 (t, 4H, J=7.5 Hz), 2.40 (t, 4H, J=7.5 Hz), 2.81 (d, 2H, J=13.2 Hz), 2.99 (dd, 2H, J=13.2, 4.6 Hz), 3.19 (t, 4H, J=6.9 Hz), 3.29 (ddd, 2H, J=10.3, 5.8, 4.6 Hz), 4.52 (dd, 2H, J=8.0, 4.6 Hz), 4.72 (dd, 2H, J=8.0, 4.6 Hz), 7.75 (d, 2H, J=1.7 Hz), 8.03 (d, 2H, J=1.7 Hz);

LRMS (ESI): m/z 829 [M+H]⁺.

N[1],N[3]-Bis{2-[2-(2-(Tert-butoxycarbonylamino)ethoxy)ethoxy]ethyl}-5-(4-iodobenzamido)isophthalamide (17)

[Chemical Formula 19]

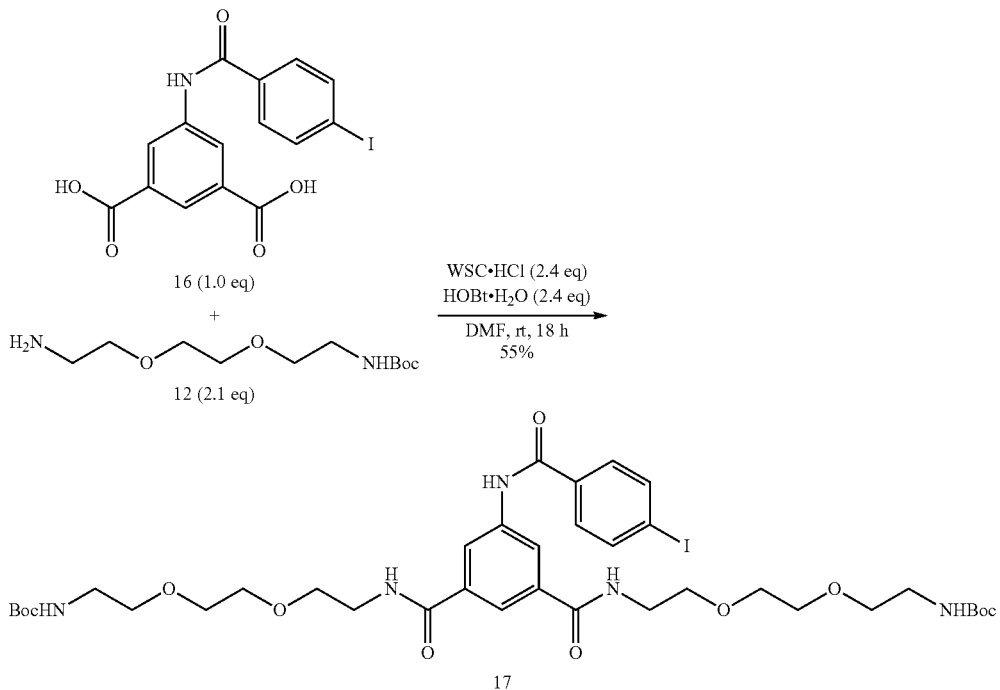

To a N,N-dimethylformamide (5 mL) solution of 5-(4-iodobenzamido)isophthalic acid 16 (0.50 g, 1.21 mmol) synthesized by a known method (Wilbur et al., Bioconjugate. Chem. (1997) 8, 161), added were 1-ethyl-3-(3-dimethylaminopropyl)carbodiimide hydrochloride (WSC.HCl, 0.556 g, 2.90 mmol) and 1-hydroxybenzotriazole monohydrate (HOBt.H$_2$O, 0.444 g, 2.90 mmol), further added was an N,N-dimethylformamide (1 mL) solution of amine 12 (0.663 g, 2.67 mmol) synthesized by a known method (Wilbur et al., Bioconjugate. Chem. (2010) 21, 1225), and the mixture was stirred at room temperature for 18 hours. After the solvent was evaporated off under reduced pressure, ethyl acetate and 0.5-N hydrochloric acid were added, the product was extracted with ethyl acetate, and the organic layer was washed successively with 0.5-N hydrochloric acid, an aqueous saturated sodium hydrogen carbonate solution, and a saturated sodium chloride solution. After the organic layer was dried over sodium sulfate, the solvent was evaporated off under reduced pressure, and the obtained crude product was purified by silica gel column chromatography (ethyl acetate→dichloromethane/methanol=10:1). Title Compound 17 (380 mg, yield=36%, highly viscous yellow oil) was thus obtained.

$^1$H NMR (400 MHz, CD$_3$OD) δ: 1.40 (s, 18H), 3.20 (t, 4H, J=5.4 Hz), 3.51 (t, 4H, J=5.4 Hz), 3.58-3.71 (m, 16H), 7.73 (dt, 2H, J=8.5, 1.8 Hz), 7.92 (dt, 2H, J=8.5, 1.8 Hz), 8.03 (t, 1H, J=1.4 Hz), 8.30 (d, 1H, J=1.4 Hz); LRMS (ESI): m/z 894 [M+Na]$^+$.

N[1],N[3]-Bis{2-[2-(2-aminoethoxy)ethoxy]ethyl}-5-(4-iodobenzamido)isophthalamide (18)

[Chemical Formula 20]

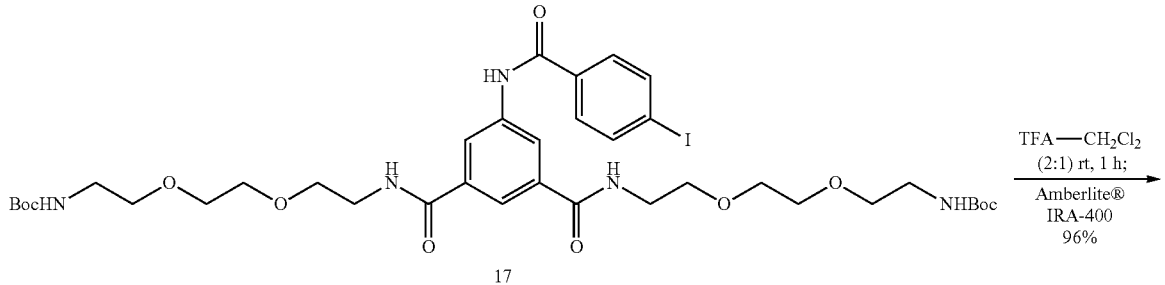

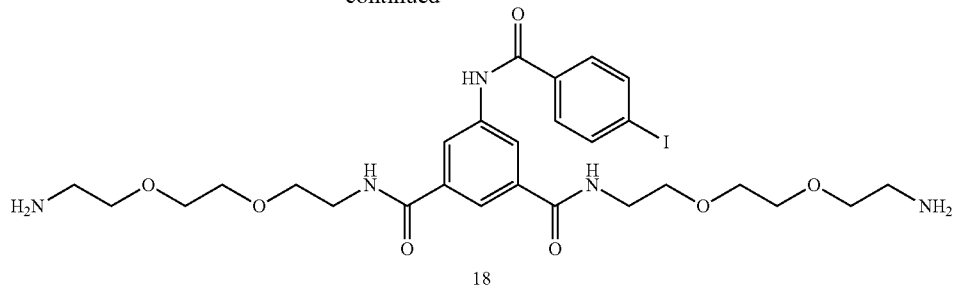

18

To a dichloromethane (1 mL) solution of dicarbamate compound 17 (0.350 g, 0.401 mmol) was added trifluoroacetic acid (2 mL), and the mixture was stirred at room temperature for one hour. The solvent was evaporated off under reduced pressure, and the residue was washed with diethyl ether. The product was dissolved in methanol (1 mL), applied to Amberlite® IRA-400 column (basic resin, 20 mm×200 mm), and eluted with methanol. After the solvent was evaporated off under reduced pressure, the residue was dried in vacuo. Title Compound 18 (0.258 g, yield 96%, yellow amorphous matter) was thus obtained.

$^1$H NMR (500 MHz, CD$_3$OD) δ: 2.74 (t, 4H, J=5.2 Hz), 3.49 (t, 4H, J=5.2 Hz), 3.59 (t, 4H, J=5.2 Hz), 3.60-3.63 (m, 4H), 3.64-3.69 (m, 8H), 7.69 (dt, 2H, J=8.6, 1.8 Hz), 7.85 (dt, 2H, J=8.6, 1.8 Hz), 7.99 (t, 1H, J=1.7 Hz), 8.27 (d, 2H, J=1.7 Hz); LRMS (ESI): m/z 672 [M+H]$^+$.

(S)-1-Tert-butyl 4-(2,5-dioxopyrrolidine-1-yl) 2-(tert-butoxycarbonylamino)succinate (19)

[Chemical Formula 21]

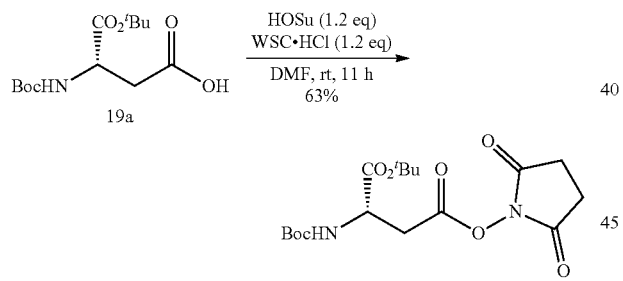

To an N,N-dimethylformamide (17 mL) solution of Boc-Asp(o$^t$bu)-OH 19a (0.50 g, 1.73 mmol) and N-hydroxysuccinimide (0.343 g, 2.08 mmol) was added 1-ethyl-3-(3-dimethylaminopropyl)carbodiimide hydrochloride (WSC.HCl, 0.399 g, 2.08 mmol), and the mixture was stirred at room temperature for 11 hours. After the solvent was evaporated off under reduced pressure, the mixture was added with ethyl acetate and 0.5-N hydrochloric acid, the product was extracted into ethyl acetate, the organic layer was washed successively with 0.5-N hydrochloric acid, an aqueous saturated sodium hydrogen carbonate solution, and a saturated sodium chloride solution. The organic layer was dried over sodium sulfate, and the solvent was evaporated off under reduced pressure. Title Compound 19 (0.431 g, yield 63%, white solid) was thus obtained. The obtained product was used for the next reaction without further purification.

$^1$H NMR (400 MHz, CD$_3$OD) δ: 1.45 (s, 9H), 1.47 (s, 9H), 2.84 (s, 4H), 3.09 (dd, 1H, J=17.5, 6.4 Hz), 3.18 (dd, 1H, J=17.4, 5.8 Hz), 4.46 (t, 1H, J=5.8 Hz); LRMS (ESI): m/z 387 [M+H]$^+$.

Tert-butyl (14S,14'S)-1,1'-[5-(4-iodobenzamido)-1,3-phenylene]bis[14-(tert-butoxycarbonylamino)-1,12-dioxo-5,8-dioxa-2,11-diazapentadecanoate] (20)

[Chemical Formula 22]

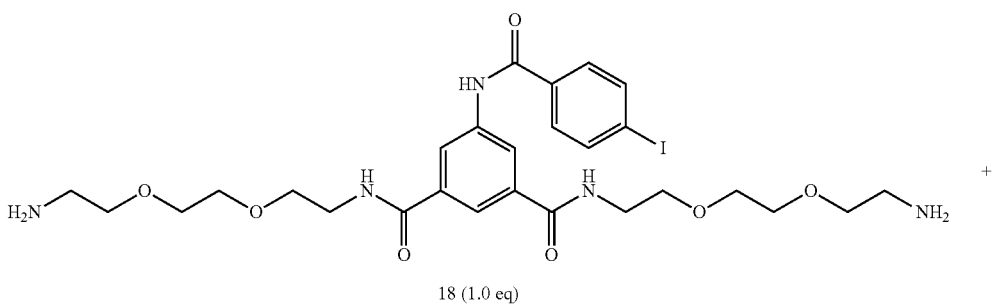

18 (1.0 eq)

+

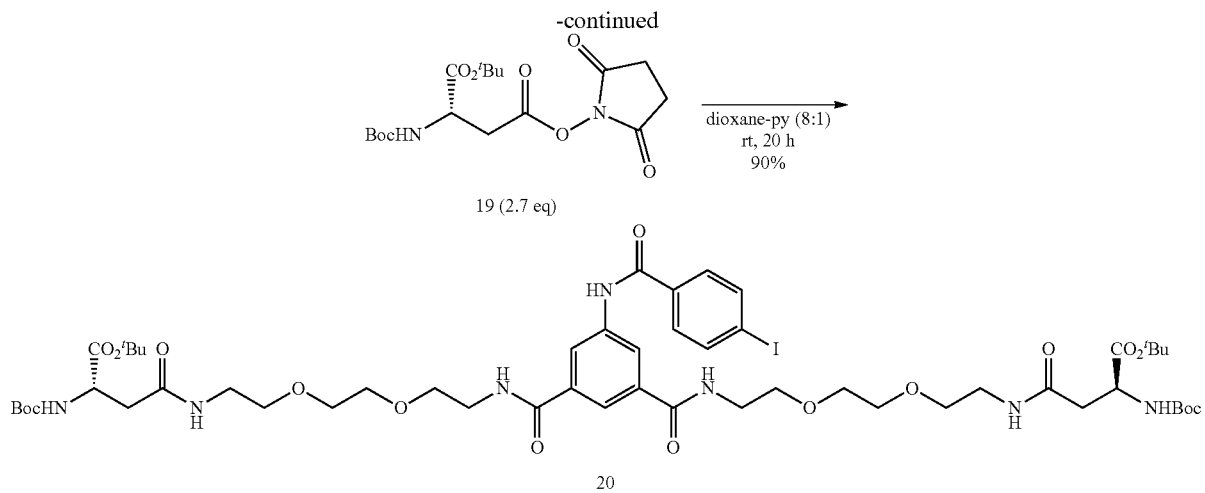

To a mixed solution of dioxane (0.8 mL) and pyridine (0.1 mL) containing diamine 18 (35.9 mg, 0.0412 mmol), activated ester 19 (33.4 mg, 0.0865 mmol) was added. The mixture was stirred at room temperature for 14 hours, an additional portion of activated ester 19 (10 mg, 0.0259 mmol) was added, and the mixture was stirred at room temperature for 6 hours. After the solvent was evaporated off under reduced pressure, the residue was added with ethyl acetate and 0.5-N hydrochloric acid, the product was extracted into ethyl acetate, the organic layer was washed successively with 0.5-N hydrochloric acid, an aqueous saturated sodium hydrogen carbonate solution, and a saturated sodium chloride solution. The organic layer was dried over sodium sulfate, the solvent was evaporated off under reduced pressure, and the obtained crude product was purified by silica gel column chromatography (dichloromethane/methanol=25:1→15:1). Title Compound 20 (47.9 mg, yield=90%, yellow amorphous matter) was thus obtained.

$^1$H NMR (500 MHz, CD$_3$OD) δ: 1.42 (s, 18H), 1.43 (s, 18H), 2.53-2.67 (m, 4H), 3.32 (t, 4H, J=5.2 Hz), 3.53 (td, 4H, J=5.2, 1.7 Hz), 3.60-3.64 (m, 8H), 3.65-3.70 (m, 8H), 4.32 (quint., 2H, J=5.8 Hz), 7.72 (dt, 2H, J=8.6, 1.7 Hz), 7.90 (dt, 2H, J=8.6, 1.7 Hz), 8.03 (t, 1H, J=1.7 Hz), 8.29 (d, 2H, J=1.7 Hz); LRMS (ESI): m/z 1236 [M+Na]$^+$.

(14S,14'S)-1,1'-[5-(4-Iodobenzamido)-1,3-phenylene]bis(14-carboxy-1,12-dioxo-5,8-dioxa-2,11-diazatetradecane-14-ammonium) di(2,2,2-trifluoroacetate) (21)

[Chemical Formula 23]

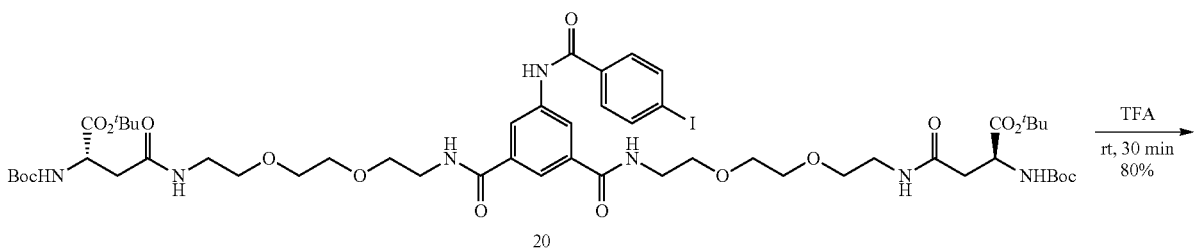

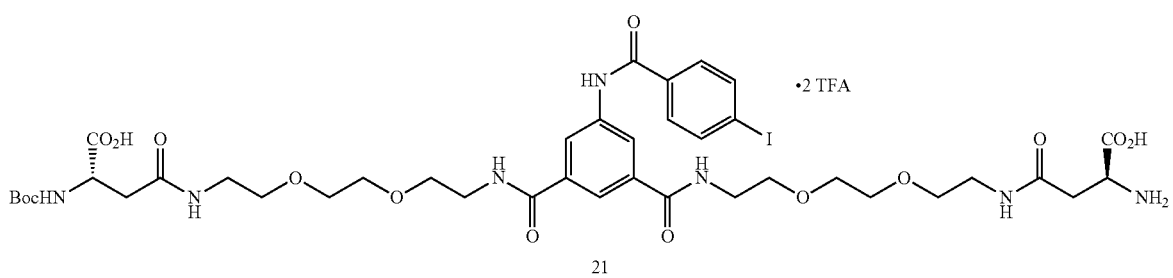

Trifluoroacetic acid (2.0 mL) was added to compound 20 (41 mg, 0.0338 mmol) to dissolve it therein, and the mixture was stirred at room temperature for 30 minutes. The solvent was evaporated off under reduced pressure, and the residue was added with diethyl ether, so that white solid was deposited. The solid was collected by suction filtration, washed with diethyl ether, and dried in vacuo. Title Compound 21 (30.4 mg, yield=80%, white solid) was thus obtained.

$^1$H NMR (500 MHz, CD$_3$OD) δ: 2.64 (dd, 2H, J=17.2, 7.5 Hz), 2.81 (dd, 2H, J=17.2, 4.0 Hz), 3.35 (t, 4H, J=5.2 Hz), 3.55 (t, 4H, J=5.2 Hz), 3.60-3.64 (m, 8H), 3.67-3.73 (m, 8H), 4.14 (dd, 2H, J=7.5, 4.0 Hz), 7.74 (d, 2H, J=8.6 Hz), 7.92 (d, 2H, J=8.6 Hz), 8.05 (t, 1H, J=1.2 Hz), 8.29 (d, 2H, J=1.2 Hz);

LRMS (ESI): m/z 902 [M+H]$^+$.

(3aS,3a'S,4S,4'S,6aR,6a'R)-4,4'-{(14S,14'S)-1,1'-[5-(4-Iodobenzamido)-1,3-phenylene]bis(14-carboxy-1,12,16-trioxo-5,8-dioxa-2,11,15-triazaeicosane-20,1-diyl)}bis(tetrahydro-1H-thieno[3,4-d]imidazole-2(3H)-iminium) di(2,2,2-trifluoroacetate) (22)

[Chemical Formula 24]

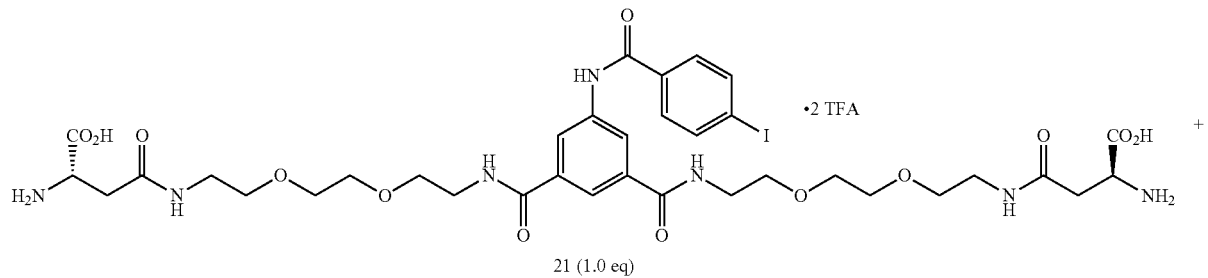

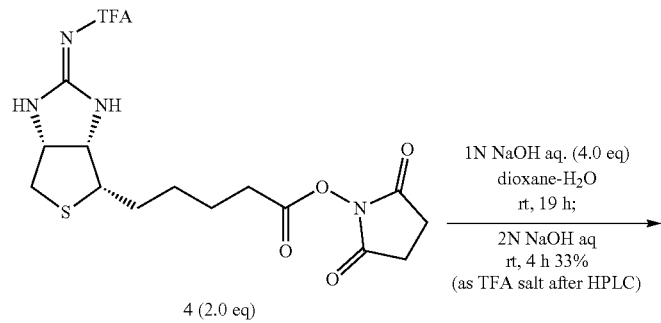

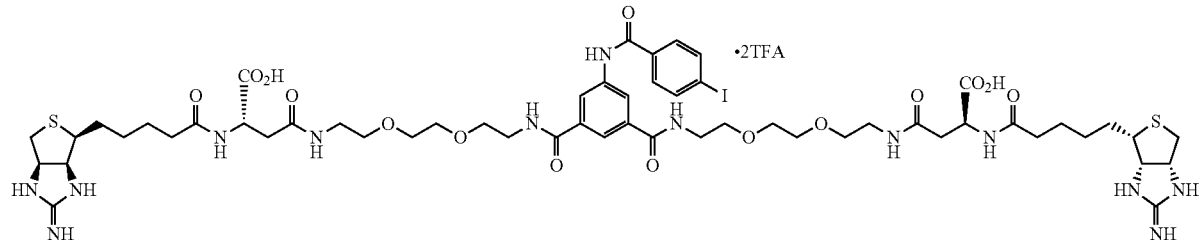

Bisamino acid 21 (5 mg, 4.43 μmol) was dissolved into a mixed solvent of dioxane (0.2 mL) and water (0.1 mL), and a 1-N aqueous sodium hydroxide solution (18 μL, 177 μmol) was then added. The mixture was stirred at room temperature for 5 minutes, and then added with EZ-Link® NHS-Iminobiotin (4, 4.0 mg, 9.07 μmol). The mixture was stirred at room temperature for 19 hours, added with a 2-N aqueous sodium hydroxide solution (150 μL), and the mixture was further stirred at room temperature for 4 hours. The aqueous layer was washed with diethyl ether, and the solvent was evaporated off under reduced pressure. The obtained crude product was purified by reversed-phase HPLC (YMC-Pack ODS-AM, gradient 0-10-11-36-37-50 min; 0-0-24-49-100-100% $CH_3CN$ in 0.1% TFA in MQ, ramp time=25 min (24-49%), $t_r$=27.2 min). Title Compound 22 (2.3 mg, yield=33%, white solid) was thus obtained.

$^1$H NMR (500 MHz, $CD_3OD$) δ: 1.40-1.51 (m, 4H), 1.52-1.81 (m, 8H), 2.25 (sext., 4H, J=7.2 Hz), 2.73 (d, 4H, J=6.3 Hz), 2.81 (d, 2H, J=13.4 Hz), 2.98 (dd, 2H, J=13.4, 4.5 Hz), 3.24-3.31 (m, 2H), 335 (t, 4H, J=5.4 Hz), 3.54 (t, 4H, J=5.4 Hz), 3.60-3.65 (m, 8H), 3.66-3.72 (m, 8H), 4.53 (dd, 2H, J=8.1, 4.5 Hz), 4.70-4.74 (m, 4H), 7.74 (d, 2H, J=8.5 Hz), 7.93 (d, 2H, J=8.5 Hz), 8.05 (s, 1H), 8.31 (d, 2H, J=1.4 Hz); LRMS (ESI): m/z 677 [M+2H]$^+$.

N,N'-[2,2'-Oxybis(ethane-2,1-diyl)]bis {6-[5-((3aS, 4S,6aR)-2-oxohexahydro-1H-thieno[3,4-d]imidazole-4-yl)pentanamido]hexanamide} (24)

[Chemical Formula 25]

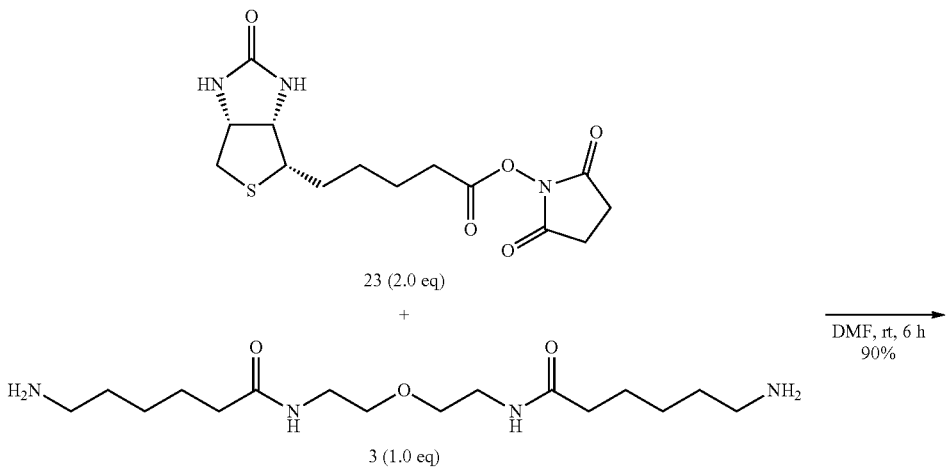

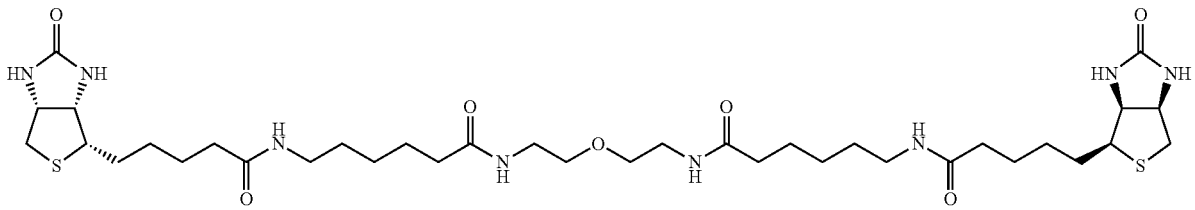

To an N,N-dimethylformamide (1.6 mL) solution of diamine 3 (21.8 mg, 0.0659 mmol), biotin N-hydroxysuccinimide ester (23, 45 mg, 0.132 mmol) was added, and the mixture was stirred at room temperature for 6 hours. The mixture was added with diethyl ether, and the deposited solid was collected by filtration. The solid was washed successively with 1-N hydrochloric acid, a saturated sodium carbonate solution, water, cold acetone, and diethyl ether, and then dried in vacuo. Title Compound 24 (46.2 mg, yield=90%, white solid) was thus obtained.

$^1$H NMR (500 MHz, CD$_3$OD) δ: 1.32-1.38 (m, 4H), 1.44 (quint., 4H, J=7.5 Hz), 1.52 (quint., 4H, J=7.5 Hz), 1.58-1.69 (m, 10H), 1.69-1.78 (m, 2H), 2.20 (q, 8H, J=7.5 Hz), 2.71 (d, 2H, J=13.2 Hz), 2.93 (dd, 2H, J=12.6, 4.6 Hz), 3.17 (t, 4H, J=6.9 Hz), 3.21 (ddd, 2H, J=10.3, 5.8, 4.6 Hz), 3.35 (t, 4H, J=5.8 Hz), 3.51 (t, 4H, J=5.8 Hz), 4.31 (dd, 2H, J=8.1, 4.6 Hz), 4.49 (dd, 2H, J=8.1, 4.6 Hz); LRMS (ESI): m/z 805 [M+Na]$^+$.

List of Compounds Used in Example 2 and Thereafter:

[Chemical Formula 26]

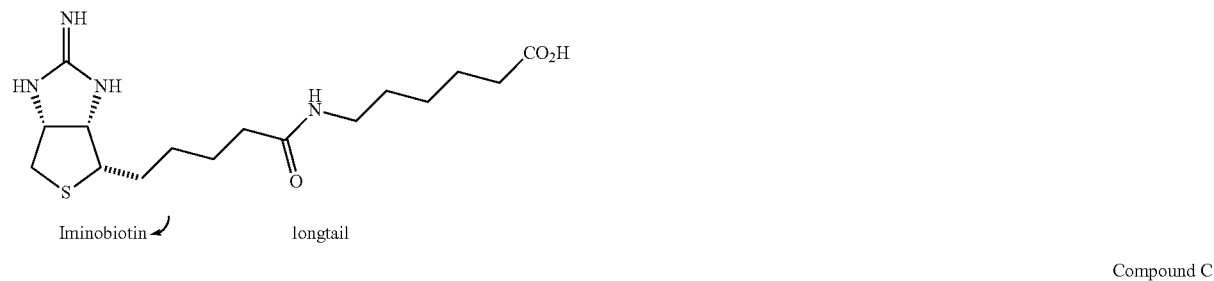

Iminobiotin   longtail

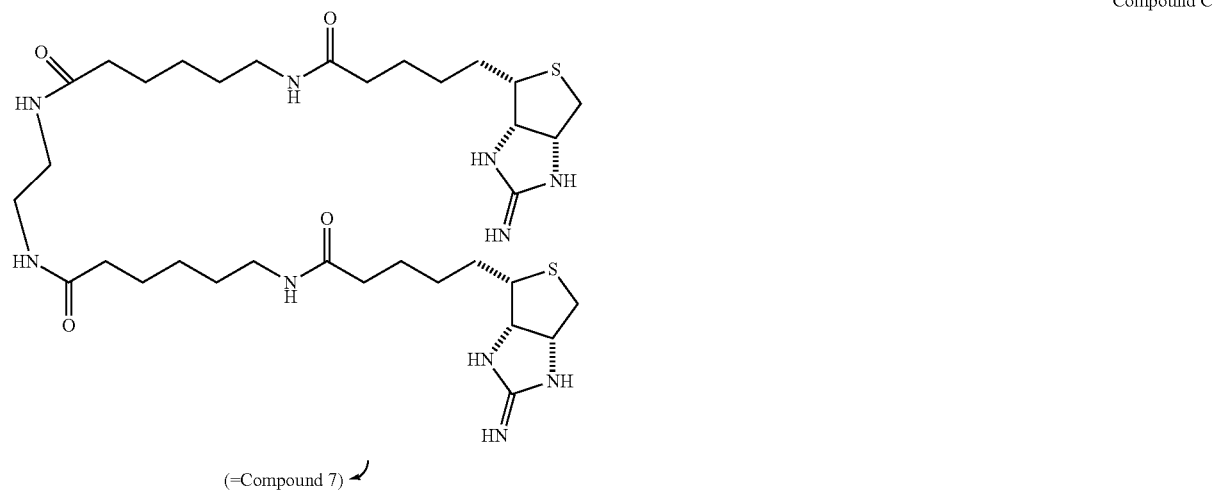

(=Compound 7)

Compound C

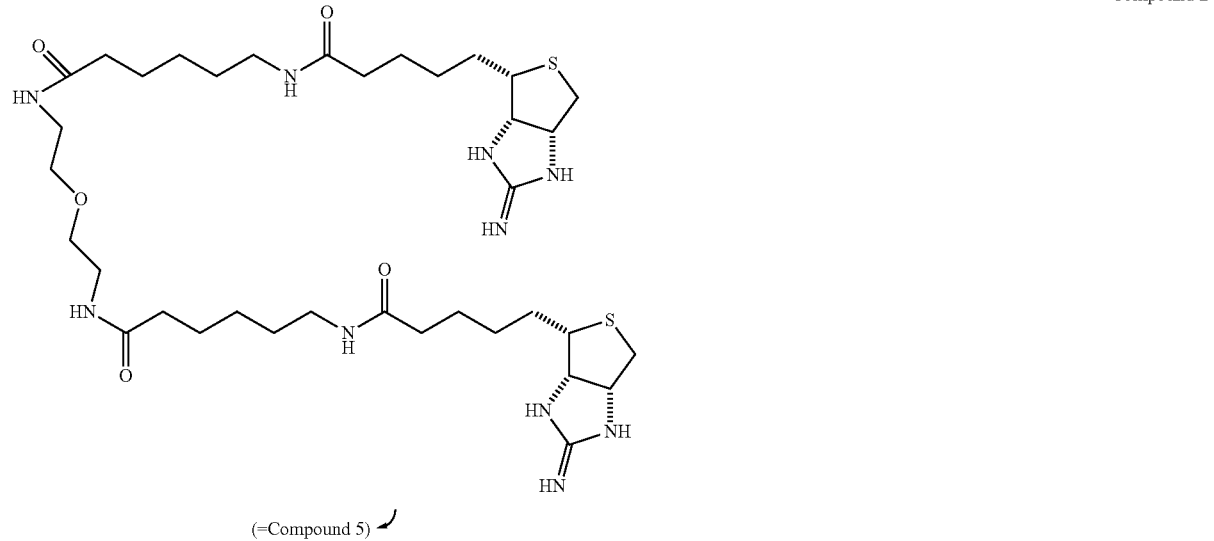

(=Compound 5)

Compound D

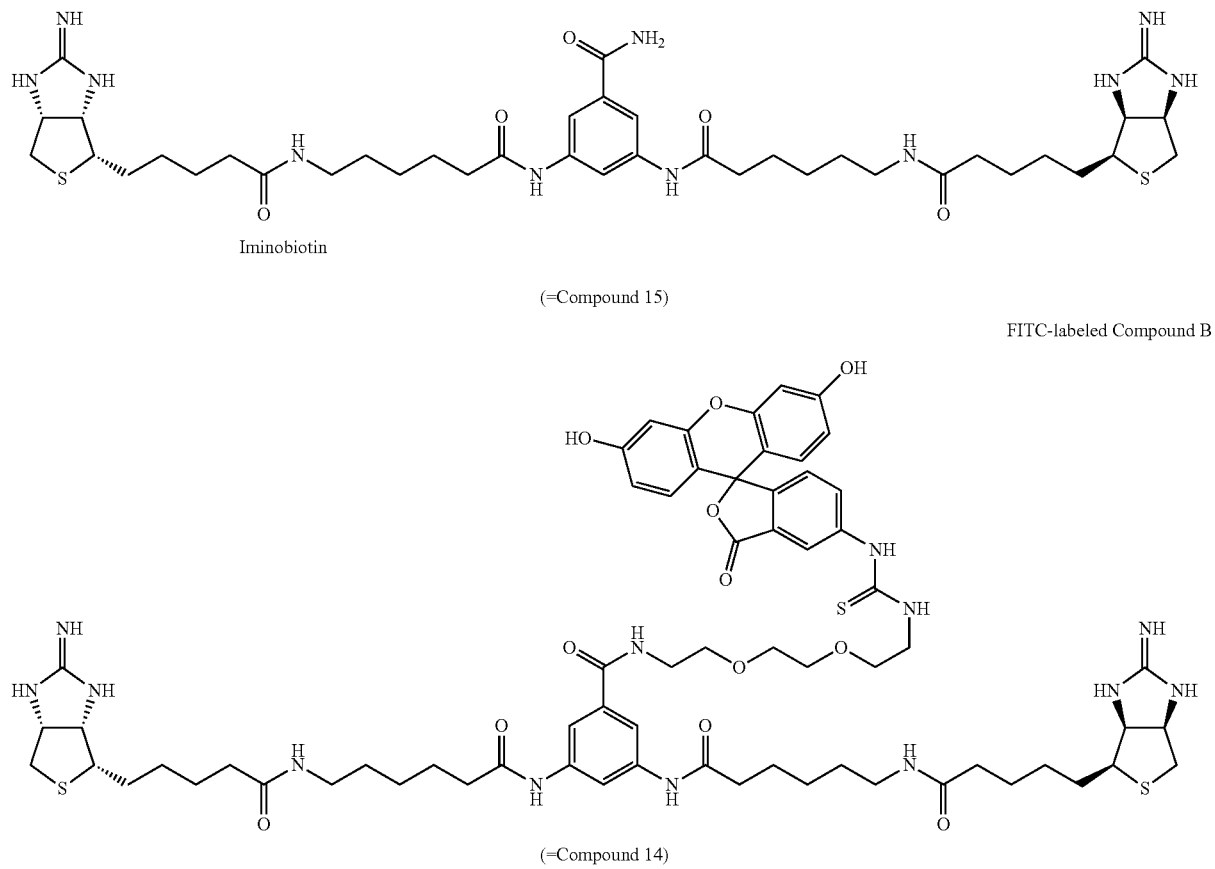

(=Compound 15)

FITC-labeled Compound B (=Compound 14)

Iminobiotin longtail may be synthesized as described below.

[Chemical Formula 27]

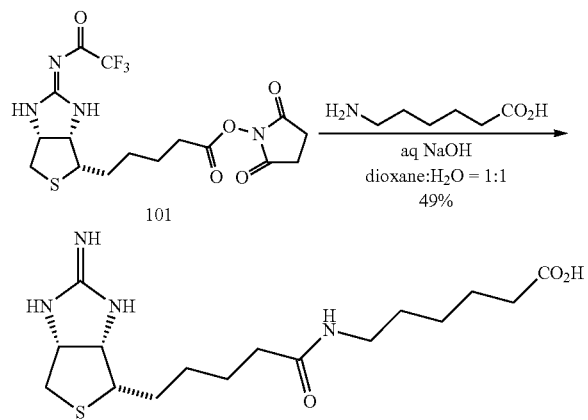

To a mixed solution of dioxane (500 μL) and H₂O (500 μL) containing 6-aminohexanoic acid (3 mg, 0.023 mmol), an aqueous sodium hydroxide solution was added to adjust pH to 9 or around. Compound 101 (10 mg, 0.023 mmol) (commercial product) was added, the mixture was stirred for 12 hours, added with ether, and the organic layer was removed. The aqueous layer was neutralized with hydrochloric acid, and then filtered. The residue was washed with acetone, and the solvent was evaporated off under reduced pressure. The obtained solid was dissolved into dioxane (500 μL) and H₂O (500 μL), 29% aqueous ammonia was added, and the mixture was stirred for 3 hours. The solvent was evaporated off under reduced pressure, and the obtained crystal was washed with a dichloromethane-methanol mixed solvent. Four milligrams of iminobiotin longtail (yield 49%, white solid) was thus obtained.

MS (ESI) m/z 357 (M+H)$^+$

Example 1B: Synthesis of Dimeric Compound of Modified Biotin Bound with Chelete Group General Method Nuclear Magnetic Resonance (NMR) spectrum was measured using JEOL ECX500 ($^1$H NMR: 500 MHz) or JEOL ECS400 ($^1$H NMR: 400 MHz) spectrometer. Chemical shift was given in ppm, as a value away from an internal reference peak assignable to a residual solvent in a deuterated solvent (CDCl$_3$: δ=7.26 ppm, CD$_3$OD: δ=3.31 ppm, acetone-d6: δ=2.05 ppm, D$_2$O: δ=4.79 ppm)). Low-resolution mass spectrum (ESI) was measured using Waters ZQ4000 spectrometer or Agilent 6120 Quadrupole LC/MS (ES) coupled with Agilent Technologies 1290 Infinity LC. Column chromatography was carried out using silica gel Merk 60 (230-400 mesh ASTM). Gel filtration chromatography was carried out using Sephadex LH-20 Lab Packs as a carrier. The reactions were monitored by thin layer chromatography (TLC), or low-resolution mass spectrometry (LRMS).

Reversed-phase high performance liquid chromatography (HPLC) was carried out using JASCO-HPLC system. Ultraviolet radiation of 210 nm or 254 nm was used for detection, and a gradient solvent system (acetonitrile/0.1% trifluoroacetic acid in MQ) was used as the mobile phase. Analysis was carried out using YMC-Triart-C18 column (150×4.6 mL) at a flow rate of 1 mL/min. Fractionation was carried out using YMC-Triart-C18 column (250×10 mL) at a flow rate of 3.5 mL/min.

EZ-Link (registered trademark) NHS-Iminobiotin was purchased from Thermo Fisher Scientific Inc. DOTA-NHS-ester was purchased from Macrocyclics, Inc. Other reagents were purchased from Aldrich, Tokyo Chemical Industry Co., Ltd. (TCI), Kanto Chemical Co., Inc. (Kanto), Wako Pure Chemical Industries, Ltd., and Watanabe Chemical Industries, Ltd. All reagents and solvents were used as sold, unless otherwise specifically noted.

Dimethyl 5-(3-(3-oxo-1-phenyl-2,7,10-trioxa-4-azadodecane-12-yl)ureido)isophthalate (28)

[Chemical Formula 28]

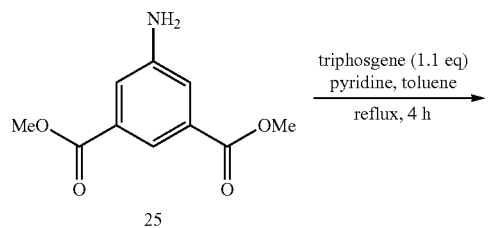

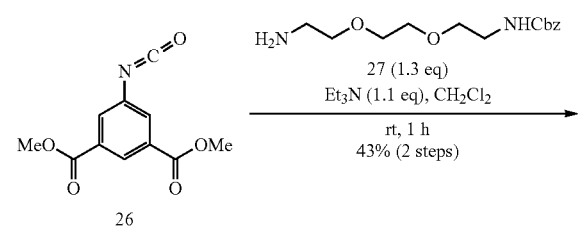

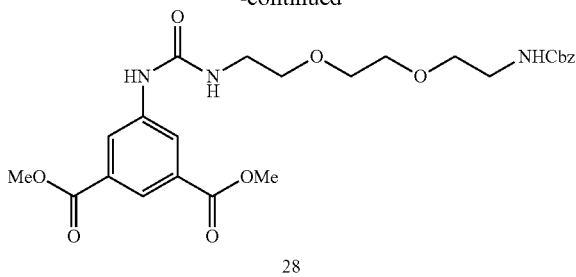

28

To a toluene solution (20 mL) of dimethyl 5-aminoisophthalate 25 (1.00 g, 4.78 mmol), triphosgene (1.48 g, 4.99 mmol) was added, and the mixture was stirred under reflux for 3 hours. The mixture was then added with pyridine, and stirred under reflux for one hour. The solvent was evaporated off under reduced pressure, the resultant crude product 26 was added with a mixed solvent of dichloromethane (25 mL) and triethylamine (728 μL, 5.24 mmol), further added with amine 27 (1.84 g, 6.52 mmol), and the mixture was stirred at room temperature for one hour. After the solvent was evaporated off under reduced pressure, the residue was added with 1-M hydrochloric acid, the product was extracted into ethyl acetate, the organic layer was washed three times with 1-N hydrochloric acid, and once with a saturated sodium chloride solution. The organic layer was dried over sodium sulfate, the solvent was evaporated off under reduced pressure, and the obtained crude product was purified by silica gel column chromatography (dichloromethane/methanol=20:1→4:1). Title Compound 28 (1.06 g, yield 43%, yellowish white solid) was thus obtained.

$^1$H NMR (400 MHz, CD$_3$OD) δ: 3.27-335 (m, 2H), 3.39 (t, 21, J=5.5 Hz), 3.55 (t, 2H, J=5.5 Hz), 3.58 (t, 2H, J=5.5 Hz), 3.63 (s, 4H), 3.91 (s, 6H), 5.06 (s, 2H), 7.20-7.47 (m, 5H), 8.21 (t, 1H, J=1.4 Hz), 8.28 (d, 2H, J=1.4 Hz); LRMS (ESI): m/z 540 [M+Na]$^+$.

5-(3-(3-Oxo-1-phenyl-2,7,10-trioxa-4-azadodecane-12-yl)ureido)isophthalic Acid (29)

[Chemical Formula 29]

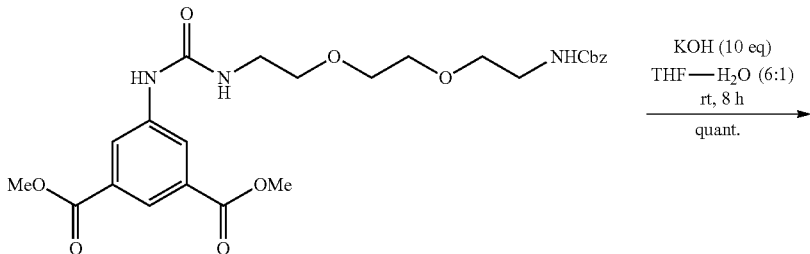

28

-continued

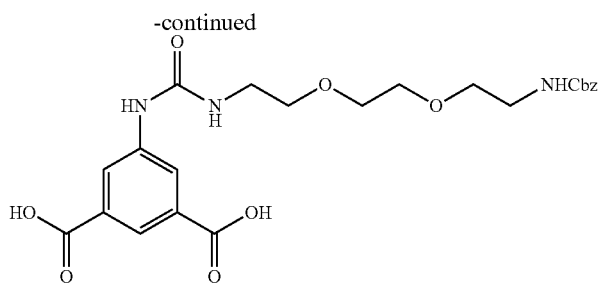

29

To a tetrahydrofuran (11.7 mL) solution of diester compound 28 (1.06 g, 2.05 mmol) was added a water (2.07 mL) solution of potassium hydroxide (1.15 g, 10.5 mmol), and the mixture was stirred at room temperature for 8 hours. Water was added until the deposited precipitate dissolved, and the solution was washed once with diethyl ether. The solution was added with 2-M hydrochloric acid, the product was extracted into ethyl acetate, and the organic layer was washed once with a saturated sodium chloride solution. The organic layer was dried over sodium sulfate, and the solvent was evaporated off under reduced pressure. A crude product (white solid) containing title compound 29 was thus obtained. The obtained crude product was used for the next reaction without further purification.

$^1$H NMR (500 MHz, CD$_3$OD) δ: 3.18-3.34 (m, 2H), 3.39 (t, 2H, J=5.7 Hz), 3.56 (t, 2H, J=5.7 Hz), 3.58 (t, 2H, J=5.2 Hz), 3.63 (s, 4H), 5.06 (s, 2H), 7.23-739 (m, 5H), 8.25 (brs, 1H), 8.28 (brs, 2H); LRMS (ESI): m/z 512 [M+Na]$^+$.

Bis(2,5-dioxopyrrolidine-1-yl) 5-(3-(3-oxo-1-phenyl-2,7,10-trioxa-4-azadodecane-12-yl)ureido)isophthalate (30)

[Chemical Formula 30]

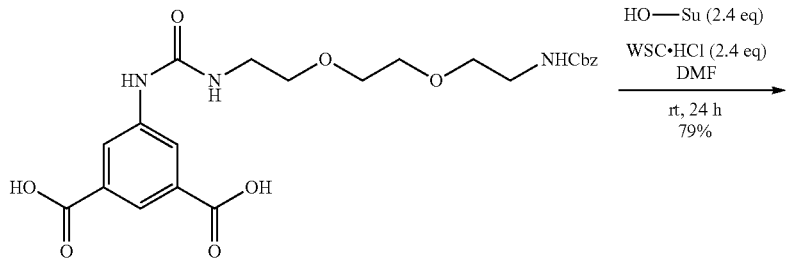

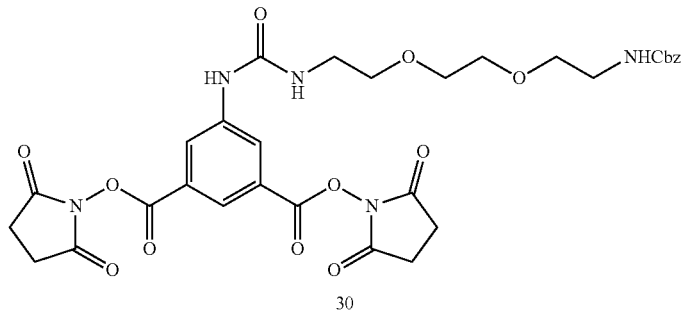

To an N,N-dimethylformamide (11.1 mL) solution of dicarboxylic acid 29 (1.09 g, 2.23 mmol) were added N-hydroxysuccinimide (0.615 g, 5.34 mmol) and 1-ethyl-3-(3-dimethylaminopropyl)carbodiimide hydrochloride (WSC.HCl, 1.03 g, 5.34 mmol), and the mixture was stirred, in an argon atmosphere, at room temperature for 24 hours. After the solvent was evaporated off under reduced pressure, the residue was added with 0.5-M hydrochloric acid, extracted into ethyl acetate, and the organic layer was washed three times with 0.5-M hydrochloric acid, once with an aqueous saturated sodium hydrogen carbonate solution, and once with a saturated sodium chloride solution. The organic layer was dried over sodium sulfate, and the solvent was evaporated off under reduced pressure. Title Compound 30 (1.2 g, yield 79%, white solid) was thus obtained.

$^1$H NMR (400 MHz, CD$_3$OD) δ: 2.90 (s, 8H), 3.25-3.35 (m, 2H), 339 (t, 2H, J=5.5 Hz), 3.54 (t, 2H, J=5.5 Hz), 3.58 (t, 2H, J=5.5 Hz), 3.62 (s, 4H), 5.05 (s, 2H), 7.20-7.40 (m, 5H), 8.36 (brs, 1H), 8.52 (brs, 2H); LRMS (ESI): m/z 342 [M+2H]$^{2+}$.

(2S,2'S)-6,6'-((5-(3-(3-Oxo-1-phenyl-2,7,10-trioxa-4-azadodecane-12-yl)ureido)isophthaloyl)bis(azanediyl))bis(2-((tert-butoxycarbonyl)amino)hexanoic Acid) (32)

[Chemical Formula 31]

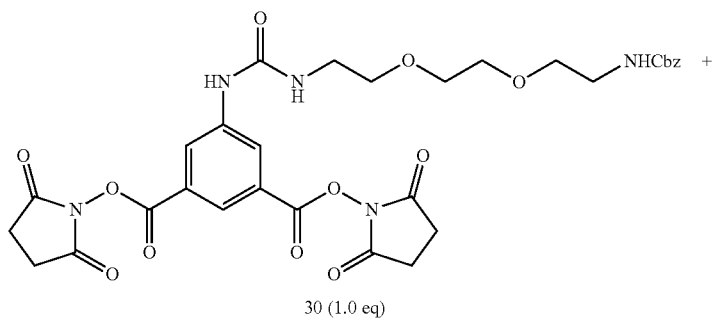

30 (1.0 eq)

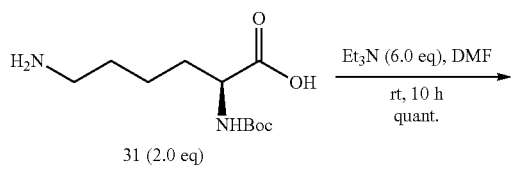

31 (2.0 eq)

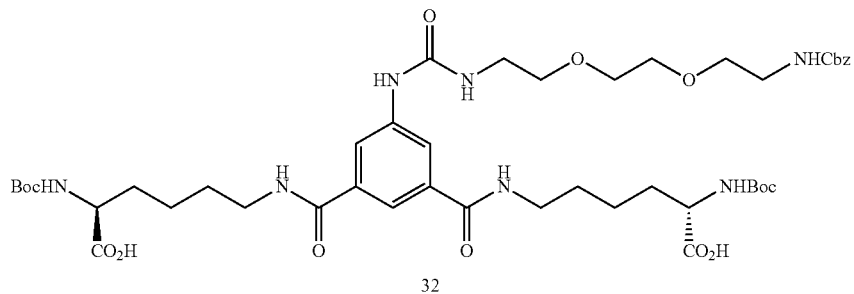

32

To a mixed solution of N,N-dimethylformamide (18.1 mL) and triethylamine (1.48 mL, 10.6 mmol) containing disuccinimide compound 30 (1.21 g, 1.76 mmol) was added Na-Boc-L-lysine (31) (974 mg, 3.52 mmol), and the mixture was stirred at room temperature for 10 hours. After the solvent was evaporated off under reduced pressure, the residue was added with water and 1-M hydrochloric acid, extracted into ethyl acetate, and the organic layer was washed once with a saturated sodium chloride solution. The organic layer was dried over sodium sulfate, the solvent was evaporated off under reduced pressure, the obtained crude product was dissolved into a small amount of dichloromethane, and the precipitate deposited from diethyl ether was collected by suction filtration. Title Compound 32 (1.68 g, yield quant., white solid) was thus obtained.

$^1$H NMR (400 MHz, CD$_3$OD) δ: 1.41 (s, 18H), 1.45-1.57 (m, 4H), 1.57-1.77 (m, 6H), 1.77-1.94 (m, 2H), 3.24-3.34 (m, 2H), 3.34-3.49 (m, 6H), 3.55 (t, 2H, J=5.4 Hz), 3.58 (t, 2H, J=5.0 Hz), 3.63 (s, 4H), 3.93-4.18 (m, 2H), 5.06 (s, 2H), 7.23-7.46 (m, 5H), 7.81 (brs, 1H), 7.93 (brs, 2H), 8.51 (brs, 1H).

(2S,2 S)-Dimethyl 6,6'-((5-(3-(3-oxo-1-phenyl-2,7,10-trioxa-4-azadodecane-12-yl)ureido)isophthaloyl)bis(azanediyl)) bis(2-((tert-butoxycarbonyl)amino)hexanoate) (33)

[Chemical Formula 32]

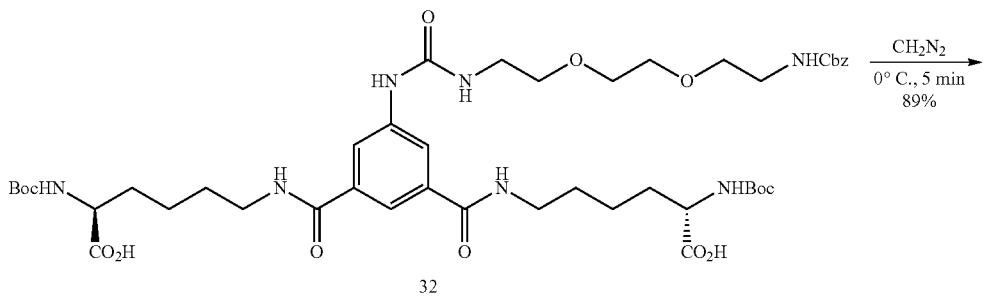

32

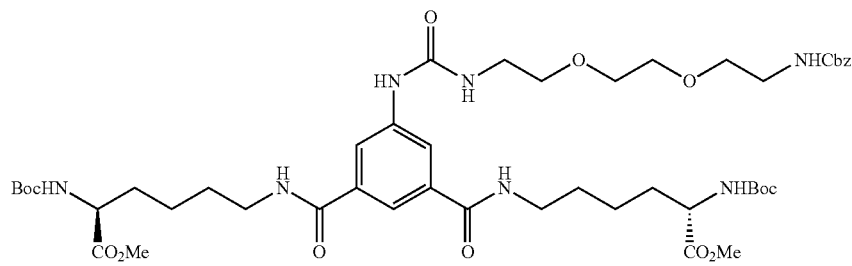

33

A methanol (530 μL) solution of dicarbamate compound 32 (100 mg, 106 μmol) was cooled on an ice bath, diazomethane (2.0 M solution in diethyl ether, 350 μL, 700 μmol) was added, and the mixture was stirred on an ice bath for 5 minutes. The mixture was added with acetic acid, the solvent was evaporated off under reduced pressure, and the obtained crude product was purified by silica gel column chromatography (dichloromethane/methanol=20:1→10:1). Title Compound 33 (91.8 mg, yield=89%, highly viscous yellow oil) was thus obtained.

¹H NMR (500 MHz, CD₃OD) δ: 1.39-1.43 (m, 22H), 1.55-1.73 (m, 6H), 1.75-1.87 (m, 2H), 3.27-3.33 (m, 2H), 3.39 (m, 6H), 3.54 (t, 2H, J=5.7 Hz), 3.57 (t, 2H, J=5.2 Hz), 3.62 (s, 4H), 3.69 (s, 6H), 4.10 (t, 2H, J=5.2 Hz), 5.06 (s, 2H), 6.86-7.05 (m, 1H), 7.24-7.35 (m, 5H), 7.81 (s, 1H), 7.93 (s, 2H), 8.46 (brs, 1H).

(2S,2'S)-Dimethyl 6,6'-((5-(3-(3-oxo-1-phenyl-2,7,10-trioxa-4-azadodecane-12-yl)ureido)isophthaloyl)bis(azanediyl))bis(2-aminohexanoate) di(2,2,2-trifluoroacetate) (34)

[Chemical Formula 33]

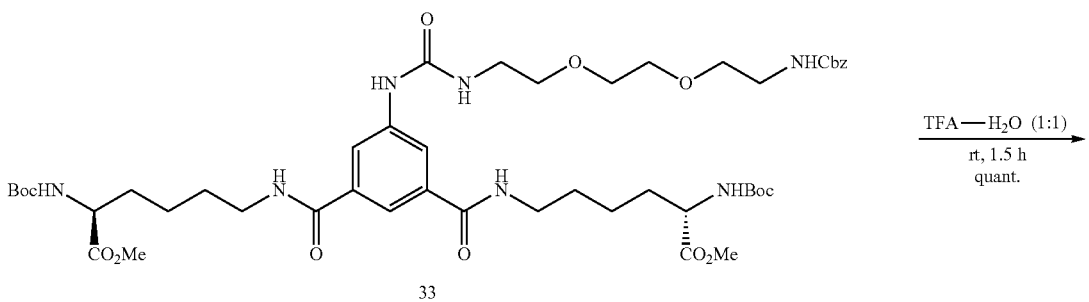

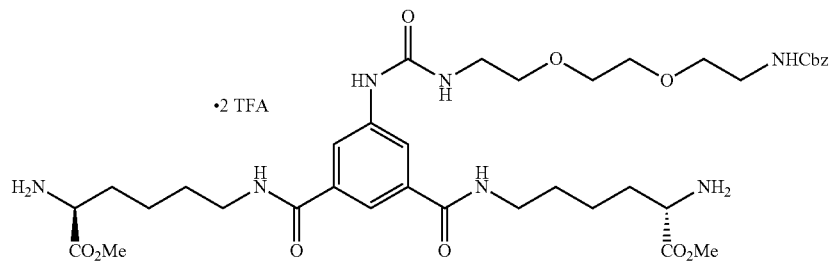

To a water (2 mL) solution of dicarbamate compound 33 (89.9 mg, 92.3 μmol), trifluoroacetic acid (2 mL) was added, and the mixture was stirred at room temperature for 1.5 hours. After the solvent was evaporated off under reduced pressure, the residue was dried in vacuo. A crude product (highly viscous yellow oil) containing title compound 34 was thus obtained. The obtained crude product was used for the next reaction without further purification.

$^1$H NMR (400 MHz, CD$_3$OD) δ: 1.38-1.60 (m, 4H), 1.60-1.73 (sext., 4H, J=7.3 Hz), 1.77-2.10 (m, 4H), 3.23-3.32 (m, 2H), 3.32-3.43 (m, 6H), 3.54 (t, 2H, J=5.5 Hz), 3.57 (t, 2H, J=5.5 Hz), 3.62 (s, 4H), 3.81 (s, 6H), 4.05 (t, 2H, J=6.4 Hz), 5.05 (s, 2H), 7.20-7.37 (m, 5H), 7.84 (brs, 1H), 7.96 (brs, 2H); LRMS (ESI): m/z 774 [M+H]$^+$.

(2S,2'S)-Dimethyl 6,6'-((5-(3-(3-oxo-1-phenyl-2,7,10-trioxa-4-azadodecane-12-yl)ureido)isophthaloyl)bis(azanediyl))bis(2-(5-(((3aS,4S,6aR)-2-iminohexahydro-1H-thieno[3,4-d]imidazole-4-yl)pentanamido)hexanoate) di(2,2,2-trifluoroacetate) (35)

[Chemical Formula 34]

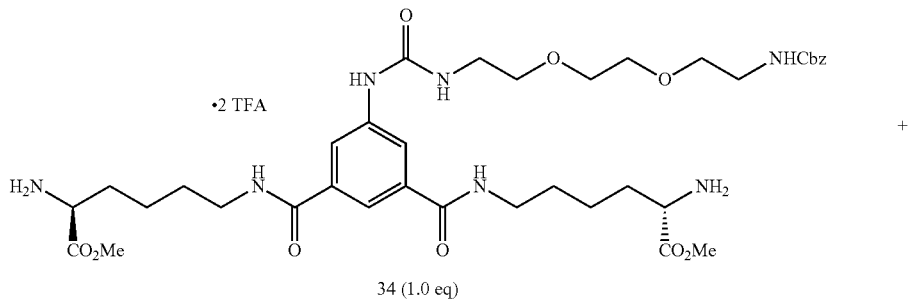

34 (1.0 eq)

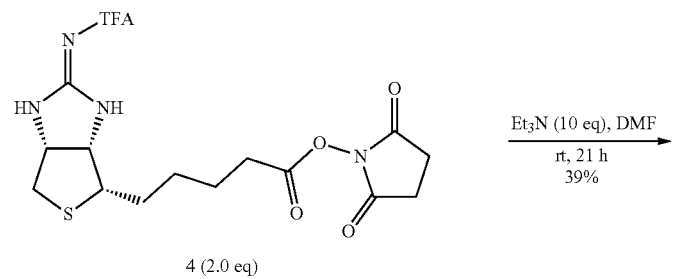

4 (2.0 eq)

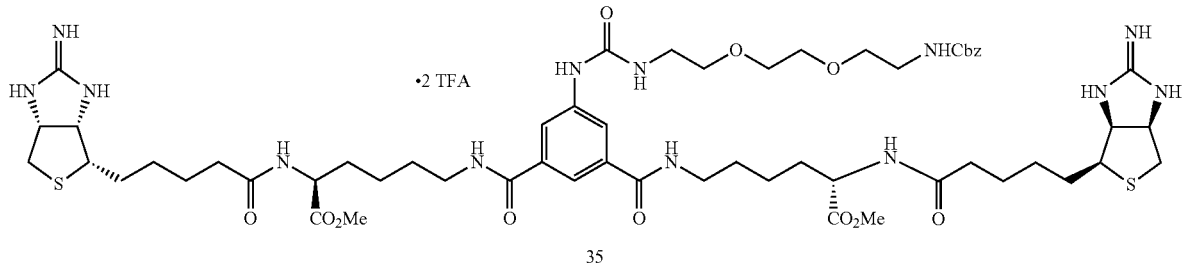

35

To a mixed solution of N,N-dimethylformamide (200 μL) and triethylamine (14.4 μL, 10.3 μmol) containing diamine 34 (10.0 mg, 10.3 μmol) was added EZ-Link® NHS-Iminobiotin 4 (9.0 mg, 20.7 μmol), and the mixture was stirred at room temperature for 21 hours. The solvent was evaporated off under reduced pressure, and the obtained crude product was purified by gel filtration chromatography (methanol). Title Compound 35 (5.6 mg, yield=39%, highly viscous yellow oil) was thus obtained.

$^1$H NMR (500 MHz, CD$_3$OD) δ: 1.32-153 (m, 8H), 1.53-1.69 (m, 10H), 1.69-1.79 (m, 4H), 1.83-1.93 (m, 2H), 2.25 (q, 4H, J=6.9 Hz), 2.88 (d, 2H, J=12.6 Hz), 3.01 (dd, 2H, J=52, 12.6 Hz), 3.27-3.33 (m, 4H), 3.34-3.45 (m, 6H), 3.55 (t, 2H, J=5.2 Hz), 3.57 (t, 2H, J=5.2 Hz), 3.63 (s, 4H), 3.71 (s, 6H), 4.40 (dd, 2H, J=4.6, 9.2 Hz), 4.49 (dd, 2H, J=4.6, 8.6 Hz), 4.75 (dd, 2H, J=4.6, 8.6 Hz), 5.06 (s, 2H), 7.21-7.38 (m, 5H), 7.81 (brs, 1H), 7.95 (brs, 2H); LRMS (ESI): m/z 613 [M+2H]$^{2+}$.

(2S,2'S)-Dimethyl 6,6'-((5-(3-(2-(2-(2-aminoethoxy)ethoxy)ethyl)ureido)isophthaloyl)bis(azanediyl))bis(2-(5-((3aS,4S,6aR)-2-iminohexahydro-1H-thieno[3,4-d]imidazole-4-yl)pentanamido)hexanoate) tri(2,2,2-trifluoroacetate) (36)

[Chemical Formula 35]

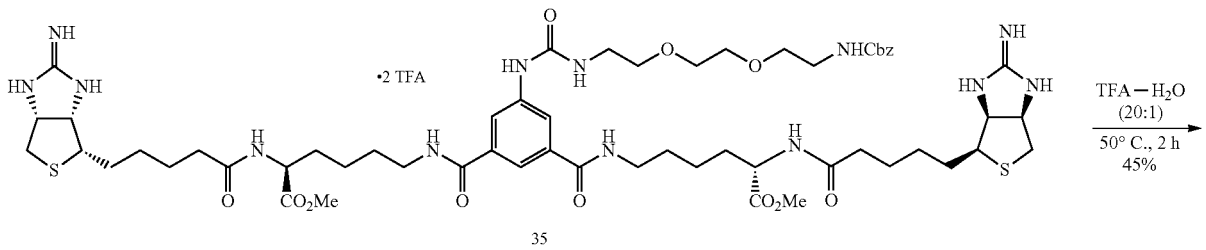

35

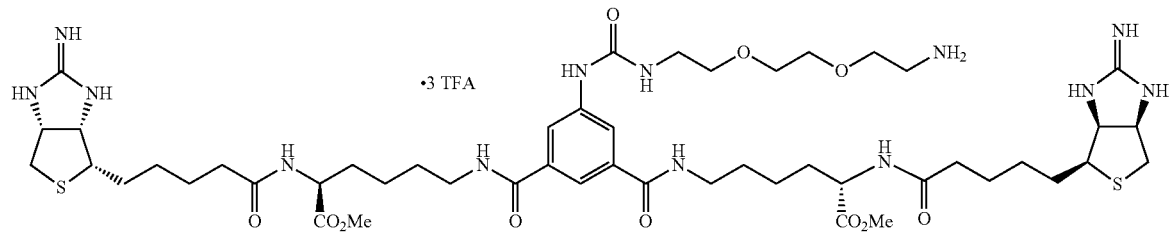

36

To an aqueous (50 µL) solution of bisiminobiotin 35 (5.8 mg, 4.1 µmol), trifluoroacetic acid (1 mL) was added, and the mixture was stirred at 50° C. for 2 hours. The solvent was evaporated off under reduced pressure, and the obtained crude product was purified by reversed-phase HPLC (0.0-20.0-20.5-60.5-61.0-75.0 min; 5.0-5.0-17.5-57.5-100.0-100.0% $CH_3CN$ in 0.1% TFA in MQ, ramp time=40 min (17.5-57.5%), $t_r$=36.5 min). Title Compound 36 (2.5 mg, yield=45%, highly viscous yellow oil) was thus obtained.

$^1$H NMR (500 MHz, $CD_3OD$) δ: 1.39-1.82 (m, 22H), 1.82-1.94 (m, 2H), 2.20-2.30 (m, 4H), 2.83 (d, 2H, J=14.2 Hz), 2.99 (dd, 2H, J=4.9, 14.2 Hz), 3.11 (t, 2H, J=5.2 Hz), 3.25-3.36 (m, 4H), 3.36-3.46 (m, 6H), 3.61 (t, 2H, J=5.3 Hz), 3.69 (s, 4H), 3.71 (s, 6H), 4.41 (dd, 2H, J=5.2, 9.7 Hz), 4.52 (dd, 2H, J=4.6, 8.1 Hz), 4.72 (dd, 5H, J=4.6, 8.1 Hz), 7.81 (s, 1H), 7.96 (d, 2H, J=1.6 Hz); LRMS (ESI): m/z 546 $[M+2H]^{2+}$.

2,2',2''-(10-(1-(((S)-5-(5-(((3aS,4S,6aR)-2-iminohexahydro-1H-thieno[3,4-d]imidazole-4-yl)pentanamido)-6-methoxy-6-oxohexyl)carbamoyl)phenyl)amino)-1,12-dioxo-5,8-dioxa-2,11-diazatridecane-13-yl)-1,4,7,10-tetraazacyclododecane-1,4,7-triyl) triacetic Acid tri(2,2,2-trifluoroacetate) (38)

To a mixed solution of N,N-dimethylformamide (100 µL) and triethylamine (15.1 µL, 10.9 mol) containing bisiminobiotin 36 (10.0 mg, 7.24 µmol), DOTA-NHS-ester 37 (6.1 mg, 7.96 µmol) was added, and the mixture was stirred at room temperature for 20 hours. The solvent was evaporated off under reduced pressure, and the obtained crude product was purified by reversed-phase HPLC (0.0-20.0-20.5-60.5-61.0-75.0 min; 5.0-5.0-17.5-57.5-100.0-100.0% $CH_3CN$ in 0.1% TFA in MQ, ramp time=40 min (17.5-57.5%), $t_r$=35.2 min). Title Compound 38 (2.0 mg, yield=16%, highly viscous yellow oil) was thus obtained.

LRMS (ESI): m/z 739 $[M+2H]^{2+}$.

Example 1C: Synthesis of Dimeric Compound of Modified Biotin Bound with Colorant, Chelete Group or Drug Nuclear magnetic resonance (NMR) spectrum was measured using JEOL ECX500 ($^1$H NMR: 500 MHz), or JEOL ECS400 ($^1$H NMR: 400 MHz) spectrometer. Chemical shift was given in ppm, as a value away from an internal reference peak assignable to a residual solvent in a deuterated solvent ($CDCl_3$: δ=7.26 ppm, $CD_3OD$: δ=3.31 ppm). Low-resolution mass spectrum (ESI) was measured using Waters ZQ4000 spectrometer or Agilent 6120 Quadrupole LC/MS (ESI) coupled with Agilent Technologies 1290 Infinity LC.

[Chemical Formula 36]

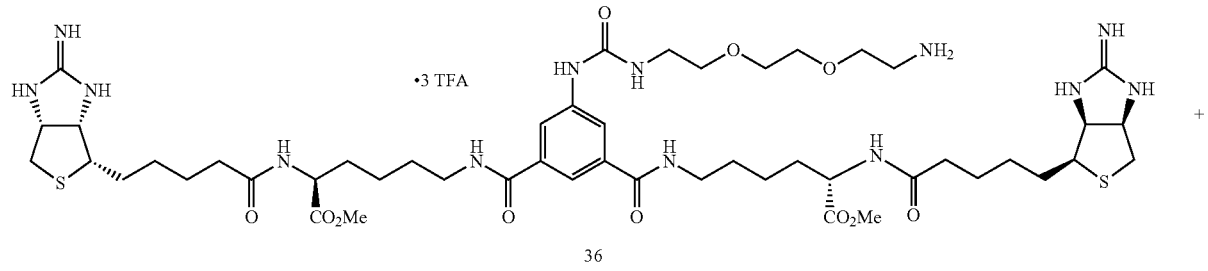

36

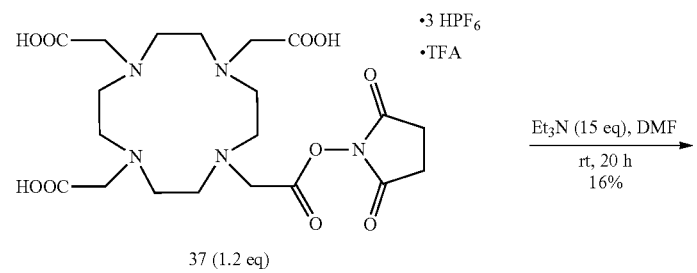

37 (1.2 eq)

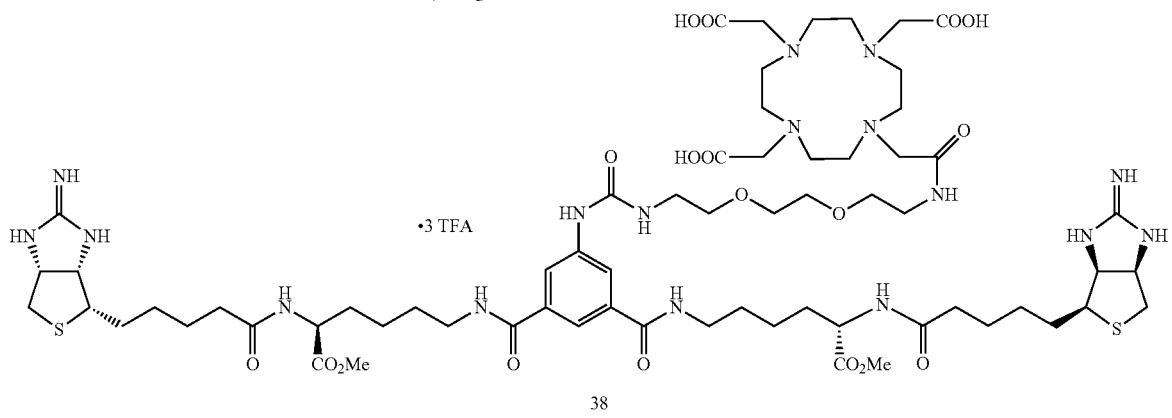

38

Column chromatography was carried out using silica gel Merk 60 (230-400 mesh ASTM), reversed-phase column chromatography was carried out using Wakosil® 40C18 (30 to 50 μm 70% up), and gel filtration chromatography was carried out using Sephadex LH-20 Lab Packs as a carrier. The reactions were monitored by thin layer chromatography (TLC), or low-resolution mass spectrometry.

Reversed-phase high performance liquid chromatography (HPLC) was carried out using JASCO-HPLC system. Ultraviolet radiation of 210 nm or 254 nm was used for detection, and a gradient solvent system (acetonitrile/0.1% trifluoroacetic acid in MQ, or a 0.1% formic acid in MQ) was used as the mobile phase. Analyses were carried out using YMC-Triart-C18 column (150×4.6 mL) at a flow rate of 1 mL/min. Fractionation was carried out using YMC-Triart-C18 column (250×10 mL) at a flow rate 3.5 mL/min.

DOTA-NHS-ester was purchased from Macrocyclics, Inc. IRDye® 800CW NHS Ester was purchased from LI-COR, Inc. Other reagents were purchased from Aldrich, Tokyo Chemical Industry Co., Ltd. (TCI, Kanto Chemical Co., Inc. (Kanto), Wako Pure Chemical Industries, Ltd., and Watanabe Chemical Industries, Ltd. All reagents and solvents were used as sold, unless otherwise specifically noted.

(3aS,4S,6aR)-4-(5-((2,5-Dioxopyrrolidine-1-yl)oxy)-5-oxopentyl)tetrahydro-1H-thieno[3,4-d]imidazole-2(3H)-iminium 2,2,2-trifluoroacetate (41)

[Chemical Formula 37]

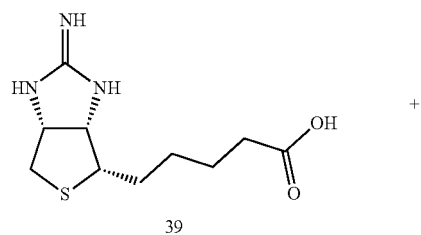

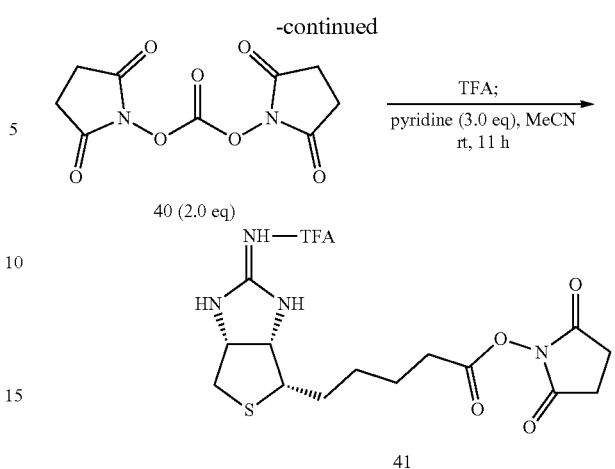

Trifluoroacetic acid was added to 2-iminobiotin 39 (88.0 mg, 0.36 mmol), the mixture was stirred, and an excessive portion of trifluoroacetic acid was evaporated off under reduced pressure. To an acetonitrile solution (3.4 mL) of the thus obtained white solid, added were pyridine (82.5 μL, 0.72 mmol) and disuccinimide 40 (175 mg, 1.08 mmol), and the mixture was stirred for 11 hours at 30° C. The solvent was evaporated off under reduced pressure, and the residue was dried in vacuo. A crude product (highly viscous yellow oil) containing title compound 41 was obtained. The thus obtained crude product was used for the next reaction, without further purification.

LRMS (ESI): m/z 341 [M+H]$^+$.

(2S,2'S)-Dimethyl 6,6-((5-(3-(3-oxo-1-phenyl-2,7,10-trioxa-4-azadodecane-12-yl)ureido)isophthaloyl)bis(azanediyl))bis(2-(5-((3aS,4S,6aR)-2-iminohexahydro-1H-thieno[3,4-d]imidazole-4-yl)pentanamido)hexanoate) di(2,2,2-trifluoroacetate) (35)

[Chemical Formula 38]

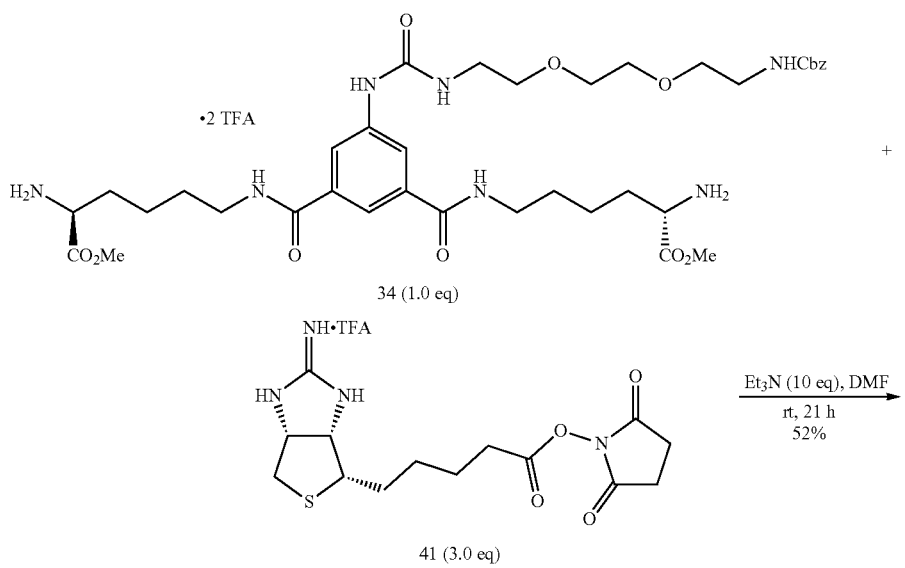

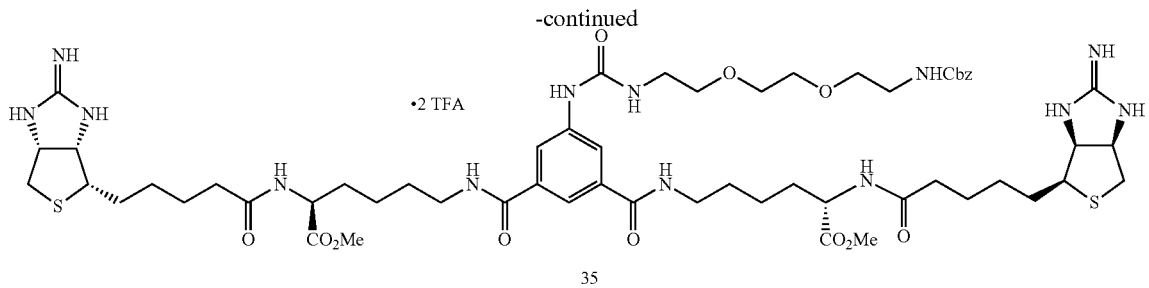

35

To a solution of diamine 34 (78.5 mg, 81.1 μmol) dissolved in a mixed solvent of N,N-dimethylformamide (5.0 mL) and triethylamine (339 μL, 2.43 mmol) was added ester 41 prepared from 2-iminobiotin 39 (88.0 mg, 0.36 mmol), the mixture was then stirred at room temperature for 21 hours. The solvent was evaporated off under reduced pressure, and the obtained crude product was purified by reversed-phase silica gel column chromatography (water/methanol=2:1→1:2). Title Compound 35 (59.3 mg, yield=52%, highly viscous yellow oil) was thus obtained.

$^1$H NMR (500 MHz, CD$_3$OD) δ: 1.32-1.53 (m, 8H), 1.53-1.69 (m, 10H), 1.69-1.79 (m, 4H), 1.83-1.93 (m, 2H), 2.25 (q, 4H, J=6.9 Hz), 2.88 (d, 2H, J=12.6 Hz), 3.01 (dd, 2H, J=5.2, 12.6 Hz), 3.27-3.33 (m, 4H), 3.34-3.45 (m, 6H), 3.55 (t, 2H, J=5.2 Hz), 3.57 (t, 2H, J=5.2 Hz), 3.63 (s, 4H), 3.71 (s, 6H), 4.40 (dd, 2H, J=4.6, 9.2 Hz), 4.49 (dd, 2H, J=4.6, 8.6 Hz), 4.75 (dd, 2H, J=4.6, 8.6 Hz), 5.06 (s, 2H), 7.21-7.38 (m, 5H), 7.81 (brs, 1H), 7.87 (brs, 2H); LRMS (ESI): m/z 613 [M+2H]$^{2+}$.

(2S,2'S)-Dimethyl 6,6'-((5-(3-(2-(2-(2-aminoethoxy)ethoxy)ethyl)ureido)isophthaloyl)bis(azanediyl))bis(2-(5-((3aS,4S,6aR)-2-iminohexahydro-1H-thieno[3,4-d]imidazole-4-yl)pentanamido)hexanoate)tri(2,2,2-trifluoroacetate) (36)

[Chemical Formula 39]

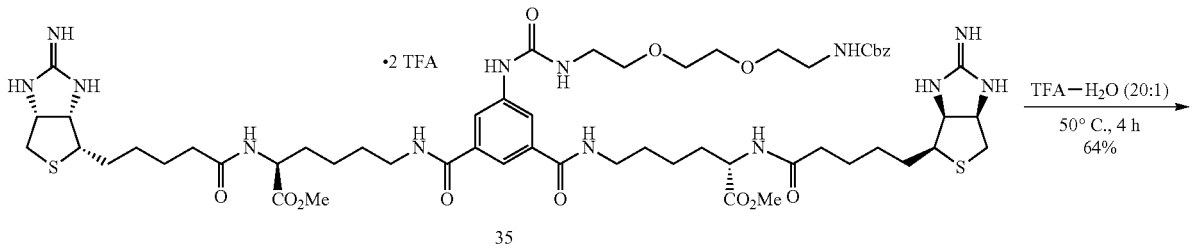

35

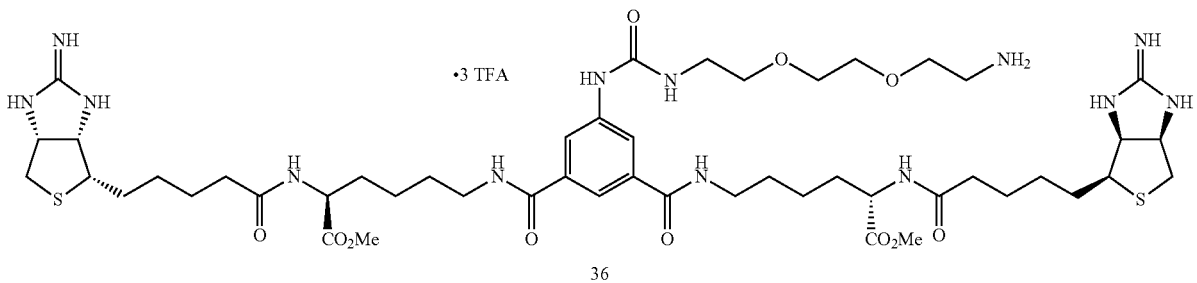

36

To a water (400 μL) solution of bisiminobiotin 35 (59.3 mg, 41.8 μmol) was added trifluoroacetic acid (8.0 mL), and the mixture was stirred at 50° C. for 4 hours. The solvent was evaporated off under reduced pressure, and the obtained crude product was purified by reversed-phase silica gel column chromatography (water/methanol=2:1→1:2). Title Compound 36 (37.1 mg, yield=64%, highly viscous yellow oil) was thus obtained.

$^1$H NMR (500 MHz, CD$_3$OD) δ 1.39-1.82 (m, 22H), 1.82-1.94 (m, 2H), 2.20-2.30 (m, 4H), 2.83 (d, 2H, J=14.2 Hz), 2.99 (dd, 2H, J=4.9, 14.2 Hz), 3.11 (t, 2H, J=5.2 Hz), 3.25-3.36 (m, 4H), 3.36-3.46 (m, 6H), 3.61 (t, 2H, J=5.3 Hz), 3.69 (s, 4H), 3.71 (s, 61H), 4.41 (dd, 2H, J=5.2, 9.7 Hz), 4.52 (dd, 2H, J=4.6, 8.1 Hz), 4.72 (dd, 5H, J=4.6, 8.1 Hz), 7.81 (s, 1H), 7.96 (d, 2H, J=1.6 Hz); LRMS (ESI): m/z 546 [M+2H]$^{2+}$.

2,2',2''-(10-(1-(((3,5-Bis(((S)-5-(5-((3aS,4S,6aR)-2-iminohexahydro-1H-thieno[3,4-d]imidazole-4-yl)pentan amido)-6-methoxy-6-oxohexyl)carbamoyl)phenyl)amino)-1,12-dioxo-5,8-dioxa-2,11-diazatridecane-13-yl)-1,4,7,10-tetraazacyclododecane-1,4,7-triyl) triacetate triformate (42)

[Chemical Formula 40]

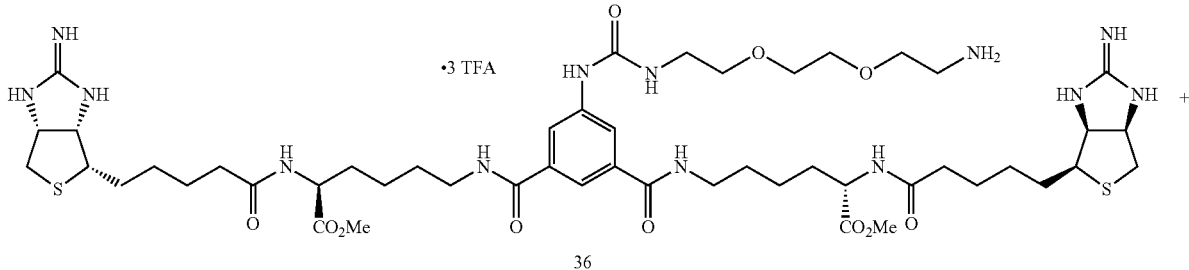

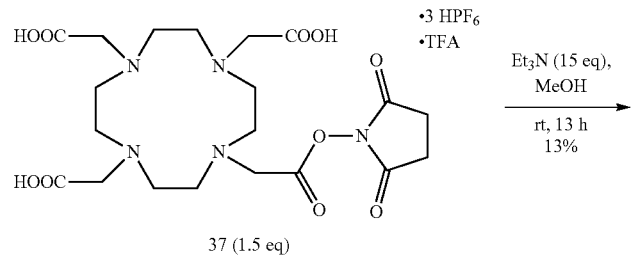

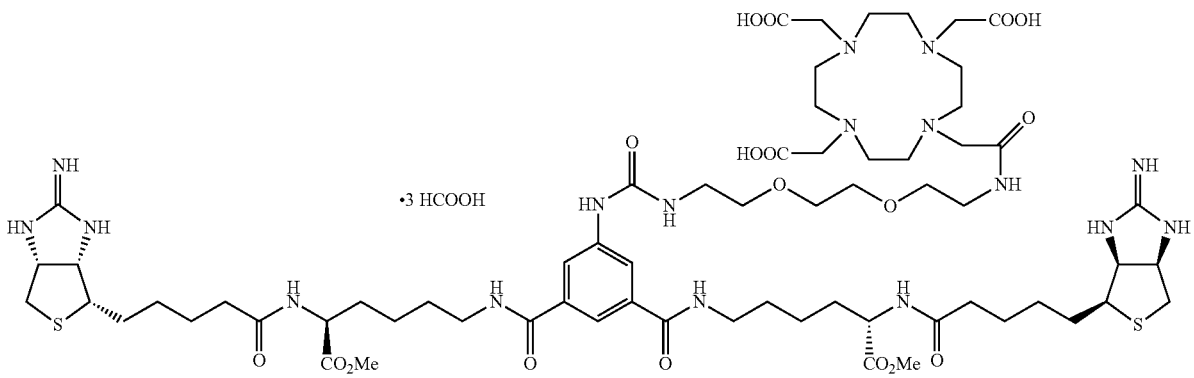

To a solution of bisiminobiotin 36 (23.4 mg, 16.9 µmol) dissolved in a mixed solvent of methanol (234 µL) and triethylamine (35.4 µL, 253 µmol) was added DOTA-NHS-ester 37 (25.8 mg, 24.9 µmol), and the mixture was stirred at room temperature for 13 hours. The solvent was evaporated off under reduced pressure, and the obtained crude product was purified by reversed-phase HPLC (0.0-20.0-20.5-60.5-61.0-75.0 min; 5.0-5.0-17.5-57.5-100.0-100.0% $CH_3CN$ in 0.1% HCOOH MQ, ramp time=40 min (17.5-57.5%), $t_r$=31.5 min). Title Compound 42 (3.55 mg, yield=13%, highly viscous yellow oil) was thus obtained.

LRMS (ESI): m/z 739 $[M+2H]^{2+}$.

1-(1-((3,5-Bis(((S)-5-(5-((3aS,4S,6aR)-2-iminohexahydro-1H-thieno[3,4-d]imidazole-4-yl)pentanamido)-6-methoxy-6-oxohexyl)carbamoyl)phenyl)amino)-1,12-dioxo-5,8-dioxa-2,11-diazaheptadecane-17-yl)-2-((E)-2-((E)-3-(2-((E)-3,3-dimethyl-5-sulfo-1-(4-sulfobutyl)indoline-2-ilidene)ethylidene)-2-(4-sulfophenoxy)cyclohex-1-ene-1-yl)vinyl)-3,3-dimethyl-3H-indol-1-ium-5-sulfonate (44)

[Chemical Formula 41]

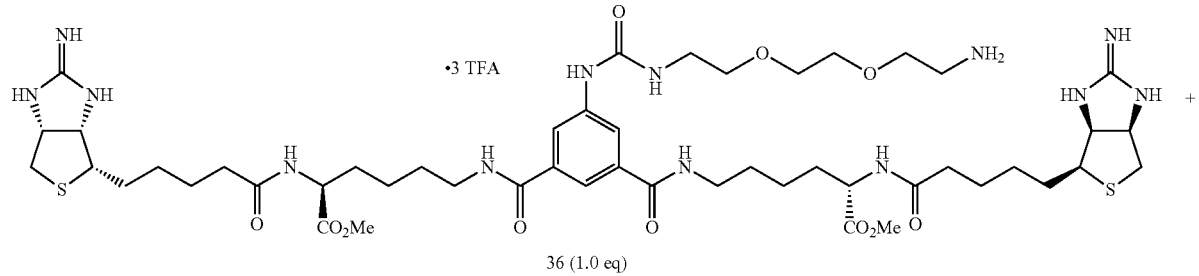

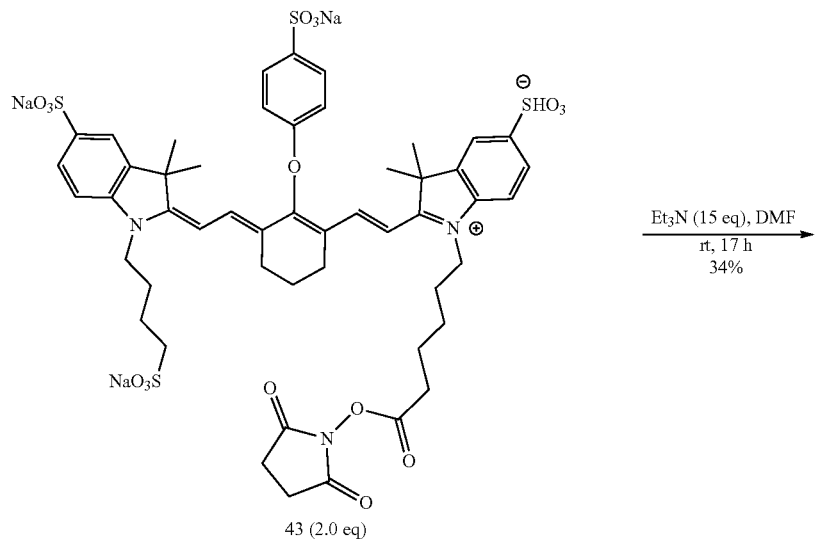

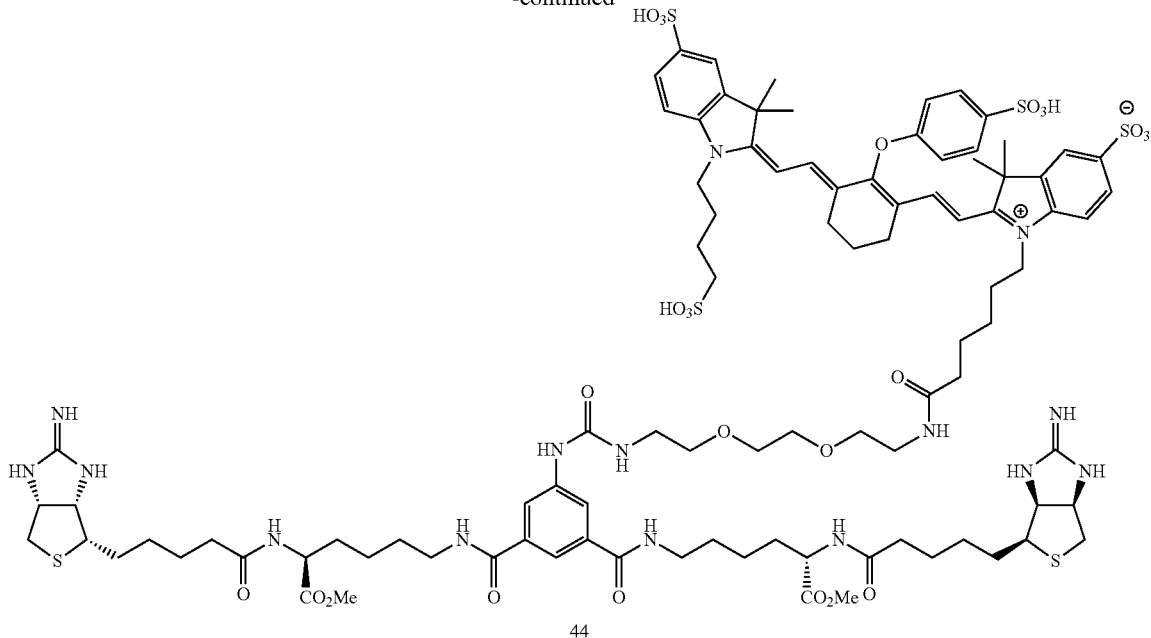

44

To a solution of bisiminobiotin 36 (1.13 mg, 0.82 μmol) dissolved in a mixed solvent of N,N-dimethylformamide (200 μL) and triethylamine (2.17 μL, 15.6 μmol) was added IRDye® 800CW NHS Ester (43, 2.41 mg, 2.06 μmol), and the mixture was stirred at room temperature for 17 hours. The solvent was evaporated off under reduced pressure, and the obtained crude product was purified by reversed-phase HPLC (0.0-20.0-20.5-60.5-61.0-75.0 min; 5.0-5.0-17.5-57.5-100.0-100.0% $CH_3CN$ in 0.1% TFA in MQ, ramp time=40 min (17.5-57.5%), $t_r$=40.9 min). Title Compound 44 (0.65 mg, yield=34%, highly viscous green oil) was thus obtained.

LRMS (ESI): m/z 1038 $[M+2H]^{2+}$.

Benzyl (2-(2-(2-(3-(3,5-bis((2-(2-((tert-butoxycarbonyl)amido)ethoxy)ethyl)carbamoyl)phenyl)ureido)ethoxy)ethoxy)ethyl)carbamate (46)

[Chemical Formula 42]

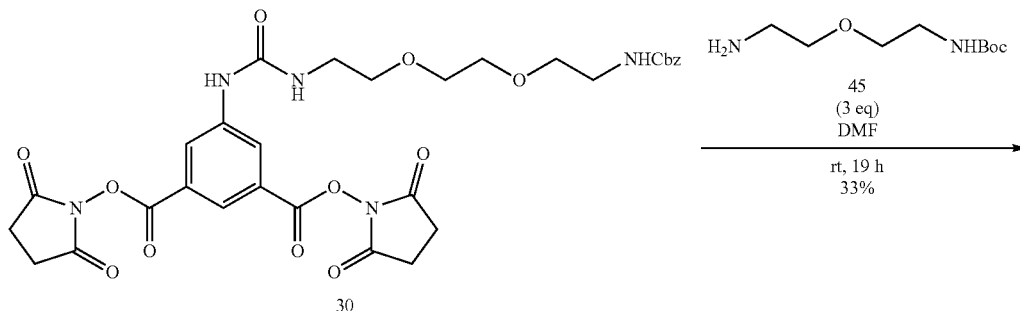

30

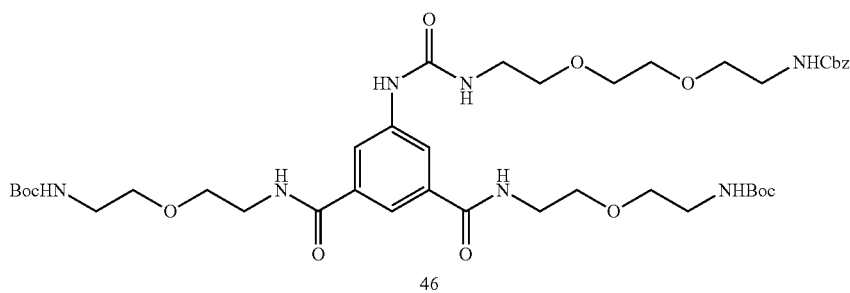

46

To an N,N-dimethylfomamide (1.9 mL) solution of disuccinimide compound 30 (198 mg, 0.290 mmol), added was amine 45 (118 mg, 0.580 mmol, N,N-dimethylformamide (1 mL) solution) synthesized by a known method (Arano et al., *Bioorg. Med Chem.* (2012) 20, 978), and the mixture was stirred at room temperature for 6.5 hours. Amine 45 (59 mg, 0.290 mmol, N,N-dimethylformamide (0.5 mL) solution) was further added, and the mixture was stirred at room temperature for 13 hours. After the solvent was evaporated off under reduced pressure, ethyl acetate was added, and the organic layer was washed successively with a 1-M aqueous sodium hydroxide solution, 1-M hydrochloric acid, and a saturated sodium chloride solution. The organic layer was dried over sodium sulfate, the solvent was evaporated off under reduced pressure, and the obtained crude product was purified by silica gel column chromatography (dichloromethane/hexane=1:30→1:20→1:10→1:5). Title Compound 46 (83.7 mg, yield=33%, white solid) was thus obtained.

$^1$H NMR (500 MHz, CD$_3$OD) δ: 1.39 (s, 18H), 3.23 (t, 2H, J=5.7 Hz), 3.29-3.35 (m, 1H), 3.40 (t, 2H, J=5.7 Hz), 3.49-3.60 (m, 13H), 3.60-3.65 (m, 8H), 5.06 (s, 2H), 7.25-7.36 (m, 5H), 7.83 (s, 1H), 7.96 (brs, 2H); LRMS (ESI): m/z 884 [M+Na]$^+$.

Benzyl (2-(2-(2-(3-(3,5-bis((2-(2-aminoethoxy)ethyl)carbamoyl)phenyl)ureido)ethoxy)ethoxy)ethyl)carbamate di(2,2,2-trifluoroacetate) (48)

[Chemical Formula 43]

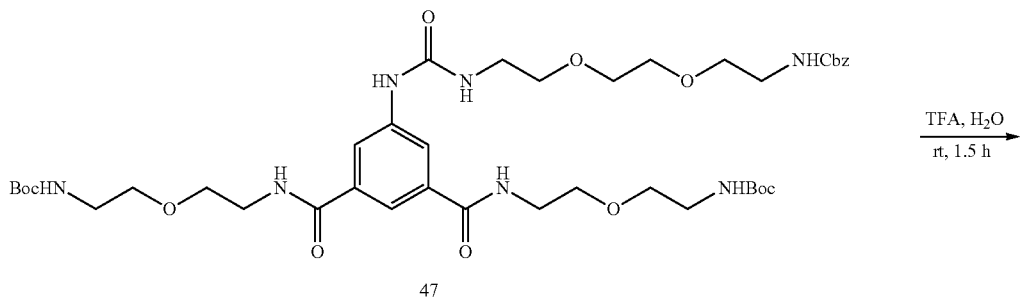

47

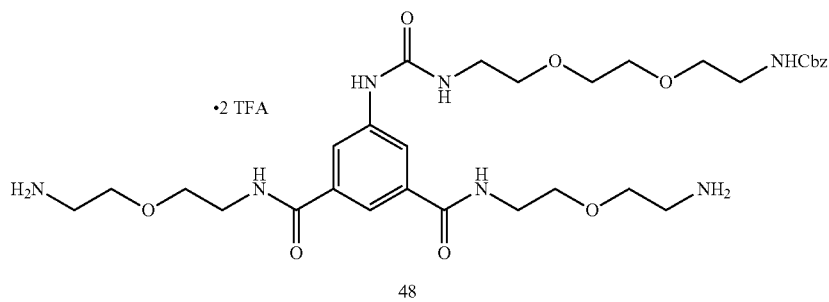

48

To a water (400 μL) solution of dicarbamate compound 47 (26.6 mg, 31 μmol), trifluoroacetic acid (200 μL) was added under cooling on ice, the mixture was stirred for 30 minutes, heated to room temperature, and further stirred for 1.5 hours. After the solvent was evaporated off under reduced pressure, the residue was dried in vacuo. A crude product (34.0 mg, colorless liquid) containing title compound 48 was thus obtained. The obtained crude product was used for the next reaction without further purification.

$^1$H NMR (400 MHz, CD$_3$OD) δ: 3.14 (t, 2H, J=5.0 Hz), 3.29-3.35 (m, 1H), 3.41 (t, 2H, J=5.0 Hz), 3.53-3.65 (m, 13H), 3.67-3.73 (m, 8H), 5.06 (s, 2H), 7.24-7.37 (m, 5H), 7.85 (t, 1H, J=1.4 Hz), 7.98 (d, 2H, J=1.4 Hz); LRMS (ESI): m/z 662 [M+H]$^+$.

Benzyl (2-(2-(2-(3-(3,5-bis((2-(2-(5-((3aS,4S,6aR)-2-iminohexahydro-1H-thieno[3,4-d]imidazole-4-yl)pentanamido)ethoxy)ethyl)carbamoyl)phenyl)ureido)ethoxy)ethoxy)ethyl)carbamate di(2,2,2-trifluoroacetate) (49)

[Chemical Formula 44]

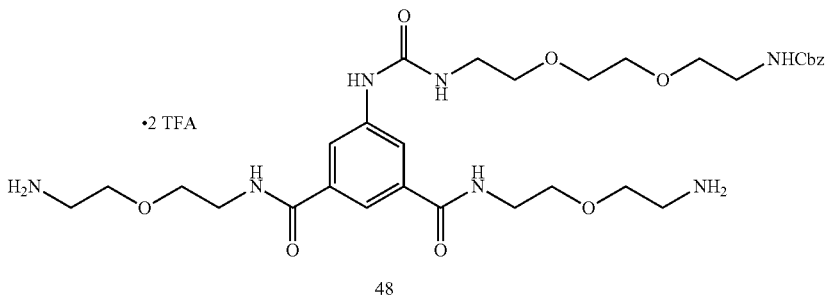

48

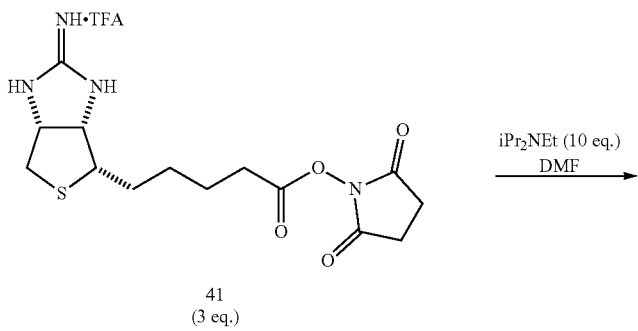

41
(3 eq.)

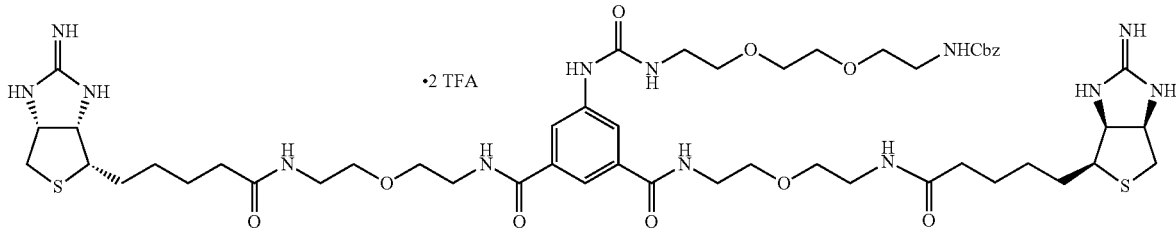

49

In a test tube containing compound 41 prepared from 2-iminobiotin 39 (16.6 mg, 68 μmol) were added an N,N-dimethylformamide (420 μL) solution of diamine 48 (252 mg) and diisopropylethylamine (40.1 μL, 23 μmol), and the mixture was stirred at room temperature for 12 hours. The solvent was evaporated off under reduced pressure, and the obtained crude product was purified by reversed-phase silica gel column chromatography (methanol/water=2:1, 0.3% TFA). Title Compound 49 (28.8 mg, colorless liquid) was thus obtained.

$^1$H NMR (500 MHz, CD$_3$OD) δ: 1.33-1.41 (m, 4H), 1.47-1.62 (m, 6H), 1.64-1.72 (m, 2H), 2.17 (q, 4H, J=6.4 Hz), 2.80 (d, 2H, J=13.2 Hz), 2.97 (dd, 2H, J=4.6, 13.2 Hz), 3.20-3.25 (m, 2H), 3.29-3.35 (m, 1H), 3.35-3.42 (m, 6H), 3.53-3.61 (m, 13H), 3.63-3.67 (m, 8H), 4.49 (dd, 2H, J=4.6, 8.1 Hz), 4.71 (dd, 2H, J=5.2, 8.1 Hz), 5.07 (s, 2H), 7.24-7.38 (m, 5H), 7.88 (brs, 1H), 7.99 (brs, 2H).

5-(3-(2-(2-(2-Aminoethoxy)ethoxy)ethyl)ureido)-N$^1$, N$^3$-bis(2-(2-(5-((3aS,4S,6aR)-2-iminohexahydro-1H-thieno[3,4-d]imidazole-4-yl)pentanamido)ethoxy)ethyl)isophthalamide tri(2,2,2-trifluoroacetate) (50)

[Chemical Formula 45]

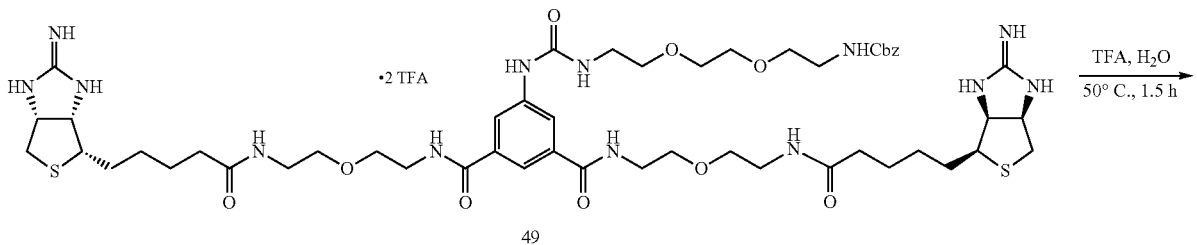

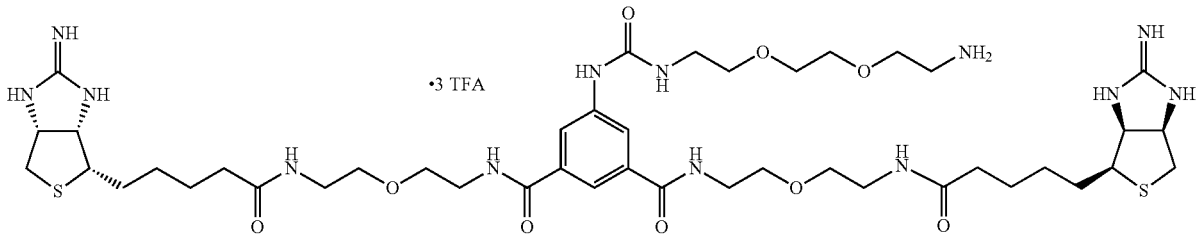

A mixed solvent of trifluoroacetic acid (1 mL) and water (50 μL) was added to bisiminobiotin 49 (6.9 mg, 5.3 μmol), the mixture was heated to 50° C., and stirred for 1.5 hours. After the solvent was evaporated off under reduced pressure, the residue was dried in vacuo. A crude product (5.3 mg, colorless liquid) containing title compound 50 was thus obtained. The obtained crude product was used for the next reaction without further purification.

$^1$H NMR (500 MHz, CD$_3$OD) δ: 1.32-1.43 (m, 4H), 1.47-1.62 (m, 6H), 1.63-1.74 (m, 2H), 2.13-2.20 (m, 4H), 2.81 (d, 2H, J=13.2 Hz), 2.98 (dd, 2H, J=4.6, 13.2 Hz), 3.08-3.14 (m, 2H), 3.20-3.27 (m, 2H), 3.35-3.45 (m, 6H), 3.52-3.73 (m, 20H), 4.51 (dd, 2H, J=4.6, 8.1 Hz), 4.72 (dd, 2H, J=5.2, 8.1 Hz), 7.87 (brs, 1H), 8.00 (brs, 2H).

2,2',2''-(10-(1-((3,5-Bis((2-(2-(5-((3aS,4S,6aR)-2-iminohexahydro-1H-thieno[3,4-d]imidazole-4-yl)pentanamido)ethoxy)ethyl)carbamoyl)phenyl)amino)-1,12-dioxo-5,8-dioxa-2,11-diazatridecane-13-yl)-1,4,7,10-tetraazacyclododecane-1,4,7-triyl)triacetic Acid tri(2,2,2-trifluoroacetate) (51)

[Chemical Formula 46]

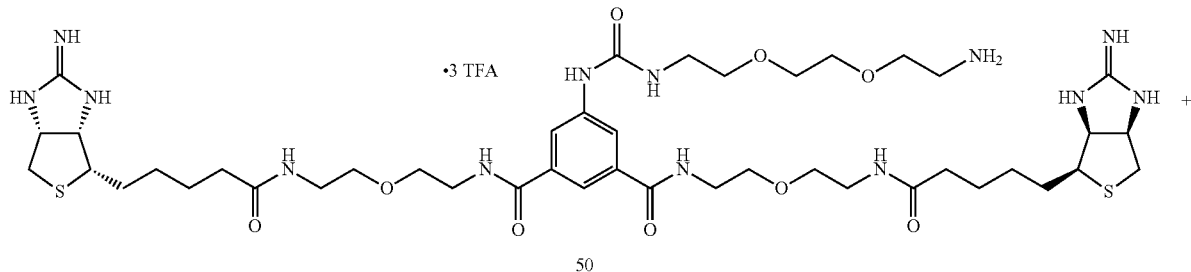

50

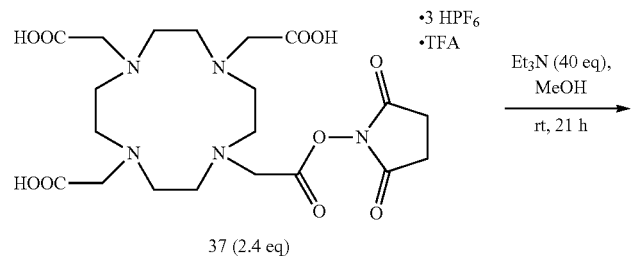

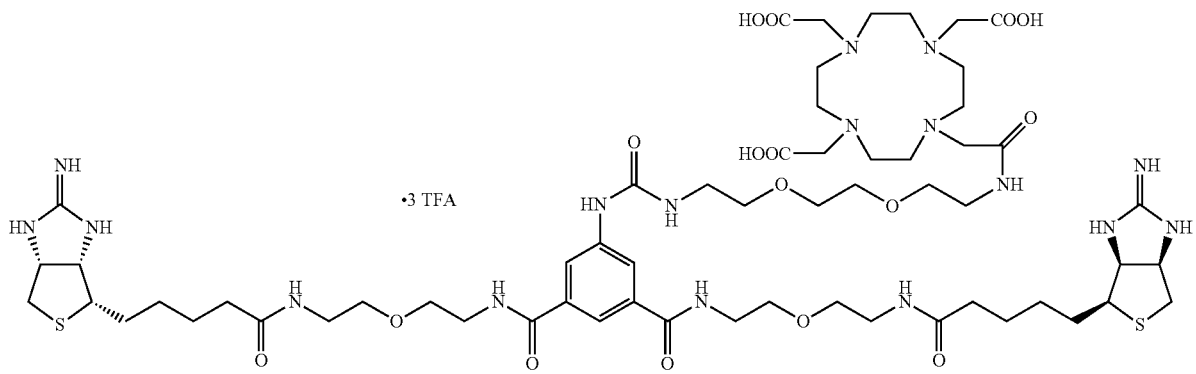

51

To a mixed solution of methanol (100 μL) and triethylamine (10 μL, 72 μmol) containing bisiminobiotin 50 (2.4 mg, 1.9 μmol), DOTA-NHS-ester 37 (3.5 mg, 4.6 μmol) was added, and the mixture was stirred at room temperature for 21 hours. The solvent was evaporated off under reduced pressure, and the obtained crude product was purified by reversed-phase HPLC (0.0-20.0-20.5-60.5-61.0-75.0 min; 5.0-5.0-17.5-57.5-100.0-100.0% $CH_3CN$ in 0.1% TFA in MQ, ramp time=40 min (17.5-57.5%), $t_r$=32.6 min). Title Compound 51 (highly viscous yellow oil) was thus obtained. LRMS (ESI): m/z 683 $[M+2H]^{2+}$.

5-(3-(2-(2-(2-(3',6'-Dihydroxy-3-oxo-3H-spiro[isobenzofuran-1,9'-xanthene]-5(6)-yl-carboxamido)ethoxy) ethoxy)ethyl)ureido)-$N^1$,$N^3$-bis(2-(2-(5-((3aS,4S,6aR)-2-iminohexahydro-1H-thieno[3,4-d]imidazole-4-yl) pentanamido)ethoxy)ethyl) isophthalamide (52)

[Chemical Formula 47]

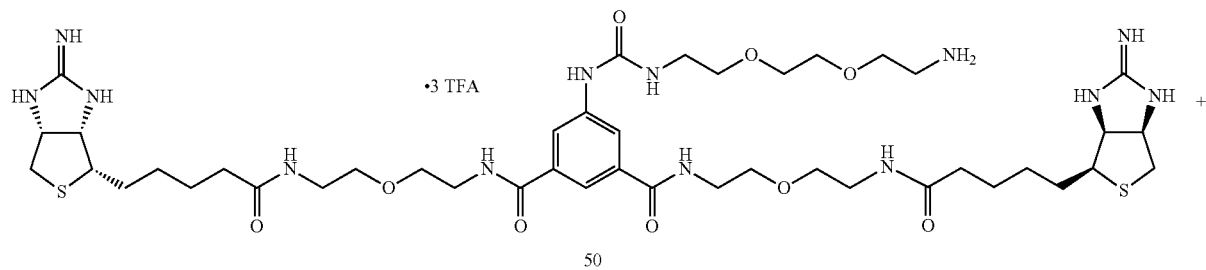

50

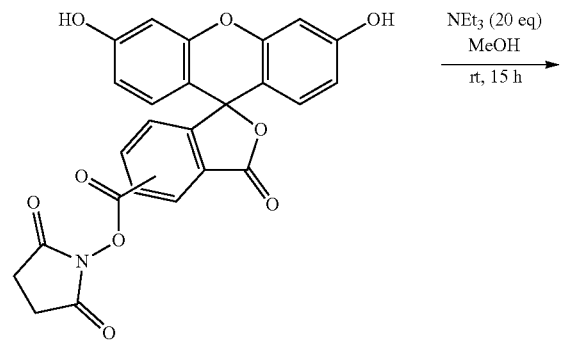

51 (3 eq.)

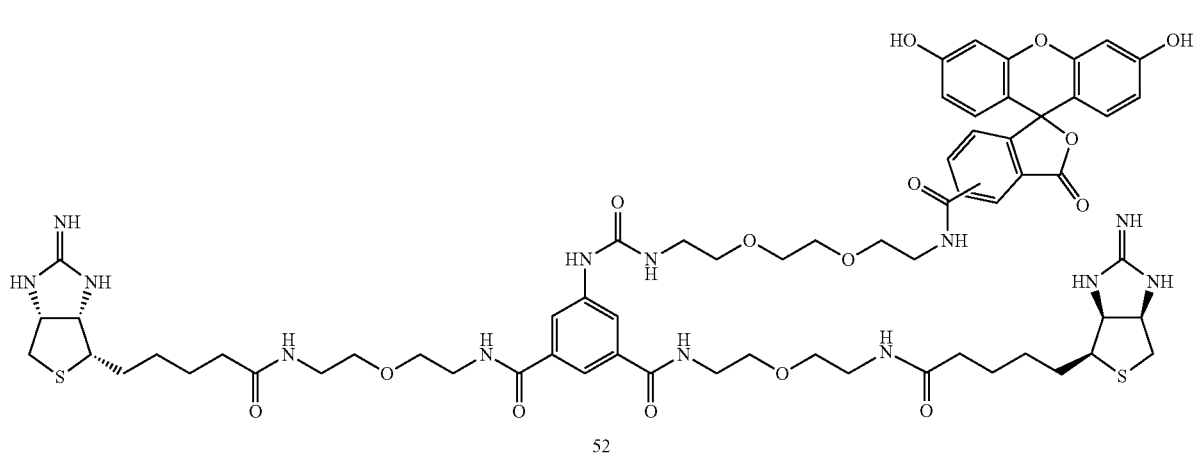

52

To a mixed solution of methanol (100 μL) and triethylamine (9.5 μL, 68 μmol) containing bisiminobiotin 50 (4.3 mg, 3.4 μmol) was added 5(6)-carboxyfluorescein N-hydroxysuccinimide ester 51 (4.8 mg, 10 μmol), and the mixture was stirred at room temperature for 16 hours. The solvent was evaporated off under reduced pressure, the obtained crude product was purified by reversed-phase column chromatography (methanol/water=1:1-2:1, 0.5% TFA), and further purified through Sephadex 20LH (methanol, 1% TFA). Title Compound 52 (2.2 mg, yield=49%) was thus obtained.

LRMS (ESI): m/z 669 [M+2H]$^{2+}$.

(S)—(S)-9-((Tert-butoxycarbonyl)oxy)-4,11-diethyl-3,14-dioxo-3,4,12,14-tetrahydro-1H-pyrano[3',4':6,7]indolizino[1,2-b]quinoline-4-yl 2-(((benzyloxy)carbonyl)amino)propanoate (55)

[Chemical Formula 48]

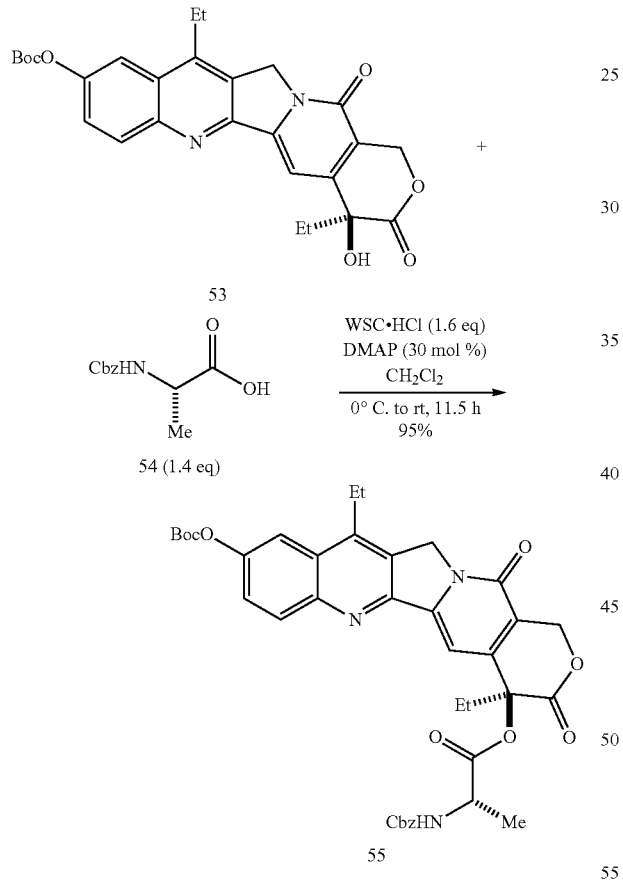

To a dichloromethane (480 μL) solution containing SN38 Boc-protected compound 53 (20.0 mg, 41 μmol) synthesized by a known method (Bioconjugate Chem. (2008) 19, 849.) and Cbz-Ala-OH 54 (12.7 mg, 57 μmol), added under cooling on ice were 1-ethyl-3-(3-dimethylaminopropyl)carbodiimide hydrochloride (WSC.HCl, 12.7 mg, 66 μmol) and dimethylaminopyridine (1.5 mg, 12 μmol), the mixture was gradually heated to room temperature, and stirred for 11.5 hours. The mixture was added with dichloromethane, and washed successively with an aqueous sodium carbonate solution, water, 0.1-M hydrochloric acid, and a saturated sodium chloride solution. The organic layer was dried over sodium sulfate, the solvent was evaporated off under reduced pressure, and the obtained crude product was purified by silica gel column chromatography (dichloromethane/methanol=30:1). Title Compound 55 (26.8 mg, yield=95%, pale yellow solid) was thus obtained.

$^1$H NMR (500 MHz, cdcl$_3$) δ: 0.94 (t, 3H, J=7.5 Hz), 1.38 (t, 3H, J=7.4 Hz), 1.53 (d, 3H, J=6.9 Hz), 1.61 (s, 9H), 2.05-2.32 (m, 2H), 3.07-3.20 (m, 2H), 4.50-4.60 (m, 1H), 5.12-5.30 (m, 5H), 5.39 (d, 1H, J=17.2 Hz), 5.68 (d, 1H, J=17.2 Hz), 7.02-7.20 (m, 2H), 7.26-7.38 (m, 3H), 7.38-7.46 (m, 1H), 7.63 (dd, 1H J=9.2, 2.3 Hz), 7.89 (brs, 1H), 8.18 (d, 1H, J=9.2 Hz); LRMS (ESI): m/z 720 [M+Na]$^+$.

(S)—(S)-9-((tert-butoxycarbonyl)oxy)-4,11-diethyl-3,14-dioxo-3,4,12,14-tetrahydro-1H-pyrano[3',4':6,7]indolizino[1,2-b]quinoline-4-yl 2-aminopropanoate (56)

[Chemical Formula 49]

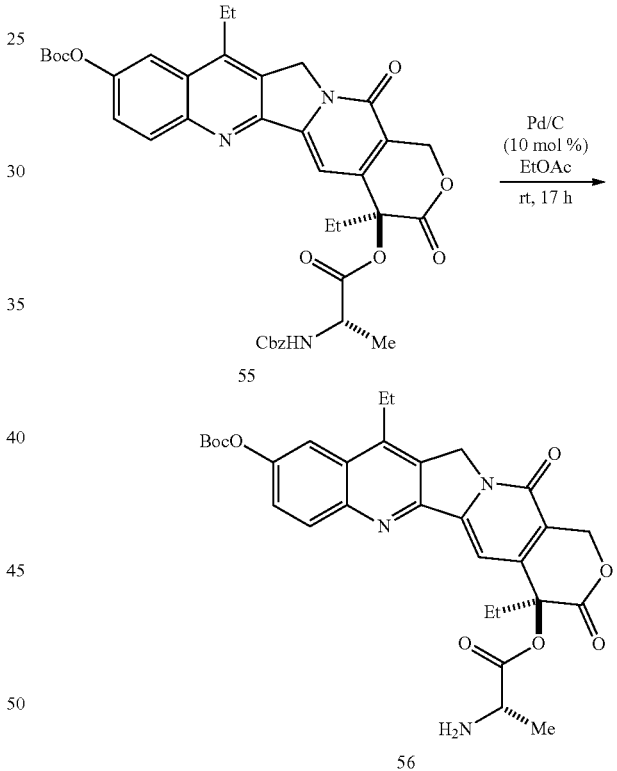

To an ethyl acetate solution (320 μL) of compound 55 (11.3 mg, 16 μmol), Pd/C (1.7 mg) was added, the atmosphere in the reaction vessel was replaced with hydrogen, the mixture was stirred at room temperature for 16 hours, then at 40° C. for one hour, and then filtered through celite. The solvent was evaporated off under reduced pressure, and the obtained crude product was purified by thin layer chromatography (dichloromethane/methanol=30:1). Title Compound 56 (2.3 mg, yield=26%) was thus obtained.

$^1$H NMR (500 MHz, cdcl$_3$) δ: 0.99 (t, 3H, J=7.5 Hz), 1.29 (t, 3H, J=8.0 Hz), 1.45 (d, 3H, J=6.9 Hz), 1.61 (s, 9H), 2.14-2.22 (m, 1H), 2.26-2.36 (m, 1H), 3.15 (q, 2H, J=8.0 Hz), 3.75 (q, 1H, J=6.9 Hz), 5.25 (d, 2H, J=3.5 Hz), 5.42 (d, 1H, J=17.2 Hz), 5.69 (d, 1H, J=17.2 Hz), 7.67 (dd, 1H J=9.2, 2.3 Hz), 7.90 (d, 1H, J=2.3 Hz), 8.21 (d, 1H, J=9.2 Hz).

(S)—(S)-9-((Tert-butoxycarbonyl)oxy)-4,11-diethyl-3,14-dioxo-3,4,12,14-tetrahydro-1H-pyrano[3',4':6,7]indolizino[1,2-b]quinoline-4-yl 2-isocyanatopropanoate (57)

[Chemical Formula 50]

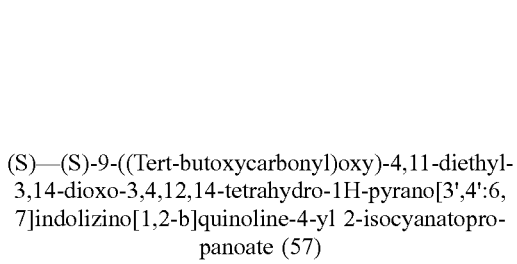

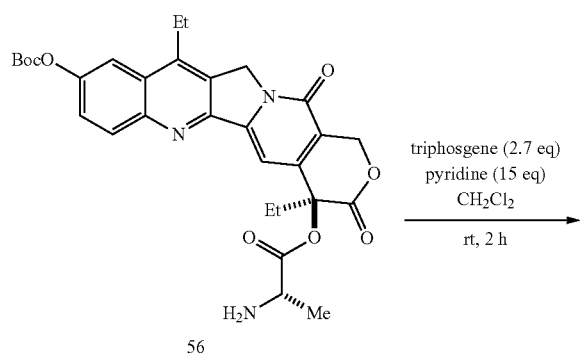

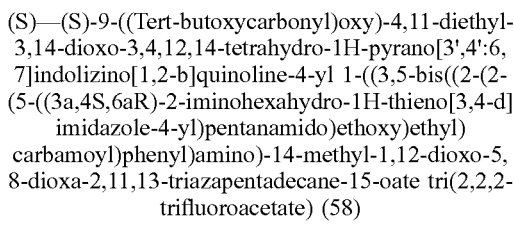

To a dichloromethane (100 μL) solution of compound 56 (2.3 mg, 4.1 μmol) were added triphosgene (3.3 mg, 11 μmol) and pyridine (5.0 μL, 62 μmol) under cooling on ice, the mixture was heated to room temperature, and stirred for 2 hours. After the solvent was evaporated off under reduced pressure, the residue was dried in vacuo. A crude product (brown liquid) containing title compound 57 was thus obtained. The obtained crude product was used for the next reaction without further purification.

(S)—(S)-9-((Tert-butoxycarbonyl)oxy)-4,11-diethyl-3,14-dioxo-3,4,12,14-tetrahydro-1H-pyrano[3',4':6,7]indolizino[1,2-b]quinoline-4-yl 1-((3,5-bis((2-(2-(5-((3a,4S,6aR)-2-iminohexahydro-1H-thieno[3,4-d]imidazole-4-yl)pentanamido)ethoxy)ethyl)carbamoyl)phenyl)amino)-14-methyl-1,12-dioxo-5,8-dioxa-2,11,13-triazapentadecane-15-oate tri(2,2,2-trifluoroacetate) (58)

[Chemical Formula 51]

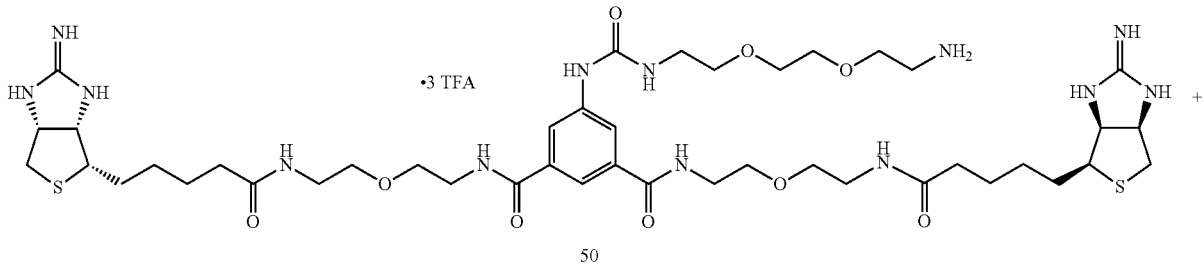

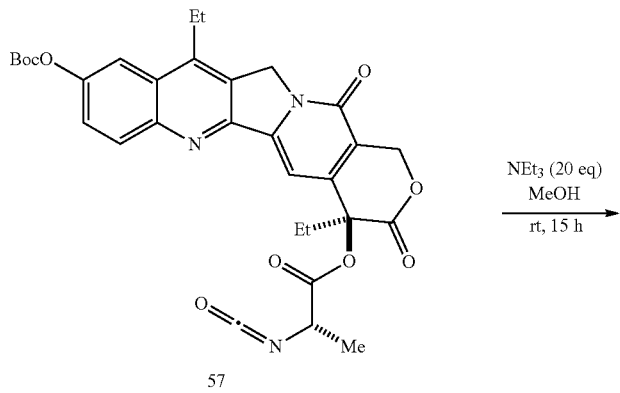

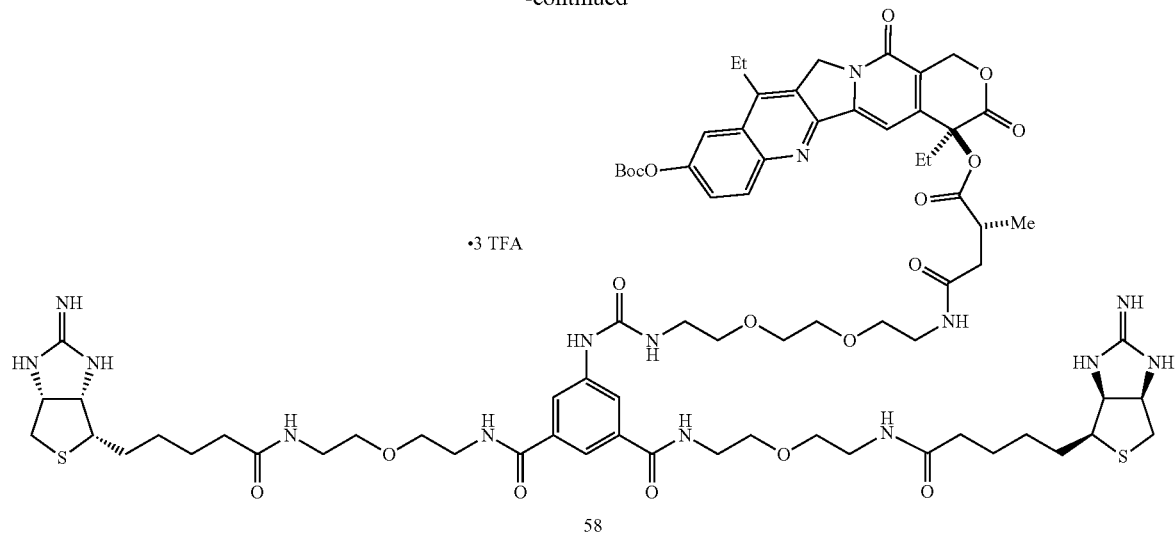

58

To a methanol (200 μL) solution of the crude product containing bisiminobiotin 50 (3.4 mg, 2.7 μmol) and compound 57, triethylamine (10 μL, 72 μmol) was added, and the mixture was stirred at room temperature for 15 hours. The solvent was evaporated off under reduced pressure, and the obtained crude product was purified by reversed-phase thin layer chromatography (methanol/water=3:1, 1% TFA). Title Compound 58 (1.5 mg, yield=30%) was thus obtained.

LRMS (ESI): m/z 785 $[M+2H]^{2+}$.

(S)—(S)-4,11-Diethyl-9-hydroxy-3,14-dioxo-3,4,12,14-tetrahydro-1H-pyrano[3',4':6,7]indolizino[,2-b]quinoline-4-yl 1-((3,5-bis((2-(2-(5-((3aS,4S,6aR)-2-iminohexahydro-1H-thieno[3,4-d]imidazole-4-yl)pentanamido)ethoxy)ethyl)carbamoyl)phenyl)amino)-14-methyl-1,12-dioxo-5,8-dioxa-2,11,13-triazapentadecane-15-oate di(2,2,2-trifluoroacetate) (59)

[Chemical Formula 52]

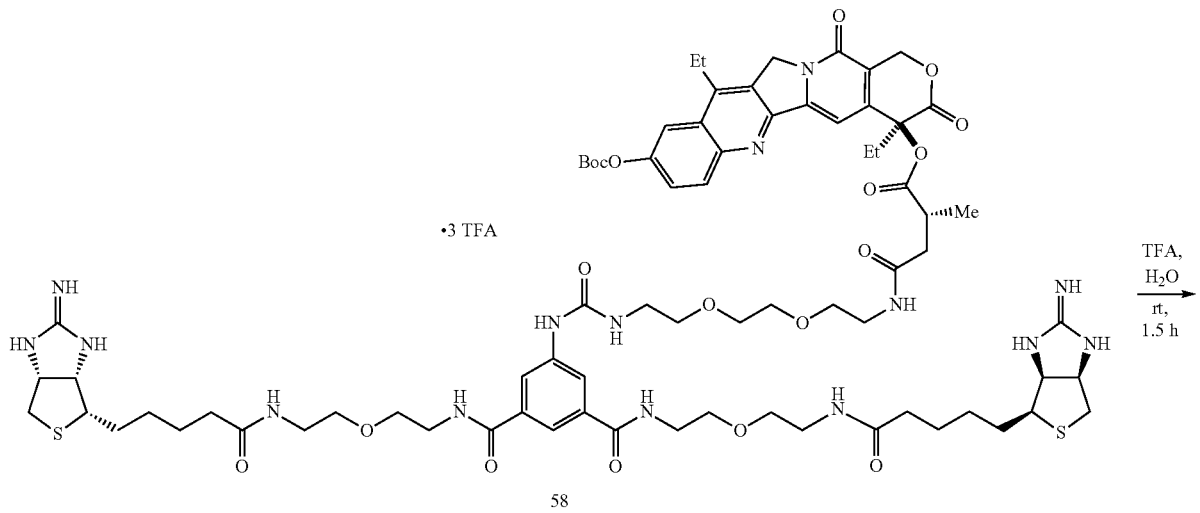

58

TFA, H₂O rt, 1.5 h

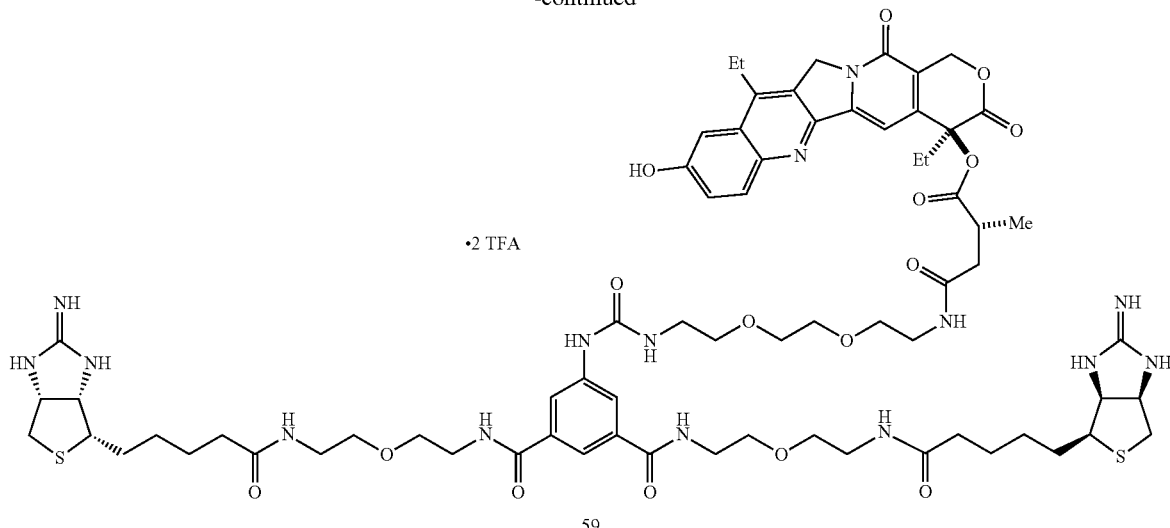

59

To a water (100 μL) solution of bisiminobiotin 58 (1.5 mg, 0.8 μmol), trifluoroacetic acid (100 L) was added, and the mixture was stirred at room temperature for 1.5 hours. The solvent was evaporated off under reduced pressure, and the obtained crude product was purified by reversed-phase thin layer chromatography (methanol/water=3:1, 1% TFA). Title Compound 59 (0.4 mg, yield=29%) was thus obtained.

LRMS (ESI): m/z 735 $[M+2H]^{2+}$.

Example 2: Expression of LISA314 Mutants V21 and V212 and Crystallographic Analysis A nucleotide sequence of a gene encoding wild-type core streptavidin is represented by SEQ ID NO: 1 in the Sequence Listing. In this invention, mcSA314 (also referred to as LISA314WT or LISA314 in this specification), described in International Patent WO2010/09455 as a low-immunogenic (modified) streptavidin, was used. mcSA314 is a streptavidin mutant having all types of mutations listed below, in the amino acid sequence of the core streptavidin represented by SEQ ID NO: 2:
(1) mutation given by substitution of tyrosine at position 10 with serine;
(2) mutation given by substitution of tyrosine at position 71 with serine;
(3) mutation given by substitution of arginine at position 72 with lysine;
(4) mutation given by substitution of glutamic acid at position 89 with aspartic acid;
(5) mutation given by substitution of arginine at position 91 with substituted with lysine; and
(6) mutation given by substitution of glutamic acid at position 104 with asparagine.

Oligo DNA used for producing each mutant was designed according to a manual attached to primerSTAR Mutagenesis Basal Kit (Takara Bio Inc.), so as to have an overlapped part over 15 bases on the 5' terminus. Using the primers below, and using pCold TF vector having LISA314 inserted therein as a template, a codon sequence was altered by substituting the nucleotide sequence according to the site-directed mutagenesis method, to thereby convert the amino acid sequence. The template plasmid was then cleaved using restriction enzyme DpnI, and E. coli was transformed.

Primers:
```
                              (SEQ ID NO: 5)
LISA314 V21 Fw:   TGGAGCgatCAGCTGGGCgatACCTTT (SEQ ID NO: 6)
LISA314 V21 Rv:   CAGCTGatcGCTCCAGGTGCCGGTAAT
```

LISA314 V21 (also referred to as V21, hereinafter), which is a LISA314 mutant, has additional mutations of N23D and S27D in LISA314. N23D means a mutation given by substitution of asparagine (N) at the 11th amino acid residue in the amino acid sequence of the core streptavidin represented by SEQ ID NO: 2, with aspartic acid (D). S27D means a mutation given by substitution of serine (S) at the 15th amino acid residue in the amino acid sequence of the core streptavidin represented by SEQ ID NO: 2, with aspartic acid (D).

Summarizing the above, V21 is a streptavidin mutant having the mutations below in the amino acid sequence of the streptavidin represented by SEQ ID NO: 2:
(1) mutation given by substitution of tyrosine at position 10 with serine;
(2) mutation given by substitution of tyrosine at position 71 with serine;
(3) mutation given by substitution of arginine at position 72 with lysine;
(4) mutation given by substitution of glutamic acid at position 89 with aspartic acid;
(5) mutation given by substitution of arginine at position 91 with substituted with lysine;
(6) mutation given by substitution of glutamic acid at position 104 with asparagine;
(7) mutation given by substitution of asparagine at position 11 with aspartic acid; and
(8) mutation given by substitution of serine at position 15 with aspartic acid.

Oligo DNA used for producing further mutant of V21 was designed according to a manual attached to primerSTAR Mutagenesis Basal Kit (Takara Bio Inc.), so as to have an overlapped part over 15 bases on the 5' terminus. Using the primers below, and using a vector having the above-described V21 inserted therein as a template, a codon sequence was altered by substituting the nucleotide sequence according to the site-directed mutagenesis method, to thereby convert the amino acid sequence. The template plasmid was then cleaved using restriction enzyme DpnI, and *E. coli* was transformed.

```
Primers:
                                        (SEQ ID NO: 7)
    S45N Fw:    TATGAAAACGCCGTGGGTAATGCGGAA (SEQ ID NO: 8)
    S45N Rv:    CACGGCGTTTTCATAGGTGCCGGTCAG
```

S45N means a mutation given by substitution of serine (S) at the 33rd amino acid residue in the amino acid sequence of the core streptavidin represented by SEQ ID NO: 2, with asparagine (N). In other words, mutant LISA314 V212 (also referred to as V212, hereinafter), which is obtained by introducing an additional amino acid mutation S45N in V21, is produced. The amino acid sequence of this mutant is represented by SEQ ID NO: 3 in the Sequence Listing.

[2] Expression and Purification of V212 Protein

V212 protein was expressed in *E. coli* (BL21 (DE3) strain), collected in the form of inclusion body, refolded by the dilution method, and then subjected to affinity purification and gel filtration purification, to obtain a tetramer fraction. More specifically, the purified inclusion body was dissolved overnight in a denaturing buffer (6 M guanidine hydrochloride, 50 mM Tris-HCl, 200 mM NaCl, 1 mM EDTA, pH8.0 at 4° C.). Since the solubilized liquid, when measured in terms of absorbance at 280 nm, showed a concentration value of 50 mg/mL, 100 μL (5 mg equivalent) of the solubilized liquid was added dropwise into 50 mL of a refolding buffer (50 mM Tris-HCl, 300 mM NaCl, 1 mM EDTA, 400 mM Arginine-HCl, pH8.0 at 4° C.) under stirring, and incubated allowed to stand still at 4° C. for two day as for. For stable refolding, the storage time was limited to two days. After the 2-day incubation storage, the product was subjected to affinity purification using Ni-NTA resin (cOmplete His-Tag Purification Resin; Roche), followed by purification by gel filtration (HiLoad 16/60 Superdex 200 pg, from GE Healthcare BioScience Corp.) to obtain a tetramer fraction.

[3] Method of Crystallizing V21 and V212

Complexes Conjugates of proteins and Compounds were purified as follows. The proteins refolded by the dilution method were concentrated by affinity purification through Ni-NTA resin, the solvent was replaced with PBS, Compound C was added at a molar ratio of 1:8, incubated for one hour, and then allowed to pass through a gel filtration column, to obtain a tetramer fraction. These purified products were concentrated to 10 mg/mL through an ultrafiltration column (Vivaspin 20).

Each product was crystallized by the sitting drop vapor diffusion method, at a crystallization temperature of 20° C. A drop prepared by mixing the protein and a reservoir solution (0.2 M sodium fluoride, 20% PEG 3350) at a ratio of 0.5 μL:0.5 μL was equilibrated with 60 μL of the reservoir solution. A 6% glycerol solution was used as an anti-freezing agent.

[4] Method of Crystallographic Analysis

Recovery intensity data was collected using SPring-8 BL44XU. The collected data was used to determine the phase of V212 crystal structure by using Phaser (molecular replacement program), based on previously-analyzed cocrystal data (FIG. 1) of a model molecule formed between previously-analyzed V21 and iminobiotin longtail complex as the search model. Refinement was carried out using REFMAC5.

[5] Results of Crystallographic Analyses

Figure 2:
FIG. 2 shows a result of crystallographic analysis.
Figure 2:
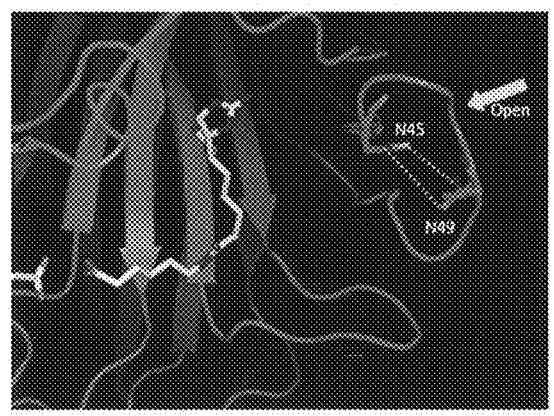

Analysis of cocrystal structure formed between V212 and Compound C revealed an opened loop structure as shown in FIG. 2. This was strongly suggested to be a result of hydrogen bonds formed between N45 and N49 (amino acids 33 and 37 in SEQ ID NO: 3).

Example 3: Design, Expression and Purification of V2122

In order to close the opened loop, it was supposedly necessary to suppress the hydrogen bonds formed between N45 and N49 (amino acids 33 and 37 in Sequence Listing 3). For this reason, asparagine (N) at position 37 in the amino acid sequence represented by SEQ ID NO: 3 was altered to alanine (A), glycine (G) or serine (S). These mutations are denoted as N49A, N49G and N49S, respectively. Method of expression was same as described previously. Using the primers below, mutant expressing vectors were constructed based on the site-directed mutagenesis.

```
Primer Set:
                                        (SEQ ID NO: 9)
    N49A Fw:    GTGGGTgcgGCGGAAAGCCGTTATGTT (SEQ ID NO: 10)
    N49A Rv:    TTCCGCcgcACCCACGGCattTTCATA (SEQ ID NO: 11)
    N49G Fw:    GTGGGTggtGCGGAAAGCCGTTATGTT (SEQ ID NO: 12)
    N49G Rv:    TTCCGCaccACCCACGGCattTTCATA (SEQ ID NO: 13)
    N49S Fw:    GTGGGTagcGCGGAAAGCCGTTATGTT (SEQ ID NO: 14)
    N49S Rv:    TTCCGCgctACCCACGGCattTTCATA
```

Figure 3:
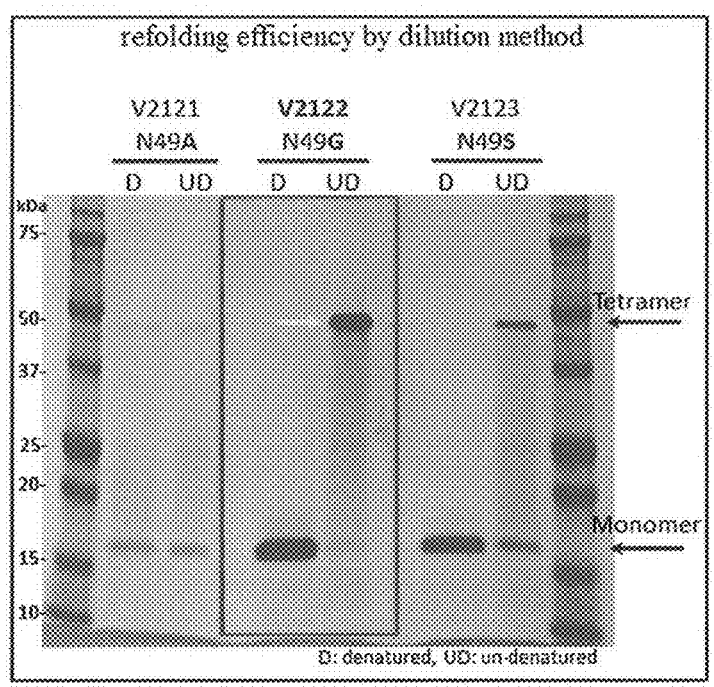
FIG. 3 shows results of measurement of refolding efficiency based on the dilution method.

The mutant protein was expressed and purified in the same way as described above, by way of denaturation of the inclusion body, and refolding by the dilution method. The refolded and purified proteins, analyzed by SDS-PAGE, revealed that, as represented by FIG. 3, the glycine mutant showed the highest efficiency in forming tetramer, in contrast to the alanine and serine mutants showing only low efficiency in the tetramer formation. The glycine mutant (N49G) was therefore selected for use in the following studies, and named LISA314-V2122 (referred to as V2122, hereinafter). The amino acid sequence of V2122 is represented by SEQ ID NO: 4 in the Sequence Listing.

Example 4: ITC Binding Analysis of V2122 and Compounds

Microcal iTC200 (MicroCal, Northampton, Mass.) was used for the measurement.

Purified V2122 was dialyzed overnight against PBS at 4° C., and stock solutions of Compound C and biotin were prepared using the external dialysis solution. For the measurement, concentration of the stock solutions was adjusted to a ten-fold concentration of V2122 to be measured. Into a cell of a calorimeter, 25 µM of V2122 was placed, and each solution was added dropwise at a stirring speed of 1000 rpm at 25° C. Obtained data was analyzed using ORIGIN, and the titration curve was fitted based on the one-site binding isotherm.

Figure 4:
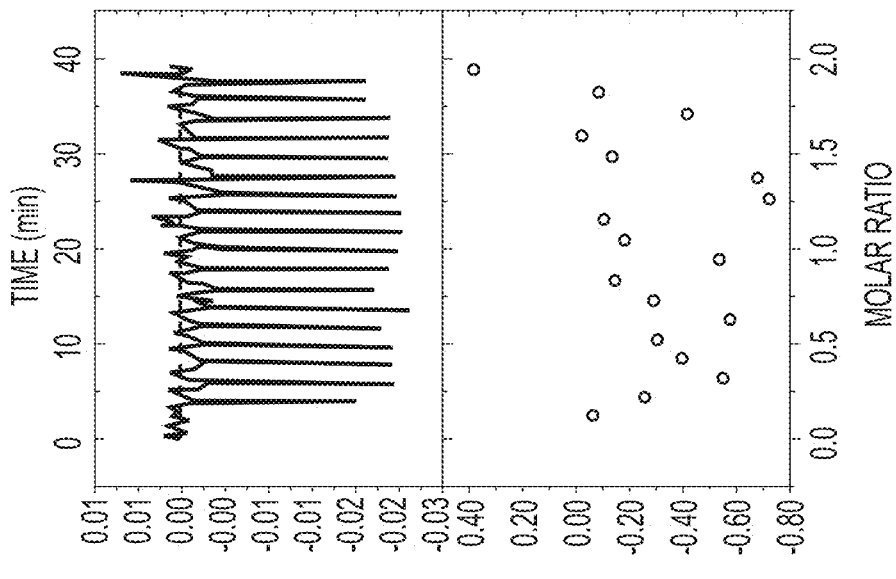
FIG. 4 shows interaction of V2122 with various compounds measured by ITC.
Figure 4:
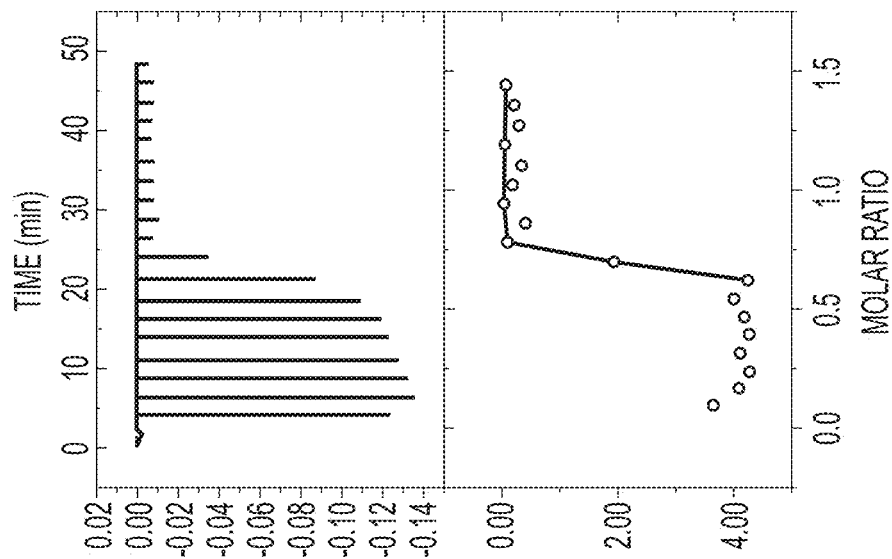

Results are shown in FIG. 4.

From the results of ITC, interaction between V2122 and Compound C was confirmed to be exothermic, suggesting a strong binding between them. Meanwhile, V2122 and biotin showed neither exothermic nor endothermic reaction, and were confirmed to be non-interactive.

Example 5: Immunogenicity Testing (1) Preparation of Protein

A protein expression vector used herein for the immunogenicity testing was obtained by altering the above-described expression vector so as not to express T7-tag attached to the N terminus, using the primer set below, according to the site-directed mutagenesis method.

```
Primer Set:
                                        (SEQ ID NO: 15)
T7tagRemove Fw:    tacatatgGCCGAAGCAGGTATTACC (SEQ ID NO: 16)
T7tagRemove Rv:    CTTCGGCcatatgtatatctccttc
```

The target protein was expressed in *E. coli* (BL21(DE3) strain), collected in the form of inclusion body, refolded by the dilution method, and then subjected to affinity purification and gel filtration purification, to obtain a tetramer fraction. More specifically, the purified inclusion body was dissolved overnight in a denaturing buffer (6 M guanidine hydrochloride, 50 mM Tris-HCl, 200 mM NaCl, 1 mM EDTA, pH8.0 at 4° C.). After measuring the absorbance of the liquid at 280 nm, a portion of the solubilized liquid containing 5 mg of product was added dropwise into 50 mL of a refolding buffer (50 mM Tris-HCl, 300 mM NaCl, 1 mM EDTA, 400 mM Arginine-HCl, pH8.0 at 4° C.) under stirring, and allowed to stand still at 4° C. for two days for. For stable refolding, the storage time was limited to two days. After the 2-day storage, the product was subjected to affinity purification using Ni-NTA resin (cOmplete His-Tag Purification Resin; Roche), followed by purification by gel filtration (HiLoad 16/60 Superdex 200 pg, from GE Healthcare BioScience Corp.) using saline as a buffer, to obtain a tetramer fraction.

(2) Immunogenicity Testing

Immunogenicity testing was conducted using four crab-eating monkeys. One milligram of the purified protein was administered three times. Before administration, blood was collected for preparing a negative control serum, followed by three times of administration of 1 mg each of purified protein. More specifically, letting the first day of administration of Day 0, the second administration fell on Day 21, and the third administration fell on Day 42. For V2122, blood was collected on Days 7, 14, 28 and 35 to prepare serum samples, and for the other, blood was collected on Days 7, 14, 28, 35, 49 and 56 to prepare serum samples.

Antibody against V2122 in the serum samples was analyzed by surface plasmon resonance (SPR). More specifically, Biacore T200 (GE Healthcare BioScience Corp.) was used as a measuring instrument, which was operated in the mode using immunogenicity package. The sensor chip was CM5. As instructed by the manual, V2122 protein (10 µg/mL) was immobilized on the CM5 sensor chip using an amine coupling kit. Serum was diluted ten-fold with a running buffer (HBS-EP, GE Healthcare BioScience Corp.) for the interaction analysis. More specifically, the serum diluted ten-fold was loaded into the running buffer at a flow rate of 10 µL/min for 5 minutes. The obtained sensorgram was analyzed using an analytical software named Biacore T200 Evaluation Software.

Figure 5:
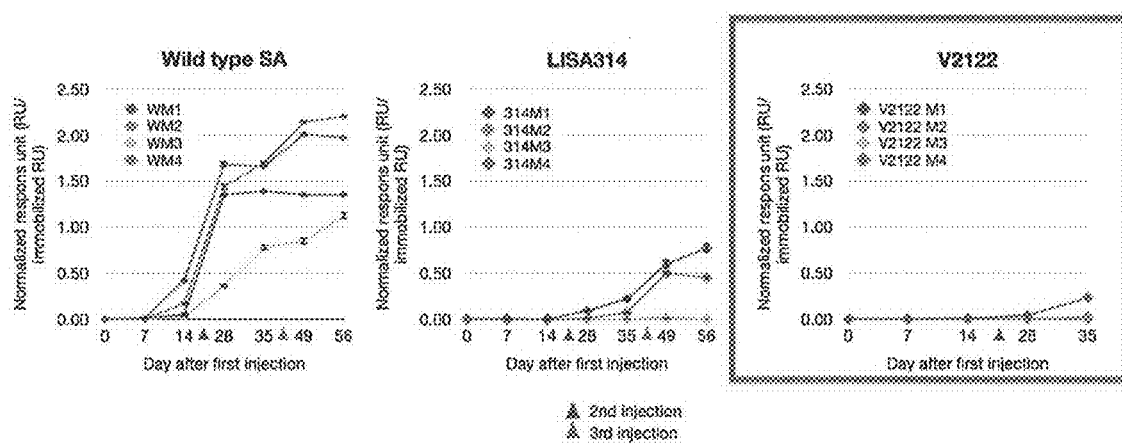
FIG. 5 shows results of immunogenicity test using crab-eating monkey (*Macaca fascicularis*).

Results are shown in FIG. 5. The immunogenicity of V2122 was found to be low as compared with the immunogenicity of the wild-type streptavidin and LISA314.

Example 6: Analysis of Affinity Between V2122 and Compound

Interaction of V2122, which is a LISA314 modified protein purified as described above, with Compound C was investigated by surface plasmon resonance (SPR). More specifically, using Biacore T200 (GE Healthcare BioScience Corp.) as a measuring instrument, and Sensor Chip NTA (GE Healthcare BioScience Corp.) as a sensor chip, the protein was immobilized on the sensor chip by way of His-Tag having been fused to the core protein. The running buffer was prepared using HBS-P(+), as described in the manual. A two-fold dilution series was prepared in nine steps by diluting a 1600 nM solution using the running buffer. The affinity was measured in the kinetics mode, and acquired data was subjected to equilibrium analysis using Biacore T200 Evaluation Software to determine the affinity.

The dissociation constant (M) between V2122 and biotin was not detected, meanwhile the dissociation constant (M) between V2122 and bisiminobiotin (Compound 7) was found to be $3.15 \times 10^{-9}$.

Example 7: Crystallographic Analysis of Cocrystal of V2122 and Compounds

For the crystallographic analysis, used was a protein from which T7-Tag has been removed, same as that used in the immunogenicity testing. The protein was expressed in *Escherichia coli* BL21-codonplus RIL, which was cultured in 2×YT medium, and an inclusion body was collected. The collected inclusion body was dissolved in 6 M Gdn.HCl, pH1.5, refolded using are folding buffer (50 mM Tris-HCl, 300 mM NaCl, 1 mM EDTA, 400 mM Arginine-HCl, pH8.0 at 4° C.) according to the dilution method described above, and then allowed to stand still at 4° C. for two days for. For stable refolding, the storage time was limited to two days. After the 2-day storage, the product was subjected to affinity purification using Ni-NTA resin (cOmplete His-Tag Purification Resin; Roche), followed by purification by gel filtration (HiLoad 16/60 Superdex 200 pg, from GE Healthcare BioScience Corp.) using PBS as a buffer, to obtain a tetramer fraction.

The thus purified tetramer fraction was added with Compound C or Compound D at a molar ratio of 1:8, and the mixture was incubated for one hour. The mixture was then concentrated to 10 mg/mL through an ultrafiltration column (Vivaspin 20), while replacing the buffer with a 20 mM Tris-HCl, pH7.5, 200 mM NaCl.

(1) Co-Crystallization of V2122 and Compound C

The co-crystallization was carried out by the sitting drop vapor diffusion method, at a crystallization temperature of 20° C. A drop prepared by mixing the protein and a reservoir solution (0.2 M citrate tribasic dehydrate, 20/(w/V) PEG 3350) at a ratio of 0.1 µL:0.1 µL was equilibrated with 60 µL of the reservoir solution. A 25% glycerol solution was used as an anti-freezing agent.

(2) Co-Crystallization of V2122 and Compound D

The crystallization was carried out by the sitting drop vapor diffusion method, at a crystallization temperature of 20° C. A drop prepared by mixing the protein and a reservoir solution (0.2 M citrate tribasic dehydrate, 20% (w/v) PEG 3350) at a ratio of 0.5 µL:0.5 µL was equilibrated with 60 µL of the reservoir solution. Oil was used as an anti-freezing agent.

(3) Method of Crystal Analysis

Recovery intensity data was collected using SPring-8 BL44XU. The collected data was used to determine the phase, using Phaser (molecular replacement program), based cocrystal data of a model molecule formed between previously-analyzed cocrystal data of V21—and iminobiotin longtail complex as the search model. Refinement was carried out using REFMAC5.

Figure 6:
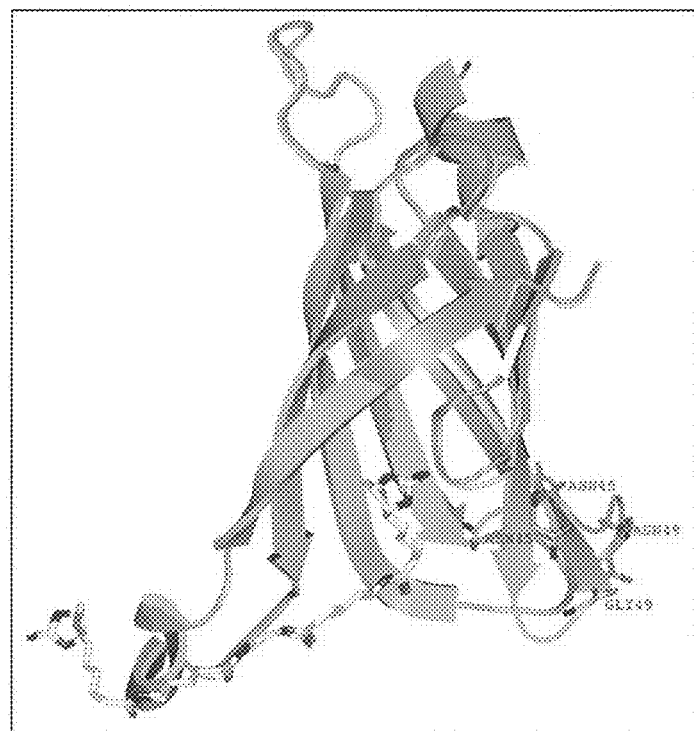
FIG. 6 shows results of crystallographic analysis. The third figure in FIG. 6 shows a crystal structure of a conjugate of V2122 and Compound C.
Figure 6:
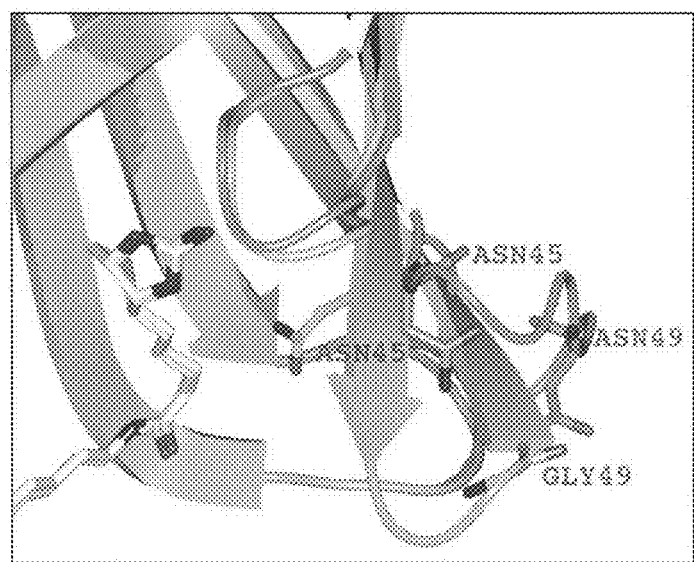
Figure 6:
Figure 7:
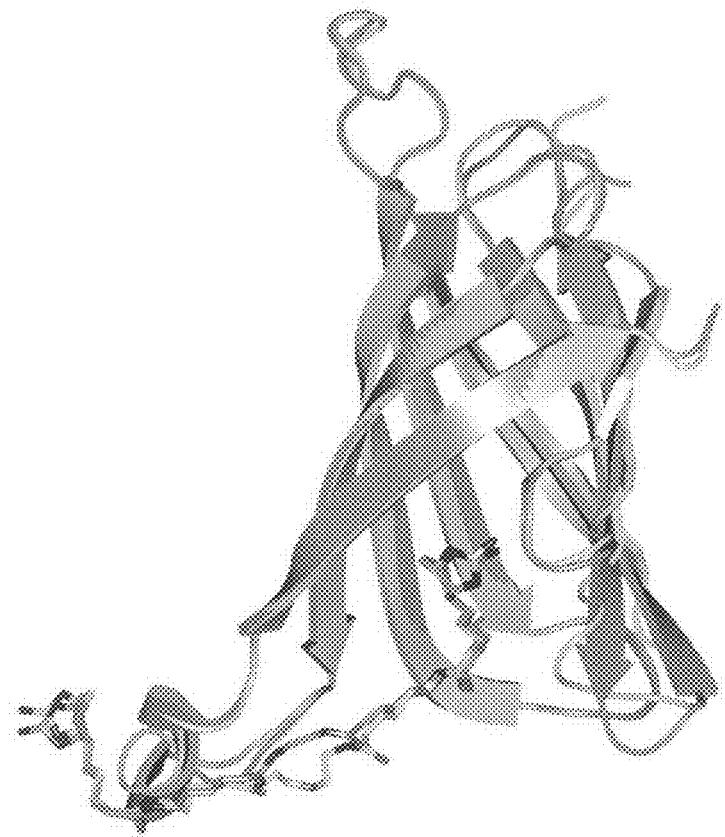
FIG. 7 shows a result of crystallographic analysis.

Results of crystallographic analysis are shown in FIGS. 6 and 7.

Comparing with a V212 crystal bound with Compound C, the crystal structure of V2122 bound with Compound C was confirmed to be altered largely in its loop structure as a result of disappearance of interaction between amino acids NO. 45 and 49 (NOs. 33 and 37 in the amino acid sequence in SEQ ID NO: 4) as planned, to have a closed loop same as found in V21, proving an advantage of mutation N49G. Also a structural difference in the loop moiety was found when comparing the structures of (V2122)s bound with Compound C or Compound D shown in FIG. 7, confirming a structural change depending on the lengths of Compounds C and D.

Example 8: Recognition Analysis of CD20 on RAMOS Cell by Flow Cytometry

A gene sequence of Rituximab-scFv-V2122 was obtained by artificial gene synthesis (Life Technologies Corp.). More specifically, amino acid sequences of light chain (VL) and heavy chain (VH) were extracted from the amino acid sequence of rituximab contained in the DrugBank database (www.drugbank.ca), and VL and VH were ligated using a linker (GGGSx4) in the order of VL-VH. For the artificial synthesis, LV-LH was further ligated with V2122 using a linker (SSGSGSA), and the product was optimized to the codon usage of *E. coli*. The nucleotide sequence and the amino acid sequence of Rituximab-scFv-V2122 are represented by SEQ ID NOs: 27 and 28. Positions of the individual sequences in the amino acid sequence represented by SEQ ID NO: 28 are listed below:
pelB signal sequence: amino acids NOs. 1-23
VL sequence: amino acid NOs. 24-130
Linker sequence 1: amino acid NOs. 131-148
VH sequence: amino acid NOs. 149-269
Linker sequence 2: amino acid NOs. 270-276
V2122 sequence: amino acid NOs. 277-405
6xHis-Tag sequence: amino acid NOs. 406-411

The gene artificially synthesized as described above was introduced into pET21a(+), the protein was expressed in *Escherichia coli* BL21(DE3), and then collected in the form of inclusion body. The collected inclusion body was refolded as described in Non-Patent Literature (Yumura et al. 2013, Protein Science) and purified.

The thus refolded and purified Rituximab-scFv-V2122 was evaluated regarding binding potential with RAMOS (human Burkitt lymphoma) cell (JCRB Cell Bank), which is a CD20 positive cell. More specifically, Rituximab-scFv-V2122 was diluted with PBS into three concentrations (0.05, 0.5, 5 µg/mL). 1×10$^6$ cells were placed in a 1.5 mL tube, centrifuged at 400×g for 4 minutes, and the supernatant was discarded to collect the cells. The collected cells were added with 100 µL of the diluted Rituximab-scFv-V2122, mixed well, and then incubated on ice for 30 minutes. The content was centrifuged again, the supernatant was discarded, added with 1 mL of PBS to wash the cells, and the cells were then collected. To 100 µL of cell, added was 13 nM or 1.3 nM of FITC-Psyche, or, 0.5 µg/mL (3.3 nM) of Anti-His-Tag mAb-Alexa Flour 488 (Medical and Biological Laboratories Co., Ltd.), the content was mixed, and incubated on ice for 30 minutes. After the incubation, the content was centrifuged again, the supernatant was discarded, added with 1 mL of PBS to wash the cells, and the cells were then collected. The collected cells were suspended in 500 µL of PBS, and measured on a flow cytometer (guava easyCyte Single System; Merck Millipore).

Figure 8:
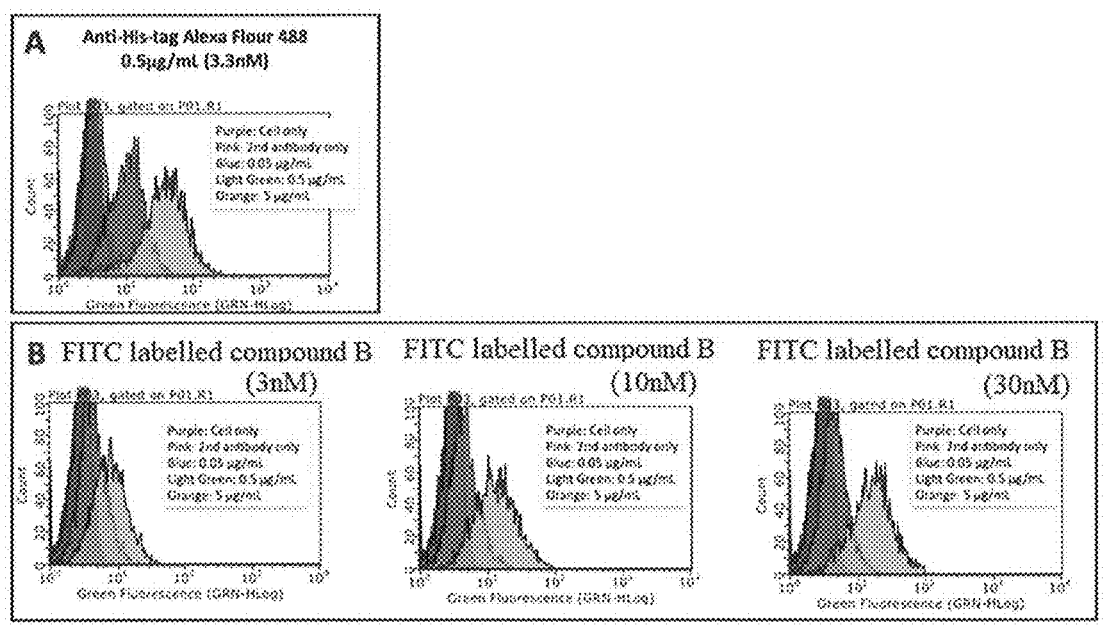
FIG. 8 shows results of CD20 recognition analysis over RAMOS cell by flow cytometry.

Results are show in FIG. 8.

Referring first to Assay Result A obtained by using Alexa Flour 488-labeled anti-His-Tag antibody (3.3 nM), shifts of fluorescence intensity were observed to be dependent on the concentration of Rituximab-scFv-V2122, proving that the thus prepared Rituximab-scFv-V2122 recognized CD20 on the RAMOS cell surface. Referring next to Assay Result B obtained by using FITC-labeled Compound B, shifts of fluorescence intensity were observed to be dependent on the concentration of Rituximab-scFv-V2122 similarly to the case with the labeled anti-His-Tag antibody. Since concentration-dependent shifts of fluorescence intensity were also confirmed at the individual concentrations of Compound (3 nM, 10 nM, 30 nM), this was the first to prove binding of the FITC-labeled Compound B with Rituximab-scFv-V2122.

Comparative Example 1: Study 1 on Performance Compared with Wild-Type Streptavidin Mutants Y43A and S45A (Comparison of Biotin Binding Potential)

First, using restriction enzyme sites NdeI and XhoI in the pET21a(+) vector, a vector having a wild-type core streptavidin sequence (Patent Literature 1, amino acid sequence in SEQ ID NO: 2) introduced therein was produced. Next, as a template for the vector, a mutant of Y43A or S45A (amino acids at positions 31 and 33 in the amino acid sequence in SEQ ID NO: 2 are substituted respectively) was produced by using the primer set listed below, by site directed mutagenesis. The target protein was expressed in *Escherichia coli* (BL21(DE3) strain), collected in the form of inclusion body, refolded by the dilution method, followed by affinity purification and gel filtration purification to obtain a tetramer forming fraction. More specifically, the purified inclusion body was dissolved overnight in a denaturing buffer (6 M guanidine hydrochloride, 50 mM Tris-HCl, 200 mM NaCl, 1 mM EDTA, pH8.0 at 4° C.). After measuring the absorbance of the liquid at 280 nm, a portion of the solubilized liquid containing 5 mg of product was added dropwise into 50 mL of a refolding buffer (50 mM Tris-HCl, 300 mM NaCl, 1 mM EDTA, 400 mM Arginine-HCl, pH8.0 at 4° C.) under stirring, and allowed to stand still at 4° C. for two days for. For stable refolding, the storage time was limited to two days. After the 2-day storage, the product was subjected to affinity purification using Ni-NTA resin (cOmplete His-Tag Purification Resin; Roche), followed by purification by gel filtration (HiLoad 16/60 Superdex 200 pg, from GE Healthcare BioScience Corp.) using PBS as a buffer, to obtain the tetramer fraction.

Using the thus purified two wild-type core streptavidin mutants (csa-Y43A, csa-S45A), purified LISA314 and V2122 protein, interaction with biotin (Sigma-Aldrich) was investigated by surface plasmon resonance (SPR). More specifically, using Biacore T200 (GE Healthcare BioScience Corp.) as a measuring instrument, and Sensor Chip NTA (GE Healthcare BioScience Corp.) as a sensor chip, the protein was immobilized on the sensor chip by way of His-Tag having been fused to the core protein. The running buffer was prepared using HBS-P(+), as described in the manual. A dilution series of Compound was prepared by using the running buffer in seven steps of 1.8 nM, 9 nM, 18 nM, 90 nM, 180 nM, 900 nM and 1800 nM, to obtain data.

```
Primer Set:
                                    (SEQ ID NO: 17)
   Y43A Fw:    GGCACCGCCGAAAGCGCCGTGGGTAAT (SEQ ID NO: 18)
   Y43A Rv:    GCTTTCGGCGGTGCCGGTCAGCGCACC (SEQ ID NO: 19)
   S45A Fw:    TATGAAGCCGCCGTGGGTAATGCGGAA (SEQ ID NO: 20)
   S45A Rv:    CACGGCGGCTTCATAGGTGCCGGTCAG
```

Figure 9:
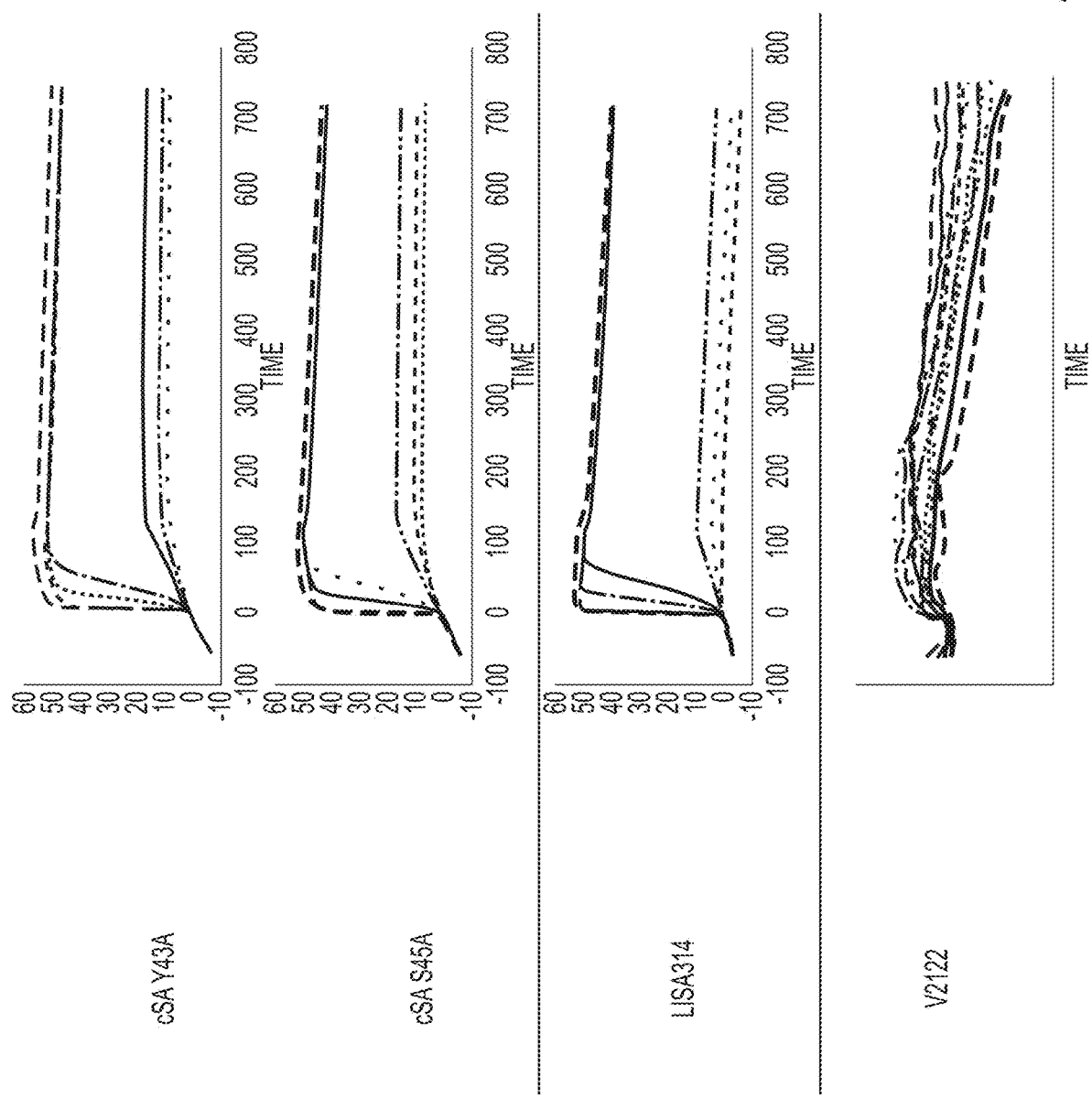
FIG. 9 shows comparison of performance of wild-type streptavidin mutants Y43A and S45A.

Results are shown in FIG. 9.

Judging from the sensorgram, both of wild-type streptavidin mutants cSA-Y43A and cSA-S45A showed interaction in a biotin concentration-dependent manner, proving a strong specific binding with biotin, equivalent to that shown by LISA314 which can dissociate from biotin only extremely slowly. Meanwhile, V2122 did not show biotin concentration-dependent interaction, proving absence of specific binding. As a consequence, wild-type streptavidin mutants cSA-Y43A and cSA-S45A, and LISA314 were confirmed to be proteins totally different from V2122 in terms of interaction with biotin.

Comparative Example 2: Study 2 on Performance Compared with Wild-Type Streptavidin Mutants Y43A and S45A (Proof of Specific Binding Potential Between Compound C and V2122)

Using the purified two wild-type core streptavidin mutants (cSA-Y43A, cSA-S45A) described above, and purified V2122 protein, interaction with Compound C was investigated by surface plasmon resonance (SPR). More specifically, using Biacore T200 (GE Healthcare BioScience Corp.) as a measuring instrument, and Sensor Chip NTA (GE Healthcare BioScience Corp.) as a sensor chip, the protein was immobilized on the sensor chip by way of His-Tag having been fused to the core protein. The running buffer was prepared using HBS-P(+), as described in the manual. A dilution series of Compound was prepared by using the running buffer in seven steps of 1.8 nM, 9 nM, 18 nM, 90 nM, 180 nM, 900 nM and 1800 nM, to obtain data.

Figure 10:
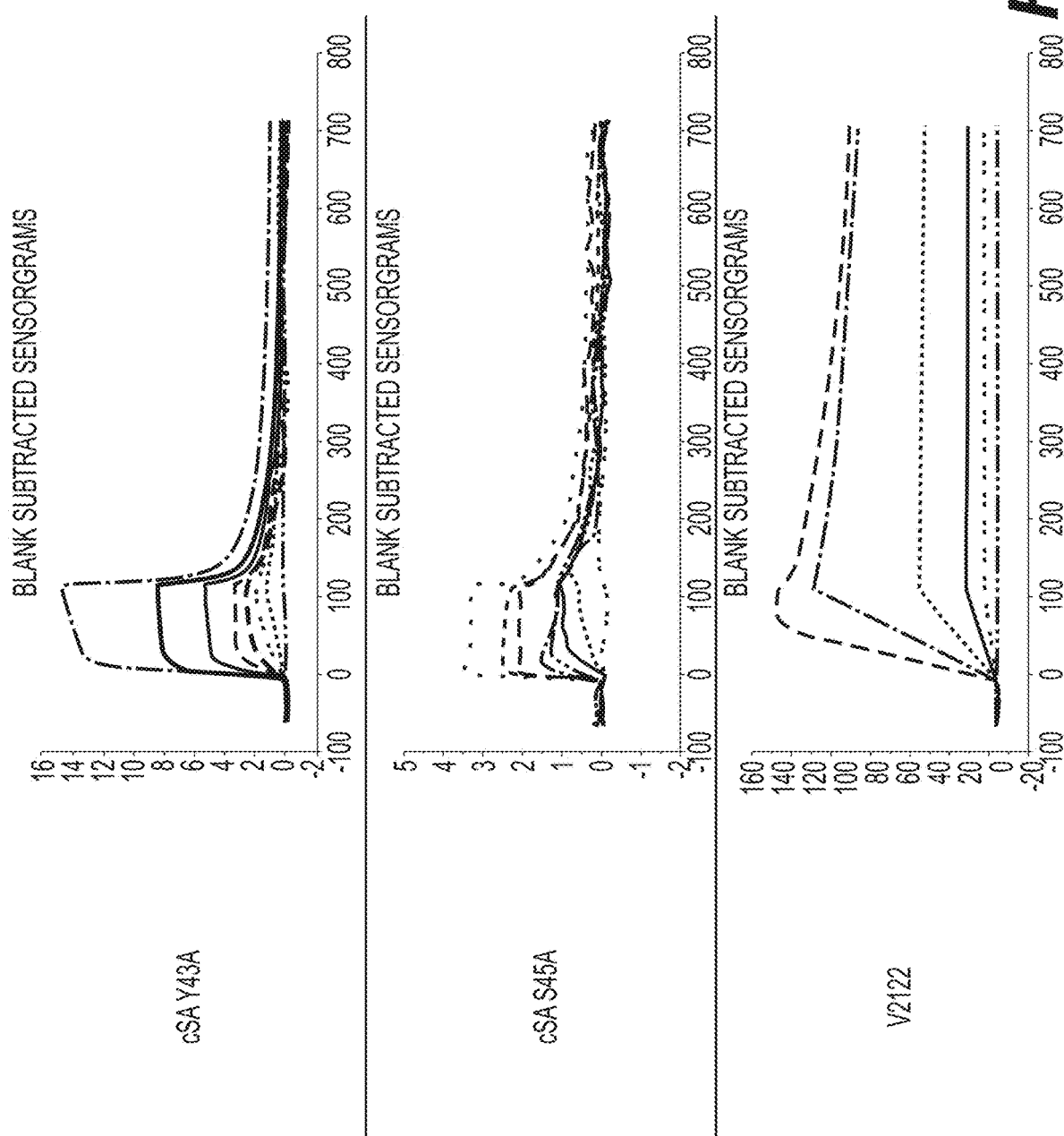
FIG. 10 shows comparison of performance of wild-type streptavidin mutants Y43A and S45A.

Results are shown in FIG. 10.

From the measurement, wild-type streptavidin mutant cSA-Y43A showed a concentration-dependent interaction with Compound C but with a fast dissociation, meanwhile wild-type streptavidin mutant cSA-S45A showed only a very weak, concentration-dependent interaction with Compound C. In contrast, V2122 and Bis-iminobiotin showed a concentration-dependent interaction, characterized by a specific binding showing only an extremely slow dissociation. As a consequence, wild-type streptavidin mutants cSA-Y43A and cSA-S45A were confined to be proteins totally different from V2122 in terms of interaction with Compound C. Compound C and V2122 were confirmed to show a highly specific strong binding.

Figure 11:
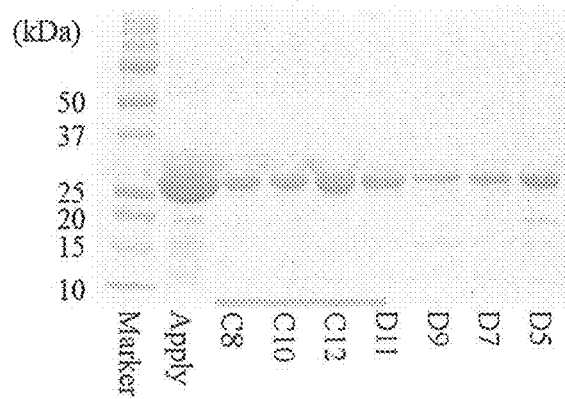
FIG. 11 shows results of SDS-PAGE of expressed anti-epiregulin scFv after purified by gel filtration.

Example 9: Crystallographic Analysis of Epiregulin Antigen and Anti-Epiregulin scFv Antibody (1) Culture for Expression, and Purification of Anti-Epiregulin scFv Antibody Escherichia coli was transformed with a plasmid encoding anti-epiregulin scFv. A colony of Escherichia coli was precultured in an LB liquid medium, the main culture was allowed to proceed in a 2×YT medium, and IPTG was added to induce expression of anti-epiregulin scFv. The collected bacterial cells were crushed in a Tris buffer, centrifuged, and the supernatant was collected. The supernatant was then purified successively through a Ni column, anion exchange column, and gel filtration column. Results of SDS-PAGE after the gel filtration are shown in FIG. 11.

The antibody was crystallized at 20° C. by the sitting drop vapor diffusion method. A good crystal was obtained by preparing a drop by mixing the purified protein solution (15 mg/mL anti-epiregulin scFv), 20 mM Tris-HCl (ph 7.5), 300 mM NaCl) with a reservoir solution (2% Tacsimate (ph 7.0), 5% 2-propanol, 0.1 M imidazole (ph 7.0), 11% PEG 3350).

The obtained crystal was analyzed by X-ray diffractometry using SPring-8 BL44XU beam line to obtain diffraction data with a 2.4-Å resolution. The data was processed using HKL2000 program, the phase was determined using Phaser based on the molecular replacement method, and the structure was further refined using Refmac5.

(2) Preparation, Crystallization and Structural Analysis of Conjugate of Anti-Epiregulin scFv and Epiregulin Five milligrams each of anti-epiregulin scFv and epiregulin (extracellular domain) were mixed, and the mixture was incubated at 25° C. for one hour. The mixture was purified through a gel filtration column, to collect a conjugate fraction.

The conjugate was crystallized by the hanging drop vapor diffusion method at 20° C. A good crystal was obtained by preparing a drop by mixing a conjugate sample (15 mg/mL scFv-epiregulin complex, 20 mM Tris-HCl (ph 7.5), 300 mM NaCl) with a reservoir solution (0.1 M magnesium chloride, 0.1 M sodium acetate (pH 5.1), 10% PEG 6,000).

The obtained crystal was analyzed by X-ray diffractometry using SPring-8 BL32XU beam line to obtain diffraction data with a 1.8-Å resolution. The data was processed using HKL2000 program, the phase was determined using Phaser based on the molecular replacement method, and the structure was further refined using Refmac5.

(3) Recognition Mechanism of Epiregulin by Anti-Epiregulin scFv Antibody

Figure 12:
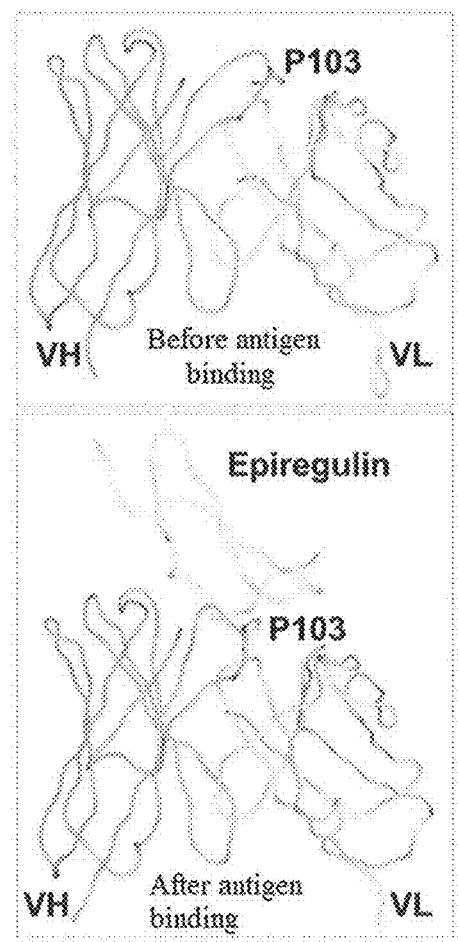
FIG. 12 shows results of structural analysis of a conjugate of anti-epiregulin scFv and epiregulin.

Crystal structures of anti-epiregulin scFv in itself, and in the form of conjugate with epiregulin revealed the followings. There were three major sites where anti-epiregulin scFv and epiregulin can interact, which were roughly classified into interaction of the N-terminus region of epiregulin with CDR1 and CDR3 in the light chain of anti-epiregulin scFv (Interaction 1); interaction of the C-terminus region of epiregulin with CDR2 in the heavy chain of anti-epiregulin scFv (Interaction 2); and interaction of the β-sheet region of epiregulin with CDR3 in the heavy chain of anti-epiregulin scFv (Interaction 3). In interactions 1 and 2, the loop structure of epiregulin changed, but without distinct change in the structure of CDR in anti-epiregulin HM (scFv). In contrast, in the region of Interaction 3, the structure of epiregulin did not change, but with a structural change in CDR3 in the heavy chain of anti-epiregulin scFv, characterized by cis-trans isomerization of P103 residue, where antigen was found to be recognized by induced fit (FIG. 12).

Example 10

(1) Production of Anti-Epiregulin scFv-V2122 Expression Vector

It is widely known that a fusion protein of single chain variable region antibody and streptavidin (scFv-SA), when expressed in *Escherichia coli*, often forms an aggregate or inclusion body, and is difficult to be recovered in a solubilized form. For this reason, a standard procedure for obtaining scFv-SA protein is such as denaturing the inclusion body and refolding the protein. Production of protein by refolding is, however, time-consuming and labor-consuming. A method employed in this invention is such as allowing both of skp, which is a protein with chaperone function, and anti-epiregulin scFv-V2122 to be expressed in *Escherichia coli*, so that the protein becomes collectable in a soluble fraction.

More specifically, the gene sequence of chaperone skp (SEQ ID NO: 23) was designed to be suited to a codon used by *Escherichia coli*, based on the protein sequence (SEQ ID NO: 24). Meanwhile, the gene sequence of a fusion protein (anti-epiregulin scFv-V2122) formed by single chain variable region antibody of anti-epiregulin antibody (anti-epiregulin scFv) and V2122 was designed in such a way that the variable regions of anti-epiregulin antibody were ligated in the direction from VH to VL using a linker (GGGGS)×4 (SEQ ID NO: 35), and VL and V2122 were ligated with a linker (GGGGSGGGG) (SEQ ID NO: 36), and then suited to a codon used by *Escherichia coli*, in the same way as skp. These two gene sequences were artificially synthesized by Artificial Gene Synthesizing Service (Life Technologies Corp.). For the variable regions VH and VL, reference was made on Lee Y H, et al., *Biochem. Biophys. Res. Commun.*, 2013 Nov. 29; 441(4):1011-7. doi: 10.1016/j.bbrc2013.11.014. Epub 2013 Nov. 12. PubMed PMID: 24239549.

The nucleotide sequence and the amino acid sequence of the single chain variable region antibody of anti-epiregulin antibody (anti-epiregulin scFv) are represented by SEQ ID NOs: 21 and 22.

Positions of the individual sequences in the amino acid sequence represented by SEQ ID NO: 22 are listed below:
pelB signal sequence: amino acid NOs. 1-22
VH sequence: amino acid NOs. 23-140
Linker sequence 1: amino acid NOs. 141-164
VL sequence: amino acid NOs. 165-273
6×His-Tag sequence: amino acid NOs. 274-279

The nucleotide sequence and the amino acid sequence of the fusion protein formed by anti-epiregulin scFv and V2122 (anti-epiregulin scFv-V2122) are represented by SEQ ID NOs: 29 and 30.

Positions of the individual sequences in the amino acid sequence represented by SEQ ID NO: 30 are listed below:
pelB signal sequence: amino acid NOs. 1-22
VH sequence: amino acid NOs. 23-140
Linker sequence 1: amino acid NO. 141-164
VL sequence: amino acid NOs. 165-272
Linker sequence 2: amino acid NOs. 273-282
V2122 sequence: amino acid NOs. 283-409
6×His-Tag sequence: amino acid NOs. 410-415

Next, of these two artificially synthesized genes, the gene sequence of skp was introduced into multicloning site 1 (MCS1) of pETDuet-1 vector (from Novagen), and the gene sequence of anti-epiregulin scFv-V2122 was introduced into MCS2. More specifically, first, the vector chain was straightened using restriction enzyme NcoI, the gene sequence of skp was amplified by PCR using primers (MCS1_skp_Fw: AGGAGATATACCATGATGAAAAAATGGCTGCTGGC (SEQ ID NO: 37) and MCS1_skp_Rv: CGCCGAGCTCGAATTTTATTTCACTTGTTTCAGAACG (SEQ ID NO: 38)), designed according to the manual of In-Fusion HD Cloning Kit (Clontech Laboratories, Inc.), purified from a cut gel, subjected to cloning using In-Fusion HD Cloning Kit based on ligation with the straightened vector, the cloned plasmid was then examined by sequence analysis, to select a target clone. Next, the plasmid vector having skp gene inserted therein was straightened using restriction NdeI, the gene sequence of anti-epiregulin scFv-V2122 was amplified in the same way as described above by PCR using primers (MCS2_scFvV2122_Fw; AAGGAGATATACATAATGAAATACCTATTGCCTACGCAG (SEQ ID NO: 39) and MCS2 scFvV2122_Rv; TTGAGATCTGCCATATCAGTGGTGGTGGTGGTGGTGGCTG (SEQ ID NO: 40)), designed according to the manual of In-Fusion HD Cloning Kit (Clontech Laboratories, Inc.), purified from a cut gel, subjected to cloning using In-Fusion HD Cloning Kit based on ligation with the straightened vector, the cloned plasmid was then examined by sequence analysis, to select a target clone. In this way, a vector (pETDuet-epiregulin-scFvV2122_skp) capable of concurrently expressing skp protein and anti-epiregulin scFv-V2122 protein was completed.

(2) Expression of Anti-Epiregulin scFv-V2122 Protein

BL21(DE3) (Nippon Gene Co., Ltd.) was transformed with pETDuet-epiregulin-scFvV2122 skp, and precultured overnight in 2×YT medium (Sigma-Aldrich) at 37° C. The medium used for the preculture was added to a new medium in a 100-fold dilution, and the culture was continued at 37° C. until OD (600 nm) becomes 0.5 to 2.0. Next, a solution containing 1 mM IPTG and 1% Triton X-100 (final concentration), was added, and the content was cultured at 16° C. for 4 hours, the supernatant was collected, and stored at 4° C.

(3) Purification of Anti-Epiregulin scFv-V2122 Protein

Anti-epiregulin scFv-V2122 protein was partially purified based on the batch process, using 6×His-Tag having been attached to the C-terminus. More specifically, cOmplete His-Tag Purification Resin equilibrated with buffer A (50 mM Tris-HCl, 0.2 M NaCl, 1 mM EDTA, 5 mM imidazole, pH8.0) was added to the supernatant of culture having been stored at 4° C., and the mixture was stirred for 2 hours up to overnight at 4° C., so as to allow the resin to bind the protein. Next, the resin was collected in a column, and washed with 20 column volumes of buffer A. The column was then eluted with buffer B (50 mM Tris-HCl, 0.2 M NaCl, 1 mM EDTA, 400 mM imidazole, pH8.0), to collect a crude product of anti-epiregulin scFv-V2122.

Figure 13:
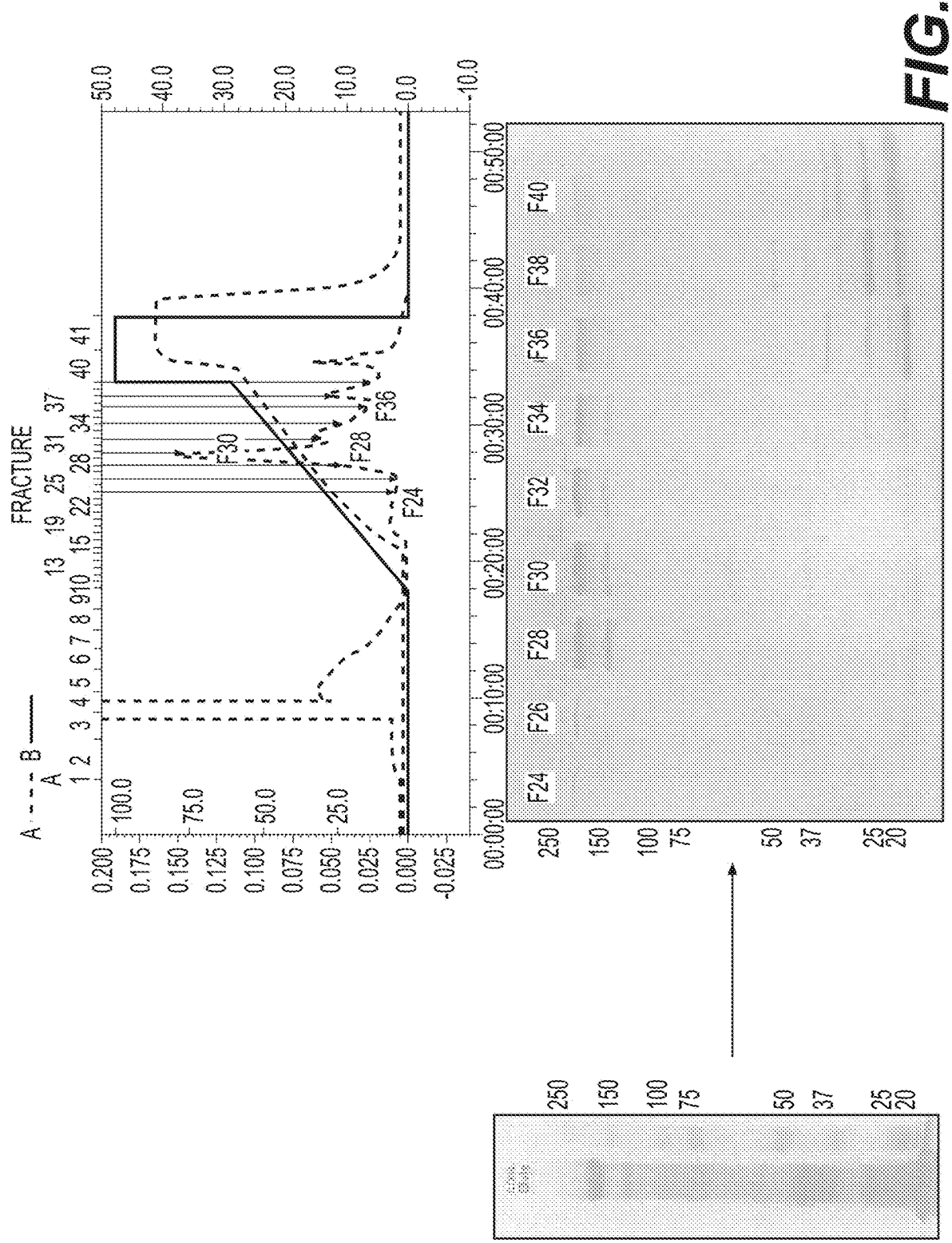
FIG. 13 shows results of purification of anti-epiregulin scFv-V2122 protein.

Next, the protein was purified using a hydroxyapatite column (Bio-Scale CHT2-I) (Bio-Rad Laboratories, Inc.). More specifically, the crude product of anti-epiregulin scFv-V2122 was concentrated through Vivaspin Turbo 15 column (molecular weight cutoff: 30,000), and then using PD-10 column, the buffer of the crude product was replaced with a starling buffer (5 mM Na$_2$PO$_4$, pH7.0). The hydroxyapatite column was fully equilibrated using the starting buffer, and the crude product whose buffer had been replaced was applied to the column. After washing with 20 column volumes, the column was eluted with 15 column volumes of elution buffer (400 mM Na$_2$PO$_4$, pH7.0) with a gradient from 0% to 60%, to prepare a target purified product (FIG. 13).

(4) Expression and Purification of Epiregulin IgG

Epiregulin IgG was expressed and purified making reference to Non-Patent Literature written by Lee et al. More specifically, gene sequences were artificially synthesized by ligating VL with a human light chain constant region, and by ligating VH with a human heavy chain constant region as described in the literature. They were denoted as light chain and heavy chain, respectively, of epiregulin IgG The nucleotide sequence and the amino acid sequence of the heavy chain of epiregulin IgG are represented by SEQ ID NOs: 31 and 32; and the nucleotide sequence and the amino acid sequence of the light chain of epiregulin IgG are represented by SEQ ID NOs: 33 and 34.

Next, the light chain and the heavy chain were introduced into pcDNA3.4 vector using pcDNA3.4 TOPO TA Cloning Kit (Life Technologies Corp.), to prepare expression vectors. The protein was expressed by introducing the vectors for the light chain and heavy chain in a ratio of 2:1, into Expi293F cell (Life Technologies Corp.) using ExpiFectamine 293 Transfection Kit. The cells were cultured following the usage and dosage instructions given in the manual of Expi293 Expression System Kit, at a $CO_2$ concentration of 8% and number of rotation for shaking of 125 rpm, in a 1 L Erlenmeyer flast (Corning Inc.), on a thermostat shaker for mammalian cell C02-BR-43FL (Titec Corp.). After 5-day culture, the cells were removed by centrifugation, and the supernatant was collected and stored at 4° C. Next, epiregulin IgG was purified from the culture supernatant stored at 4° C., using Bio-Scale MiniUNOspher SUPrA affinity cartridge (Bio-Rad Laboratories, Inc.) following the usage and dosage instructions given in the manual.

Expression and Purification of Pro-EPR-mFc Protein (Pro-EPR-mFc), obtained by fusing the extracellular domain of epiregulin with the Fc region in the heavy chain of murine IgG1 antibody, was expressed and purified. The nucleotide sequence and the amino acid sequence of Pro-PR-mFc are represented by SEQ ID NOs: 25 and 26. More specifically, a gene produced by fusing the extracellular domain of epiregulin with the Fc region in the heavy chain of murine IgG1 antibody was introduced into pcDNA3.4 vector, and the protein was expressed and purified in the same way as described above in "Expression and Purification of Epiregulin IgG".

(5) FITC Labeling of Purified Product, and Test of Labeled Product

An FITC-labeled product of the thus purified anti-epiregulin scFv-V2122 (anti-epiregulin scFv-V2122-FITC) was produced using Fluorescein Labeling Kit-NH (Dojindo Laboratories) following the usage and dosage instructions of the kit. Also epiregulin IgG and anti-epiregulin scFv protein were labeled in the same way.

Figure 14:
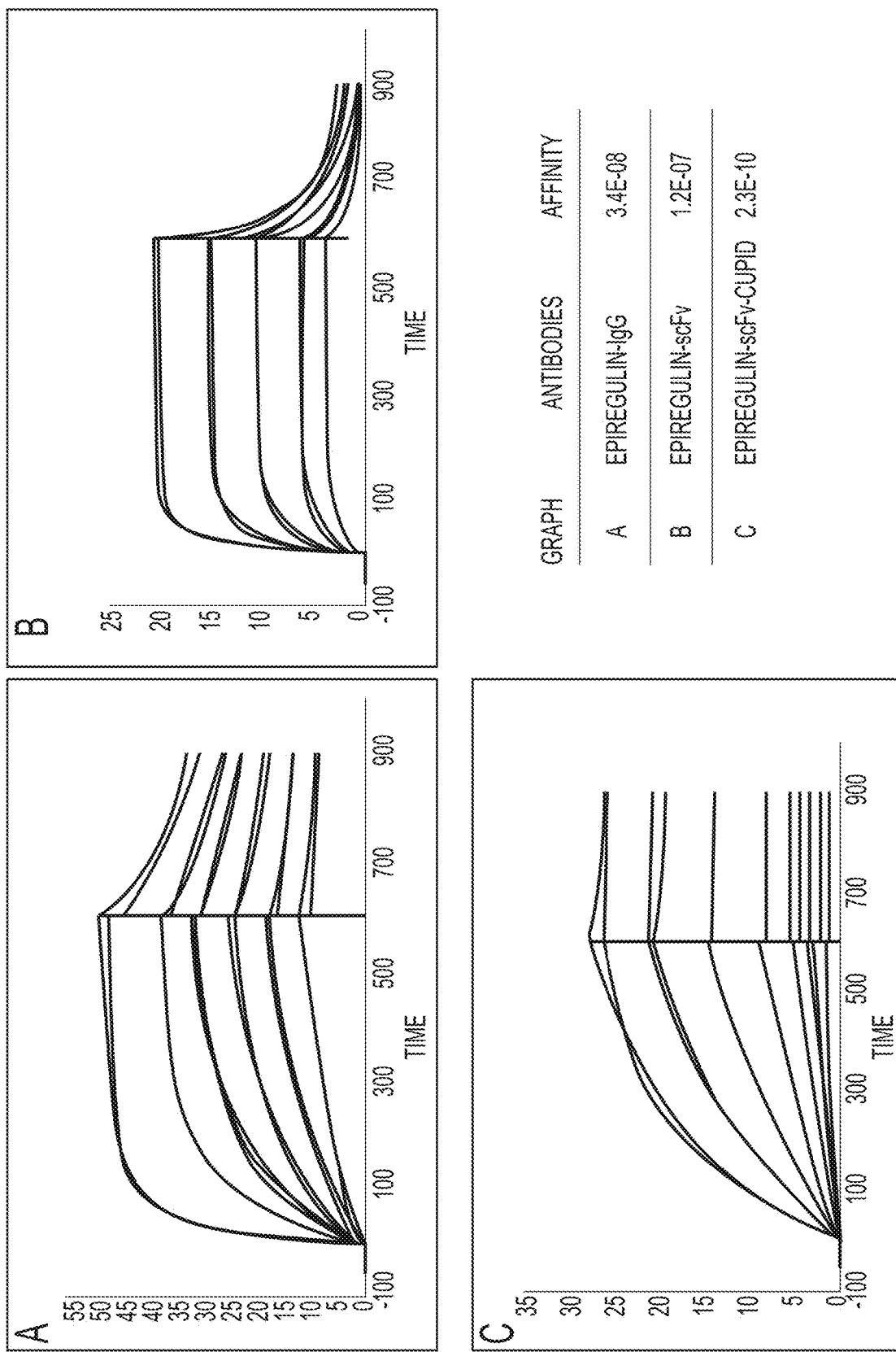
FIG. 14 shows results of antigen-binding ability of anti-epiregulin scFv-V2122-FITC, confirmed by SPR (Biacore T200).

Next, in order to confirm whether the labeling reduced the binding potential or not, the antigen binding potential of anti-epiregulin scFv-V2122-FITC was confirmed by SPR (Biacore T200). More specifically, protein (Pro-EPR-mFc) obtained by fusing the extracellular domain of epiregulin which functions as a ligand with murine Fe region is captured on the sensor chip CM5 having anti-Murine IgG antibody immobilized thereon, and then eluted for kinetics assay with an analyte composed of a two-fold dilution series prepared by diluting a 20 nM anti-epiregulin scFv-V2122-FITC solution into nine steps (FIG. 14). From the study, anti-epiregulin scFv-V2122-FITC was confirmed to keep the binding potential to the antigen, showing an affinity of 2.3E-10, even after labeling. Also epiregulin IgG and anti-epiregulin scFv protein were investigated in the binding test in the same way as described above, using a two-fold dilution series prepared by diluting a 300 nM solution into nine steps (FIG. 14). Data was analyzed using Biacore evaluation software. Both of epiregulin IgG-FITC and anti-epiregulin scFv-FTC were confirmed to keep the binding potential even after being labeled, showing affinity values of 3.4E-08 and 1.2E-07, respectively, proving that anti-epiregulin scFv-V2122-FITC has an affinity approximately 100 to 1000 times larger than the affinity demonstrated by epiregulin IgG-FITC and anti-epiregulin scFv-FITC.

(6) Cell Staining Using Anti-Epiregulin scFv-V2122-FITC, and Analysis of Internalization Human colorectal cancer-derived DLD1 cells, used for cell staining, were cultured in a complete medium RPNI1640 (containing 10% FBS), and seeded in uClear 96-well plate (Greiner) in a density of $1\times10^4$ cells/well, two days before the assay. In the cell staining, first the medium was replaced with a complete medium added with Hoechst 33342 so as to adjust the concentration to 1 µM, and 15 minutes after, each of anti-epiregulin scFv-V2122-FITC, epiregulin IgG-FITC and anti-epiregulin scFv-FITC was added to the individual wells so as to adjust the concentration to 25 nM, 50 nM and 100 nM.

Binding of antibody to the cell surface, and internalization were analyzed using IN Cell Analyzer 6000 (GE Healthcare BioScience Corp.), and recorded by time lapse imaging at 5 minute intervals.

Figure 15:
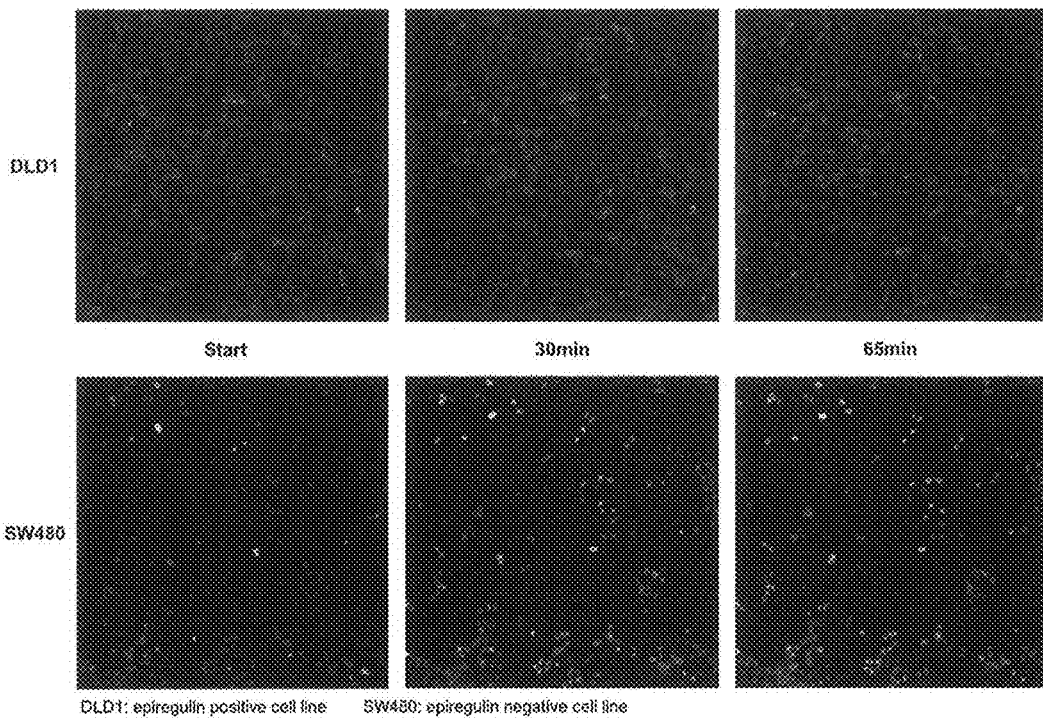
FIG. 15 shows analytical results of cell staining and internalization using anti-epiregulin scFv-V2122-FITC.

From the study, staining of the surface of the cell membrane was observed for all of anti-epiregulin scFv-V2122-FITC, epiregulin IgG-FITC and anti-epiregulin scFv-FTC. A distinct internalization was observed particularly for anti-epiregulin scFv-V2122-FITC, which began to be observed approximately 10 minutes after the addition of antibody. Sixty-five minutes after, the almost entire part of fluorescence was found to migrate into the cytoplasm (FIG. 15).

(7) FACS Analysis Using Anti-Epiregulin scFv-V2122-FITC

Cell surface binding potential was determined by FACS, using labeled antibodies that are anti-epiregulin scFv-V2122-FITC, epiregulin IgG-FITC and anti-epiregulin scFv-FITC. More specifically, dilute solutions of the labeled antibodies having concentrations of 0 nM, 0.5 nM, 5 nM and 50 nM were allowed to react on ice for 30 minutes with DLD1 cells ($1\times10^6$ cells/mL, 500 mL) having epiregulin expressed therein, and then fluorescence was measured using flow cytometer guava easyCyte 5. The measurement followed the usage and dosage instructions given in the manual of the instrument.

Figure 16:
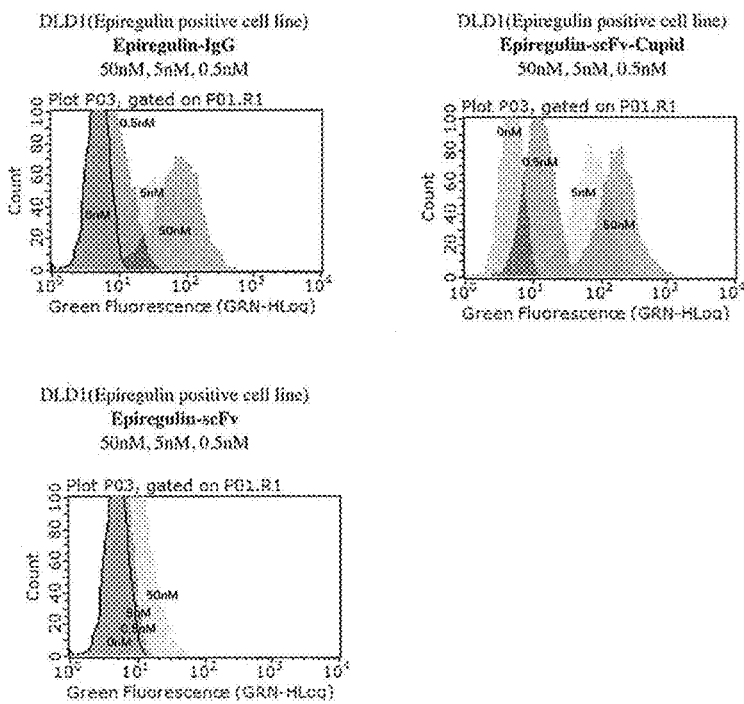
FIG. 16 shows results of FACS analysis using anti-epiregulin scFv-V2122-FITC.

In this study, among the labeled antibodies, anti-epiregulin scFv-V2122-FITC and epiregulin IgG-FITC showed equivalent levels of binding potential, whereas anti-epiregulin scFv-FITC showed a level of binding potential lower than those shown by the former two (FIG. 16).

Example 11: In Vivo Imaging of Rituximab-scFv-V2122

(1) Construction of Expression Vector

Rituximab single chain antibody (single chain variable fragment; scFv) was designed so that the light chain variable region VL and the heavy chain variable region VH were ligated in the order of VL and VH using a linker (GGGGS)× 4. VL was attached with PelB sequence as a secretion signal, to produce a sequence of PelB-VL-(GGGGS)$_4$—VH. scFv was ligated with V2122 using a linker (GGGGSGGGG) (referred to as Rituximab-scFv-V2122, hereinafter) (amino acid sequence: SEQ ID NO: 42). A gene sequence for expressing protein was synthesized by Artificial Gene Synthesizing Service (Life Technologies Corp.) (gene sequence: SEQ ID NO: 41). An expression vector was produced by incorporating Rituximab-scFv-V2122 to multicloning site 2 (MCS2) of pETDuet-1, in the same way as described in "(1) Production of Anti-Epiregulin scFv-V2122 Expression Vector" in Example 10.

The amino acid sequence and the nucleotide sequence of Rituximab-scFv-V2122 are shown below.

Gene Sequence of Rituximab-scFv-V2122
(SEQ ID NO: 41)
ATGAAATATCTGCTGCCGACCGCAGCAGCGGGTCTGCTGCTGCTGGCAGC

ACAGCCTGCAATGGCACAGATTGTTCTGAGCCAGAGTCCGGCAATTCTGA

GCGCATCACCGGGTGAAAAAGTTACCATGACCTGTCGTGCAAGCAGCAGC

GTTAGCTATATTCATTGGTTTCAGCAGAAACCGGGTAGCAGCCCGAAACC

GTGGATTTATGCAACCAGCAATCTGGCAAGCGGTGTTCCGGTTCGTTTTA

GCGGTAGCGGTAGTGGCACCAGCTATAGCCTGACCATTAGCCGTGTTGAA

GCAGAAGATGCAGCAACCTATTATTGTCAGCAGTGGACCAGTAATCCGCC

TACCTTTGGTGGTGGCACCAAACTGGAAATTAAAGGAGGTGGTGGTTCAG

GAGGTGGTGGTAGCGGTGGCGGTGGTAGCGGAGGTGGTGGTAGCCAGGTT

CAGCTGCAGCAGCCTGGTGCAGAACTGGTTAAACCGGGTGCAAGCGTTAA

AATGAGCTGTAAAGCAAGCGGTTATACCTTTACCAGCTACAATATGCATT

GGGTTAAACAGACACCGGGTCGTGGTCTGGAATGGATTGGTGCAATTTAT

CCGGGTAATGGTGATACGAGCTATAACCAGAAATTCAAAGGCAAAGCAAC

CCTGACCGCAGATAAAAGCAGCAGTACCGCCTATATGCAGCTGAGCAGTC

TGACCAGCGAAGATAGCGCAGTTTATTACTGTGCACGTAGCACCTATTAC

GGTGGTGATTGGTATTTTAACGTTTGGGGTGCAGGCACCACCGTTACCGT

TAGCGCAGGCGGAGGTGGAAGCGGTGGAGGTGGAGCAGAAGCAGGTATTA

CCGGCACCTGGTCAGATCAGCTGGGTGATACCTTTATTGTTACCGCAGGC

GCAGATGGTGCACTGACCGGTACATATGAAATGCAGTTGGTAATGCAGA

AAGCCGTTATGTTCTGACCGGTCGTTATGATAGCGCACCGGCAACCGATG

GTAGCGGCACCGCACTGGGTTGGACCGTTGCATGGAAAAATAACAGCAAA

AATGCACATAGCGCAACCACATGGTCAGGTCAGTATGTTGGTGGTGCAGA

TGCCAAAATTAACACCCAGTGGCTGCTGACCAGTGGTACAACCAATGCAA

ATGCCTGGAAAAGCACCCTGGTTGGTCATGATACATTTACCAAAGTTAAA

CCGAGCGCAGCGAGCGGTGGTCATCATCATCACCATCAT

Amino Acid Sequence of Rituximab-scFv-V2122
(SEQ ID NO: 42)
MKYLLPTAAAGLLLLAAQPAMAQIVLSQSPAILSASPGEKYTMTCRASSS

VSYIHWFQQKPGSSPKPWIYATSNLASGVPVRFSGSGSGTSYSLTISRVE

AEDAATYYCQQWTSNPPTFGGGTKLEIKGGGGSGGGGSGGGGSGGGGSQV

QLQQPGAELVKPGASVKMSCKASGYTFTSYNMHWVKQTPGRGLEWIGAIY

PGNGDTSYNQKFKGKATLTADKSSSTAYMQLSSLTSEDSAVYYCARSTYY

GGDWYFNVWGAGTTVTVSAGGGSGGGGAEAGITGTWSDQLGDTFIVTAG

ADGALTGTYENAVGNAESRYVLTGRYDSAPATDGSGTALGWTVAWKNNSK

NAHSATTWSGQYVGGADAKINTQWLLTSGTTNANAWKSTLVGHDTFTKVK

PSAASGGHHHHHH (2) Expression and Partial Purification of Protein

Figure 17:
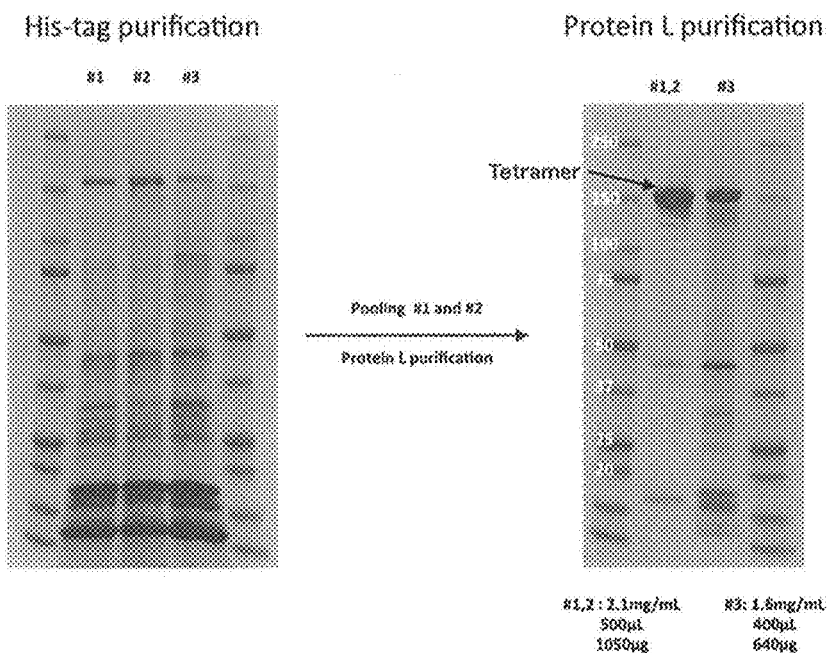
FIG. 17 shows results of purification of Rituximab-scFv-V2122 protein through Protein L column.

Rituximab-scFv-V2122 protein was expressed in *Escherichia coli*. More specifically, pETDuet-1(skp)Rituximab-scFv-V2122, which is a plasmid vector, was introduced into BL21 (DE3) (Nippon Gene Co., Ltd.) for transformation. The transformed *Escherichia coli* was cultured overnight in 100 mL of 2×YT medium at 37° C. Next, 20 mL of the preculture liquid was added to 1 L of 2×YT medium, and the mixture was cultured at 37° C. Upon confirming $OD_{600nm}$=2.0, IPTG and Triton X-100 were added while adjusting the final concentration to 1 mM and 1%, respectively, and the mixture was cultured for 18 hours to 24 hours at 20° C. The supernatant of culture was then collected by centrifugation, and 4 L of supernatant was pooled. Next, the protein was partially purified using Ni-NTA resin. More specifically, 5 mL equivalent of cOomplete His-Tag Purification Resin (Roche) was added to the 4-L pool, the mixture was kept stirred using a stirrer overnight at 4° C. so as to allow a binding process to proceed. The resin was then collected into a column, washed with 50 mL of washing buffer (50 mM Tris-HCl, 0.2 M NaCl, 1 mM EDTA, 5 mM imidazole, pH8.0), and then eluted with 40 mL of elution buffer (50 mM Tris-HCl, 0.2 M NaCl, 1 mM EDTA, 400 mM imidazole, pH8.0). The eluate was concentrated using Vivaspin Turbo 15, MWCO=30,000 (Sartorius AG) to 1 to 3 mL, and then stored frozen (−80° C.) (FIG. 17).

(3) Purification of Rituximab-scFv-V2122 Protein Through Protein L Column

The protein was further purified by using Protein L 1 mL column (HiTrap L (GE Healthcare BioScience Corp.)). More specifically, the column was equilibrated using 10 column volumes of PBS, and a sample diluted 2-fold with PBS was applied. The column was washed with 10 column volumes of PBS, and then eluted with 10 column volumes of 10 mM glycine-HCl buffer pH2.5. The buffer in the eluate was immediately replaced with PBS using PD10 column, and then concentrated using Vivaspin Turbo 15, MWCO=100,000 (Sartorius AG) to 0.3 to 1 mL, and then stored cool (FIG. 17).

(4) Fluorescent Labeling

The thus purified Rituximab-scFv-V2122 was preliminarily mixed with Psyche F-IRDye 800 (Compound 44 in Example) dissolved in DMSO (final concentration is tenfold molar concentration), and incubated on ice for 10 minutes. The buffer was then replaced with Japanese Pharmacopoeia physiological saline (Otsuka Pharmaceutical Co., Ltd.) using Zeba Spin Desalting Column (Thermo Fisher Scientific Inc.).

(5) Flow Cytometer

Figure 18:
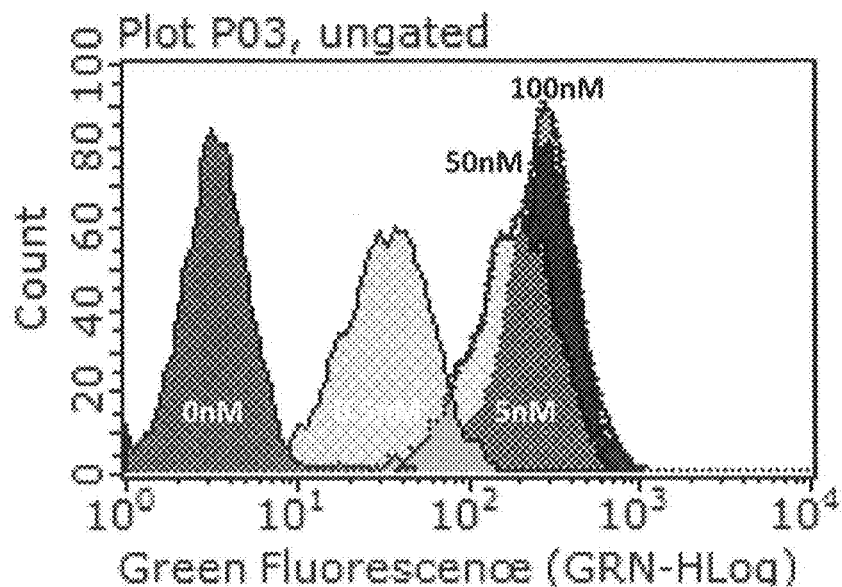
FIG. 18 shows results of flow cytometry using Rituximab-scFv-V2122.

Ramos cell (human Burkitt lymphoma-derived cell) (JCR Cell Bank), in which human CD20 antigen is abundantly expressed, was collected by centrifugation. The cells were suspended in PBS (1×10$^6$ cells/mL), and incubated with an antibody to be tested (0 nM, 0.5 nM, 5 nM, 50 nM, 100 nM) at room temperature for 30 minutes. The cells were washed twice with PBS, added with 0.1 mL of anti 6×His-tag antibody Alexa Flour 488 (500 ng/mL), and the mixture was incubated at room temperature for 30 minutes. The cells were washed twice with PBS, and binding mode and specificity of the test antibody were evaluated using guava easyCyte (Merck Millipore), according to the user's manual available from the manufacturer (FIG. 18).

(6) Heterotransplantation Model

Ramos cell suspension and Matrigel Matrix (Corning) were mixed in a ratio of 1:1 (5×10$^6$ cells/0.1 mL), and 0.1 mL of the mixed liquid was administered subcutaneously in the left side of 5 to 6-week-old female nude mice (Sankyo Labo Service Corporation, Inc.). The mice were bred for several weeks to produce tumor. One week before imaging, the feed was switched to a low fluorescence feed (iVid #1, Oriental Yeast Co., Ltd.) and the breeding was continued. Mice in which an average tumor volume had reached 100 to 600 mm$^3$ were used for fluorescent imaging test.

(7) In Vivo Imaging

Figure 19:
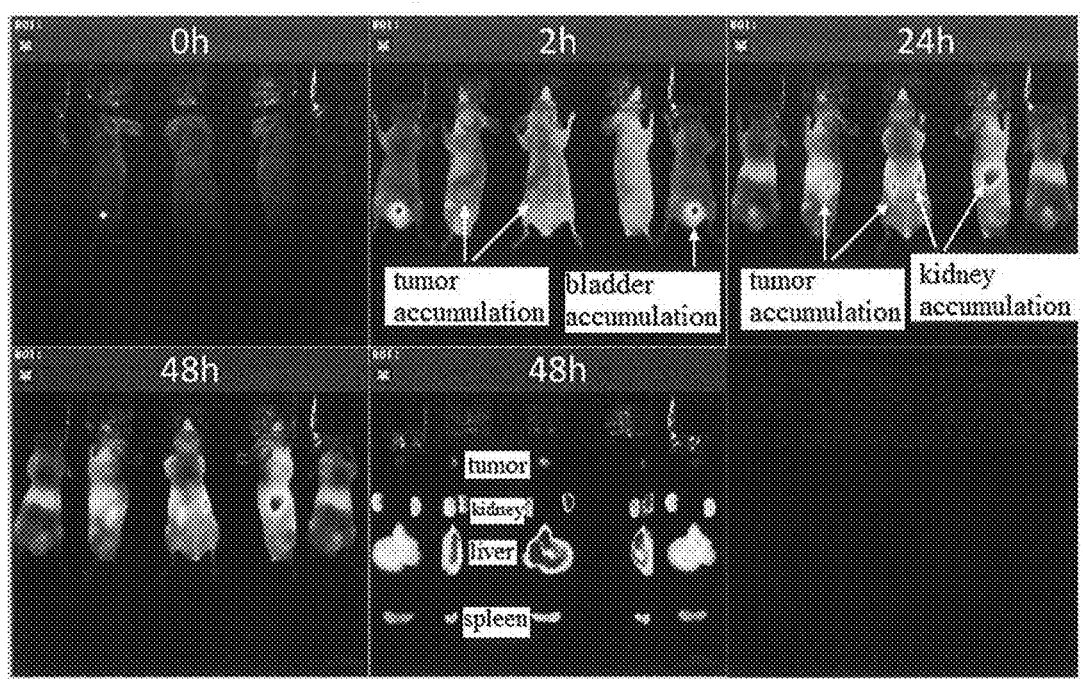
FIG. 19 shows results of in vivo imaging using Rituximab-scFv-V2122.

Rituximab-scFv-V2122 antibody (25 µg, 50 µg, 100 µg), preliminarily labeled with fluorescence by reacting it with Psyche F-IRDye 800 (Compound 44 in Example), was intravenously administered to nude mice having established human Burkitt lymphoma Ramos. For investigation into accumulation in tumor, accumulation of IRDye 800 in the tumor was evaluated 2, 24 and 48 hours after the administration, using in vivo photo-imaging instrument Clairvivo OPT plus (Shimadzu Corporation) (FIG. 19).

(8) Results

First; as shown in FIG. 18, Rituximab-scFv-V2122 antibody was found to be bound to the target cells in a concentration-dependent manner. Second, as shown in FIG. 19, the Rituximab-scFv-V2122 antibody was found to be accumulated in the tumor of the model mice 2 hours after the administration. In conclusion, Rituximab-scFv-V2122 antibody and Psyche F-IRDye 800 (Compound 44 in Example) remain bound in vivo, and can quickly accumulate in the site in a tumor-specific manner. Rituximab-scFv-V2122 antibody can therefore deliver a diagnostic drug or therapeutic drug quickly to the tumor site, and is therefore a leading candidate for diagnostic and therapeutic drugs.

Example 12: In Vivo Imaging Using Anti-Epiregulin scFv-V2122

(1) Expression and Partial Purification of Protein

Anti-epiregulin scFv-V2122 protein was expressed using anti-epiregulin scFv-V2122 expression vector described in Example 10 (1). More specifically, pETDuet-epiregulin-scFvV2122 skp, which is a plasmid vector, was introduced into BL21 (DE3) (Nippon Gene Co., Ltd.) for transformation. The transformed *Escherichia coli* was cultured overnight in 100 mL of 2×YT medium (Difco Laboratories) at 37° C. Next, 20 mL of the preculture liquid was added to 1 L of 2×YT medium, and the mixture was cultured at 37° C. Upon confirming $OD_{600nm}$=2.0, IPTG and Triton X-100 were added adjusting the final concentration to 1 mM and 1%, respectively, and the mixture was cultured for 18 hours to 24 hours at 20° C. The supernatant of culture was then collected by centrifugation, and 4 L of supernatant was pooled.

Next, the protein was partially purified using Ni-NTA resin. More specifically, 5 mL of cOomplete His-Tag Purification Resin (Roche) was added to 4 L of the pooled sample, the mixture was kept stirred using a stirrer overnight at 4° C. so as to allow a binding process to proceed. The resin was then collected into a column, washed with 50 mL of washing buffer (50 mM Tris-HCl, 0.2 M NaCl, 1 mM EDTA, 5 mM imidazole, pH8.0), and then eluted with 40 mL of elution buffer (50 mM Tris-HCl, 0.2 M NaCl, 1 mM EDTA, 400 mM imidazole, pH8.0). The eluate was concentrated using Vivaspin Turbo 15, MWCO=30,000 (Sartorius AG) to 1 to 3 mL, and then stored frozen (−80° C.) (FIG. 17).

(2) Purification Through Protein L Column

Figure 20:
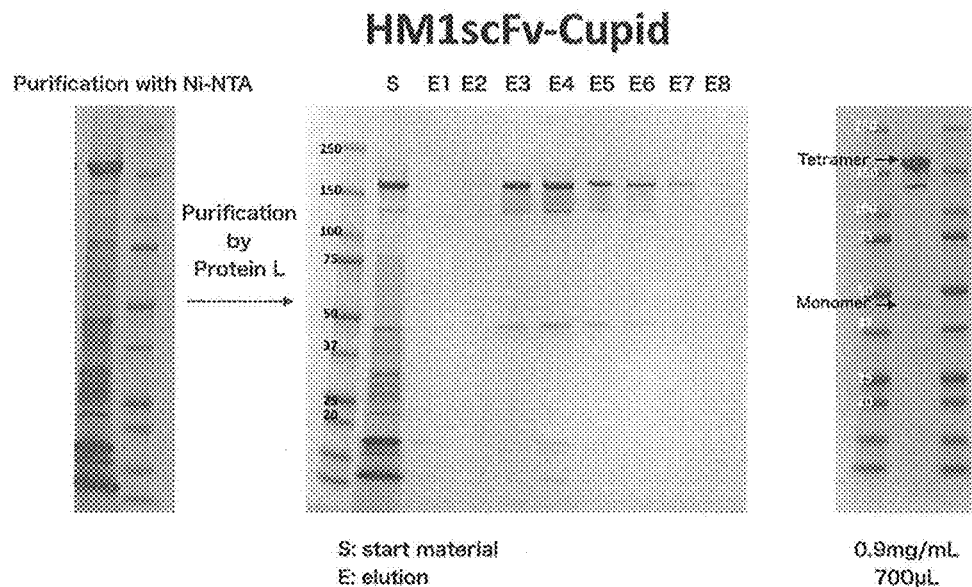
FIG. 20 shows results of purification of anti-epiregulin scFv-V2122 through Protein L column.

The protein was further purified by using Protein L 1 mL column (HiTrap L (GE Healthcare BioScience Corp.)). More specifically, the column was equilibrated using 10 column volumes of PBS, and a sample diluted 2-fold with PBS was applied. The column was washed with 10 column volumes of PBS, and then eluted with 10 column volumes of 10 mM glycine-HCl buffer pH2.5. The buffer in the eluate was immediately replaced with PBS using PD10 column, and then concentrated using Vivaspin Turbo 15, MWCO=100,000 (Sartorius AG) to 0.3 to 1 mL, and then stored cool (FIG. 20).

(3) Fluorescent Labeling

The thus purified anti-epiregulin scFv-V2122 was mixed with Psyche F-IRDye 800 (Compound 44 in Example) dissolved in DMSO (final concentration was ten-fold molar concentration), and the mixture was incubated on ice for 10 minutes. The buffer was then replaced with Japanese Pharmacopoeia physiological saline (Otsuka Pharmaceutical Co., Ltd.) using Zeba Spin Desalting Column (Thermo Fisher Scientific Inc.) and was stored under cooling. Epiregulin IgG was labeled using ICG Labeling Kit-NH2 (Dojindo Laboratories).

(4) Heterotransplantation Model

Suspension liquid of human colorectal cancer-derived DLD1 cell and Matrigel Matrix (Corning) were mixed in a ratio of 1:1 (5×10$^6$ cells/0.1 mL), and 0.1 mL of the mixed liquid was administered subcutaneously in the left side of 5 to 6-week-old female nude mice (Sankyo Labo Service Corporation, Inc.). The mice were bred for several weeks to produce tumor. One week before imaging, the feed was switched to a low fluorescence feed (iVid #1, Oriental Yeast Co., Ltd.) and the breeding was continued. Mice in which an average tumor volume had reached 100 to 600 mm$^3$ were used for fluorescent imaging test.

(5) In Vivo Imaging

Anti-epiregulin scFv-V2122 antibody (25 µg, 50 µg, 100 µg) preliminarily labeled with fluorescence by allowing it to react with Psyche F-IRDye 800 (Compound 44 in Example), or fluorescent-labeled epiregulin IgG (50 µg) was intravenously administered to nude mice having established DLD1 tumor. For investigation into accumulation in tumor, accumulation of IRDye 800 in the tumor was evaluated 2, 24 and 48 hours after the administration, using in vivo photo-imaging instrument Clairvivo OPT plus (Shimadzu Corporation) (FIG. 21).

(6) Results

Figure 21:
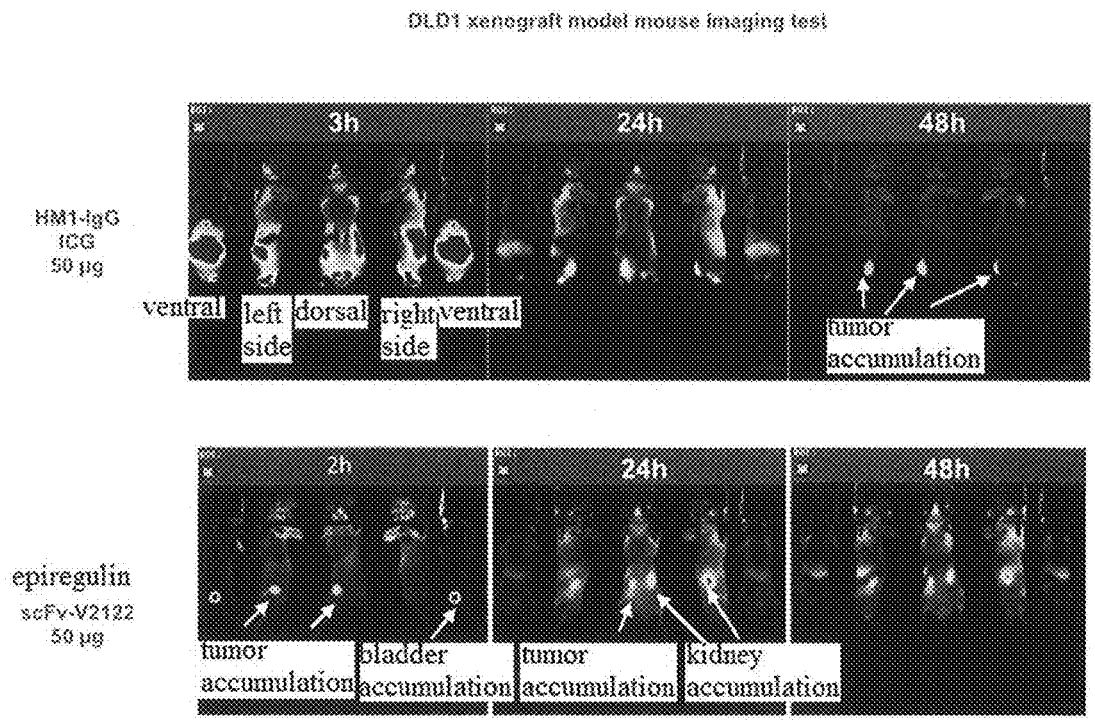
FIG. 21 shows results of in vivo imaging using anti-epiregulin scFv-V2122.

First, as shown in FIG. 21, anti-epiregulin scFv-V2122 antibody and Psyche F-IRDye 800 (Compound 44 in Example) were demonstrated to be bound also in vivo, since the tumor site was depicted. Second, as shown in FIG. 21, the labeled anti-epiregulin scFv-V2122 antibody was found to accumulate in the tumor of the model mice earlier (2 hours after administration) than the labeled IgG. In conclusion, anti-epiregulin scFv-V2122 antibody and Psyche F-IRDye 800 (Compound 44 in Example) remain bound in vivo, and can quickly accumulate in the site in a tumor-specific manner. Anti-epiregulin scFv-V2122 antibody can therefore deliver a diagnostic drug or therapeutic drug quickly to the tumor site, and is therefore a leading candidate for diagnostic and therapeutic drugs.

The invention claimed is:

1. A streptavidin mutant comprising an amino acid sequence in which Asn at amino acid residue 37 in the amino acid sequence represented by SEQ ID NO: 3 is substituted with other amino acid residue.

2. A streptavidin mutant comprising an amino acid sequence represented by SEQ ID NO: 4.

3. A DNA encoding the streptavidin mutant described in claim 1.

4. A streptavidin mutant-molecular probe conjugate, obtained by combining the streptavidin mutant described in claim 1 with a molecular probe.

5. The streptavidin mutant-molecular probe conjugate of claim 4, wherein the molecular probe is an anti-human CD20 antibody.

6. The streptavidin mutant-molecular probe conjugate of claim 4, wherein the molecular probe is rituximab.

7. The streptavidin mutant-molecular probe conjugate of claim 4, wherein the molecular probe is an anti-epiregulin single chain antibody.

8. A therapeutic agent, or in vivo or in vitro diagnostic agent, comprising the streptavidin mutant-molecular probe conjugate described in claim 4.

9. A therapeutic, or in vivo or in vitro diagnostic kit, comprising (a) a streptavidin mutant-molecular probe conjugate obtained by combining a streptavidin mutant comprising an amino acid sequence in which Asn at amino acid residue 37 in the amino acid sequence represented by SEQ ID NO: 3 is substituted with other amino acid residue, with a molecular probe; and (b) an in vivo or in vitro diagnostic substance, or a therapeutic substance, labeled with a compound represented by Formula (1) below:

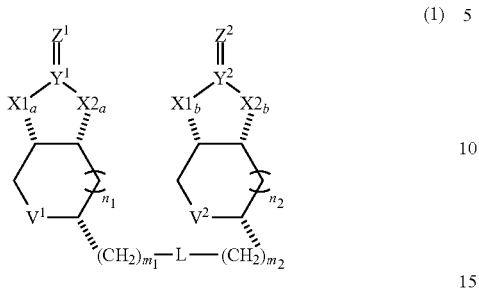

wherein, each of X1a, X1b, X2a and X2b independently represents O or NH, each of $Y^1$ and $Y^2$ independently represents C or S, each of $Z^1$ and $Z^2$ independently represents O, S or NH, each of $V^1$ and $V^2$ independently represents S or $S^+$—$O^-$, each of n1 and n2 independently represents 0 or 1, each of m1 and m2 independently represents and integer from 1 to 10, and L represents a linking group.

* * * * *

UNITED STATES PATENT AND TRADEMARK OFFICE
CERTIFICATE OF CORRECTION

PATENT NO. : 11,161,884 B2
APPLICATION NO. : 16/512894
DATED : November 2, 2021
INVENTOR(S) : Sugiyama et al.

Page 1 of 1

It is certified that error appears in the above-identified patent and that said Letters Patent is hereby corrected as shown below:

On the Title Page

Item (57)/Abstract, Line 7, please change "angsd" to -- and --

In the Claims

Column 163, Line 23, (Claim 9) please change "and integer" to -- an integer --

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 44

<210> SEQ ID NO 1
<211> LENGTH: 381
<212> TYPE: DNA
<213> ORGANISM: Streptomyces avidinii
<220> FEATURE:
<221> NAME/KEY: CDS
<222> LOCATION: (1)..(381)

<400> SEQUENCE: 1

```
gcc gaa gct ggt atc act ggc acc tgg tat aac caa ctg ggg tcg act      48
Ala Glu Ala Gly Ile Thr Gly Thr Trp Tyr Asn Gln Leu Gly Ser Thr
1               5                   10                  15 ttc att gtg acc gct ggt gcg gac gga gct ctg act ggc acc tac gaa      96
Phe Ile Val Thr Ala Gly Ala Asp Gly Ala Leu Thr Gly Thr Tyr Glu
            20                  25                  30 tct gcg gtt ggt aac gca gaa tcc cgc tac gta ctg act ggc cgt tat     144
Ser Ala Val Gly Asn Ala Glu Ser Arg Tyr Val Leu Thr Gly Arg Tyr
        35                  40                  45 gac tct gca cct gcc acc gat ggc tct ggt acc gct ctg ggc tgg act     192
Asp Ser Ala Pro Ala Thr Asp Gly Ser Gly Thr Ala Leu Gly Trp Thr
    50                  55                  60 gtg gct tgg aaa aac aac tat cgt aat gcg cac agc gcc act acg tgg     240
Val Ala Trp Lys Asn Asn Tyr Arg Asn Ala His Ser Ala Thr Thr Trp
65                  70                  75                  80 tct ggc caa tac gtt ggc ggt gct gag gct cgt atc aac act cag tgg     288
Ser Gly Gln Tyr Val Gly Gly Ala Glu Ala Arg Ile Asn Thr Gln Trp
                85                  90                  95 ctg tta aca tcc ggc act acc gaa gcg aat gca tgg aaa tcg aca cta     336
Leu Leu Thr Ser Gly Thr Thr Glu Ala Asn Ala Trp Lys Ser Thr Leu
            100                 105                 110 gta ggt cat gac acc ttt acc aaa gtt aag cct tct gct gct agc         381
Val Gly His Asp Thr Phe Thr Lys Val Lys Pro Ser Ala Ala Ser
        115                 120                 125
```

<210> SEQ ID NO 2
<211> LENGTH: 127
<212> TYPE: PRT
<213> ORGANISM: Streptomyces avidinii

<400> SEQUENCE: 2

```
Ala Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125
```

<210> SEQ ID NO 3

<211> LENGTH: 127
<212> TYPE: PRT
<213> ORGANISM: Artificial Sequence
<220> FEATURE:
<223> OTHER INFORMATION: Description of Artificial Sequence: Synthetic recombinant polypeptide

<400> SEQUENCE: 3

```
Ala Glu Ala Gly Ile Thr Gly Thr Trp Ser Asp Gln Leu Gly Asp Thr
1               5                   10                  15
Phe Ile Val Thr Ala Gly Ala Asp Gly Ala Leu Thr Gly Thr Tyr Glu
            20                  25                  30
Asn Ala Val Gly Asn Ala Glu Ser Arg Tyr Val Leu Thr Gly Arg Tyr
        35                  40                  45
Asp Ser Ala Pro Ala Thr Asp Gly Ser Gly Thr Ala Leu Gly Trp Thr
    50                  55                  60
Val Ala Trp Lys Asn Asn Ser Lys Asn Ala His Ser Ala Thr Thr Trp
65                  70                  75                  80
Ser Gly Gln Tyr Val Gly Gly Ala Asp Ala Lys Ile Asn Thr Gln Trp
                85                  90                  95
Leu Leu Thr Ser Gly Thr Thr Asn Ala Asn Ala Trp Lys Ser Thr Leu
            100                 105                 110
Val Gly His Asp Thr Phe Thr Lys Val Lys Pro Ser Ala Ala Ser
        115                 120                 125
```

<210> SEQ ID NO 4
<211> LENGTH: 127
<212> TYPE: PRT
<213> ORGANISM: Artificial Sequence
<220> FEATURE:
<223> OTHER INFORMATION: Description of Artificial Sequence: Synthetic recombinant polypeptide

<400> SEQUENCE: 4

```
Ala Glu Ala Gly Ile Thr Gly Thr Trp Ser Asp Gln Leu Gly Asp Thr
1               5                   10                  15
Phe Ile Val Thr Ala Gly Ala Asp Gly Ala Leu Thr Gly Thr Tyr Glu
            20                  25                  30
Asn Ala Val Gly Gly Ala Glu Ser Arg Tyr Val Leu Thr Gly Arg Tyr
        35                  40                  45
Asp Ser Ala Pro Ala Thr Asp Gly Ser Gly Thr Ala Leu Gly Trp Thr
    50                  55                  60
Val Ala Trp Lys Asn Asn Ser Lys Asn Ala His Ser Ala Thr Thr Trp
65                  70                  75                  80
Ser Gly Gln Tyr Val Gly Gly Ala Asp Ala Lys Ile Asn Thr Gln Trp
                85                  90                  95
Leu Leu Thr Ser Gly Thr Thr Asn Ala Asn Ala Trp Lys Ser Thr Leu
            100                 105                 110
Val Gly His Asp Thr Phe Thr Lys Val Lys Pro Ser Ala Ala Ser
        115                 120                 125
```

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
tggagcgatc agctgggcga taccttt                                          27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cagctgatcg ctccaggtgc cggtaat                                          27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tatgaaaacg ccgtgggtaa tgcggaa                                          27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cacggcgttt tcataggtgc cggtcag                                          27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtgggtgcgg cggaaagccg ttatgtt                                          27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttccgccgca cccacggcat tttcata                                          27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtgggtggtg cggaaagccg ttatgtt                                          27

```
<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttccgcacca cccacggcat tttcata                                           27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gtgggtagcg cggaaagccg ttatgtt                                           27

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ttccgcgcta cccacggcat tttcata                                           27

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tacatatggc cgaagcaggt attacc                                            26

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cttcggccat atgtatatct ccttc                                             25

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggcaccgccg aaagcgccgt gggtaat                                           27
```

```
<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gctttcggcg gtgccggtca gcgcacc                                              27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tatgaagccg ccgtgggtaa tgcggaa                                              27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cacggcggct tcataggtgc cggtcag                                              27

<210> SEQ ID NO 21
<211> LENGTH: 840
<212> TYPE: DNA
<213> ORGANISM: Artificial Sequence
<220> FEATURE:
<223> OTHER INFORMATION: Description of Artificial Sequence: Synthetic
      recombinant polynucleotide
<220> FEATURE:
<221> NAME/KEY: CDS
<222> LOCATION: (1)..(837)

<400> SEQUENCE: 21 atg aaa tac cta ttg cct acg gca gcc gct gga ttg tta tta ctc gcg         48
Met Lys Tyr Leu Leu Pro Thr Ala Ala Ala Gly Leu Leu Leu Leu Ala
1               5                   10                  15 gcc cag ccg gcc atg gcc cag gtg cag ctg cag cag tct ggc gcc gaa         96
Ala Gln Pro Ala Met Ala Gln Val Gln Leu Gln Gln Ser Gly Ala Glu
                20                  25                  30 gtg aag aaa cct ggc gcc tcc gtg aag gtg tcc tgc aag gcc tcc ggc        144
Val Lys Lys Pro Gly Ala Ser Val Lys Val Ser Cys Lys Ala Ser Gly
            35                  40                  45 ttc aac atc aag gac acc tac atg cac tgg gtg cga cag gcc cct gag        192
Phe Asn Ile Lys Asp Thr Tyr Met His Trp Val Arg Gln Ala Pro Glu
        50                  55                  60 cag ggc ctg gaa tgg atg ggc aga atc gac ccc ctg aac gac aag act        240
Gln Gly Leu Glu Trp Met Gly Arg Ile Asp Pro Leu Asn Asp Lys Thr
65                  70                  75                  80 aag tac gac ccc aag ttc cag ggc aga gtg acc atc acc gcc gac acc        288
Lys Tyr Asp Pro Lys Phe Gln Gly Arg Val Thr Ile Thr Ala Asp Thr
                85                  90                  95 tct acc aac acc gcc tac ctg gaa ctg tcc tcc ctg acc tct gag gac        336
Ser Thr Asn Thr Ala Tyr Leu Glu Leu Ser Ser Leu Thr Ser Glu Asp
```

```
acc gcc gtg tac tac tgc gct aga ggc gga gga gat ccc gtg ttc gtg    384
Thr Ala Val Tyr Tyr Cys Ala Arg Gly Gly Gly Asp Pro Val Phe Val
            115                 120                 125 tat tgg ggc cag ggc acc ctc gtg acc gtg tct gct tct tct ggc gga    432
Tyr Trp Gly Gln Gly Thr Leu Val Thr Val Ser Ala Ser Ser Gly Gly
        130                 135                 140 ggc gga tct ggg ggc gga ggt tct ggt ggt ggt gga agc ggt ggc ggt    480
Gly Gly Ser Gly Gly Gly Gly Ser Gly Gly Gly Ser Gly Gly Gly
145                 150                 155                 160 gga tct ggc ggc gat atc cag atg acc cag tcc ccc agc tcc ctg tct    528
Gly Ser Gly Gly Asp Ile Gln Met Thr Gln Ser Pro Ser Ser Leu Ser
                165                 170                 175 gcc tct gtg ggc gac cgc gtg acc att aca tgc aag gcc agc cag gac    576
Ala Ser Val Gly Asp Arg Val Thr Ile Thr Cys Lys Ala Ser Gln Asp
            180                 185                 190 atc aac aag tac ctg gcc tgg tat cag cac aag ccc ggc cag gct cct    624
Ile Asn Lys Tyr Leu Ala Trp Tyr Gln His Lys Pro Gly Gln Ala Pro
        195                 200                 205 cgg ctg ctg atc cac tat acc tcc acc ctg cac ccc ggc atc cct tcc    672
Arg Leu Leu Ile His Tyr Thr Ser Thr Leu His Pro Gly Ile Pro Ser
    210                 215                 220 aga ttc tcc ggc tct ggc tcc ggc acc gac ttt acc ttc tcc atc tcc    720
Arg Phe Ser Gly Ser Gly Ser Gly Thr Asp Phe Thr Phe Ser Ile Ser
225                 230                 235                 240 agc ctg cag ccc gag gat atc gct acc tac tac tgc ctg cag tac gac    768
Ser Leu Gln Pro Glu Asp Ile Ala Thr Tyr Tyr Cys Leu Gln Tyr Asp
                245                 250                 255 aac ctg cgg acc ttc gga ggc ggc acc aag gtg gaa atc aag cgg acc    816
Asn Leu Arg Thr Phe Gly Gly Gly Thr Lys Val Glu Ile Lys Arg Thr
            260                 265                 270 agc cac cac cac cac cac cac tga                                    840
Ser His His His His His His
        275
```

<210> SEQ ID NO 22
<211> LENGTH: 279
<212> TYPE: PRT
<213> ORGANISM: Artificial Sequence
<220> FEATURE:
<223> OTHER INFORMATION: Description of Artificial Sequence: Synthetic recombinant polypeptide

<400> SEQUENCE: 22

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Ser Gly Ala Glu
            20                  25                  30

Val Lys Lys Pro Gly Ala Ser Val Lys Val Ser Cys Lys Ala Ser Gly
        35                  40                  45

Phe Asn Ile Lys Asp Thr Tyr Met His Trp Val Arg Gln Ala Pro Glu
    50                  55                  60

Gln Gly Leu Glu Trp Met Gly Arg Ile Asp Pro Leu Asn Asp Lys Thr
65                  70                  75                  80

Lys Tyr Asp Pro Lys Phe Gln Gly Arg Val Thr Ile Thr Ala Asp Thr
                85                  90                  95

Ser Thr Asn Thr Ala Tyr Leu Glu Leu Ser Ser Leu Thr Ser Glu Asp
            100                 105                 110

Thr Ala Val Tyr Tyr Cys Ala Arg Gly Gly Gly Asp Pro Val Phe Val
```

```
            115                 120                 125
Tyr Trp Gly Gln Gly Thr Leu Val Thr Val Ser Ala Ser Ser Gly Gly
        130                 135                 140

Gly Gly Ser Gly Gly Gly Ser Gly Gly Gly Ser Gly Gly Gly
145                 150                 155                 160

Gly Ser Gly Gly Asp Ile Gln Met Thr Gln Ser Pro Ser Ser Leu Ser
                165                 170                 175

Ala Ser Val Gly Asp Arg Val Thr Ile Thr Cys Lys Ala Ser Gln Asp
            180                 185                 190

Ile Asn Lys Tyr Leu Ala Trp Tyr Gln His Lys Pro Gly Gln Ala Pro
        195                 200                 205

Arg Leu Leu Ile His Tyr Thr Ser Thr Leu His Pro Gly Ile Pro Ser
    210                 215                 220

Arg Phe Ser Gly Ser Gly Ser Gly Thr Asp Phe Thr Phe Ser Ile Ser
225                 230                 235                 240

Ser Leu Gln Pro Glu Asp Ile Ala Thr Tyr Tyr Cys Leu Gln Tyr Asp
                245                 250                 255

Asn Leu Arg Thr Phe Gly Gly Gly Thr Lys Val Glu Ile Lys Arg Thr
            260                 265                 270

Ser His His His His His
        275
```

```
<210> SEQ ID NO 23
<211> LENGTH: 486
<212> TYPE: DNA
<213> ORGANISM: Artificial Sequence
<220> FEATURE:
<223> OTHER INFORMATION: Description of Artificial Sequence: Synthetic
      recombinant polynucleotide
<220> FEATURE:
<221> NAME/KEY: CDS
<222> LOCATION: (1)..(483)

<400> SEQUENCE: 23
```

```
atg aaa aaa tgg ctg ctg gca gca ggt ctg ggt ctg gca ctg gca acc      48
Met Lys Lys Trp Leu Leu Ala Ala Gly Leu Gly Leu Ala Leu Ala Thr
1               5                   10                  15 agc gca cag gca gca gat aaa att gcc att gtt aat atg ggt agc ctg      96
Ser Ala Gln Ala Ala Asp Lys Ile Ala Ile Val Asn Met Gly Ser Leu
            20                  25                  30 ttt cag cag gtt gca cag aaa acc ggt gtt agc aat acc ctg gaa aat     144
Phe Gln Gln Val Ala Gln Lys Thr Gly Val Ser Asn Thr Leu Glu Asn
        35                  40                  45 gaa ttt aaa ggt cgt gca agc gaa ctg cag cgt atg gaa acc gat ctg     192
Glu Phe Lys Gly Arg Ala Ser Glu Leu Gln Arg Met Glu Thr Asp Leu
    50                  55                  60 cag gca aaa atg aaa aaa ctg cag agc atg aaa gca ggt agc gat cgt     240
Gln Ala Lys Met Lys Lys Leu Gln Ser Met Lys Ala Gly Ser Asp Arg
65                  70                  75                  80 acc aaa ctg gaa aaa gat gtt atg gca cag cgt cag acc ttt gcc cag     288
Thr Lys Leu Glu Lys Asp Val Met Ala Gln Arg Gln Thr Phe Ala Gln
                85                  90                  95 aaa gca cag gca ttt gaa cag gat cgt gca cgt cgt agc aat gaa gaa     336
Lys Ala Gln Ala Phe Glu Gln Asp Arg Ala Arg Arg Ser Asn Glu Glu
            100                 105                 110 cgt ggt aaa ctg gtt acc cgt att cag acc gca gtt aaa agc gtt gca     384
Arg Gly Lys Leu Val Thr Arg Ile Gln Thr Ala Val Lys Ser Val Ala
        115                 120                 125 aat agc cag gat att gat ctg gtt gtt gat gca aat gcc gtt gcc tat     432
```

```
         Asn Ser Gln Asp Ile Asp Leu Val Val Asp Ala Asn Ala Val Ala Tyr
             130                 135                 140 aat agc agt gat gtg aaa gat att acc gca gac gtt ctg aaa caa gtg          480
Asn Ser Ser Asp Val Lys Asp Ile Thr Ala Asp Val Leu Lys Gln Val
145                 150                 155                 160 aaa tag                                                                   486
Lys
```

<210> SEQ ID NO 24
<211> LENGTH: 161
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 24

```
Met Lys Lys Trp Leu Leu Ala Ala Gly Leu Gly Leu Ala Leu Ala Thr
 1               5                  10                  15

Ser Ala Gln Ala Ala Asp Lys Ile Ala Ile Val Asn Met Gly Ser Leu
             20                  25                  30

Phe Gln Gln Val Ala Gln Lys Thr Gly Val Ser Asn Thr Leu Glu Asn
         35                  40                  45

Glu Phe Lys Gly Arg Ala Ser Glu Leu Gln Arg Met Glu Thr Asp Leu
     50                  55                  60

Gln Ala Lys Met Lys Lys Leu Gln Ser Met Lys Ala Gly Ser Asp Arg
 65                  70                  75                  80

Thr Lys Leu Glu Lys Asp Val Met Ala Gln Arg Gln Thr Phe Ala Gln
                 85                  90                  95

Lys Ala Gln Ala Phe Glu Gln Asp Arg Ala Arg Arg Ser Asn Glu Glu
            100                 105                 110

Arg Gly Lys Leu Val Thr Arg Ile Gln Thr Ala Val Lys Ser Val Ala
        115                 120                 125

Asn Ser Gln Asp Ile Asp Leu Val Val Asp Ala Asn Ala Val Ala Tyr
    130                 135                 140

Asn Ser Ser Asp Val Lys Asp Ile Thr Ala Asp Val Leu Lys Gln Val
145                 150                 155                 160

Lys
```

<210> SEQ ID NO 25
<211> LENGTH: 984
<212> TYPE: DNA
<213> ORGANISM: Artificial Sequence
<220> FEATURE:
<223> OTHER INFORMATION: Description of Artificial Sequence: Synthetic
      recombinant polynucleotide
<220> FEATURE:
<221> NAME/KEY: CDS
<222> LOCATION: (1)..(981)

<400> SEQUENCE: 25

```
atg gaa acc gat aca ctg ctg ctg tgg gtg ctg ctg ctg tgg gtc cct           48
Met Glu Thr Asp Thr Leu Leu Leu Trp Val Leu Leu Leu Trp Val Pro
 1               5                  10                  15 ggg tca act ggc gat gtc ctc agt aca act gtg att cca tca tgt atc           96
Gly Ser Thr Gly Asp Val Leu Ser Thr Thr Val Ile Pro Ser Cys Ile
             20                  25                  30 cca gga gag tcc agt gat aac tgc aca gct tta gtt cag aca gaa gac          144
Pro Gly Glu Ser Ser Asp Asn Cys Thr Ala Leu Val Gln Thr Glu Asp
         35                  40                  45
```

| | | |
|---|---|---|
| aat cca cgt gtg gct caa gtg tca ata aca aag tgt agc tct gac atg<br>Asn Pro Arg Val Ala Gln Val Ser Ile Thr Lys Cys Ser Ser Asp Met<br>50 55 60 | | 192 |
| aat ggc tat tgt ttg cat gga cag tgc atc tat ctg gtg gac atg agt<br>Asn Gly Tyr Cys Leu His Gly Gln Cys Ile Tyr Leu Val Asp Met Ser<br>65 70 75 80 | | 240 |
| caa aac tac tgc agg tgt gaa gtg ggt tat act ggt gtc cga tgt gaa<br>Gln Asn Tyr Cys Arg Cys Glu Val Gly Tyr Thr Gly Val Arg Cys Glu<br>85 90 95 | | 288 |
| cac ttc ttt tta acc gtc cac caa cct gga gcc aaa cct gcc att gcc<br>His Phe Phe Leu Thr Val His Gln Pro Gly Ala Lys Pro Ala Ile Ala<br>100 105 110 | | 336 |
| aca gtc cca gaa gta tca tct gtc ttc atc ttc ccc cca aag ccc aag<br>Thr Val Pro Glu Val Ser Ser Val Phe Ile Phe Pro Pro Lys Pro Lys<br>115 120 125 | | 384 |
| gat gtg ctc acc att act ctg act cct aag gtc acg tgt gtt gtg gta<br>Asp Val Leu Thr Ile Thr Leu Thr Pro Lys Val Thr Cys Val Val Val<br>130 135 140 | | 432 |
| gac atc agc aag gat gat ccc gag gtc cag ttc agc tgg ttt gta gat<br>Asp Ile Ser Lys Asp Asp Pro Glu Val Gln Phe Ser Trp Phe Val Asp<br>145 150 155 160 | | 480 |
| gat gtg gag gtg cac aca gct cag acg caa ccc cgg gag gag cag ttc<br>Asp Val Glu Val His Thr Ala Gln Thr Gln Pro Arg Glu Glu Gln Phe<br>165 170 175 | | 528 |
| aac agc act ttc cgc tca gtc agt gaa ctt ccc atc atg cac cag gac<br>Asn Ser Thr Phe Arg Ser Val Ser Glu Leu Pro Ile Met His Gln Asp<br>180 185 190 | | 576 |
| tgg ctc aat ggc aag gag ttc aaa tgc agg gtc aac agt gca gct ttc<br>Trp Leu Asn Gly Lys Glu Phe Lys Cys Arg Val Asn Ser Ala Ala Phe<br>195 200 205 | | 624 |
| cct gcc ccc atc gag aaa acc atc tcc aaa acc aaa ggc aga ccg aag<br>Pro Ala Pro Ile Glu Lys Thr Ile Ser Lys Thr Lys Gly Arg Pro Lys<br>210 215 220 | | 672 |
| gct cca cag gtg tac acc att cca cct ccc aag gag cag atg gcc aag<br>Ala Pro Gln Val Tyr Thr Ile Pro Pro Pro Lys Glu Gln Met Ala Lys<br>225 230 235 240 | | 720 |
| gat aaa gtc agt ctg acc tgc atg ata aca gac ttc ttc cct gaa gac<br>Asp Lys Val Ser Leu Thr Cys Met Ile Thr Asp Phe Phe Pro Glu Asp<br>245 250 255 | | 768 |
| att act gtg gag tgg cag tgg aat ggg cag cca gcg gag aac tac aag<br>Ile Thr Val Glu Trp Gln Trp Asn Gly Gln Pro Ala Glu Asn Tyr Lys<br>260 265 270 | | 816 |
| aac act cag ccc atc atg gac aca gat ggc tct tac ttc gtc tac agc<br>Asn Thr Gln Pro Ile Met Asp Thr Asp Gly Ser Tyr Phe Val Tyr Ser<br>275 280 285 | | 864 |
| aag ctc aat gtg cag aag agc aac tgg gag gca gga aat act ttc acc<br>Lys Leu Asn Val Gln Lys Ser Asn Trp Glu Ala Gly Asn Thr Phe Thr<br>290 295 300 | | 912 |
| tgc tct gtg tta cat gag ggc ctg cac aac cac cat act gag aag agc<br>Cys Ser Val Leu His Glu Gly Leu His Asn His His Thr Glu Lys Ser<br>305 310 315 320 | | 960 |
| ctc tcc cac tct cct ggt aaa tga<br>Leu Ser His Ser Pro Gly Lys<br>325 | | 984 |

<210> SEQ ID NO 26
<211> LENGTH: 327
<212> TYPE: PRT
<213> ORGANISM: Artificial Sequence
<220> FEATURE:
<223> OTHER INFORMATION: Description of Artificial Sequence: Synthetic -continued recombinant polypeptide

<400> SEQUENCE: 26

Met Glu Thr Asp Thr Leu Leu Leu Trp Val Leu Leu Leu Trp Val Pro
1               5                   10                  15

Gly Ser Thr Gly Asp Val Leu Ser Thr Thr Val Ile Pro Ser Cys Ile
            20                  25                  30

Pro Gly Glu Ser Ser Asp Asn Cys Thr Ala Leu Val Gln Thr Glu Asp
        35                  40                  45

Asn Pro Arg Val Ala Gln Val Ser Ile Thr Lys Cys Ser Ser Asp Met
    50                  55                  60

Asn Gly Tyr Cys Leu His Gly Gln Cys Ile Tyr Leu Val Asp Met Ser
65                  70                  75                  80

Gln Asn Tyr Cys Arg Cys Glu Val Gly Tyr Thr Gly Val Arg Cys Glu
                85                  90                  95

His Phe Phe Leu Thr Val His Gln Pro Gly Ala Lys Pro Ala Ile Ala
            100                 105                 110

Thr Val Pro Glu Val Ser Ser Val Phe Ile Phe Pro Pro Lys Pro Lys
        115                 120                 125

Asp Val Leu Thr Ile Thr Leu Thr Pro Lys Val Thr Cys Val Val Val
    130                 135                 140

Asp Ile Ser Lys Asp Asp Pro Glu Val Gln Phe Ser Trp Phe Val Asp
145                 150                 155                 160

Asp Val Glu Val His Thr Ala Gln Thr Gln Pro Arg Glu Glu Gln Phe
                165                 170                 175

Asn Ser Thr Phe Arg Ser Val Ser Glu Leu Pro Ile Met His Gln Asp
            180                 185                 190

Trp Leu Asn Gly Lys Glu Phe Lys Cys Arg Val Asn Ser Ala Ala Phe
        195                 200                 205

Pro Ala Pro Ile Glu Lys Thr Ile Ser Lys Thr Lys Gly Arg Pro Lys
    210                 215                 220

Ala Pro Gln Val Tyr Thr Ile Pro Pro Lys Glu Gln Met Ala Lys
225                 230                 235                 240

Asp Lys Val Ser Leu Thr Cys Met Ile Thr Asp Phe Phe Pro Glu Asp
                245                 250                 255

Ile Thr Val Glu Trp Gln Trp Asn Gly Gln Pro Ala Glu Asn Tyr Lys
            260                 265                 270

Asn Thr Gln Pro Ile Met Asp Thr Asp Gly Ser Tyr Phe Val Tyr Ser
        275                 280                 285

Lys Leu Asn Val Gln Lys Ser Asn Trp Glu Ala Gly Asn Thr Phe Thr
    290                 295                 300

Cys Ser Val Leu His Glu Gly Leu His Asn His His Thr Glu Lys Ser
305                 310                 315                 320

Leu Ser His Ser Pro Gly Lys
                325

<210> SEQ ID NO 27
<211> LENGTH: 1236
<212> TYPE: DNA
<213> ORGANISM: Artificial Sequence
<220> FEATURE:
<223> OTHER INFORMATION: Description of Artificial Sequence: Synthetic
      recombinant polynucleotide
<220> FEATURE:
<221> NAME/KEY: CDS
<222> LOCATION: (1)..(1233)

<400> SEQUENCE: 27

```
atg aaa tac ctg ctg ccg acc gct gct gct ggt ctg ctg ctc ctc gct        48
Met Lys Tyr Leu Leu Pro Thr Ala Ala Ala Gly Leu Leu Leu Leu Ala
1               5                   10                  15 gcc cag ccg gcg atg gcc atg gat cag atc gtg ctg tct cag agt ccc        96
Ala Gln Pro Ala Met Ala Met Asp Gln Ile Val Leu Ser Gln Ser Pro
            20                  25                  30 gcc atc ctg tcc gca agc cct ggg gaa aaa gtc act atg acc tgt aga       144
Ala Ile Leu Ser Ala Ser Pro Gly Glu Lys Val Thr Met Thr Cys Arg
        35                  40                  45 gcc tcc tca agc gtg tcc tac atc cac tgg ttc cag cag aaa cca ggg       192
Ala Ser Ser Ser Val Ser Tyr Ile His Trp Phe Gln Gln Lys Pro Gly
    50                  55                  60 agc tcc cca aag ccc tgg atc tac gct aca agt aac ctg gca tca gga       240
Ser Ser Pro Lys Pro Trp Ile Tyr Ala Thr Ser Asn Leu Ala Ser Gly
65                  70                  75                  80 gtg ccc gtc cgg ttt tca ggg agc gga tcc ggc aca tct tac agt ctg       288
Val Pro Val Arg Phe Ser Gly Ser Gly Ser Gly Thr Ser Tyr Ser Leu
                85                  90                  95 act atc tcc aga gtg gag gcc gaa gac gcc gct aca tac tat tgc cag       336
Thr Ile Ser Arg Val Glu Ala Glu Asp Ala Ala Thr Tyr Tyr Cys Gln
            100                 105                 110 cag tgg acc tct aat ccc cct aca ttc ggc ggg gga act aaa ctg gag       384
Gln Trp Thr Ser Asn Pro Pro Thr Phe Gly Gly Gly Thr Lys Leu Glu
        115                 120                 125 att aag ggc tca act agc gga gga gga agc gga gga gga tcc gga gga       432
Ile Lys Gly Ser Thr Ser Gly Gly Gly Ser Gly Gly Gly Ser Gly Gly
    130                 135                 140 gga gga tct agt cag gtg cag ctg cag cag cct gga gca gaa ctg gtg       480
Gly Gly Ser Ser Gln Val Gln Leu Gln Gln Pro Gly Ala Glu Leu Val
145                 150                 155                 160 aaa cca ggc gcc tct gtc aaa atg agt tgt aag gct agc ggc tac acc       528
Lys Pro Gly Ala Ser Val Lys Met Ser Cys Lys Ala Ser Gly Tyr Thr
                165                 170                 175 ttc aca agc tat aac atg cat tgg gtc aag cag act cca gga agg gga       576
Phe Thr Ser Tyr Asn Met His Trp Val Lys Gln Thr Pro Gly Arg Gly
            180                 185                 190 ctg gag tgg atc gga gca atc tac cct ggc aac ggg gac acc agc tat       624
Leu Glu Trp Ile Gly Ala Ile Tyr Pro Gly Asn Gly Asp Thr Ser Tyr
        195                 200                 205 aat cag aag ttt aaa ggg aag gca act ctg acc gcc gat aaa tca agc       672
Asn Gln Lys Phe Lys Gly Lys Ala Thr Leu Thr Ala Asp Lys Ser Ser
    210                 215                 220 tcc acc gct tac atg cag ctg tct agt ctg aca tcc gaa gat tct gcc       720
Ser Thr Ala Tyr Met Gln Leu Ser Ser Leu Thr Ser Glu Asp Ser Ala
225                 230                 235                 240 gtg tac tat tgc gct cgg tct acc tat tat ggc ggg gac tgg tat ttc       768
Val Tyr Tyr Cys Ala Arg Ser Thr Tyr Tyr Gly Gly Asp Trp Tyr Phe
                245                 250                 255 aat gtg tgg ggg gca gga act act gtg act gtc tca gcc tcc tcc ggc       816
Asn Val Trp Gly Ala Gly Thr Thr Val Thr Val Ser Ala Ser Ser Gly
            260                 265                 270 agc ggc tct gct gct gag gct gga atc acc ggc acc tgg tct gac cag       864
Ser Gly Ser Ala Ala Glu Ala Gly Ile Thr Gly Thr Trp Ser Asp Gln
        275                 280                 285 ctg ggc gac acc ttc atc gtg acc gct ggt gct gat ggc gct ctg acc       912
Leu Gly Asp Thr Phe Ile Val Thr Ala Gly Ala Asp Gly Ala Leu Thr
    290                 295                 300 ggc aca tac gag aac gcc gtg ggc gga gcc gag tcc aga tat gtg ctg       960
```

| | | | | | | | | | | | | |
|---|---|---|---|---|---|---|---|---|---|---|---|---|
|Gly|Thr|Tyr|Glu|Asn|Ala|Val|Gly|Gly|Ala|Glu|Ser|Arg|Tyr|Val|Leu|
|305| | | |310| | | |315| | | |320|

```
acc gga aga tac gac tcc gcc cct gcc acc gat ggc tct gga aca gct      1008
Thr Gly Arg Tyr Asp Ser Ala Pro Ala Thr Asp Gly Ser Gly Thr Ala
            325                 330                 335 ctg ggc tgg acc gtg gcc tgg aag aac aac tcc aag aac gcc cac tcc      1056
Leu Gly Trp Thr Val Ala Trp Lys Asn Asn Ser Lys Asn Ala His Ser
        340                 345                 350 gcc acc act tgg agc ggc cag tat gtg ggc gga gcc gac gcc aag atc      1104
Ala Thr Thr Trp Ser Gly Gln Tyr Val Gly Gly Ala Asp Ala Lys Ile
    355                 360                 365 aac acc cag tgg ctg ctg acc agc ggc acc acc aat gcc aac gcc tgg      1152
Asn Thr Gln Trp Leu Leu Thr Ser Gly Thr Thr Asn Ala Asn Ala Trp
370                 375                 380 aag tcc acc ctc gtg ggc cac gat acc ttc acc aaa gtg aag ccc tct      1200
Lys Ser Thr Leu Val Gly His Asp Thr Phe Thr Lys Val Lys Pro Ser
385                 390                 395                 400 gcc gcc tct ggc ggc cac cac cat cac cat cat tga                      1236
Ala Ala Ser Gly Gly His His His His His His
                405                 410

<210> SEQ ID NO 28
<211> LENGTH: 411
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 28

Met Lys Tyr Leu Leu Pro Thr Ala Ala Gly Leu Leu Leu Leu Ala
1               5                   10                  15

Ala Gln Pro Ala Met Ala Met Asp Gln Ile Val Leu Ser Gln Ser Pro
                20                  25                  30

Ala Ile Leu Ser Ala Ser Pro Gly Glu Lys Val Thr Met Thr Cys Arg
            35                  40                  45

Ala Ser Ser Ser Val Ser Tyr Ile His Trp Phe Gln Gln Lys Pro Gly
        50                  55                  60

Ser Ser Pro Lys Pro Trp Ile Tyr Ala Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Arg Val Glu Ala Glu Asp Ala Ala Thr Tyr Tyr Cys Gln
            100                 105                 110

Gln Trp Thr Ser Asn Pro Pro Thr Phe Gly Gly Gly Thr Lys Leu Glu
        115                 120                 125

Ile Lys Gly Ser Thr Ser Gly Gly Gly Ser Gly Gly Gly Ser Gly Gly
    130                 135                 140

Gly Gly Ser Ser Gln Val Gln Leu Gln Gln Pro Gly Ala Glu Leu Val
145                 150                 155                 160

Lys Pro Gly Ala Ser Val Lys Met Ser Cys Lys Ala Ser Gly Tyr Thr
                165                 170                 175

Phe Thr Ser Tyr Asn Met His Trp Val Lys Gln Thr Pro Gly Arg Gly
            180                 185                 190

Leu Glu Trp Ile Gly Ala Ile Tyr Pro Gly Asn Gly Asp Thr Ser Tyr
        195                 200                 205

Asn Gln Lys Phe Lys Gly Lys Ala Thr Leu Thr Ala Asp Lys Ser Ser
    210                 215                 220
```

```
Ser Thr Ala Tyr Met Gln Leu Ser Ser Leu Thr Ser Glu Asp Ser Ala
225                 230                 235                 240

Val Tyr Tyr Cys Ala Arg Ser Thr Tyr Tyr Gly Gly Asp Trp Tyr Phe
            245                 250                 255

Asn Val Trp Gly Ala Gly Thr Thr Val Thr Val Ser Ala Ser Ser Gly
        260                 265                 270

Ser Gly Ser Ala Ala Glu Ala Gly Ile Thr Gly Thr Trp Ser Asp Gln
    275                 280                 285

Leu Gly Asp Thr Phe Ile Val Thr Ala Gly Ala Asp Gly Ala Leu Thr
290                 295                 300

Gly Thr Tyr Glu Asn Ala Val Gly Gly Ala Glu Ser Arg Tyr Val Leu
305                 310                 315                 320

Thr Gly Arg Tyr Asp Ser Ala Pro Ala Thr Asp Gly Ser Gly Thr Ala
            325                 330                 335

Leu Gly Trp Thr Val Ala Trp Lys Asn Asn Ser Lys Asn Ala His Ser
        340                 345                 350

Ala Thr Thr Trp Ser Gly Gln Tyr Val Gly Gly Ala Asp Ala Lys Ile
    355                 360                 365

Asn Thr Gln Trp Leu Leu Thr Ser Gly Thr Thr Asn Ala Asn Ala Trp
370                 375                 380

Lys Ser Thr Leu Val Gly His Asp Thr Phe Thr Lys Val Lys Pro Ser
385                 390                 395                 400

Ala Ala Ser Gly Gly His His His His His His
            405                 410

<210> SEQ ID NO 29
<211> LENGTH: 1248
<212> TYPE: DNA
<213> ORGANISM: Artificial Sequence
<220> FEATURE:
<223> OTHER INFORMATION: Description of Artificial Sequence: Synthetic
      recombinant polynucleotide
<220> FEATURE:
<221> NAME/KEY: CDS
<222> LOCATION: (1)..(1245)

<400> SEQUENCE: 29 atg aaa tac cta ttg cct acg gca gcc gct gga tta tta ctc gcg         48
Met Lys Tyr Leu Leu Pro Thr Ala Ala Ala Gly Leu Leu Leu Leu Ala
1               5                   10                  15 gcc cag ccg gcc atg gcc cag gtg cag ctg cag cag tct ggc gcc gaa    96
Ala Gln Pro Ala Met Ala Gln Val Gln Leu Gln Gln Ser Gly Ala Glu
                20                  25                  30 gtg aag aaa cct ggc gcc tcc gtg aag gtg tcc tgc aag gcc tcc ggc    144
Val Lys Lys Pro Gly Ala Ser Val Lys Val Ser Cys Lys Ala Ser Gly
            35                  40                  45 ttc aac atc aag gac acc tac atg cac tgg gtg cga cag gcc cct gag   192
Phe Asn Ile Lys Asp Thr Tyr Met His Trp Val Arg Gln Ala Pro Glu
        50                  55                  60 cag ggc ctg gaa tgg atg ggc aga atc gac ccc ctg aac gac aag act   240
Gln Gly Leu Glu Trp Met Gly Arg Ile Asp Pro Leu Asn Asp Lys Thr
65                  70                  75                  80 aag tac gac ccc aag ttc cag ggc aga gtg acc atc acc gcc gac acc   288
Lys Tyr Asp Pro Lys Phe Gln Gly Arg Val Thr Ile Thr Ala Asp Thr
                85                  90                  95 tct acc aac acc gcc tac ctg gaa ctg tcc tcc ctg acc tct gag gac   336
Ser Thr Asn Thr Ala Tyr Leu Glu Leu Ser Ser Leu Thr Ser Glu Asp
            100                 105                 110
```

| | | |
|---|---|---|
| acc gcc gtg tac tac tgc gct aga ggc ggc gga gat ccc gtg ttc gtg<br>Thr Ala Val Tyr Tyr Cys Ala Arg Gly Gly Gly Asp Pro Val Phe Val<br>                 115                      120                    125 | | 384 |
| tat tgg ggc cag ggc acc ctc gtg acc gtg tct gct tct tct ggc gga<br>Tyr Trp Gly Gln Gly Thr Leu Val Thr Val Ser Ala Ser Ser Gly Gly<br>130                      135                      140 | | 432 |
| ggc gga tct ggg ggc gga ggt tct ggt ggt ggt gga agc ggt ggc ggt<br>Gly Gly Ser Gly Gly Gly Gly Ser Gly Gly Gly Gly Ser Gly Gly Gly<br>145                      150                      155                      160 | | 480 |
| gga tct ggc ggc gat atc cag atg acc cag tcc ccc agc tcc ctg tct<br>Gly Ser Gly Gly Asp Ile Gln Met Thr Gln Ser Pro Ser Ser Leu Ser<br>                 165                      170                      175 | | 528 |
| gcc tct gtg ggc gac cgc gtg acc att aca tgc aag gcc agc cag gac<br>Ala Ser Val Gly Asp Arg Val Thr Ile Thr Cys Lys Ala Ser Gln Asp<br>                    180                      185                      190 | | 576 |
| atc aac aag tac ctg gcc tgg tat cag cac aag ccc ggc cag gct cct<br>Ile Asn Lys Tyr Leu Ala Trp Tyr Gln His Lys Pro Gly Gln Ala Pro<br>         195                      200                      205 | | 624 |
| cgg ctg ctg atc cac tat acc tcc acc ctg cac ccc ggc atc cct tcc<br>Arg Leu Leu Ile His Tyr Thr Ser Thr Leu His Pro Gly Ile Pro Ser<br>210                      215                      220 | | 672 |
| aga ttc tcc ggc tct ggc tcc ggc acc gac ttt acc ttc tcc atc tcc<br>Arg Phe Ser Gly Ser Gly Ser Gly Thr Asp Phe Thr Phe Ser Ile Ser<br>225                      230                      235                      240 | | 720 |
| agc ctg cag ccc gag gat atc gct acc tac tac tgc ctg cag tac gac<br>Ser Leu Gln Pro Glu Asp Ile Ala Thr Tyr Tyr Cys Leu Gln Tyr Asp<br>                    245                      250                      255 | | 768 |
| aac ctg cgg acc ttc gga ggc ggc acc aag gtg gaa atc aag cgg acc<br>Asn Leu Arg Thr Phe Gly Gly Gly Thr Lys Val Glu Ile Lys Arg Thr<br>                    260                      265                      270 | | 816 |
| agc ggc gga ggt gga agc ggt gga ggt gga gcc gaa gca ggt att acc<br>Ser Gly Gly Gly Gly Ser Gly Gly Gly Gly Ala Glu Ala Gly Ile Thr<br>                275                      280                      285 | | 864 |
| ggc acc tgg agc gat cag ctg ggc gat acc ttt att gtg acc gcc ggc<br>Gly Thr Trp Ser Asp Gln Leu Gly Asp Thr Phe Ile Val Thr Ala Gly<br>290                      295                      300 | | 912 |
| gca gat ggt gcg ctg acc ggc acc tat gaa aat gcc gtg ggt ggt gcg<br>Ala Asp Gly Ala Leu Thr Gly Thr Tyr Glu Asn Ala Val Gly Gly Ala<br>305                      310                      315                      320 | | 960 |
| gaa agc cgt tat gtt ctg acc ggt cgt tat gat agc gca ccg gca acc<br>Glu Ser Arg Tyr Val Leu Thr Gly Arg Tyr Asp Ser Ala Pro Ala Thr<br>                    325                      330                      335 | | 1008 |
| gat ggc agc ggc acc gcc ctg ggt tgg acc gtg gcg tgg aaa aac aat<br>Asp Gly Ser Gly Thr Ala Leu Gly Trp Thr Val Ala Trp Lys Asn Asn<br>                    340                      345                      350 | | 1056 |
| agc aaa aac gcc cat agc gcg acc acc tgg agc ggc cag tat gtt ggc<br>Ser Lys Asn Ala His Ser Ala Thr Thr Trp Ser Gly Gln Tyr Val Gly<br>         355                      360                      365 | | 1104 |
| ggt gcc gat gcg aaa att aac acc cag tgg ctg ctg acc agc ggc acc<br>Gly Ala Asp Ala Lys Ile Asn Thr Gln Trp Leu Leu Thr Ser Gly Thr<br>370                      375                      380 | | 1152 |
| acc aat gcc aat gcg tgg aaa agc acc ctg gtg ggt cat gat acc ttt<br>Thr Asn Ala Asn Ala Trp Lys Ser Thr Leu Val Gly His Asp Thr Phe<br>385                      390                      395                      400 | | 1200 |
| acc aaa gtt aaa ccg agc gcg gcc agc cac cac cac cac cac cac tga<br>Thr Lys Val Lys Pro Ser Ala Ala Ser His His His His His His<br>                    405                      410                      415 | | 1248 |

<210> SEQ ID NO 30
<211> LENGTH: 415

<212> TYPE: PRT
<213> ORGANISM: Artificial Sequence
<220> FEATURE:
<223> OTHER INFORMATION: Description of Artificial Sequence: Synthetic recombinant polypeptide

<400> SEQUENCE: 30

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Ser Gly Ala Glu
            20                  25                  30

Val Lys Lys Pro Gly Ala Ser Val Lys Val Ser Cys Lys Ala Ser Gly
        35                  40                  45

Phe Asn Ile Lys Asp Thr Tyr Met His Trp Val Arg Gln Ala Pro Glu
    50                  55                  60

Gln Gly Leu Glu Trp Met Gly Arg Ile Asp Pro Leu Asn Asp Lys Thr
65                  70                  75                  80

Lys Tyr Asp Pro Lys Phe Gln Gly Arg Val Thr Ile Thr Ala Asp Thr
                85                  90                  95

Ser Thr Asn Thr Ala Tyr Leu Glu Leu Ser Ser Leu Thr Ser Glu Asp
            100                 105                 110

Thr Ala Val Tyr Tyr Cys Ala Arg Gly Gly Gly Asp Pro Val Phe Val
        115                 120                 125

Tyr Trp Gly Gln Gly Thr Leu Val Thr Val Ser Ala Ser Ser Gly Gly
    130                 135                 140

Gly Gly Ser Gly Gly Gly Gly Ser Gly Gly Gly Ser Gly Gly Gly Gly
145                 150                 155                 160

Gly Ser Gly Gly Asp Ile Gln Met Thr Gln Ser Pro Ser Ser Leu Ser
                165                 170                 175

Ala Ser Val Gly Asp Arg Val Thr Ile Thr Cys Lys Ala Ser Gln Asp
            180                 185                 190

Ile Asn Lys Tyr Leu Ala Trp Tyr Gln His Lys Pro Gly Gln Ala Pro
        195                 200                 205

Arg Leu Leu Ile His Tyr Thr Ser Thr Leu His Pro Gly Ile Pro Ser
    210                 215                 220

Arg Phe Ser Gly Ser Gly Ser Gly Thr Asp Phe Thr Phe Ser Ile Ser
225                 230                 235                 240

Ser Leu Gln Pro Glu Asp Ile Ala Thr Tyr Tyr Cys Leu Gln Tyr Asp
                245                 250                 255

Asn Leu Arg Thr Phe Gly Gly Gly Thr Lys Val Glu Ile Lys Arg Thr
            260                 265                 270

Ser Gly Gly Gly Gly Ser Gly Gly Gly Gly Ala Glu Ala Gly Ile Thr
        275                 280                 285

Gly Thr Trp Ser Asp Gln Leu Gly Asp Thr Phe Ile Val Thr Ala Gly
    290                 295                 300

Ala Asp Gly Ala Leu Thr Gly Thr Tyr Glu Asn Ala Val Gly Gly Ala
305                 310                 315                 320

Glu Ser Arg Tyr Val Leu Thr Gly Arg Tyr Asp Ser Ala Pro Ala Thr
                325                 330                 335

Asp Gly Ser Gly Thr Ala Leu Gly Trp Thr Val Ala Trp Lys Asn Asn
            340                 345                 350

Ser Lys Asn Ala His Ser Ala Thr Thr Trp Ser Gly Gln Tyr Val Gly
        355                 360                 365

Gly Ala Asp Ala Lys Ile Asn Thr Gln Trp Leu Leu Thr Ser Gly Thr
    370                 375                 380
```

```
Thr Asn Ala Asn Ala Trp Lys Ser Thr Leu Val Gly His Asp Thr Phe
385                 390                 395                 400

Thr Lys Val Lys Pro Ser Ala Ala Ser His His His His His
            405                 410                 415

<210> SEQ ID NO 31
<211> LENGTH: 1410
<212> TYPE: DNA
<213> ORGANISM: Artificial Sequence
<220> FEATURE:
<223> OTHER INFORMATION: Description of Artificial Sequence: Synthetic
      recombinant polynucleotide
<220> FEATURE:
<221> NAME/KEY: CDS
<222> LOCATION: (1)..(1407)

<400> SEQUENCE: 31 atg gaa acc gat aca ctg ctg ctg tgg gtg ctg ctg ctg tgg gtc cct      48
Met Glu Thr Asp Thr Leu Leu Leu Trp Val Leu Leu Leu Trp Val Pro
1               5                   10                  15 ggg tca act ggc gat cag gtt cag ctg cag cag tct ggt gcg gaa gtt     96
Gly Ser Thr Gly Asp Gln Val Gln Leu Gln Gln Ser Gly Ala Glu Val
                20                  25                  30 aaa aaa ccg ggt gcg tct gtt aaa gtt tct tgc aaa gcg tct ggt ttc    144
Lys Lys Pro Gly Ala Ser Val Lys Val Ser Cys Lys Ala Ser Gly Phe
            35                  40                  45 aac atc aaa gac acc tac atg cac tgg gtt cgt cag gcg ccg gaa cag    192
Asn Ile Lys Asp Thr Tyr Met His Trp Val Arg Gln Ala Pro Glu Gln
        50                  55                  60 ggt ctg gaa tgg atg ggt cgt atc gac ccg ctg aac gac aaa acc aaa    240
Gly Leu Glu Trp Met Gly Arg Ile Asp Pro Leu Asn Asp Lys Thr Lys
65                  70                  75                  80 tac gac ccg aaa ttc cag ggt cgt gtt acc atc act gct gat acc tct    288
Tyr Asp Pro Lys Phe Gln Gly Arg Val Thr Ile Thr Ala Asp Thr Ser
                85                  90                  95 acc aac acc gcg tac ctg gaa ctg tct tct ctg acc tct gaa gac act    336
Thr Asn Thr Ala Tyr Leu Glu Leu Ser Ser Leu Thr Ser Glu Asp Thr
            100                 105                 110 gct gtc tac tac tgc gcg cgt ggt ggt ggt gac ccg gtt ttc gtt tac    384
Ala Val Tyr Tyr Cys Ala Arg Gly Gly Gly Asp Pro Val Phe Val Tyr
        115                 120                 125 tgg ggt cag ggt acc ctg gtt acc gtt tct gcg gct agc acc aag ggc    432
Trp Gly Gln Gly Thr Leu Val Thr Val Ser Ala Ala Ser Thr Lys Gly
130                 135                 140 cca tcg gtc ttc ccc ctg gca ccc tcc tcc aag agc acc tct ggg ggc    480
Pro Ser Val Phe Pro Leu Ala Pro Ser Ser Lys Ser Thr Ser Gly Gly
145                 150                 155                 160 aca gcg gcc ctg ggc tgc ctg gtc aag gac tac ttc ccc gaa ccg gtg    528
Thr Ala Ala Leu Gly Cys Leu Val Lys Asp Tyr Phe Pro Glu Pro Val
                165                 170                 175 acg gtg tcg tgg aac tca ggc gcc ctg acc agc ggc gtg cac acc ttc    576
Thr Val Ser Trp Asn Ser Gly Ala Leu Thr Ser Gly Val His Thr Phe
            180                 185                 190 ccg gct gtc cta cag tcc tca gga ctc tac tcc ctc agc agc gtg gtg    624
Pro Ala Val Leu Gln Ser Ser Gly Leu Tyr Ser Leu Ser Ser Val Val
        195                 200                 205 acc gtg ccc tcc agc agc ttg ggc acc cag acc tac atc tgc aac gtg    672
Thr Val Pro Ser Ser Ser Leu Gly Thr Gln Thr Tyr Ile Cys Asn Val
    210                 215                 220 aat cac aag ccc agc aac acc aag gtg gac aag aaa gtt gag ccc aaa    720
Asn His Lys Pro Ser Asn Thr Lys Val Asp Lys Lys Val Glu Pro Lys
```

-continued

|  |  |  |  |  |
|---|---|---|---|---|
| 225 | 230 | 235 | 240 | |

```
tct tgt gac aaa act cac aca tgc cca ccg tgc cca gca cct gaa ctc      768
Ser Cys Asp Lys Thr His Thr Cys Pro Pro Cys Pro Ala Pro Glu Leu
                245                 250                 255 ctg ggg gga ccg tca gtc ttc ctc ttc ccc cca aaa ccc aag gac acc      816
Leu Gly Gly Pro Ser Val Phe Leu Phe Pro Pro Lys Pro Lys Asp Thr
            260                 265                 270 ctc atg atc tcc cgg acc cct gag gtc aca tgc gtg gtg gtg gac gtg      864
Leu Met Ile Ser Arg Thr Pro Glu Val Thr Cys Val Val Val Asp Val
        275                 280                 285 agc cac gaa gac cct gag gtc aag ttc aac tgg tac gtg gac ggc gtg      912
Ser His Glu Asp Pro Glu Val Lys Phe Asn Trp Tyr Val Asp Gly Val
    290                 295                 300 gag gtg cat aat gcc aag aca aag ccg cgg gag gag cag tac aac agc      960
Glu Val His Asn Ala Lys Thr Lys Pro Arg Glu Glu Gln Tyr Asn Ser
305                 310                 315                 320 acg tac cgt gtg gtc agc gtc ctc acc gtc ctg cac cag gac tgg ctg     1008
Thr Tyr Arg Val Val Ser Val Leu Thr Val Leu His Gln Asp Trp Leu
                325                 330                 335 aat ggc aag gag tac aag tgc aag gtc tcc aac aaa gcc ctc cca gcc     1056
Asn Gly Lys Glu Tyr Lys Cys Lys Val Ser Asn Lys Ala Leu Pro Ala
            340                 345                 350 ccc atc gag aaa acc atc tcc aaa gcc aaa ggg cag ccc cga gaa cca     1104
Pro Ile Glu Lys Thr Ile Ser Lys Ala Lys Gly Gln Pro Arg Glu Pro
        355                 360                 365 cag gtg tac acc ctg ccc cca tcc cgg gag gag atg acc aag aac cag     1152
Gln Val Tyr Thr Leu Pro Pro Ser Arg Glu Glu Met Thr Lys Asn Gln
    370                 375                 380 gtc agc ctg acc tgc ctg gtc aaa ggc ttc tat ccc agc gac atc gcc     1200
Val Ser Leu Thr Cys Leu Val Lys Gly Phe Tyr Pro Ser Asp Ile Ala
385                 390                 395                 400 gtg gag tgg gag agc aat ggg cag ccg gag aac aac tac aag acc acg     1248
Val Glu Trp Glu Ser Asn Gly Gln Pro Glu Asn Asn Tyr Lys Thr Thr
                405                 410                 415 cct ccc gtg ctg gac tcc gac ggc tcc ttc ttc ctc tac agc aag ctc     1296
Pro Pro Val Leu Asp Ser Asp Gly Ser Phe Phe Leu Tyr Ser Lys Leu
            420                 425                 430 acc gtg gac aag agc agg tgg cag cag ggg aac gtc ttc tca tgc tcc     1344
Thr Val Asp Lys Ser Arg Trp Gln Gln Gly Asn Val Phe Ser Cys Ser
        435                 440                 445 gtg atg cat gag gct ctg cac aac cac tac acg cag aag agc ctc tcc     1392
Val Met His Glu Ala Leu His Asn His Tyr Thr Gln Lys Ser Leu Ser
    450                 455                 460 ctg tct ccg ggt aaa tga                                             1410
Leu Ser Pro Gly Lys
465

<210> SEQ ID NO 32
<211> LENGTH: 469
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 32

Met Glu Thr Asp Thr Leu Leu Leu Trp Val Leu Leu Leu Trp Val Pro
1               5                   10                  15

Gly Ser Thr Gly Asp Gln Val Gln Leu Gln Gln Ser Gly Ala Glu Val
            20                  25                  30
```

-continued

Lys Lys Pro Gly Ala Ser Val Lys Val Ser Cys Lys Ala Ser Gly Phe
         35                  40                  45

Asn Ile Lys Asp Thr Tyr Met His Trp Val Arg Gln Ala Pro Glu Gln
 50                  55                  60

Gly Leu Glu Trp Met Gly Arg Ile Asp Pro Leu Asn Asp Lys Thr Lys
 65                  70                  75                  80

Tyr Asp Pro Lys Phe Gln Gly Arg Val Thr Ile Thr Ala Asp Thr Ser
                 85                  90                  95

Thr Asn Thr Ala Tyr Leu Glu Leu Ser Ser Leu Thr Ser Glu Asp Thr
             100                 105                 110

Ala Val Tyr Tyr Cys Ala Arg Gly Gly Gly Asp Pro Val Phe Val Tyr
         115                 120                 125

Trp Gly Gln Gly Thr Leu Val Thr Val Ser Ala Ala Ser Thr Lys Gly
     130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
             165                 170                 175

Thr Val Ser Trp Asn Ser Gly Ala Leu Thr Ser Gly Val His Thr Phe
         180                 185                 190

Pro Ala Val Leu Gln Ser Ser Gly Leu Tyr Ser Leu Ser Ser Val Val
     195                 200                 205

Thr Val Pro Ser Ser Ser Leu Gly Thr Gln Thr Tyr Ile Cys Asn Val
 210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
             245                 250                 255

Leu Gly Gly Pro Ser Val Phe Leu Phe Pro Pro Lys Pro Lys Asp Thr
         260                 265                 270

Leu Met Ile Ser Arg Thr Pro Glu Val Thr Cys Val Val Val Asp Val
     275                 280                 285

Ser His Glu Asp Pro Glu Val Lys Phe Asn Trp Tyr Val Asp Gly Val
 290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
             325                 330                 335

Asn Gly Lys Glu Tyr Lys Cys Lys Val Ser Asn Lys Ala Leu Pro Ala
         340                 345                 350

Pro Ile Glu Lys Thr Ile Ser Lys Ala Lys Gly Gln Pro Arg Glu Pro
     355                 360                 365

Gln Val Tyr Thr Leu Pro Pro Ser Arg Glu Glu Met Thr Lys Asn Gln
 370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
             405                 410                 415

Pro Pro Val Leu Asp Ser Asp Gly Ser Phe Phe Leu Tyr Ser Lys Leu
         420                 425                 430

Thr Val Asp Lys Ser Arg Trp Gln Gln Gly Asn Val Phe Ser Cys Ser
     435                 440                 445

Val Met His Glu Ala Leu His Asn His Tyr Thr Gln Lys Ser Leu Ser

```
                        450                 455                 460

Leu Ser Pro Gly Lys
465

<210> SEQ ID NO 33
<211> LENGTH: 705
<212> TYPE: DNA
<213> ORGANISM: Artificial Sequence
<220> FEATURE:
<223> OTHER INFORMATION: Description of Artificial Sequence: Synthetic
      recombinant polynucleotide
<220> FEATURE:
<221> NAME/KEY: CDS
<222> LOCATION: (1)..(702)

<400> SEQUENCE: 33 atg gaa acc gat aca ctg ctg ctg tgg gtg ctg ctg ctg tgg gtc cct      48
Met Glu Thr Asp Thr Leu Leu Leu Trp Val Leu Leu Leu Trp Val Pro
1               5                   10                  15 ggg tca act ggc gat gac atc cag atg acc cag tct ccg tct tct ctg      96
Gly Ser Thr Gly Asp Asp Ile Gln Met Thr Gln Ser Pro Ser Ser Leu
            20                  25                  30 tct gcg tct gtt ggt gac cgt gtt acc atc acc tgc aaa gcg tct cag     144
Ser Ala Ser Val Gly Asp Arg Val Thr Ile Thr Cys Lys Ala Ser Gln
        35                  40                  45 gac atc aac aaa tac ctg gcg tgg tac cag cac aaa ccg ggt cag gcg     192
Asp Ile Asn Lys Tyr Leu Ala Trp Tyr Gln His Lys Pro Gly Gln Ala
    50                  55                  60 ccg cgt ctg ctg atc cac tac acc tct acc ctg cac ccg ggt atc ccg     240
Pro Arg Leu Leu Ile His Tyr Thr Ser Thr Leu His Pro Gly Ile Pro
65                  70                  75                  80 tct cgt ttc tct ggt tct ggt tct ggt acc gac tac acc ttc tct atc     288
Ser Arg Phe Ser Gly Ser Gly Ser Gly Thr Asp Tyr Thr Phe Ser Ile
                85                  90                  95 tct tct ctg cag ccg gaa gac atc gcg acc tac tac tgc ctg cag tac     336
Ser Ser Leu Gln Pro Glu Asp Ile Ala Thr Tyr Tyr Cys Leu Gln Tyr
            100                 105                 110 gac aac ctg cgt acc ttc ggt ggt ggt acc aaa gtt gaa atc aaa cgt     384
Asp Asn Leu Arg Thr Phe Gly Gly Gly Thr Lys Val Glu Ile Lys Arg
        115                 120                 125 acg gtg gct gca cca tct gtc ttc atc ttc ccg cca tct gat gag cag     432
Thr Val Ala Ala Pro Ser Val Phe Ile Phe Pro Pro Ser Asp Glu Gln
    130                 135                 140 ttg aaa tct gga act gcc tct gtt gtg tgc ctg ctg aat aac ttc tat     480
Leu Lys Ser Gly Thr Ala Ser Val Val Cys Leu Leu Asn Asn Phe Tyr
145                 150                 155                 160 ccc aga gag gcc aaa gta cag tgg aag gtg gat aac gcc ctc caa tcg     528
Pro Arg Glu Ala Lys Val Gln Trp Lys Val Asp Asn Ala Leu Gln Ser
                165                 170                 175 ggt aac tcc cag gag agt gtc aca gag cag gac agc aag gac agc acc     576
Gly Asn Ser Gln Glu Ser Val Thr Glu Gln Asp Ser Lys Asp Ser Thr
            180                 185                 190 tac agc ctc agc agc acc ctg acg ctg agc aaa gca gac tac gag aaa     624
Tyr Ser Leu Ser Ser Thr Leu Thr Leu Ser Lys Ala Asp Tyr Glu Lys
        195                 200                 205 cac aaa gtc tac gcc tgc gaa gtc acc cat cag ggc ctg agc tcg ccc     672
His Lys Val Tyr Ala Cys Glu Val Thr His Gln Gly Leu Ser Ser Pro
    210                 215                 220 gtc aca aag agc ttc aac agg gga gag tgt tag                         705
Val Thr Lys Ser Phe Asn Arg Gly Glu Cys
225                 230
```

<210> SEQ ID NO 34
<211> LENGTH: 234
<212> TYPE: PRT
<213> ORGANISM: Artificial Sequence
<220> FEATURE:
<223> OTHER INFORMATION: Description of Artificial Sequence: Synthetic recombinant polypeptide

<400> SEQUENCE: 34

Met Glu Thr Asp Thr Leu Leu Leu Trp Val Leu Leu Leu Trp Val Pro
1               5                   10                  15

Gly Ser Thr Gly Asp Asp Ile Gln Met Thr Gln Ser Pro Ser Ser Leu
            20                  25                  30

Ser Ala Ser Val Gly Asp Arg Val Thr Ile Thr Cys Lys Ala Ser Gln
        35                  40                  45

Asp Ile Asn Lys Tyr Leu Ala Trp Tyr Gln His Lys Pro Gly Gln Ala
    50                  55                  60

Pro Arg Leu Leu Ile His Tyr Thr Ser Thr Leu His Pro Gly Ile Pro
65                  70                  75                  80

Ser Arg Phe Ser Gly Ser Gly Ser Gly Thr Asp Tyr Thr Phe Ser Ile
                85                  90                  95

Ser Ser Leu Gln Pro Glu Asp Ile Ala Thr Tyr Tyr Cys Leu Gln Tyr
            100                 105                 110

Asp Asn Leu Arg Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Gly Gly Gly Gly Ser Gly Gly Gly Ser Gly Gly Gly Gly Ser Gly
1               5                   10                  15

Gly Gly Gly Ser
            20

<210> SEQ ID NO 36
<211> LENGTH: 9
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 36

Gly Gly Gly Gly Ser Gly Gly Gly Gly
1               5

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aggagatata ccatgatgaa aaaatggctg ctggc                                 35

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cgccgagctc gaattttatt tcacttgttt cagaacg                               37

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
aaggagatat acataatgaa atacctattg cctacggcag                            40

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttgagatctg ccatatcagt ggtggtggtg gtggtggctg                            40

<210> SEQ ID NO 41
<211> LENGTH: 1239
<212> TYPE: DNA
<213> ORGANISM: Artificial Sequence
<220> FEATURE:
<223> OTHER INFORMATION: Description of Artificial Sequence: Synthetic
      recombinant polynucleotide
<220> FEATURE:
<221> NAME/KEY: CDS
<222> LOCATION: (1)..(1239)

<400> SEQUENCE: 41 atg aaa tat ctg ctg ccg acc gca gca gcg ggt ctg ctg ctg ctg gca        48
Met Lys Tyr Leu Leu Pro Thr Ala Ala Ala Gly Leu Leu Leu Leu Ala
1               5                   10                  15 gca cag cct gca atg gca cag att gtt ctg agc cag agt ccg gca att        96
```

|  |  |  |  |  |  |  |  |  |  |  |  |  |  |  |  |
|---|---|---|---|---|---|---|---|---|---|---|---|---|---|---|---|
| Ala | Gln | Pro | Ala | Met | Ala | Gln | Ile | Val | Leu | Ser | Gln | Ser | Pro | Ala | Ile |
|  |  |  | 20 |  |  |  | 25 |  |  |  | 30 |  |  |  |  |

```
ctg agc gca tca ccg ggt gaa aaa gtt acc atg acc tgt cgt gca agc      144
Leu Ser Ala Ser Pro Gly Glu Lys Val Thr Met Thr Cys Arg Ala Ser
         35                  40                  45 agc agc gtt agc tat att cat tgg ttt cag cag aaa ccg ggt agc agc      192
Ser Ser Val Ser Tyr Ile His Trp Phe Gln Gln Lys Pro Gly Ser Ser
     50                  55                  60 ccg aaa ccg tgg att tat gca acc agc aat ctg gca agc ggt gtt ccg      240
Pro Lys Pro Trp Ile Tyr Ala Thr Ser Asn Leu Ala Ser Gly Val Pro
 65                  70                  75                  80 gtt cgt ttt agc ggt agc ggt agt ggc acc agc tat agc ctg acc att      288
Val Arg Phe Ser Gly Ser Gly Ser Gly Thr Ser Tyr Ser Leu Thr Ile
                 85                  90                  95 agc cgt gtt gaa gca gaa gat gca gca acc tat tat tgt cag cag tgg      336
Ser Arg Val Glu Ala Glu Asp Ala Ala Thr Tyr Tyr Cys Gln Gln Trp
            100                 105                 110 acc agt aat ccg cct acc ttt ggt ggt ggc acc aaa ctg gaa att aaa      384
Thr Ser Asn Pro Pro Thr Phe Gly Gly Gly Thr Lys Leu Glu Ile Lys
        115                 120                 125 gga ggt ggt ggt tca gga ggt ggt ggt agc ggt ggc ggt ggt agc gga      432
Gly Gly Gly Gly Ser Gly Gly Gly Ser Gly Gly Gly Gly Ser Gly
    130                 135                 140 ggt ggt ggt agc cag gtt cag ctg cag cag cct ggt gca gaa ctg gtt      480
Gly Gly Gly Ser Gln Val Gln Leu Gln Gln Pro Gly Ala Glu Leu Val
145                 150                 155                 160 aaa ccg ggt gca agc gtt aaa atg agc tgt aaa gca agc ggt tat acc      528
Lys Pro Gly Ala Ser Val Lys Met Ser Cys Lys Ala Ser Gly Tyr Thr
                165                 170                 175 ttt acc agc tac aat atg cat tgg gtt aaa cag aca ccg ggt cgt ggt      576
Phe Thr Ser Tyr Asn Met His Trp Val Lys Gln Thr Pro Gly Arg Gly
            180                 185                 190 ctg gaa tgg att ggt gca att tat ccg ggt aat ggt gat acg agc tat      624
Leu Glu Trp Ile Gly Ala Ile Tyr Pro Gly Asn Gly Asp Thr Ser Tyr
        195                 200                 205 aac cag aaa ttc aaa ggc aaa gca acc ctg acc gca gat aaa agc agc      672
Asn Gln Lys Phe Lys Gly Lys Ala Thr Leu Thr Ala Asp Lys Ser Ser
    210                 215                 220 agt acc gcc tat atg cag ctg agc agt ctg acc agc gaa gat agc gca      720
Ser Thr Ala Tyr Met Gln Leu Ser Ser Leu Thr Ser Glu Asp Ser Ala
225                 230                 235                 240 gtt tat tac tgt gca cgt agc acc tat tac ggt ggt gat tgg tat ttt      768
Val Tyr Tyr Cys Ala Arg Ser Thr Tyr Tyr Gly Gly Asp Trp Tyr Phe
                245                 250                 255 aac gtt tgg ggt gca ggc acc acc gtt acc gtt agc gca ggc gga ggt      816
Asn Val Trp Gly Ala Gly Thr Thr Val Thr Val Ser Ala Gly Gly Gly
            260                 265                 270 gga agc ggt gga ggt gga gca gaa gca ggt att acc ggc acc tgg tca      864
Gly Ser Gly Gly Gly Gly Ala Glu Ala Gly Ile Thr Gly Thr Trp Ser
        275                 280                 285 gat cag ctg ggt gat acc ttt att gtt acc gca ggc gca gat ggt gca      912
Asp Gln Leu Gly Asp Thr Phe Ile Val Thr Ala Gly Ala Asp Gly Ala
    290                 295                 300 ctg acc ggt aca tat gaa aat gca gtt ggt aat gca gaa agc cgt tat      960
Leu Thr Gly Thr Tyr Glu Asn Ala Val Gly Asn Ala Glu Ser Arg Tyr
305                 310                 315                 320 gtt ctg acc ggt cgt tat gat agc gca ccg gca acc gat ggt agc ggc     1008
Val Leu Thr Gly Arg Tyr Asp Ser Ala Pro Ala Thr Asp Gly Ser Gly
                325                 330                 335
```

```
acc gca ctg ggt tgg acc gtt gca tgg aaa aat aac agc aaa aat gca         1056
Thr Ala Leu Gly Trp Thr Val Ala Trp Lys Asn Asn Ser Lys Asn Ala
            340                 345                 350 cat agc gca acc aca tgg tca ggt cag tat gtt ggt ggt gca gat gcc         1104
His Ser Ala Thr Thr Trp Ser Gly Gln Tyr Val Gly Gly Ala Asp Ala
            355                 360                 365 aaa att aac acc cag tgg ctg ctg acc agt ggt aca acc aat gca aat         1152
Lys Ile Asn Thr Gln Trp Leu Leu Thr Ser Gly Thr Thr Asn Ala Asn
        370                 375                 380 gcc tgg aaa agc acc ctg gtt ggt cat gat aca ttt acc aaa gtt aaa         1200
Ala Trp Lys Ser Thr Leu Val Gly His Asp Thr Phe Thr Lys Val Lys
385                 390                 395                 400 ccg agc gca gcg agc ggt ggt cat cat cat cac cat cat                     1239
Pro Ser Ala Ala Ser Gly Gly His His His His His His
                405                 410

<210> SEQ ID NO 42
<211> LENGTH: 413
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 42

Met Lys Tyr Leu Leu Pro Thr Ala Ala Ala Gly Leu Leu Leu Leu Ala
1               5                   10                  15

Ala Gln Pro Ala Met Ala Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Phe Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
        115                 120                 125

Gly Gly Gly Gly Ser Gly Gly Gly Ser Gly Gly Gly Ser Gly
    130                 135                 140

Gly Gly Gly Ser Gln Val Gln Leu Gln Gln Pro Gly Ala Glu Leu Val
145                 150                 155                 160

Lys Pro Gly Ala Ser Val Lys Met Ser Cys Lys Ala Ser Gly Tyr Thr
                165                 170                 175

Phe Thr Ser Tyr Asn Met His Trp Val Lys Gln Thr Pro Gly Arg Gly
            180                 185                 190

Leu Glu Trp Ile Gly Ala Ile Tyr Pro Gly Asn Gly Asp Thr Ser Tyr
        195                 200                 205

Asn Gln Lys Phe Lys Gly Lys Ala Thr Leu Thr Ala Asp Lys Ser Ser
    210                 215                 220

Ser Thr Ala Tyr Met Gln Leu Ser Ser Leu Thr Ser Glu Asp Ser Ala
225                 230                 235                 240

Val Tyr Tyr Cys Ala Arg Ser Thr Tyr Tyr Gly Gly Asp Trp Tyr Phe
                245                 250                 255
```

Asn Val Trp Gly Ala Gly Thr Thr Val Thr Val Ser Ala Gly Gly Gly
                260                 265                 270

Gly Ser Gly Gly Gly Ala Glu Ala Gly Ile Thr Gly Thr Trp Ser
        275                 280                 285

Asp Gln Leu Gly Asp Thr Phe Ile Val Thr Ala Gly Ala Asp Gly Ala
        290                 295                 300

Leu Thr Gly Thr Tyr Glu Asn Ala Val Gly Asn Ala Glu Ser Arg Tyr
305                 310                 315                 320

Val Leu Thr Gly Arg Tyr Asp Ser Ala Pro Ala Thr Asp Gly Ser Gly
                325                 330                 335

Thr Ala Leu Gly Trp Thr Val Ala Trp Lys Asn Asn Ser Lys Asn Ala
                340                 345                 350

His Ser Ala Thr Thr Trp Ser Gly Gln Tyr Val Gly Gly Ala Asp Ala
                355                 360                 365

Lys Ile Asn Thr Gln Trp Leu Leu Thr Ser Gly Thr Thr Asn Ala Asn
                370                 375                 380

Ala Trp Lys Ser Thr Leu Val Gly His Asp Thr Phe Thr Lys Val Lys
385                 390                 395                 400

Pro Ser Ala Ala Ser Gly Gly His His His His His His
                405                 410

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Ser Gly Ser Gly Ser Ala
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 44

His His His His His His
1               5